(12) United States Patent
Drummond et al.

(10) Patent No.: US 12,331,264 B2
(45) Date of Patent: Jun. 17, 2025

(54) LIPID NANOPARTICLES FOR DELIVERY OF NUCLEIC ACIDS AND METHODS OF USE THEREOF

(71) Applicant: Akagera Medicines, Inc., Boxford, MA (US)

(72) Inventors: Daryl C. Drummond, Lincoln, MA (US); Dmitri B. Kirpotin, San Francisco, CA (US); Mark E. Hayes, Mill Valley, CA (US); Alexander Koshkaryev, Norwood, MA (US); Ross B. Fulton, Southborough, MA (US)

(73) Assignee: Akagera Medicines, Inc., Boxford, MA (US)

( * ) Notice: Subject to any disclaimer, the term of this patent is extended or adjusted under 35 U.S.C. 154(b) by 528 days.

(21) Appl. No.: 17/818,052

(22) Filed: Aug. 8, 2022

(65) Prior Publication Data
US 2022/0411394 A1    Dec. 29, 2022

Related U.S. Application Data

(63) Continuation of application No. PCT/US2021/060877, filed on Nov. 24, 2021.

(60) Provisional application No. 63/118,534, filed on Nov. 25, 2020.

(51) Int. Cl.
| | | |
|---|---|---|
| C11C 3/00 | (2006.01) | |
| C07D 317/28 | (2006.01) | |
| C07F 9/09 | (2006.01) | |

(52) U.S. Cl.
CPC ............ C11C 3/003 (2013.01); C07D 317/28 (2013.01); C07F 9/091 (2013.01)

(58) Field of Classification Search
CPC .................................................. C11C 3/003
USPC ........................................................ 549/451
See application file for complete search history.

(56) References Cited

U.S. PATENT DOCUMENTS

| | | |
|---|---|---|
| 4,394,448 A | 7/1983 | Szoka, Jr. et al. |
| 4,438,052 A | 3/1984 | Weder et al. |
| 4,515,736 A | 5/1985 | Deamer |
| 4,598,051 A | 7/1986 | Papahadjopoulos et al. |
| 4,897,355 A | 1/1990 | Eppstein et al. |
| 5,013,556 A | 5/1991 | Woodle et al. |
| 5,171,678 A | 12/1992 | Behr et al. |
| 5,208,036 A | 5/1993 | Eppstein et al. |
| 5,225,212 A | 7/1993 | Martin et al. |
| 5,264,618 A | 11/1993 | Feigner et al. |
| 5,279,833 A | 1/1994 | Rose |
| 5,283,185 A | 2/1994 | Epand et al. |
| 5,316,771 A | 5/1994 | Barenholz et al. |
| 5,320,906 A | 6/1994 | Eley et al. |
| 5,334,761 A | 8/1994 | Gebeyehu et al. |
| 5,545,412 A | 8/1996 | Eppstein et al. |
| 5,578,475 A | 11/1996 | Jessee |
| 5,627,159 A | 5/1997 | Shih et al. |
| 5,641,662 A | 6/1997 | Debs et al. |
| 5,656,743 A | 8/1997 | Busch et al. |
| 5,674,908 A | 10/1997 | Haces et al. |
| 5,703,055 A | 12/1997 | Feigner et al. |
| 5,705,385 A | 1/1998 | Bally et al. |
| 5,736,392 A | 4/1998 | Hawley-Nelson et al. |
| 5,800,833 A | 9/1998 | Hope et al. |
| 5,820,873 A | 10/1998 | Choi et al. |
| 5,877,220 A | 3/1999 | Schwartz et al. |
| 5,885,613 A | 3/1999 | Holland et al. |
| 5,958,901 A | 9/1999 | Dwyer et al. |
| 5,976,567 A | 11/1999 | Wheeler et al. |
| 5,981,501 A | 11/1999 | Wheeler et al. |
| 6,020,202 A | 2/2000 | Jessee |
| 6,020,526 A | 2/2000 | Schwartz et al. |
| 6,034,135 A | 3/2000 | Schwartz et al. |
| 6,051,429 A | 4/2000 | Hawley-Nelson et al. |
| 6,075,012 A | 6/2000 | Gebeyehu et al. |
| 6,110,491 A | 8/2000 | Kirpotin |
| 6,165,501 A | 12/2000 | Tirosh et al. |
| 6,172,049 B1 | 1/2001 | Dwyer et al. |
| 6,251,939 B1 | 6/2001 | Schwartz et al. |
| 6,284,267 B1 | 9/2001 | Aneja |
| 6,287,591 B1 | 9/2001 | Semple et al. |
| 6,339,173 B1 | 1/2002 | Schwartz et al. |

(Continued)

FOREIGN PATENT DOCUMENTS

| | | |
|---|---|---|
| CA | 2 271 582 | 11/1989 |
| CA | 2 309 727 | 4/1999 |

(Continued)

OTHER PUBLICATIONS

Akinc et al., "Development of Lipidoid—siRNA Formulations for Systemic Delivery to the Liver" Molecular Therapy, vol. 17, No. 5, pp. 872-879, May 2009.

(Continued)

*Primary Examiner* — Taofiq A Solola

(74) *Attorney, Agent, or Firm* — Greenberg Traurig, LLP; David J. Dykeman; Natalie Salem

(57) ABSTRACT

The present disclosure provides for improved compositions of ionizable lipid nanoparticles for the delivery of therapeutic nucleic acids to cells. Cationic ionizable lipids are engineered with improved stability to oxidative degradation while in storage, while retaining high transfection activity or potency in cells. These lipids are designed to be biodegradable, thus improving the tolerability of nanoparticles formed with them in vivo. In addition, targeting of these nanoparticles in a highly specific manner to dendritic cells is provided for through inclusion of antibody conjugates directed against cell surface receptors.

20 Claims, 22 Drawing Sheets

Specification includes a Sequence Listing.

(56) References Cited

U.S. PATENT DOCUMENTS

| | | |
|---|---|---|
| 6,376,248 B1 | 4/2002 | Hawley-Nelson et al. |
| 6,534,484 B1 | 3/2003 | Wheeler et al. |
| 6,586,410 B1 | 7/2003 | Wheeler et al. |
| 6,638,529 B2 | 10/2003 | Schwartz et al. |
| 6,649,780 B1 | 11/2003 | Eibl et al. |
| 6,671,393 B2 | 12/2003 | Hays et al. |
| 6,689,779 B2 | 2/2004 | Lee et al. |
| 6,696,424 B1 | 2/2004 | Wheeler |
| 6,815,432 B2 | 11/2004 | Wheeler et al. |
| 6,858,224 B2 | 2/2005 | Wheeler et al. |
| 7,074,596 B2 | 7/2006 | Darzynkiewicz |
| 7,166,745 B1 | 1/2007 | Chu et al. |
| 7,422,902 B1 | 9/2008 | Wheeler et al. |
| 7,462,615 B2 | 12/2008 | Guedat et al. |
| 7,479,573 B2 | 1/2009 | Chu et al. |
| 7,601,872 B2 | 10/2009 | Chu et al. |
| 7,687,070 B2 | 3/2010 | Gebeyehu et al. |
| 7,744,921 B2 | 6/2010 | Tardi et al. |
| 7,745,651 B2 | 6/2010 | Heyes et al. |
| 7,799,565 B2 | 9/2010 | Maclachlan et al. |
| 7,803,397 B2 | 9/2010 | Heyes et al. |
| 7,807,815 B2 | 10/2010 | Maclachlan et al. |
| 7,816,379 B2 | 10/2010 | Rhee et al. |
| 7,838,658 B2 | 11/2010 | Maclachlan et al. |
| 7,901,708 B2 | 3/2011 | Maclachlan et al. |
| 7,915,450 B2 | 3/2011 | Chu et al. |
| 7,982,027 B2 | 7/2011 | MacLachlan et al. |
| 8,021,686 B2 | 9/2011 | Semple et al. |
| 8,058,068 B2 | 11/2011 | Hawley-Nelson et al. |
| 8,058,069 B2 | 11/2011 | Yaworski et al. |
| 8,101,741 B2 | 1/2012 | Maclachlan et al. |
| 8,147,867 B2 | 4/2012 | Hong et al. |
| 8,158,827 B2 | 4/2012 | Chu et al. |
| 8,188,263 B2 | 5/2012 | Maclachlan et al. |
| 8,227,443 B2 | 7/2012 | Maclachlan et al. |
| 8,278,036 B2 | 10/2012 | Kariko et al. |
| 8,283,333 B2 | 10/2012 | Yaworski et al. |
| 8,349,360 B2 | 1/2013 | Bally et al. |
| 8,455,455 B1 | 6/2013 | Robbins et al. |
| 8,492,359 B2 | 7/2013 | Yaworski et al. |
| 8,513,403 B2 | 8/2013 | Maclachlan et al. |
| 8,569,256 B2 | 10/2013 | Heyes et al. |
| 8,598,333 B2 | 12/2013 | Maclachlan et al. |
| 8,822,668 B2 | 9/2014 | Yaworski et al. |
| 9,061,063 B2 | 6/2015 | Maier et al. |
| 9,139,554 B2 | 9/2015 | Hope et al. |
| 9,220,683 B2 | 12/2015 | Manoharan et al. |
| 9,364,435 B2 | 6/2016 | Yaworski et al. |
| 9,404,127 B2 | 8/2016 | Yaworski et al. |
| 9,504,651 B2 | 11/2016 | MacLachlan et al. |
| 9,549,939 B2 | 1/2017 | Weers |
| 9,657,295 B2 | 5/2017 | Schrum et al. |
| 9,764,036 B2 | 9/2017 | Manoharan et al. |
| 10,072,057 B2 | 9/2018 | Hoge et al. |
| 10,221,127 B2 | 3/2019 | Du et al. |
| 10,369,226 B2 | 8/2019 | Maier et al. |
| 10,632,191 B2 | 4/2020 | Reed et al. |
| 10,653,780 B2 | 5/2020 | Hope et al. |
| 11,071,784 B2 | 7/2021 | Maier et al. |
| 11,141,378 B2 | 10/2021 | Yaworski et al. |
| 11,246,933 B1 | 2/2022 | Maier et al. |
| 11,591,544 B2 | 2/2023 | Drummond et al. |
| 12,064,479 B2 | 8/2024 | Drummond et al. |
| 12,077,725 B2 | 9/2024 | Drummond et al. |
| 2001/0048940 A1 | 12/2001 | Tousignant et al. |
| 2003/0069173 A1 | 4/2003 | Hawley-Nelson et al. |
| 2003/0072794 A1 | 4/2003 | Boulikas |
| 2003/0077829 A1 | 4/2003 | Maclachlan |
| 2003/0143732 A1 | 7/2003 | Fosnaugh et al. |
| 2004/0009126 A1 | 1/2004 | Pilkiewicz et al. |
| 2004/0063654 A1 | 4/2004 | Davis et al. |
| 2004/0142892 A1 | 7/2004 | Finn et al. |
| 2004/0253723 A1 | 12/2004 | Tachas et al. |
| 2004/0258651 A1 | 12/2004 | Pascaly et al. |
| 2004/0258652 A1 | 12/2004 | Pascaly et al. |
| 2004/0259247 A1 | 12/2004 | Tuschl et al. |
| 2005/0000030 A1 | 1/2005 | Dupont et al. |
| 2005/0064595 A1 | 3/2005 | Maclachlan et al. |
| 2005/0118253 A1 | 6/2005 | Maclachlan et al. |
| 2005/0187218 A1 | 8/2005 | Marinier et al. |
| 2005/0260757 A1 | 11/2005 | Gebeyehu et al. |
| 2006/0008519 A1 | 1/2006 | Davidsen et al. |
| 2006/0008910 A1 | 1/2006 | Maclachlan et al. |
| 2006/0083780 A1 | 4/2006 | Heyes et al. |
| 2006/0147514 A1 | 7/2006 | Gebeyehu et al. |
| 2006/0228406 A1 | 10/2006 | Chiou et al. |
| 2006/0240093 A1 | 10/2006 | Maclachlan et al. |
| 2007/0042031 A1 | 2/2007 | Maclachlan et al. |
| 2007/0148220 A1 | 6/2007 | Muller et al. |
| 2007/0202598 A1 | 8/2007 | Chu et al. |
| 2007/0202600 A1 | 8/2007 | Chu et al. |
| 2008/0021071 A1 | 1/2008 | Gravestock et al. |
| 2009/0023729 A1 | 1/2009 | Nakamura et al. |
| 2009/0143583 A1 | 6/2009 | Chu et al. |
| 2009/0291131 A1 | 11/2009 | Maclachlan et al. |
| 2010/0130588 A1 | 5/2010 | Yaworski et al. |
| 2010/0159593 A1 | 6/2010 | Chu et al. |
| 2010/0192814 A1 | 8/2010 | Herzog et al. |
| 2011/0060032 A1 | 3/2011 | MacLachlan et al. |
| 2011/0262527 A1 | 10/2011 | Heyes et al. |
| 2012/0058188 A1 | 3/2012 | Maclachlan et al. |
| 2012/0095075 A1 | 4/2012 | Manoharan et al. |
| 2012/0136073 A1 | 5/2012 | Zhiwei et al. |
| 2012/0183581 A1 | 7/2012 | Yaworski et al. |
| 2012/0238747 A1 | 9/2012 | Chu et al. |
| 2012/0276209 A1 | 11/2012 | Cullis et al. |
| 2014/0065228 A1 | 3/2014 | Yaworski et al. |
| 2016/0106842 A1 | 4/2016 | Baryza et al. |
| 2016/0317676 A1 | 11/2016 | Hope et al. |
| 2018/0064807 A1 | 3/2018 | Manoharan et al. |
| 2018/0125985 A1 | 5/2018 | Manoharan |
| 2018/0170866 A1 | 6/2018 | Payne et al. |
| 2018/0353434 A1 | 12/2018 | Hatanaka et al. |
| 2018/0369143 A1 | 12/2018 | Bally et al. |
| 2019/0083593 A1 | 3/2019 | Sahin et al. |
| 2019/0262448 A1 | 8/2019 | Brito et al. |
| 2019/0380963 A1 | 12/2019 | Chen et al. |
| 2020/0078345 A1 | 3/2020 | Rhee et al. |
| 2020/0206362 A1 | 7/2020 | Besin et al. |
| 2020/0254086 A1 | 8/2020 | Hoge et al. |
| 2020/0282060 A1 | 9/2020 | Heyes et al. |
| 2020/0289638 A1 | 9/2020 | Ciaramella et al. |
| 2021/0290756 A1 | 9/2021 | Sullivan et al. |
| 2021/0323914 A1 | 10/2021 | Payne et al. |
| 2022/0105187 A1 | 4/2022 | Maier et al. |
| 2022/0111053 A1 | 4/2022 | Maier et al. |
| 2022/0162521 A1 | 5/2022 | Drummond et al. |
| 2022/0175928 A1 | 6/2022 | Maier et al. |
| 2022/0175929 A1 | 6/2022 | Maier et al. |
| 2022/0175930 A1 | 6/2022 | Maier et al. |
| 2022/0370624 A1 | 11/2022 | Rajappan et al. |
| 2022/0389422 A1 | 12/2022 | Rajappan et al. |
| 2023/0126953 A1 | 4/2023 | Drummond et al. |
| 2023/0381303 A1 | 11/2023 | Drummond et al. |
| 2024/0309291 A1 | 9/2024 | Drummond et al. |
| 2024/0325525 A1 | 10/2024 | Drummond et al. |

FOREIGN PATENT DOCUMENTS

| | | |
|---|---|---|
| CA | 2 330 741 | 11/1999 |
| CA | 2 397 016 | 7/2001 |
| CN | 110974954 A | 4/2020 |
| EP | 2 350 043 | 3/2014 |
| JP | 03-126211 | 5/1991 |
| JP | 2002522442 A | 7/2002 |
| JP | 2002525063 | 8/2002 |
| JP | 2003524349 | 2/2003 |
| JP | 2005-202085 | 7/2005 |
| JP | 2006-080560 | 3/2006 |
| JP | 2009-051827 | 3/2009 |
| JP | 2009-051828 | 3/2009 |
| WO | WO1990001405 | 2/1990 |
| WO | WO1991016024 | 10/1991 |
| WO | WO1993005162 | 3/1993 |

(56) References Cited

FOREIGN PATENT DOCUMENTS

| | | |
|---|---|---|
| WO | WO1993012240 | 6/1993 |
| WO | WO1993012756 | 7/1993 |
| WO | WO1993024640 | 12/1993 |
| WO | WO1993025673 | 12/1993 |
| WO | WO1995002698 | 1/1995 |
| WO | WO1995018863 | 7/1995 |
| WO | WO1995035301 | 12/1995 |
| WO | WO1996002655 | 2/1996 |
| WO | WO1996010390 | 4/1996 |
| WO | WO1996040964 | 12/1996 |
| WO | WO1996041873 | 12/1996 |
| WO | WO1998051285 | 11/1998 |
| WO | WO2000003683 | 1/2000 |
| WO | 2000008031 A1 | 2/2000 |
| WO | WO2000015820 | 3/2000 |
| WO | WO2000062813 | 10/2000 |
| WO | WO2001005374 | 1/2001 |
| WO | WO2001005873 | 1/2001 |
| WO | WO2001075164 | 10/2001 |
| WO | WO2001093836 | 12/2001 |
| WO | WO2002020492 | 3/2002 |
| WO | WO2002034236 | 5/2002 |
| WO | WO2002040614 | 5/2002 |
| WO | WO2002087541 | 11/2002 |
| WO | WO2003097805 | 11/2003 |
| WO | WO2004039409 | 5/2004 |
| WO | WO2004041752 | 5/2004 |
| WO | WO2004065546 | 8/2004 |
| WO | WO2004072069 | 8/2004 |
| WO | WO2004087117 | 10/2004 |
| WO | WO2004110499 | 12/2004 |
| WO | WO2005007196 | 1/2005 |
| WO | WO2005026372 | 3/2005 |
| WO | WO2005035764 | 4/2005 |
| WO | WO2005115992 | 12/2005 |
| WO | WO2005120152 | 12/2005 |
| WO | WO2006002538 | 1/2006 |
| WO | WO2006053430 | 5/2006 |
| WO | WO2006124687 | 11/2006 |
| WO | WO2007015877 | 2/2007 |
| WO | WO2007036366 | 4/2007 |
| WO | WO2007048046 | 4/2007 |
| WO | WO2007056861 | 5/2007 |
| WO | WO2007066200 | 6/2007 |
| WO | WO2007088999 | 8/2007 |
| WO | WO2007116922 | 10/2007 |
| WO | WO2008038136 | 4/2008 |
| WO | WO2008127714 | 4/2008 |
| WO | WO2088037635 | 4/2008 |
| WO | WO2008064317 | 5/2008 |
| WO | WO2008064318 | 5/2008 |
| WO | WO2008091681 | 7/2008 |
| WO | WO2008101029 | 8/2008 |
| WO | WO2008101905 | 8/2008 |
| WO | WO2009024221 | 2/2009 |
| WO | WO2009025983 | 2/2009 |
| WO | 2009086558 A1 | 7/2009 |
| WO | WO2009086558 | 7/2009 |
| WO | WO2009103064 | 8/2009 |
| WO | WO2009105782 | 8/2009 |
| WO | WO2009111658 | 9/2009 |
| WO | WO2009114763 | 9/2009 |
| WO | WO2009132131 | 10/2009 |
| WO | WO2009156535 | 12/2009 |
| WO | WO2010006432 | 1/2010 |
| WO | WO2010042877 | 4/2010 |
| WO | WO2010048228 | 4/2010 |
| WO | WO2010048536 | 4/2010 |
| WO | WO2010054406 | 5/2010 |
| WO | WO2010074327 | 7/2010 |
| WO | WO2010088537 | 8/2010 |
| WO | WO2010105209 | 9/2010 |
| WO | WO2010129709 | 11/2010 |
| WO | WO2010138652 | 12/2010 |
| WO | WO2010138659 | 12/2010 |
| WO | WO2010138685 | 12/2010 |
| WO | WO2010138695 | 12/2010 |
| WO | WO2010138706 | 12/2010 |
| WO | WO2010138758 | 12/2010 |
| WO | WO2010148422 | 12/2010 |
| WO | WO2011000106 | 1/2011 |
| WO | WO2011000107 | 1/2011 |
| WO | WO2011000108 | 1/2011 |
| WO | WO2011011447 | 1/2011 |
| WO | WO2011017548 | 1/2011 |
| WO | WO2011021218 | 2/2011 |
| WO | WO2011045415 | 4/2011 |
| WO | WO2011066651 | 6/2011 |
| WO | WO2011079315 | 6/2011 |
| WO | WO2011103189 | 8/2011 |
| WO | WO2011140627 | 11/2011 |
| WO | WO2021123332 | 6/2012 |
| WO | 2013149140 A1 | 10/2013 |
| WO | WO2014089239 | 6/2014 |
| WO | WO2015130584 | 9/2015 |
| WO | WO2016176330 | 3/2016 |
| WO | WO2016118697 | 7/2016 |
| WO | 2017070624 A1 | 4/2017 |
| WO | WO2017066964 | 4/2017 |
| WO | WO2017112865 | 6/2017 |
| WO | WO2017173054 | 10/2017 |
| WO | 2017201346 A1 | 11/2017 |
| WO | WO2017218704 | 12/2017 |
| WO | WO2018064755 | 4/2018 |
| WO | WO2018075592 | 4/2018 |
| WO | WO2018078053 | 5/2018 |
| WO | WO2018081480 | 5/2018 |
| WO | WO2018081638 | 5/2018 |
| WO | WO2018089540 | 5/2018 |
| WO | WO2018119514 | 7/2018 |
| WO | WO2018126084 | 7/2018 |
| WO | WO2018170306 | 9/2018 |
| WO | WO2018170336 | 9/2018 |
| WO | WO2018200613 | 11/2018 |
| WO | WO2018208856 | 11/2018 |
| WO | WO2018213789 | 11/2018 |
| WO | WO2018232120 | 12/2018 |
| WO | WO2018232357 | 12/2018 |
| WO | WO2019046809 | 3/2019 |
| WO | WO2019051289 | 3/2019 |
| WO | WO2019067992 | 4/2019 |
| WO | WO2019089828 | 5/2019 |
| WO | WO2019126593 | 6/2019 |
| WO | WO2019141814 | 7/2019 |
| WO | WO2019147749 | 8/2019 |
| WO | WO2019200171 | 10/2019 |
| WO | WO2019202035 | 10/2019 |
| WO | WO2019210394 | 11/2019 |
| WO | WO2020028133 | 2/2020 |
| WO | WO2020056304 | 3/2020 |
| WO | WO2020061332 | 3/2020 |
| WO | WO2020061367 | 3/2020 |
| WO | WO2020061457 | 3/2020 |
| WO | WO2020069169 | 4/2020 |
| WO | WO2020069718 | 4/2020 |
| WO | WO2020070040 | 4/2020 |
| WO | WO2020077007 | 4/2020 |
| WO | WO2020123300 | 6/2020 |
| WO | WO2020160397 | 8/2020 |
| WO | WO2020191103 | 9/2020 |
| WO | WO2020198697 | 10/2020 |
| WO | WO2020198706 | 10/2020 |
| WO | WO2020201383 | 10/2020 |
| WO | WO2020205644 | 10/2020 |
| WO | WO2020210901 | 10/2020 |
| WO | WO2020219941 | 10/2020 |
| WO | WO2020227510 | 11/2020 |
| WO | WO2020252589 | 12/2020 |
| WO | WO2020263985 | 12/2020 |
| WO | WO2021000041 | 1/2021 |
| WO | WO2021016430 | 1/2021 |
| WO | WO2021022173 | 2/2021 |
| WO | WO2021026358 | 2/2021 |
| WO | WO2021030701 | 2/2021 |

(56) References Cited

FOREIGN PATENT DOCUMENTS

| WO | WO2021046265 | 3/2021 |
|---|---|---|
| WO | WO2021050986 | 3/2021 |
| WO | WO2021055833 | 3/2021 |
| WO | WO2021055835 | 3/2021 |
| WO | WO2021055849 | 3/2021 |
| WO | WO2021076805 | 4/2021 |
| WO | WO2021077066 | 4/2021 |
| WO | WO2021077067 | 4/2021 |
| WO | WO2021102411 | 5/2021 |
| WO | WO2021142336 | 7/2021 |
| WO | WO2021148511 | 7/2021 |
| WO | WO2021155274 | 8/2021 |
| WO | WO2021156267 | 8/2021 |
| WO | WO2021159130 | 8/2021 |
| WO | WO2021178510 | 9/2021 |
| WO | WO2021178725 | 9/2021 |
| WO | WO2021183563 | 9/2021 |
| WO | WO2021191265 | 9/2021 |
| WO | WO2021195529 | 9/2021 |
| WO | WO2021198157 | 10/2021 |
| WO | WO2021207020 | 10/2021 |
| WO | WO2021207710 | 10/2021 |
| WO | WO2021207712 | 10/2021 |
| WO | WO2021214204 | 10/2021 |
| WO | WO2021222287 | 11/2021 |
| WO | WO2021222801 | 11/2021 |
| WO | WO2021231901 | 11/2021 |
| WO | 2022115645 A1 | 6/2022 |
| WO | 2023230587 A1 | 11/2023 |
| WO | 2024138121 A1 | 6/2024 |

OTHER PUBLICATIONS

Lopresti et al., "The Replacement of Helper Lipids with Charged Alternatives in Lipid Nanoparticles Facilitates Targeted mRNA Delvery to the Spleen and Lungs" Journal of Controlled Release, vol. 345, pp. 819-831, May 1, 2022.

Luozhong et al., "Phosphatidylserine Lipid Nanoparticles Promote Systemic RNA Delivery to Secondary Lymphoid Organs" Nano Letters, vol. 22, No. 20, pp. 8304-8311, Oct. 4, 2022. https://doi.org/10.1021/acs.nanolett.2c03234.

Hauser et al., "Crystallization of Phosphatidylserine Bilayers Induced by Lithium," The Journal of Biological Chemistry, vol. 256, No. 22, pp. 11377-11380, Nov. 25, 1981.

Allen et al., "Pharmacokinetics and Anti-Tumor Activity of Vincristine Encapsulated in Sterically Stabilized Liposomes", Int. J. Cancer, vol. 62, No. 2, pp. 199-204, Jul. 17, 1995.

Anderluzzi et al., "Investigating the Impact of Delivery System Design on the Efficacy of Self-Amplifying RNA Vaccines," Vaccines, vol. 8, No. 2, pp. 212-233, May 8, 2020.

Anderson et al., "Safety and Immunogenicity of SARS-COV-2 mRNA-1273 Vaccine in Older Adults," New England Journal of Medicine, vol. 383, No. 25, pp. 2427-2438, Sep. 29, 2020.

Arpicco et al., "Preparation and Characterization of Novel Cationic Lipids Developed for Gene Transfection," Proceed. Int'l Symp. Control. Rel. Bioact. Mater. (Controlled Release Society, Inc.), 1999, vol. 26, pp. 759-760.

Arpicco et al., "Synthesis, characterization and transfection activity of new saturated and unsaturated cationic lipids," IL Farmaco, vol. 59, No. 11, pp. 869-878, Nov. 2004.

Ballas et al., "Liposomes bearing a quaternary ammonium detergent as an efficient vehicle for functional transfer of TMV-RNA into plant protoplasts," Biochimica et Biophysica Acta, vol. 939, No. 1, pp. 8-18, Mar. 22, 1988.

Barinaga, M., "Step Taken Toward Improved Vectors for Gene Transfer," Science, vol. 266, Issue 5189, pp. 1326-1327, Nov. 25, 1994.

Bass, "The Short Answer," Nature, vol. 411, No. 6836, pp. 428-429, May 24, 2001.

Beale et al., "Gene Silencing Nucleic Acids Designed by Scanning Arrays: Anti-EGFR Activity of siRNA, Ribozyme and DNA Enzymes Targeting a Single Hybridization-accessible Region using the Same Delivery System," Journal of Drug Targeting, vol. 11, No. 7, pp. 449-456, Aug. 1, 2003.

Behr, J.-P., "Synthetic Gene-Transfer Vectors," Acc. Chem. Res., vol. 26, No. 5, pp. 274-278, May 1, 1993.

Birkkholz et al., "Targeting of DEC-205 on Human Dendritic Cells Results in Efficient MHC Class II—Restricted Antigen Presentation," Blood, vol. 116, No. 13, pp. 2277-2286, Sep. 2010.

Bloom et al., "Self-Amplifying RNA Vaccines for Infectious Diseases," Gene Therapy, vol. 28, pp. 117-129, Oct. 22, 2020.

Bonifaz et al., "In Vivo Targeting of Antigens to Maturing Dendritic Cells via the DEC-205 Receptor Improves T Cell Vaccination," J. Exp. Med., vol. 199, No. 6, pp. 815-824, Mar. 15, 2004.

Brigham et al., "Rapid Communication: In vivo Transfection of Murine Lungs with a Functioning Prokaryotic Gene Using a Liposome Vehicle," The American Journal of the Medical Sciences, vol. 298, No. 4, pp. 278-281, Oct. 1, 1989.

Brummelkamp et al., "A System for Stable Expression of Short Interfering RNAs in Mammalian Cells," Science, vol. 296, No. 5567, pp. 550-553, Mar. 21, 2002.

Cevc, G., "How Membrane Chain-Melting Phase-Transition Temperature is Affected by the Lipid Chain Asymmetry and Degree of Unsaturation: An Effective Chain-Length Model," Biochemistry, vol. 30, No. 29, pp. 7186-7193, Jul. 23, 1991.

Chonn et al., "Recent Advances in Liposomal Drug-Delivery Systems," Current Opinion in Biotechnology, vol. 6, No. 6, pp. 698-708, Jan. 1, 1995.

Check, "RNA to the Rescue", Nature, vol. 425:10-12 (2003), https://222.nature.com/articles/425010a.

Chung et al., "COVID-19 Vaccine Frontrunners and Their Nanotechnology Design," ACS Nano, vol. 14, No. 10, pp. 12522-12537, Oct. 2020.

Corbett et al., "Evaluation of the mRNA-1273 Vaccine Against SARS-COV-2 in Nonhuman Primates", New England Journal of Medicine, vol. 383, Issue 16, pp. 1544-1555, Jul. 28, 2020.

Corbett et al., "SARS-COV-2 mRNA Vaccine Development Enabled by Prototype Pathogen Preparedness" bioRvix.org Jun. 11, 2020, https://www.biorxiv.org/content/10.1101/2020.06.11.145920v1.full.

Cortesi et al., "Effect of cationic liposome composition on in vitro cytotoxicity and protective effect on carried DNA," International Journal of Pharmaceutics, vol. 139, No. 1-2, pp. 69-78, Aug. 9, 1996.

COVID-19 Vaccinations in the United States, CDC (last visited Feb. 25, 2022) https://covid.cdc.gov/covid-data-tracker/#vaccinations_vacc-total-admin-rate-total.

Cross, Ryan, "Without These Lipid Shells, There Would be no mRNA Vaccines for COVID-19", Chemical & Engineering News, Mar. 6, 2021, https://cen.acs.org/pharmaceuticals/drugdelivery/Without-lipid-shells-mRNA-vaccines/99/18.

Cruz et al., "Targeting Nanoparticles fo CD40, DEC-205 or CD11c Molecules on Dendritic Cells for Efficient CD8+ T Cell Response: A Comparative Study," Journal of Controlled Release, vol. 192, pp. 209-218 (2004).

Crystal, R., "Transfer of Genes to Humans: Early Lessons and Obstacles to Success," Science, vol. 270, No. 5235, pp. 404-410, Oct. 20, 1995.

Culver K., "The First Human Gene Therapy Experiment," Gene Therapy: A Handbook for Physicians, pp. 33-40, 1994.

Delaware Environmental Public Health Tracking Network, Vaccine Tracker, https://myhealthycommunity.dhss.delaware.gove/locations/state/vaccine-tracker.

Dhodapkar et al., "Induction of Antigen-Specific Immunity with a Vaccine Targeting NY-ESO-1 to the Dendritic Cell Receptor DEC-205," Sci. Transl. Med., vol. 6(232), pp. 1-22, Apr. 16, 2014.

Dolgin, "Startups Set Off New Wave of mRNA Therapeutics," Nature Biotechnology, vol. 39, No. 9, pp. 1029-1031, Sep. 2021.

Dolgin, "The Tangled History of MRNA Vaccines," Nature, vol. 597, pp. 318-324, Sep. 16, 2021.

Duzgunes, N., "Membrane Fusion," Subcellular Biochemistry, vol. 11, pp. 195-286, 1985.

(56) References Cited

OTHER PUBLICATIONS

Dwarki et al., "Cationic Liposome-Mediated RNA Transfection," Methods in Enzymology, vol. 217, pp. 644-654, 1993.

Elbashir, et al., "Duplexes of 21-nucleotide RNAs Mediate RNA Interference in Cultured Mammalian Cells," Nature, vol. 411, No. 6836, pp. 494-498, May 2001.

Enoch et al., "Formation and Properties of 1000-A-Diameter, Single-Bilayer Phospholipid Vesicles," Proc. Natl. Acad. Sci., vol. 76, No. 1, pp. 145-149, Jan. 1, 1979.

Fadok et al., "Apoptosis: Giving Phosphatidylserine Recognition an Assist—With a Twist", Curr Biol. vol. 13, No. 16, pp. R655-R657, Aug. 19, 2003.

Fahey et al., "A Comprehensive Classification System for Lipids," J. Lipid Res. vol. 46, No. 5, pp. 839-861, May 1, 2005.

Felgner et al., "Cationic Lipid-Mediated Transfection in Mammalian Cells: 'Lipofection,'" J. Tiss. Cult. Meth., vol. 15, No. 2, pp. 63-68, Jun. 1, 1993.

Felgner et al., "Enhanced Gene Delivery and Mechanism Studies with a Novel Series of Cationic Lipid Formulations," The Journal of Biological Chemistry, vol. 269, No. 4, pp. 2550-2561, Jan. 28, 1994.

Felgner et al., "Lipofection: A Highly Efficient, Lipid-Mediated DNA-Transfection Procedure," Proc. Natl. Acad. Sci. vol. 84, No. 21, pp. 7413-7417, Nov. 1, 1987.

Felgner et al., "Cationic Liposome Mediated Transfection," Proc. West. Pharmacol. Soc., vol. 32, pp. 115-121, 1989.

Filion et al., "Toxicity and Immunomodulatory Activity of Liposomal Vectors Formulated with Cationic Lipids Toward Immune Effector Cells," Biochim Biophys Acta. vol. 1329, No. 2, pp. 345-356, Oct. 23, 1997.

Fossom et al., "Targeting Antigens to Different Receptors on Conventional Type 1 Dendritic Cells Impacts the Immune Response," J. Immnol., vol. 205, pp. 661-673, Jun. 26, 2020.

Gao, X., et al., "A Novel Cationic Liposome Reagent for Efficient Transfection of Mammalian Cells," Biochem. Biophys. Res. Comm., vol. 179, No. 1, pp. 280-285, Aug. 30, 1991.

Gauthier et al., "Quantification of Surface GalNAc Ligands Decorating Nanostructured Lipid Carriers by UPLC-ELSD," J Mol Sci. vol. 20, No. 22, pp. 5669-5684, Nov. 12, 2019.

Gershon, H., et al., "Mode of Formation and Structural Feature of DNA-Cationic Liposome Complexes Used forTransfection," Biochemistry, vol. 32, No. 28, pp. 7143-7151, Jul. 1, 1993.

Global Newswire, retrieved from http://globalnewswire.com on Feb. 27, 13, Tekmira sues Alnylam Pharmaceuticals for repeated misuse of tradesecrets and confidential information, Mar. 16, 2011, pp. 1-3.

Guy-Caffey et al., "Novel Polyaminolipids Enhance the Cellular Uptake of Oligonucleotides," The Journal of Biological Chemistry, vol. 270, No. 52, pp. 31391-31396, Dec. 29, 1995.

Hassett et al., "Optimization of Lipid Nanoparticles for Intramuscular Administration of mRNA Vaccines", Molecular Therapy: Nucleic Acids, vol. 15, Issue 1, pp. 1-11, Apr. 2019.

Hawley-Nelson et al., "LipofectAmine™ Reagent: A New, Higher Efficiency Polycationic Liposome Transfection Reagent," Focus, vol. 15, No. 3, pp. 73-79, 1993.

Heinz et al., "Distinguishing Features of Current COVID-19 Vaccines: Knowns and Unknowns of Antigen Presentation and Modes of Action," npj Vaccines, vol. 6, No. 1, pp. 1-13, Aug. 16, 2021.

Heyes et al., "Cationic lipid saturation influences intracellular delivery of encapsulated nucleic acids," Journal of Controlled Release, 2005, vol. 107, pp. 276-287.

Heyes et al., "Synthesis of novel cationic lipids: effect of structural modification on the efficiency of gene transfer," J. Med. Chem., vol. 45, No. 1, pp. 99-114, Jan. 3, 2002.

Hoge, Stephen, "Turns Out, Designing a COVID Vaccine Was Easy", UCSF Alumni, https://alumni.ucsf.edu/stories/stephen-hoge.

Hou et al., "Lipid Nanoparticles for mRNA Delivery", Nature, vol. 6, pp. 1078-1094, Dec. 2021.

Huang et al., "Thiocholesterol-Based Lipids for Ordered Assembly of Bioresponsive Gene Carriers," Molecular Therapy, vol. 11, No. 3, pp. 409-417, Mar. 2005.

Hyde, S., et al., "Correction of the Ion Transport Defect in Cystic Fibrosis Transgenic Mice by Gene Therapy," Nature, vol. 362, pp. 250-255, Mar. 18, 1993.

International Search Report and Written Opinion in PCT International Application No. PCT/US2021/060877 mailed Apr. 8, 2022.

Jackson et al., "An mRNA Vaccine Against SARS-COV-2—Preliminary Report," New Engl. J. Med., vol. 383, No. 20, pp. 1920-1931, Nov. 12, 2020.

Jayaraman et al., "Maximizing the Potency of siRNA Lipid Nanoparticles for Hepatic Gene Silencing In Vivo**," Angew. Chem. Int. Ed., vol. 51, No. 34, pp. 8529-8533, Aug. 20, 2012.

Jiang, L., et al., "Comparison of protein precipitation methods for sample preparation prior to proteomic analysis," Journal of Chromatography A, vol. 1023, No. 2, pp. 317-320, Jan. 16, 2004.

Juliano et al., "The Effect of Particle Size and Charge on the Clearance Rates of Liposomes and Liposome Encapsulated Drugs," Biochem. Biophys. Res. Commun., vol. 63, No. 3, pp. 651-658, Apr. 7, 1975.

Keough, K., "Influence of Chain Unsaturation and Chain Position on Thermotropism and Intermolecular Interactions in Membranes," Biochem. Soc. Transactions, vol. 18, No. 5, pp. 835-837, 1990.

Krichevsky et al., "RNAi Functions in Cultured Mammalian Neurons," PNAS, vol. 99, No. 18, pp. 11926-11929, Sep. 3, 2002.

Lawrence et al. "The formation, characterization and stability of non-ionic surfactant vesicles," S.T.P. Pharma Sciences, vol. 6, No. 1, pp. 49-60, 1996.

Lawrence et al., "Synthesis and Aggregation Properties of Dialkyl Polyoxyethylene Glycerol Ethers," Chemistry and Physics of Lipids, vol. 82, No. 2, pp. 89-100, Aug. 19, 1996.

Legendre et al., "Delivery of Plasmid DNA into Mammalian Cell Lines Using pH-Sensitive Liposomes: Comparison with Cationic Liposomes," Pharm. Res., vol. 9, No. 10, pp. 1235-1242, Oct. 9, 1992.

Leventis et al., "Interactions of mammalian cells with lipid dispersions containing novel metabolizable cationic amphiphiles," Biochem. Biophys. Acta, vol. 1023, No. 1, pp. 124-132, Mar. 30, 1990.

Li et al., "A Review on Phospholipids and Their Main Applications in Drug Delivery Systems," Asian J. Pharm. Sci. vol. 10, pp. 81-98, 2015.

Liu et al., "Cationic Liposome-Mediated Intravenous Gene Delivery", J. Biol. Chem., vol. 270, No. 42, pp. 24864-24870, Oct. 20, 1995.

Loh, Tim, "Lipids are Delivering the Vaccine Revolution", Bloomberg, Mar. 6, 2021, https://www.bloomberg.com/news/newsletters/2021-03-06/lipids-are-delivering-the-vaccine-revolution.

Lotter et al., "Incorporation of Phosphatidylserine Improves Efficiency of Lipid Based Gene Delivery Systems" European Journal of Pharmaceutics and Biopharmaceutics, vol. 172, pp. 134-143, Mar. 2022.

Lotter et al., "Incorporation of Phosphatidylserine Improves Efficiency of Lipid Based Gene Delivery Systems" Supporting Information Document.

Maloy et al., "Intralymphatic Immunization Enhances DNA Vaccination," Proc Natl Acad Sci USA, vol. No. 6, pp. 3299-3033, Mar. 13, 2001.

Marshall, E., "Gene Therapy's Growing Pains," Science, vol. 269, No. 5227, pp. 1050-1055, Aug. 25, 1995.

Murahashi et al., "Synthesis and Evaluation of Neoglycolipid for Liposome Modification," Biol. Pharm. Bull., vol. 20, No. 6, pp. 704-707, Jun. 15, 1997.

Nellis et al., "Preclinical Manufacture of an Anti-HER2 scFv-PEG-DSPE, Liposome-Inserting Conjugate. 1. Gram-Scale Production and Purification," Biotechnol Prog., vol. 21, pp. 205-220, Jan. 2005.

Nellis et al., "Preclinical Manufacture of Anti-HER2 Liposome-Inserting, scFv-PEG-Lipid Conjugate. 2. Conjugate Micelle Identity, Purity, Stability, and Potency Analysis," Biotechnol Prog., vol. 21, pp. 221-232, Jan. 2005.

Offutt-Powell et al., "Delaware's My Healthy Community Data Platform: At the Intersection of Public Health Informatics and Epidemiology" Delaware Journal of Public Health, vol. 7, No. 3, p. 58, Jul. 2021.

(56) References Cited

OTHER PUBLICATIONS

Orkin, S., et al., NIH Report, Report and Recommendations of the Panel to Assess the NIH Investment in Research on Gene Therapy, vol. 7, Dec. 7, 1995.

Pardi, et al., "mRNA Vaccines—A New Era in Vaccinology," Nat. Rev. Drug Discov. vol. 17, No. 4, pp. 261-279, Apr. 19, 2018.

Parr et al., "Factors Influencing the Retention and Chemical Stability of Polly (Ethylene Glycol)-Lipid Conjugates Incorporated into Large Unilamellar Vesicles," Biochimica et Biophysica Acta, vol. 1195, No. 1, pp. 21-30, Oct. 12, 1994.

Paul, C., et al., "Effective Expression of Small Interfering RNA in Human Cells," Nature Biotech., vol. 20, No. 5, pp. 505-508, May 2002.

Press Release, Moderna and Baxter Announce Agreement for Fill/Finish Manufacturing of the Moderna COVID-19 Vaccine in the U.S. https://investors.modernatx.com/news-releases/news-release-details/baxter-biopharma-solutions-and-moderna-announce-agreement.

Press Release, Moderna and Lonza Announce Worldwide Strategic Collaboration to Manufacture Moderna's Vaccine (mRNA-1273) Against Novel Coronavirus (May 1, 2020), https://investors.modernatx.com/news-releases/news-release-details/moderna-and-lonza-announce-worldwide-strategic-collaboration.

Press Release, Moderna Announces Initiation of Rolling Submission of Biologics License Application (BLA) with U.S. FDA for the Moderna COVID-19 Vaccine (Jun. 1, 2021) https://investors.modernatx.com/news-releases/news-release-details/moderna-announces-initiation-rolling-submission-biologics.

Press Release, Moderna Receives Full U.S. FDA Approval for COVID 19 Vaccine Spikevax 2022.

Press Release, Moderna, Moderna Reports Fourth Quarter and Fiscal Year 2021 Financial Results and Provides Business Updates, Feb. 24, 2022, https://investors.modernatx.com/news/news-details/2022/Moderna-Reports-Fourth-Quarter-and-Fiscal-Year-2021-Financial-Results-and-Provides-Business-Updates/default.aspx.

Press Release, Moderna, Vaccine Exports from U.S. Accelerate as Moderna Ships Abroad, Bloomberg.com, May 20, 2021, https://www.bloomberg.com/news/articles/2021-05-20/moderna-starts-shipping-vaccine-from-US-boosting-shot-exports.

Puyal, C., et al., "A New Cationic Liposome Encapsulating Genetic Material: A Potential Delivery System for Polynucleotides," Eur. J. Biochem., vol. 228, No. 3, pp. 697-703, Mar. 1995.

Regalado, Antonio, "None of US Were Ready to Manufacture Genetic Vaccines for a Billion People", MIT Technology Review, Dec. 17, 2020, https://www.technologyreview.com/2020/12/17/1014989/moderna-vaccine-availability-stephane-bancel-ceo/.

Sabnis et al., "A Novel Amino Lipid Series for mRNA Delivery: Improved Endosomal Escape and Sustained Pharmacology and Safety in Non-Human Primates," Molecular Ther., vol. 26, No. 6, pp. 1509-1519, Jun. 2018.

Sahin et al., "Personalized RNA Mutanome Vaccines Mobilize Poly-Specific Therapeutic Immunity Against Cancer," Nature, vol. 547, pp. 222-240, Jul. 13, 2017.

Sawada et al., "Microemulsions in Supercritical CO2 Utilizing the Polyethyleneglycol Dialkylglycerol and Their Use for the Solubilization of Hydrophiles," Dyes and Pigments, vol. 65, No. 1, pp. 67-74, Apr. 1, 2005.

Semple et al., "Rational Design of Cationic Lipids for siRNA Delivery," Nature Biotechnology, vol. 28, No. 2, pp. 172-178, Feb. 2010.

Sharma, et al., "A Review of the Progress and Challenges of Developing a Vaccine for COVID-19," Frontiers in Immunology, vol. 11, pp. 1-17, Oct. 2020.

Shin, et al. "Acid-Triggered Release via dePEGylation of DOPE Liposomes Containing Acid-Labile Vinyl Ether PEG-lipids," Journal of Controlled Release, vol. 91, No. 1-2, pp. 187-200, Aug. 28, 2003.

Shirley et al., "Amikacin Liposome Inhalation Suspension: A Review in *Mycobacterium avium* Complex Lung Disease", Drugs, vol. 79, No. 5, pp. 555-562, Apr. 2019.

Shurin, et al., "Recognition of Live Phosphatidylserine-Labeled Tumor Cells by Dendritic Cells: A Novel Approach to Immunotherapy of Skin Cancer," Cancer Res. Vol. 69, No. 6, pp. 2487-2496, Mar. 15, 2009.

Song et al., "Characterization of the Inhibitory Effect of PEG-lipid Conjugates on the Intracellular Delivery of Plasmid and Antisense DNA Mediated by Cationic Lipid Liposomes," Biochimica et Biophysica Acta, vol. 1558, No. 1, pp. 1-13, Jan. 2, 2002.

Sorensen, et al., "Gene Silencing by Systemic Delivery of Synthetic siRNAs in Adult Mice", J. Biol. Chem., vol. 327, No. 4, pp. 761-766, Apr. 4, 2003.

Spagnou, S., et al., "Lipidic Carriers of siRNA: Differences in the Formulation, Cellular Uptake, and Delivery with Plasmid DNA," Biochemistry, vol. 43, No. 42, pp. 13348-13356, Oct. 26, 2004.

Stamatatos, L., et al., "Interactions of Cationic Lipid Vesicles with Negatively Charged Phospholipid Vesicles and Biological Membranes," Biochemistry, vol. 27, No. 11, pp. 3917-3925, May 1, 1988.

Swadling et al., "Pre-Existing Polymerase-Specific T Cells Expand in Abortive Seronegative SARS-CoV2," Nature, vol. 601, pp. 110-142, Jan. 6, 2022.

Szoka, F., et al., "Comparative Properties and Methods of Preparation of Lipid Vesicles (Liposomes)," Ann. Rev. Biophys. Bioeng., vol. 9, No. 1, pp. 467-508, Jun. 1980.

Szoka et al., "Procedure for preparation of liposomes with large internal aqueous space and high capture by reverse-phase evaporation," Proc. Natl. Acad. Sci., vol. 75, No. 9, pp. 4194-4198, Sep. 1, 1978.

Tada, et al., "Comparison of Neutralizing Antibody Titers Elicited by mRNA and Adenoviral Vector Vaccine Against SARS-COV-2 Variants," Biorxiv, Jan. 2021.

Templeton, "Cationic Liposome-mediated Gene Delivery In vivo", Bioscience Reports, vol. 22, No. 2, pp. 283-295, Apr. 2002.

Vanderwoude, I., et al., "Parameters influencing the introduction of plasmid DNA into cells by the use of synthetic amphiphiles as a carrier system," Biochimica et Biophysica Acta, vol. 1240, No. 1, pp. 34-40, Nov. 22, 1995.

Vardi, Nathan, "Moderna's Mysterious Coronavirus Vaccine Delivery System", Forbes.com, Jul. 29, 2020, www.forbes.com/sites/nathanvardi/2020/7/29/modernas-mysterious-coronavirus-vaccine-delivery-system/.

Walsh, et al., "Safety and Immunogenicity of Two RNA-Based Covid-19 Vaccine Candidates," N. Engl. J. Med., vol. 383, No. 25, pp. 2439-2450, Dec. 17, 2020.

Wheeler, et al., "Stabilized Plasmid-lipid Particles: Constructions and Characterization," Gene Therapy, vol. 6, No. 2, pp. 271-281, Feb. 5, 1999.

Wilson, R., et al., "Counterion-Induced Condensation of Deoxyribonucleic Acid," A Light-Scattering Study, Biochemistry, vol. 18, No. 11, pp. 2192-2196, May 1, 1979.

Woodle, M.C., et al., "Versatility in lipid compositions showing prolonged circulation with sterically stabilized liposomes," Biochimica et Biophysica Acta, vol. 1105, pp. 193-200, Apr. 13, 1992.

Yu et al., "RNA Drugs and RNA Targets for Small Molecules: Principles, Progress, and Challenges," Pharmacological Reviews, vol. 72, pp. 862-898, Oct. 2020.

Zhu, N., et al., "Systemic Gene Expression After Intravenous DNA Delivery into Adult Mice," Science, vol. 261, No. 5118, pp. 209-211, Jul. 9, 1993.

International Search Report in PCT Application No. PCT/US2021/060877 mailed Apr. 8, 2022.

Non-Final Office Action in U.S. Appl. No. 17/456,567 dated May 18, 2022.

Final Office Action in U.S. Appl. No. 17/456,567 dated Aug. 8, 2022.

Han et al., "An Ionizable Lipid Toolbox for RNA Delivery", Nature Communications, vol. 12, No. 1, pp. 7233 (1-6), Dec. 2021.

Li, et al., "Tailoring Combinatorial Lipid Nanoparticles for Intracellular Delivery of Nucleic Acids, Proteins, and Drugs," Acta Pharm. Scinica, vol. 12, No. 6, pp. 2624-2639, 2022.

Oberli et al., "Lipid Nanoparticle Assisted mRNA for Potent Cancer Immunotherapy", Nano Letters, vol. 17, No. 3, pp. 1326-1335, Mar. 8, 2017.

(56) References Cited

OTHER PUBLICATIONS

Sun et al., "Structure and Function of Cationic and Ionizable Lipids for Nucleic Acid Delivery", Pharmaceutical Research, vol. 40, No. 1, pp. 27-46, Jan. 2023.
Tang et al., "Ionizable Lipid Nanoparticles for mRNA Delivery", Advanced NanoBiomed Research, vol. 3, No., 8, pp. 2300006 (1-21), Aug. 2023.
Witten et al., Recent Advances in Nanoparticulate RNA Delivery Systems, PNAS, vol. 121, No. 11, pp. e2307798120 (1-9), Mar. 2024.
Xu, et al., "Lipid-Mediated Targeting with Membrane Wrapped Nanoparticles in the Presence of Corona Formation", ACS Nano, vol. 10, No. 1, pp. 1189-1200, Jan. 26, 2016.
Zhang et al., "Modification of Lipid-Based Nanoparticles: An Efficient Delivery System for Nucleic Acid-Based Immunotherapy", Molecules, vol. 27, No. 6, pp. 1943 (1-29), Mar. 2022.
European Search Report and Written Opinion in European Application No. 21899145.3 mailed Feb. 13, 2025.

FIG. 3A (Example 12)
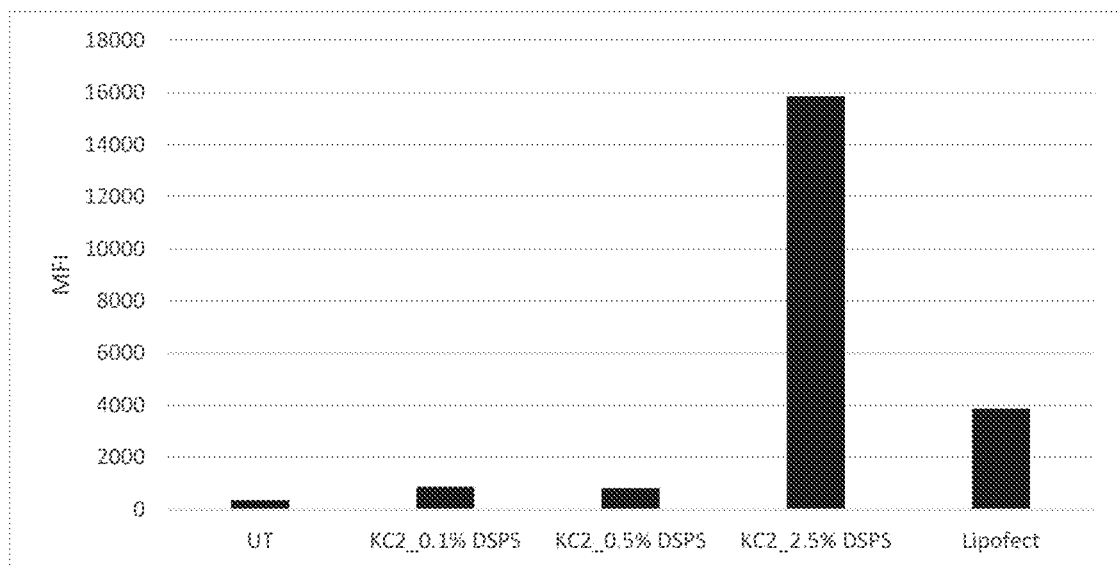
FIG. 3B (Example 12)
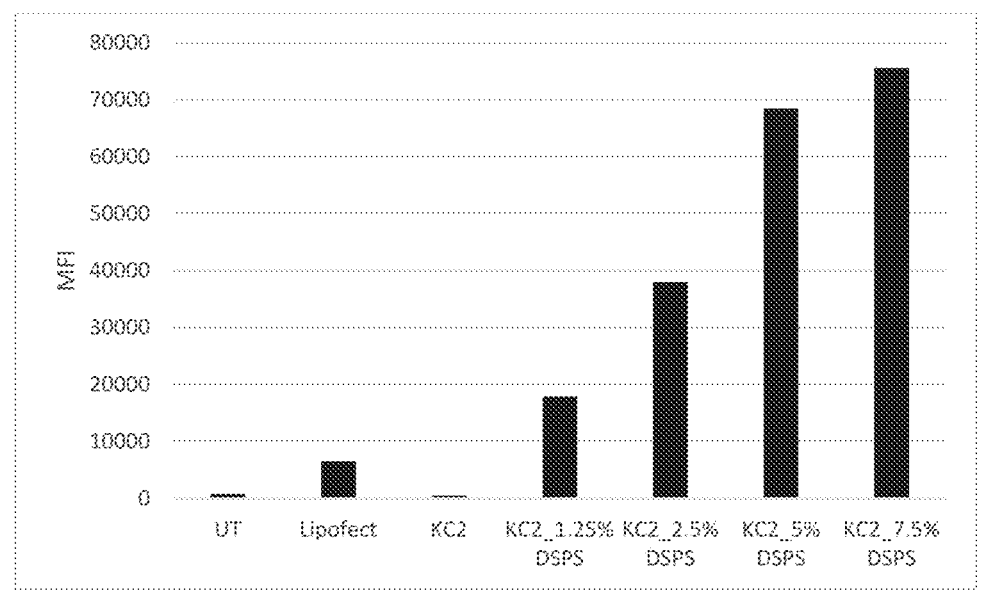

FIG. 3C (Example 12)
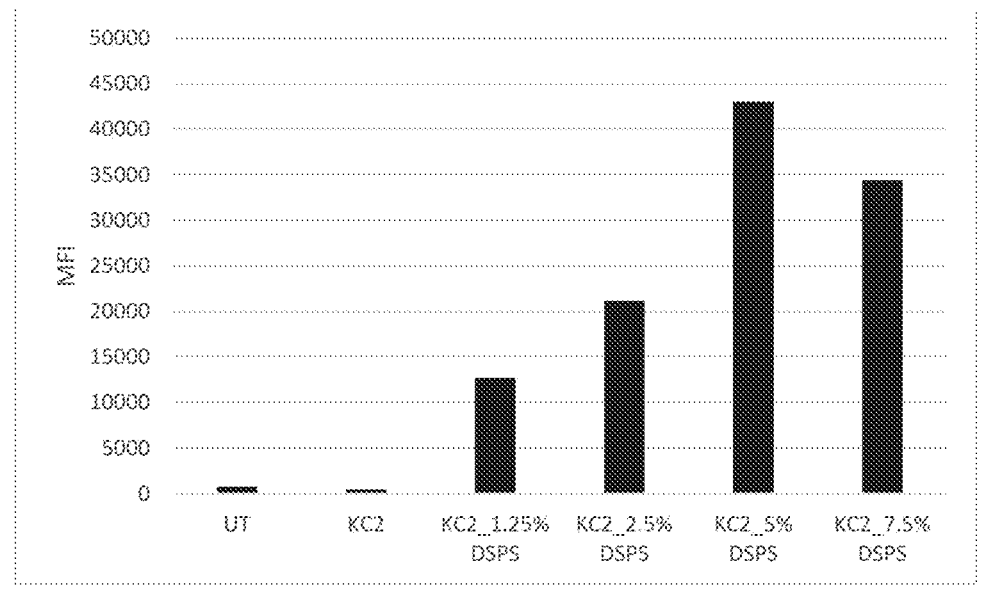
FIG. 3D (Example 12)
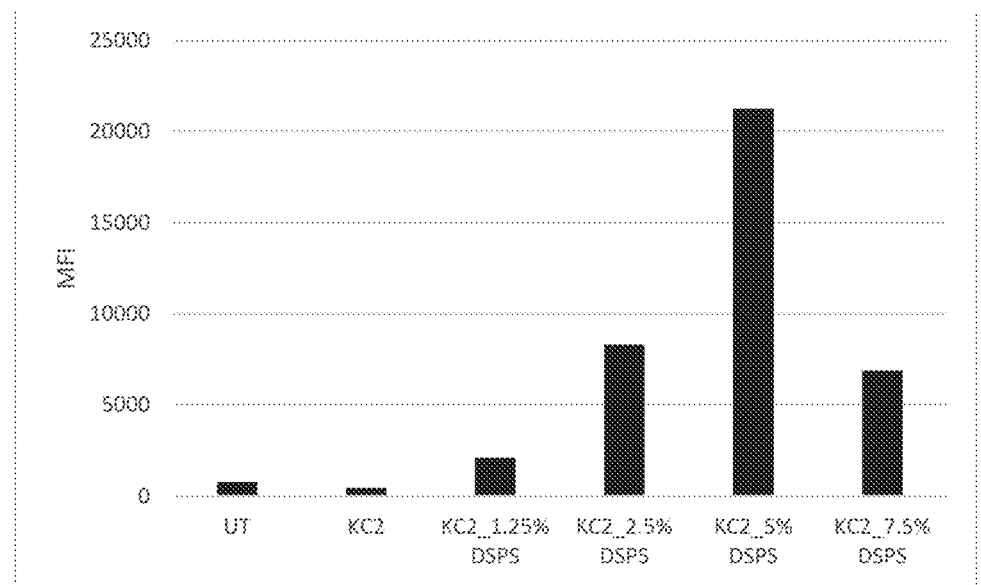

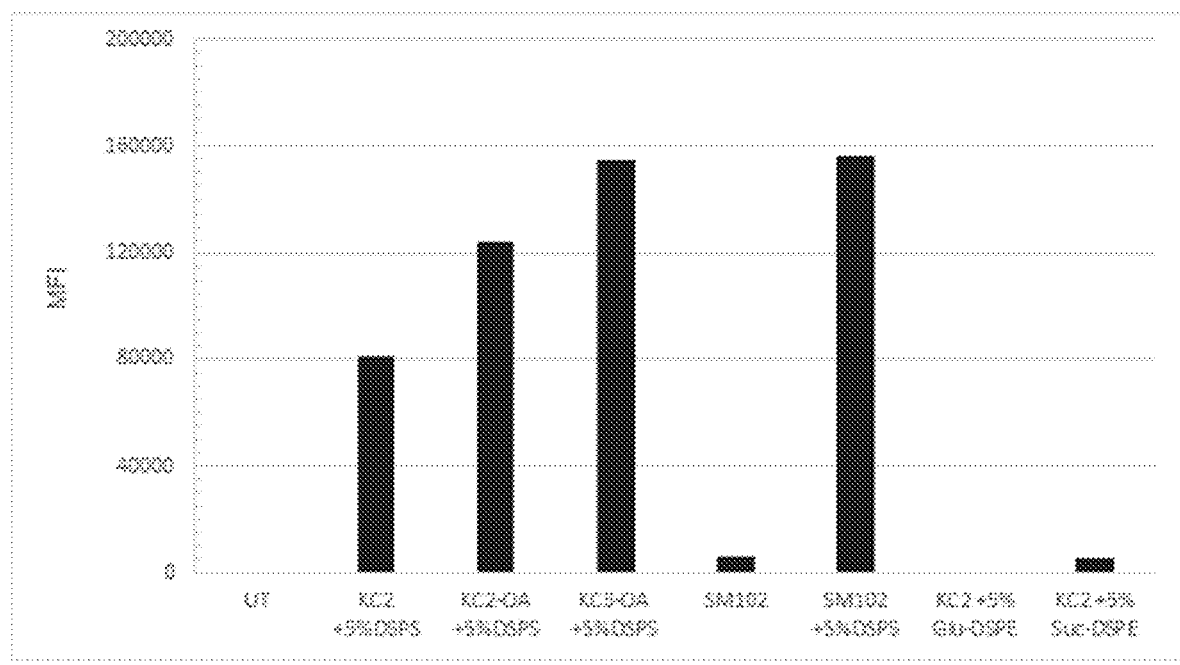
FIG. 4 (Example 13) – SM102 comparison with KC series

FIG. 5 (Example 14) – PS targeting KC series
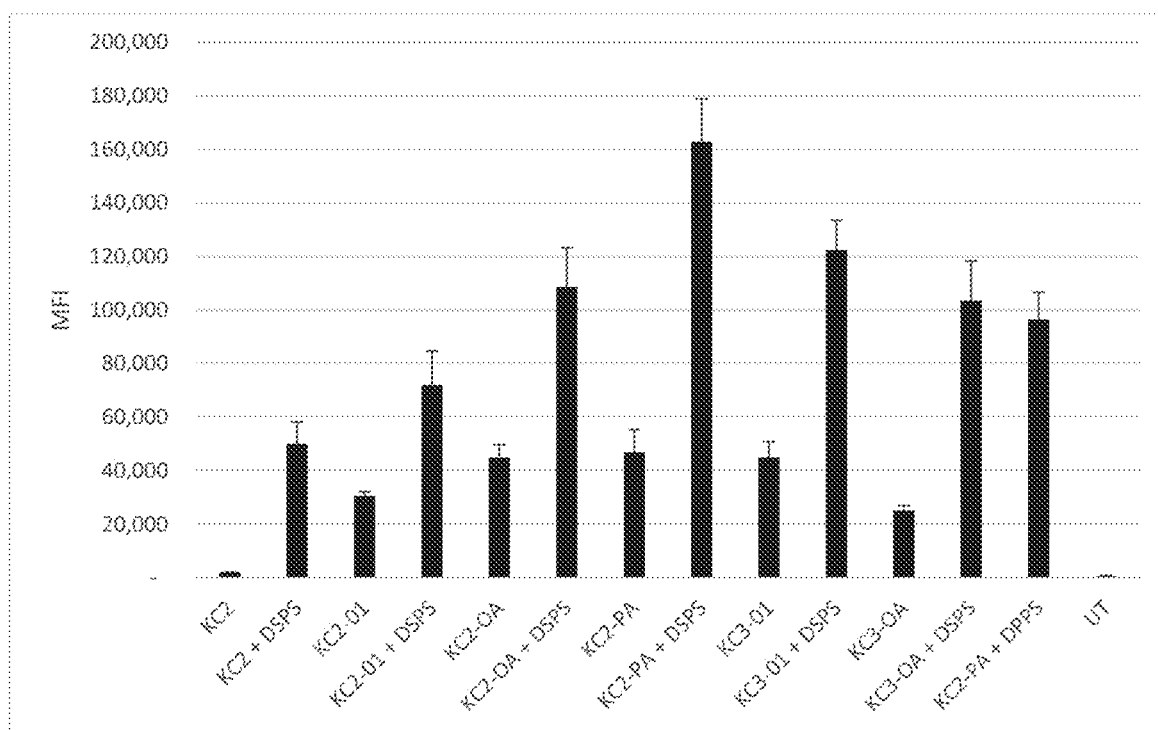

FIG. 6A (Example 15)
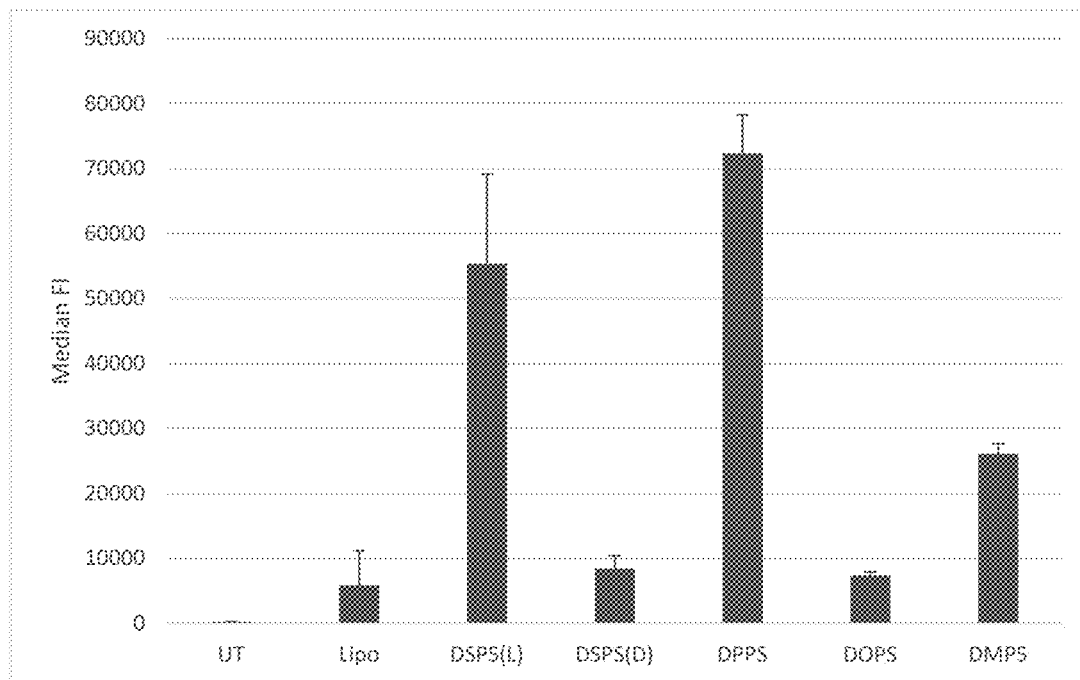
FIG. 6B (Example 15)
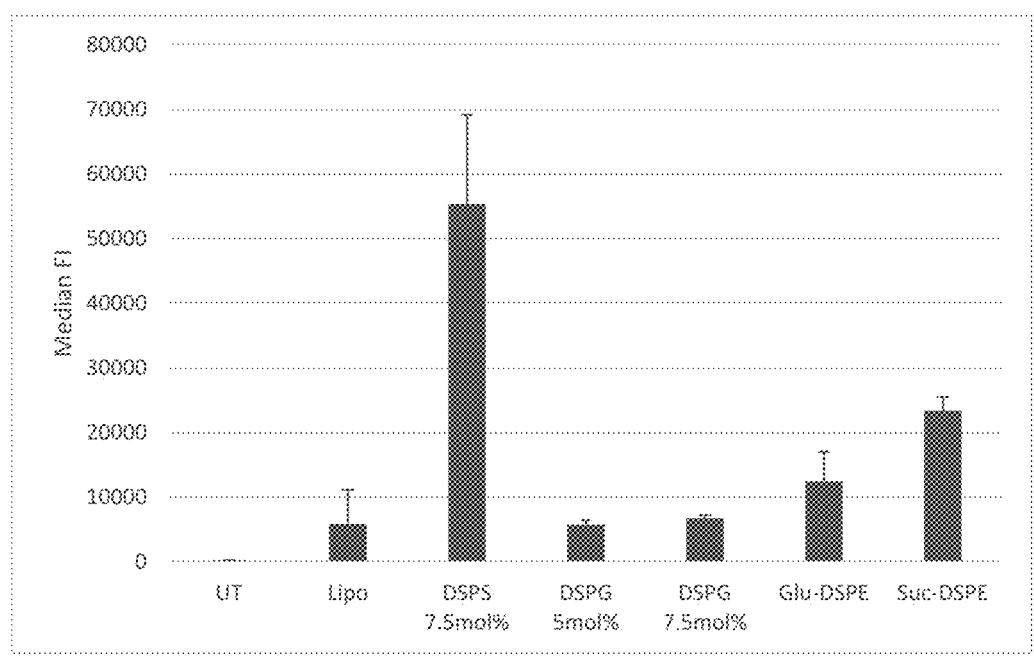

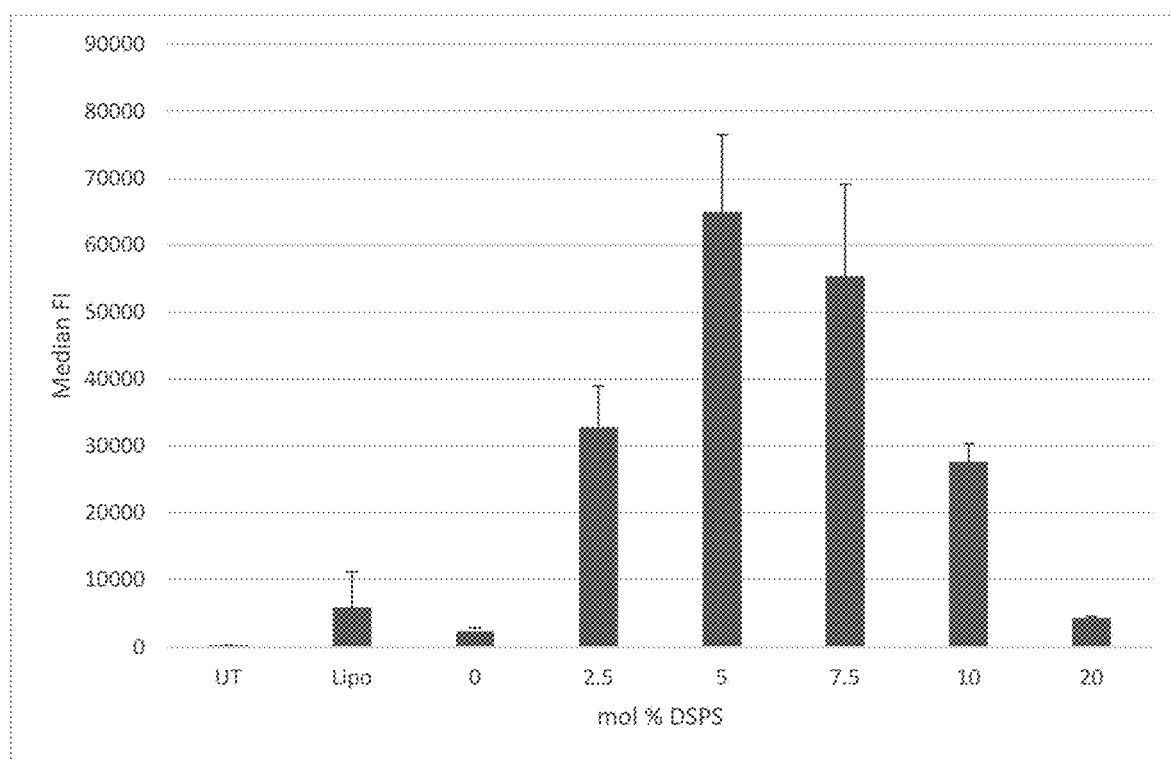
FIG. 7 (Example 16)

FIG. 8 (Example 17)
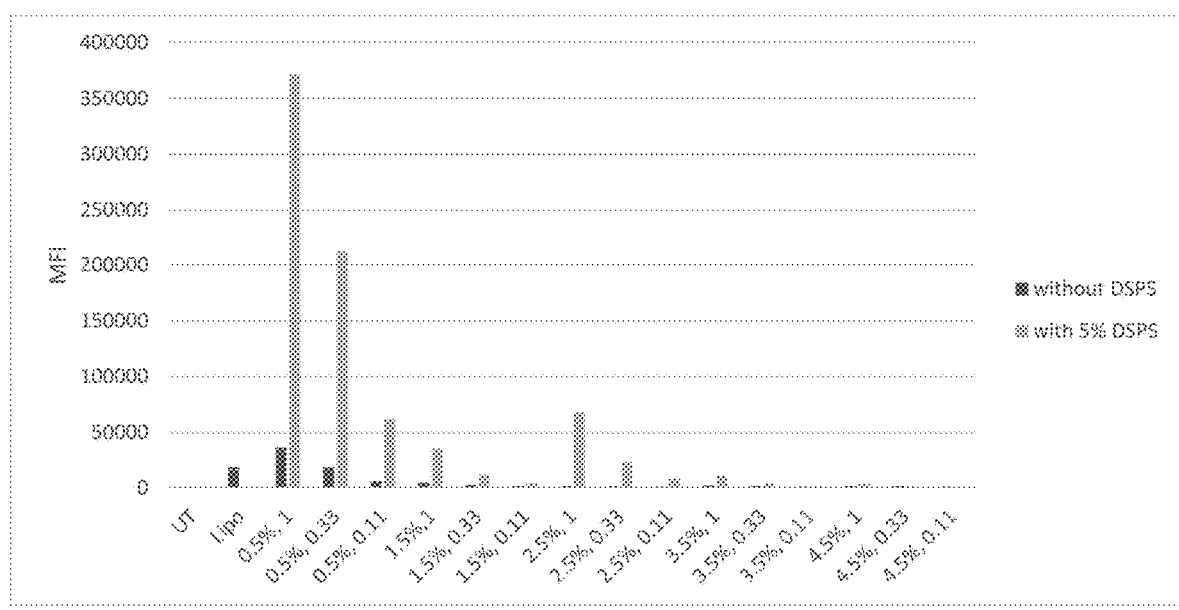

FIG. 9A (Example 18)
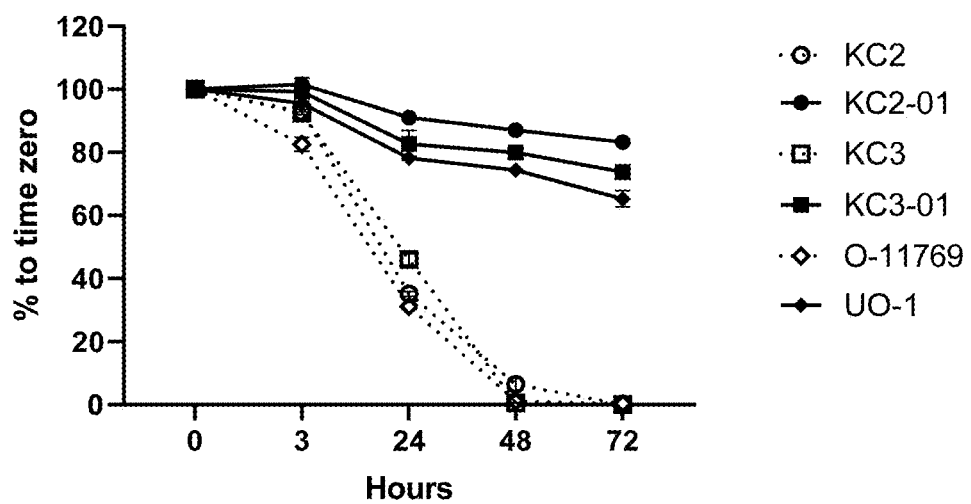
FIG. 9B (Example 18)
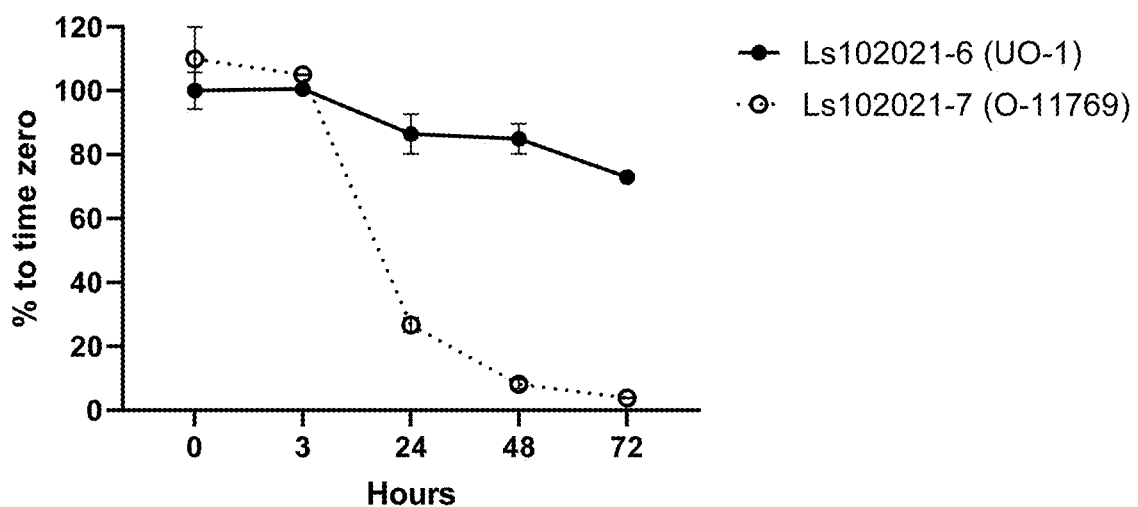

FIG. 10A (Example 19)
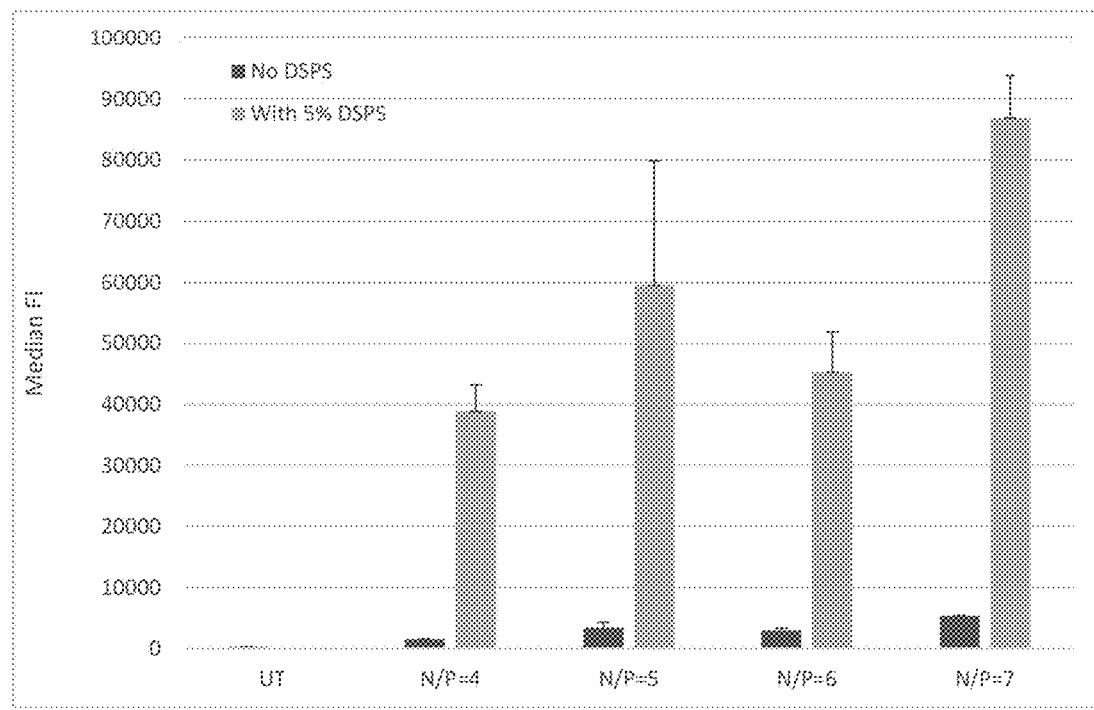
FIG. 10B (Example 19)
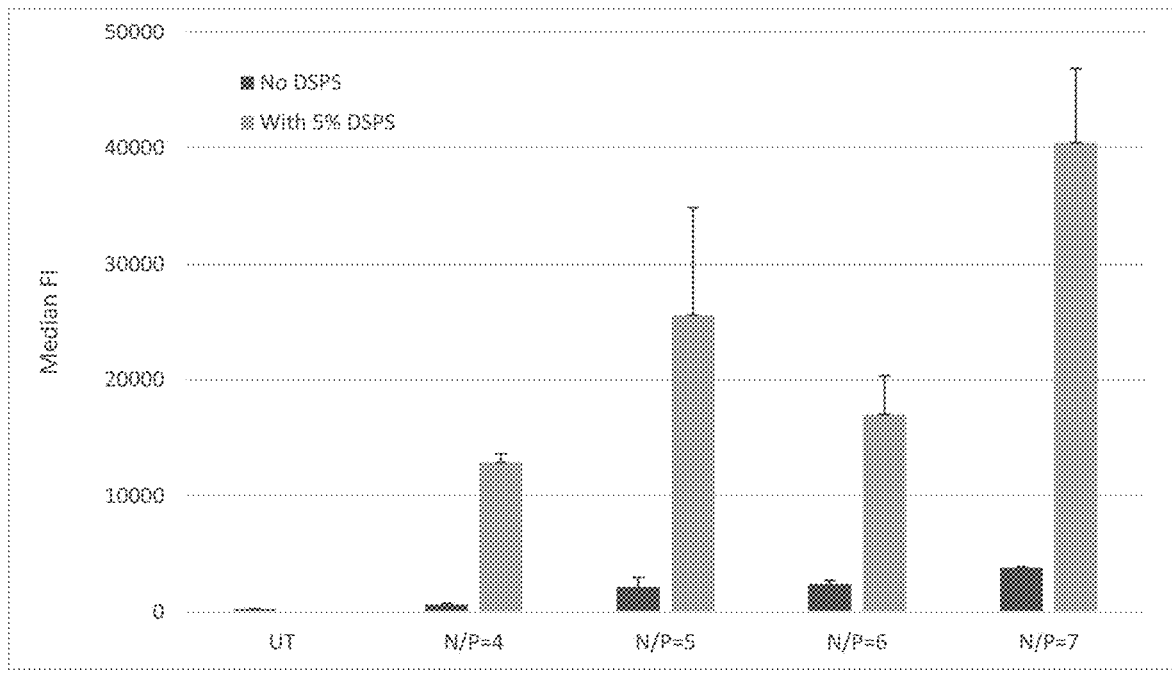

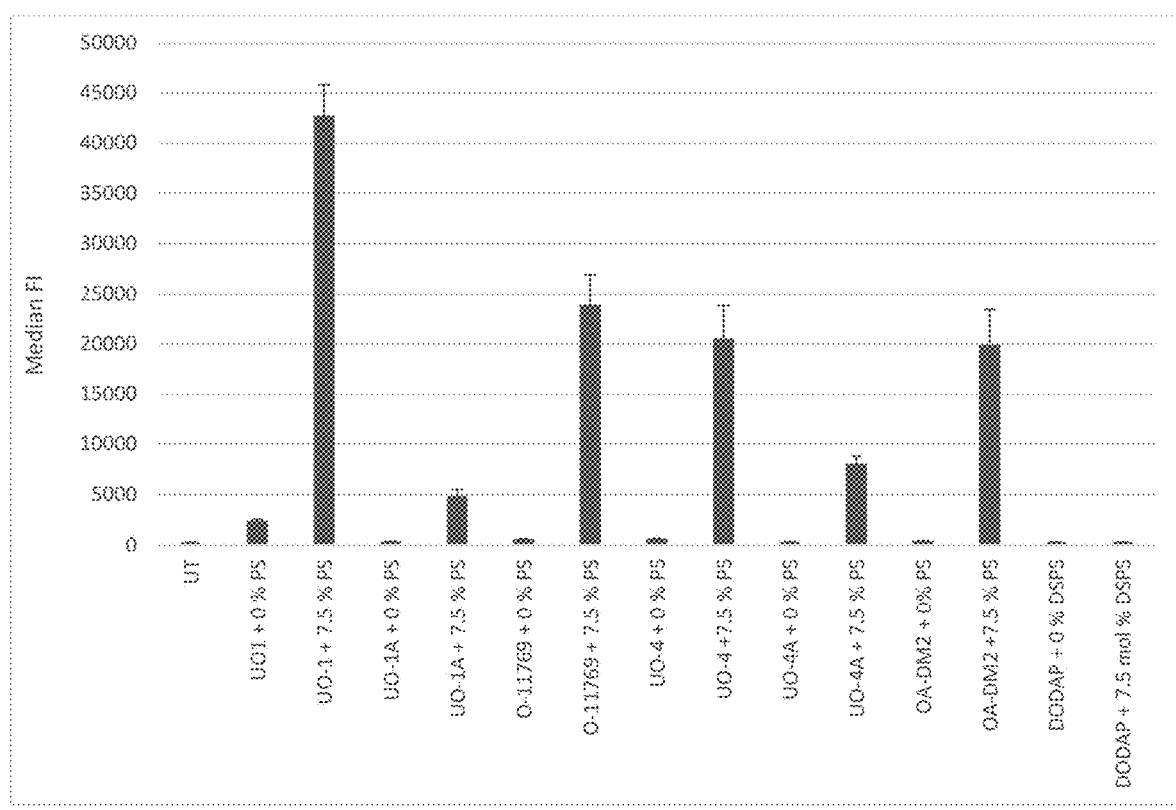
FIG. 11 (Example 20)

FIG. 12 (Example 21)
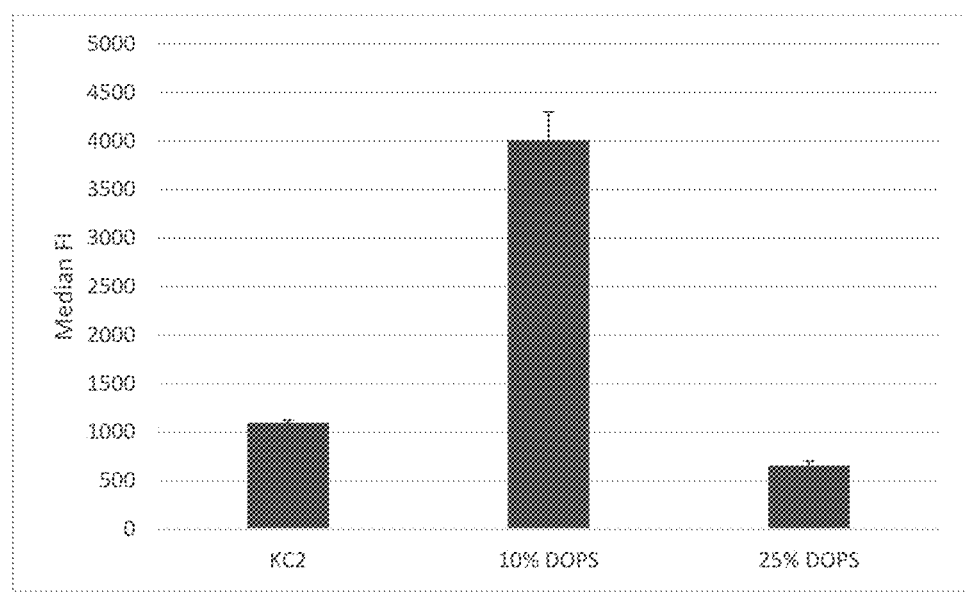

FIG. 13A (Example 22)

mVRN029 (SEQ ID NO: 2)

```
GGGAATAAACTAGTATTCTTCTGGTCCCCACAGACTCAGAGAGAACCCGCCACCATGTTCGTGTTCCTGG
TGCTGCTGCCTCTGGTGTCCAGCCAGTGTGTGAACCTGACCACCAGAACACAGCTGCCTCCAGCCTACAC
CAACAGCTTTACCAGAGGCGTGTACTACCCCGACAAGGTGTTCAGATCCAGCGTGCTGCACTCTACCCAG
GACCTGTTCCTGCCTTTCTTCAGCAACGTGACCTGGTTCCACGCCATCCACGTGTCCGGCACCAATGGCA
CCAAGAGATTCGACAACCCCGTGCTGCCCTTCAACGACGGGGTGTACTTTGCCAGCACCGAGAAGTCCAA
CATCATCAGAGGCTGGATCTTCGGCACCACACTGGACAGCAAGACCCAGAGCCTGCTGATCGTGAACAAC
GCCACCAACGTGGTCATCAAAGTGTGCGAGTTCCAGTTCTGCAACGACCCCTTCCTGGGCGTCTACTACC
ACAAGAACAACAAGAGCTGGATGGAAAGCGAGTTCCGGGTGTACAGCAGCGCCAACAACTGCACCTTCGA
GTACGTGTCCCAGCCTTTCCTGATGGACCTGGAAGGCAAGCAGGGCAACTTCAAGAACCTGCGCGAGTTC
GTGTTTAAGAACATCGACGGCTACTTCAAGATCTACAGCAAGCACACCCCTATCAACCTCGTGCGGGATC
TGCCTCAGGGCTTCTCTGCTCTGGAACCCCTGGTGGATCTGCCCATCGGCATCAACATCACCCGGTTTCA
GACACTGCTGGCCCTGCACAGAAGCTACCTGACACCTGGCGATAGCAGCAGCGGATGGACAGCTGGTGCC
GCCGCTTACTATGTGGGCTACCTGCAGCCTAGAACCTTCCTGCTGAAGTACAACGAGAACGGCACCATCA
CCGACGCCGTGGATTGTGCTCTGGATCCTCTGAGCGAGACAAAGTGCACCCTGAAGTCCTTCACCGTGGA
AAAGGGCATCTACCAGACCAGCAACTTCCGGGTGCAGCCCACCGAATCCATCGTGCGGTTCCCCAATATC
ACCAATCTGTGCCCCTTCGGCGAGGTGTTCAATGCCACCAGATTCGCCTCTGTGTACGCCTGGAACCGGA
AGCGGATCAGCAATTGCGTGGCCGACTACTCCGTGCTGTACAACTCCGCCAGCTTCAGCACCTTCAAGTG
CTACGGCGTGTCCCCTACCAAGCTGAACGACCTGTGCTTCACAAACGTGTACGCCGACAGCTTCGTGATC
CGGGGAGATGAAGTGCGGCAGATTGCCCCTGGACAGACAGGCAAGATCGCCGACTACAACTACAAGCTGC
CCGACGACTTCACCGGCTGTGTGATTGCCTGGAACAGCAACAACCTGGACTCCAAAGTCGGCGGCAACTA
CAATTACCTGTACCGGCTGTTCCGGAAGTCCAATCTGAAGCCCTTCGAGCGGGACATCTCCACCGAGATC
TATCAGGCCGGCAGCACCCCTTGTAACGGCGTGGAAGGCTTCAACTGCTACTTCCCACTGCAGTCCTACG
GCTTTCAGCCCACAAATGGCGTGGGCTATCAGCCCTACAGAGTGGTGGTGCTGAGCTTCGAACTGCTGCA
TGCCCCTGCCACAGTGTGCGGCCCTAAGAAAAGCACCAATCTCGTGAAGAACAAATGCGTGAACTTCAAC
TTCAACGGCCTGACCGGCACCGGCGTGCTGACAGAGAGCAACAAGAAGTTCCTGCCATTCCAGCAGTTTG
GCCGGGATATCGCCGATACCACAGACGCCGTTAGAGATCCCCAGACACTGGAAATCCTGGACATCACCCC
TTGCAGCTTCGGCGGAGTGTCTGTGATCACCCCTGGCACCAACACCAGCAATCAGGTGGCAGTGCTGTAC
CAGGACGTGAACTGTACCGAAGTGCCCGTGGCCATTCACGCCGATCAGCTGACACCTACATGGCGGGTGT
ACTCCACCGGCAGCAATGTGTTTCAGACCAGAGCCGGCTGTCTGATCGGAGCCGAGCACGTGAACAATAG
CTACGAGTGCGACATCCCCATCGGCGCTGGAATCTGCGCCAGCTACCAGACACAGACAAACAGCCCTCGG
AGAGCCAGAAGCGTGGCCAGCCAGAGCATCATTGCCTACACAATGTCTCTGGGCGCCGAGAACAGCGTGG
CCTACTCCAACAACTCTATCGCTATCCCCACCAACTTCACCATCAGCGTGACCACAGAGATCCTGCCTGT
GTCCATGACCAAGACCAGCGTGGACTGCACCATGTACATCTGCGGCGATTCCACCGAGTGCTCCAACCTG
CTGCTGCAGTACGGCAGCTTCTGCACCCAGCTGAATAGAGCCCTGACAGGGATCGCCGTGGAACAGGACA
AGAACACCCAAGAGGTGTTCGCCCAAGTGAAGCAGATCTACAAGACCCCTCCTATCAAGGACTTCGGCGG
CTTCAATTTCAGCCAGATTCTGCCCGATCCTAGCAAGCCCAGCAAGCGGAGCTTCATCGAGGACCTGCTG
TTCAACAAAGTGACACTGGCCGACGCCGGCTTCATCAAGCAGTATGGCGATTGTCTGGGCGACATTGCCG
CCAGGGATCTGATTTGCGCCCAGAAGTTTAACGGACTGACAGTGCTGCCTCCTCTGCTGACCGATGAGAT
GATCGCCCAGTACACATCTGCCCTGCTGGCCGGCACAATCACAAGCGGCTGGACATTTGGAGCAGGCGCC
GCTCTGCAGATCCCCTTTGCTATGCAGATGGCCTACCGGTTCAACGGCATCGGAGTGACCCAGAATGTGC
TGTACGAGAACCAGAAGCTGATCGCCAACCAGTTCAACAGCGCCATCGGCAAGATCCAGGACAGCCTGAG
CAGCACAGCAAGCGCCCTGGGAAAGCTGCAGGACGTGGTCAACCAGAATGCCCAGGCACTGAACACCCTG
GTCAAGCAGCTGTCCTCCAACTTCGGCGCCATCAGCTCTGTGCTGAACGATATCCTGAGCAGACTGGACC
CTCCTGAGGCCGAGGTGCAGATCGACAGACTGATCACAGGCAGACTGCAGAGCCTCCAGACATACGTGAC
CCAGCAGCTGATCAGAGCCGCCGAGATTAGAGCCTCTGCCAATCTGGCCGCCACCAAGATGTCTGAGTGT
GTGCTGGGCCAGAGCAAGAGAGTGGACTTTTGCGGCAAGGGCTACCACCTGATGAGCTTCCCTCAGTCTG
CCCCTCACGGCGTGGTGTTTCTGCACGTGACATATGTGCCCGCTCAAGAGAAGAATTTCACCACCGCTCC
```

FIG. 13A (Example 22) Continued

```
AGCCATCTGCCACGACGGCAAAGCCCACTTTCCTAGAGAAGGCGTGTTCGTGTCCAACGGCACCCATTGG
TTCGTGACACAGCGGAACTTCTACGAGCCCCAGATCATCACCACCGACAACACCTTCGTGTCTGGCAACT
GCGACGTCGTGATCGGCATTGTGAACAATACCGTGTACGACCCTCTGCAGCCCGAGCTGGACAGCTTCAA
AGAGGAACTGGACAAGTACTTTAAGAACCACACAAGCCCCGACGTGGACCTGGGCGATATCAGCGGAATC
AATGCCAGCGTCGTGAACATCCAGAAAGAGATCGACCGGCTGAACGAGGTGGCCAAGAATCTGAACGAGA
GCCTGATCGACCTGCAAGAACTGGGGAAGTACGAGCAGTACATCAAGTGGCCCTGGTACATCTGGCTGGG
CTTTATCGCCGGACTGATTGCCATCGTGATGGTCACAATCATGCTGTGTTGCATGACCAGCTGCTGTAGC
TGCCTGAAGGGCTGTTGTAGCTGTGGCAGCTGCTGCAAGTTCGACGAGGACGATTCTGAGCCCGTGCTGA
AGGGCGTGAAACTGCACTACACATGATGACTCGAGCTGGTACTGCATGCACGCAATGCTAGCTGCCCCTT
TCCCGTCCTGGGTACCCCGAGTCTCCCCCGACCTCGGGTCCCAGGTATGCTCCCACCTCCACCTGCCCCA
CTCACCACCTCTGCTAGTTCCAGACACCTCCCAAGCACGCAGCAATGCAGCTCAAAACGCTTAGCCTAGC
CACACCCCACGGGAAACAGCAGTGATTAACCTTTAGCAATAAACGAAAGTTTAACTAAGCTATACTAAC
CCCAGGGTTGGTCAATTTCGTGCCAGCCACACCCTGGAGCTAGCAGCGGCCGCGGCCGCAAAAAAAAAA
AAAAAAAAAAAAAAAAAAAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA
```

FIG. 13B (Example 22)
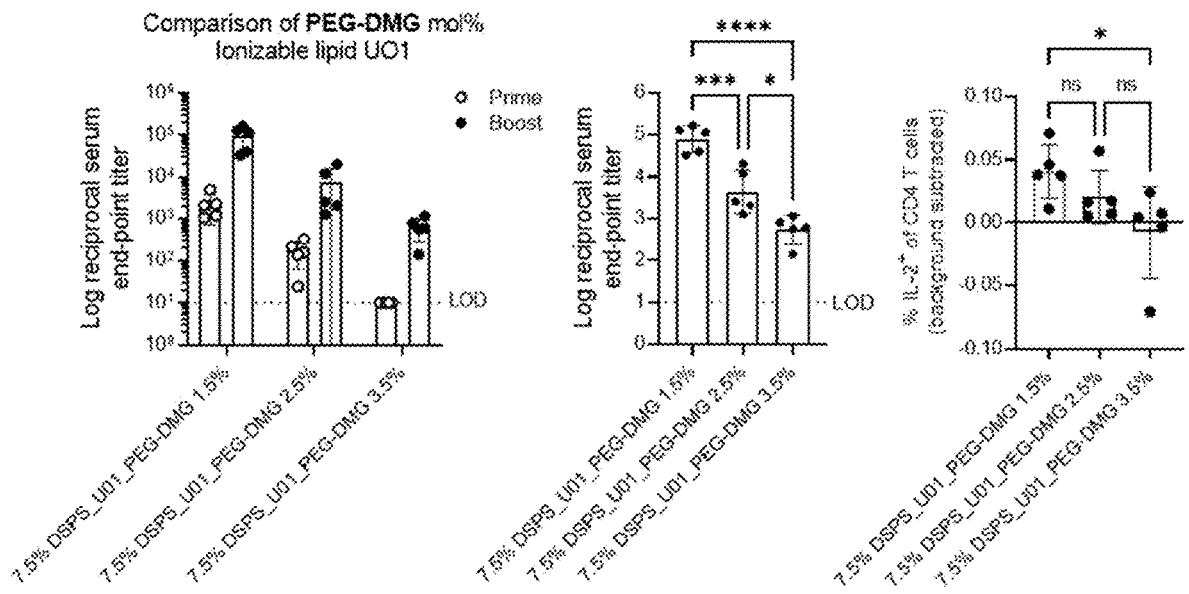
FIG. 13C (Example 22)
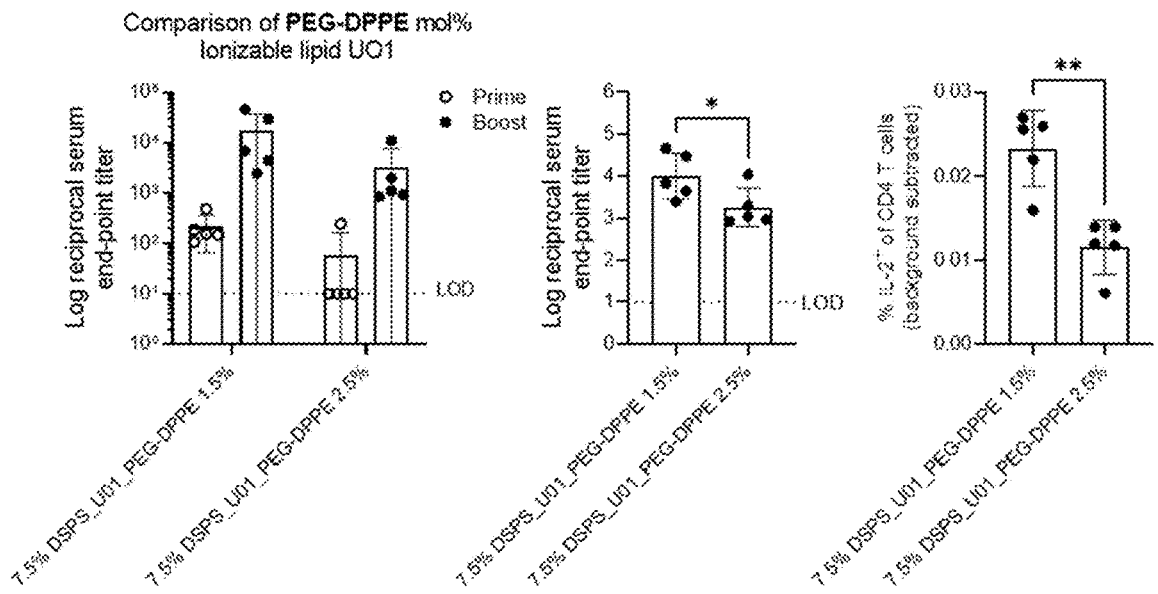

FIG. 13D (Example 22).
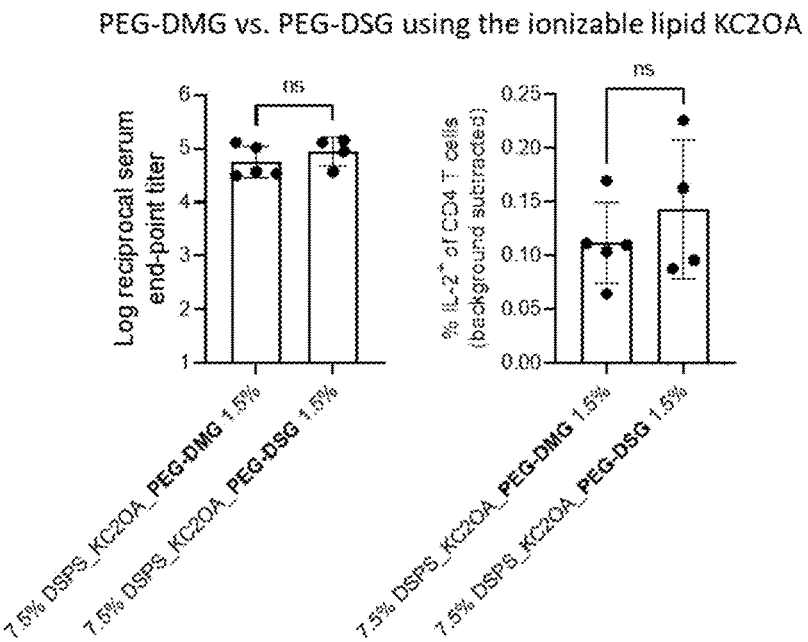
FIG. 13E (Example 22).
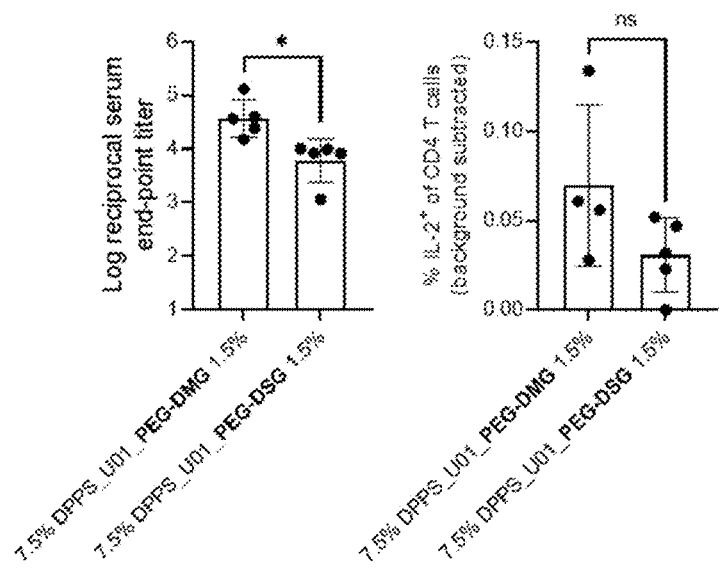

FIG. 13F (Example 22).
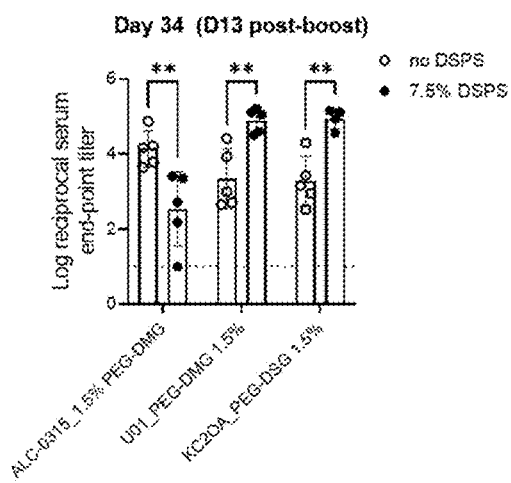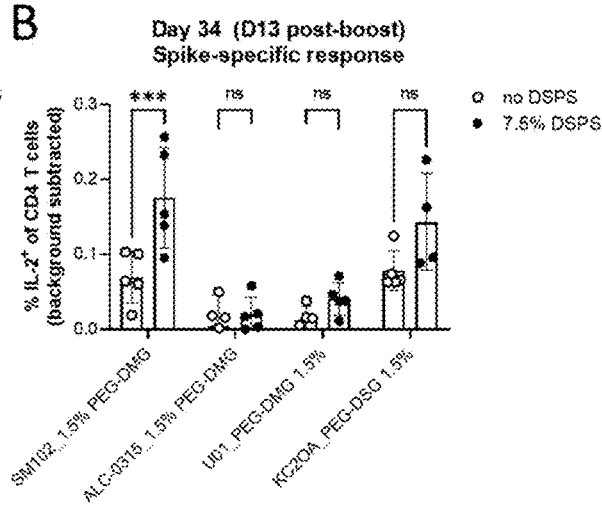
FIG. 13G (Example 22).
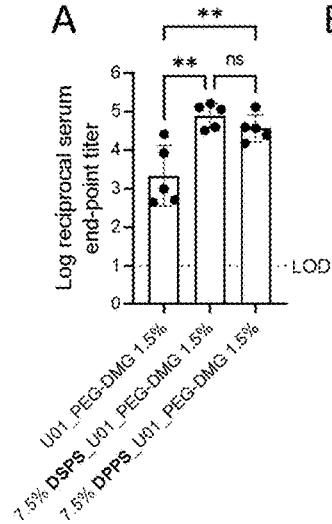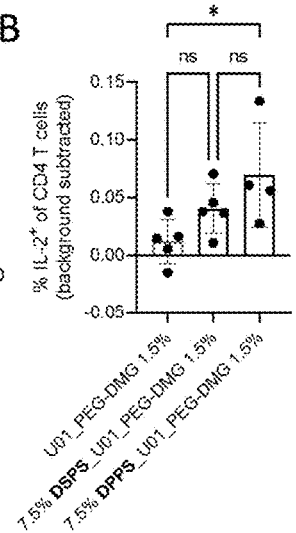

FIG. 14A (Example 23).
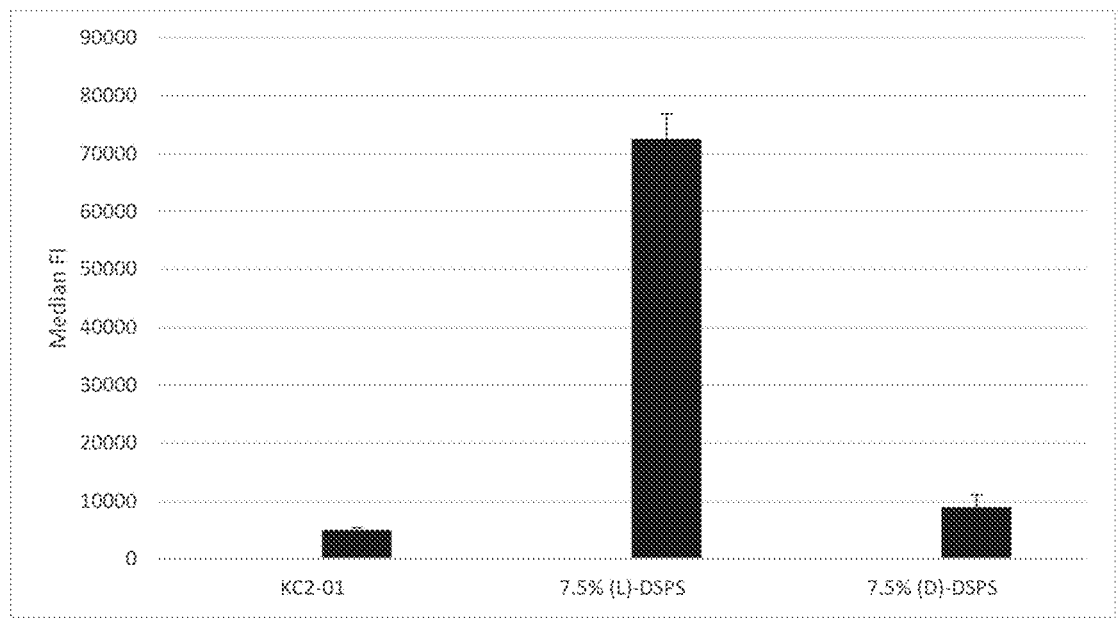
FIG. 14B (Example 23).
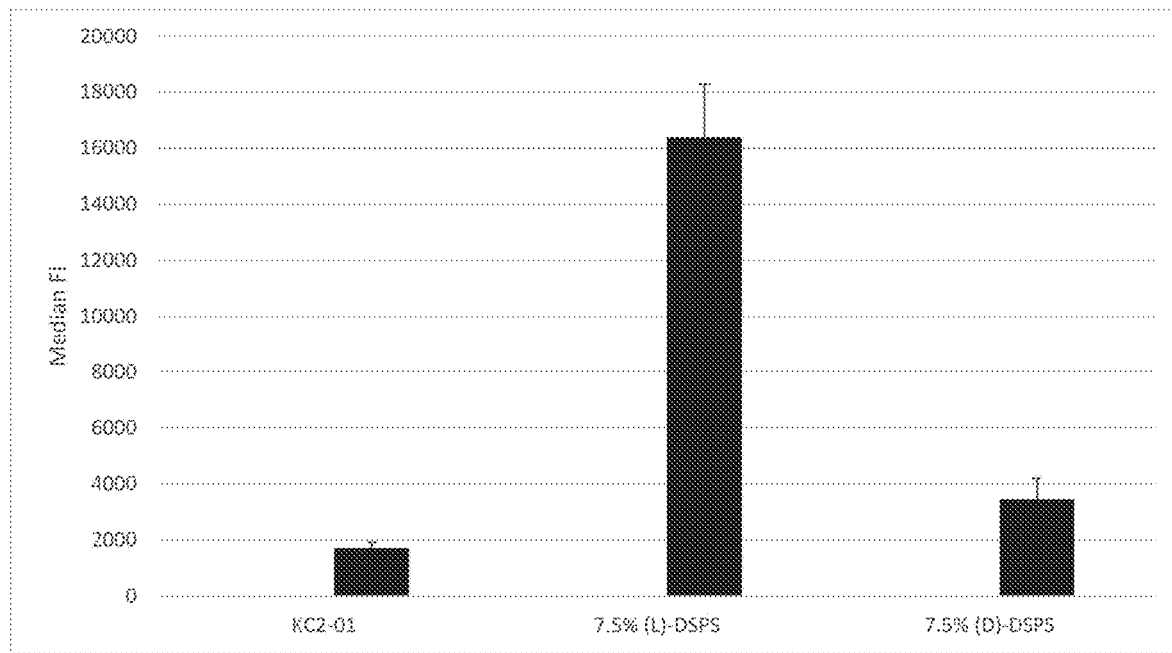

FIG. 15 (Example 24).
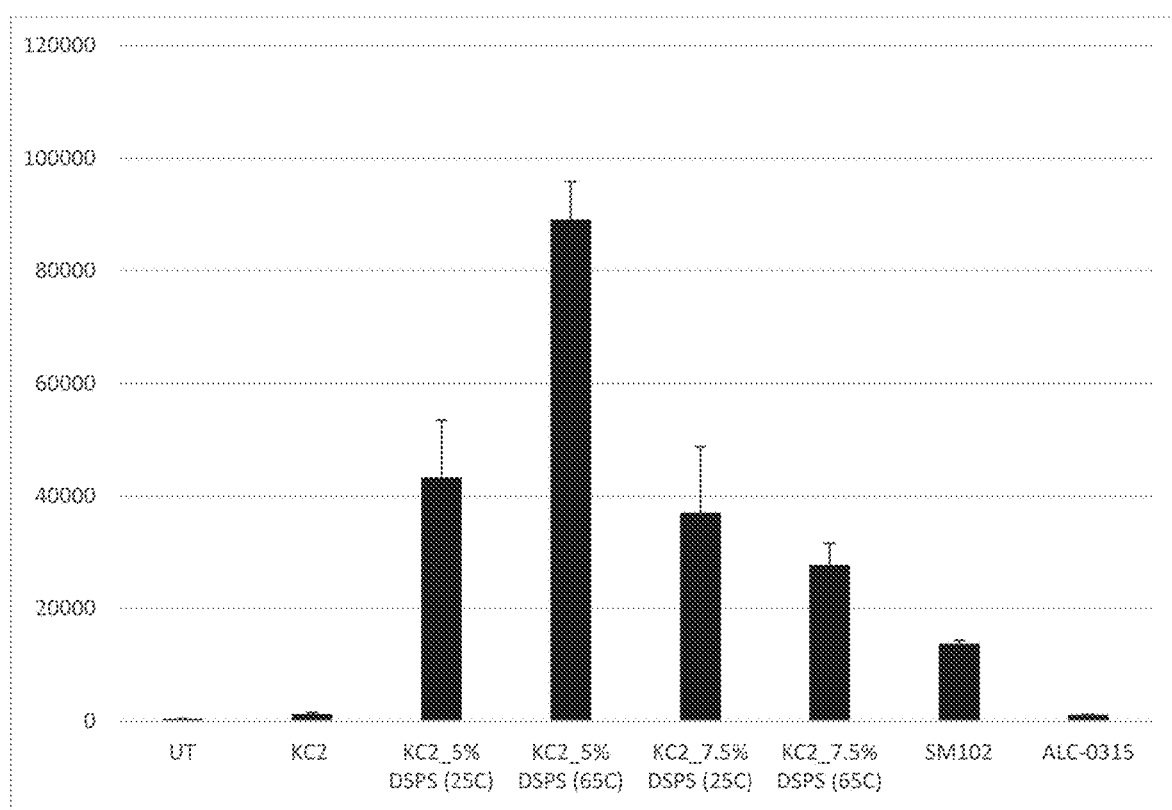

FIG. 16 (Example 25).
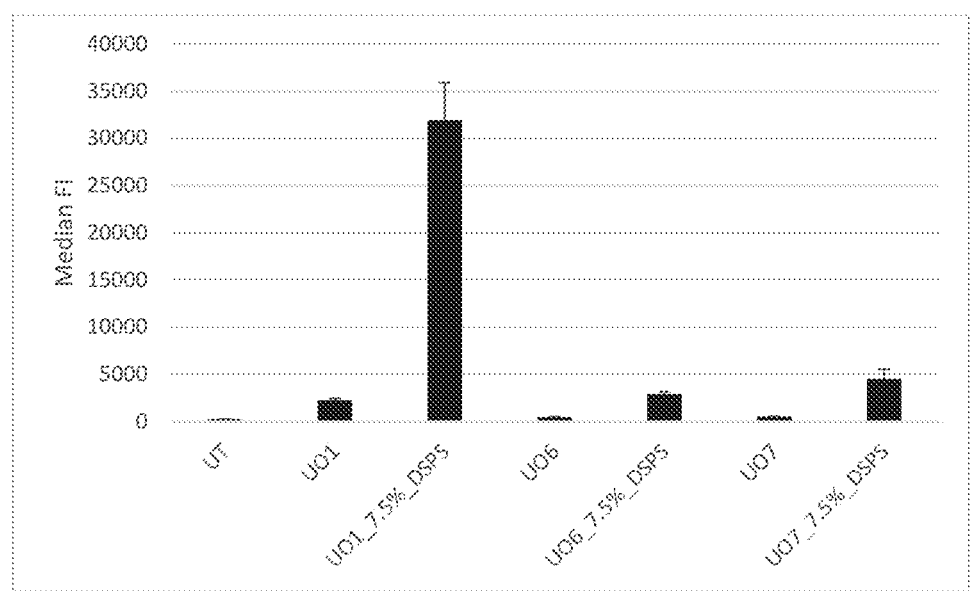

FIG. 17 (Example 26).
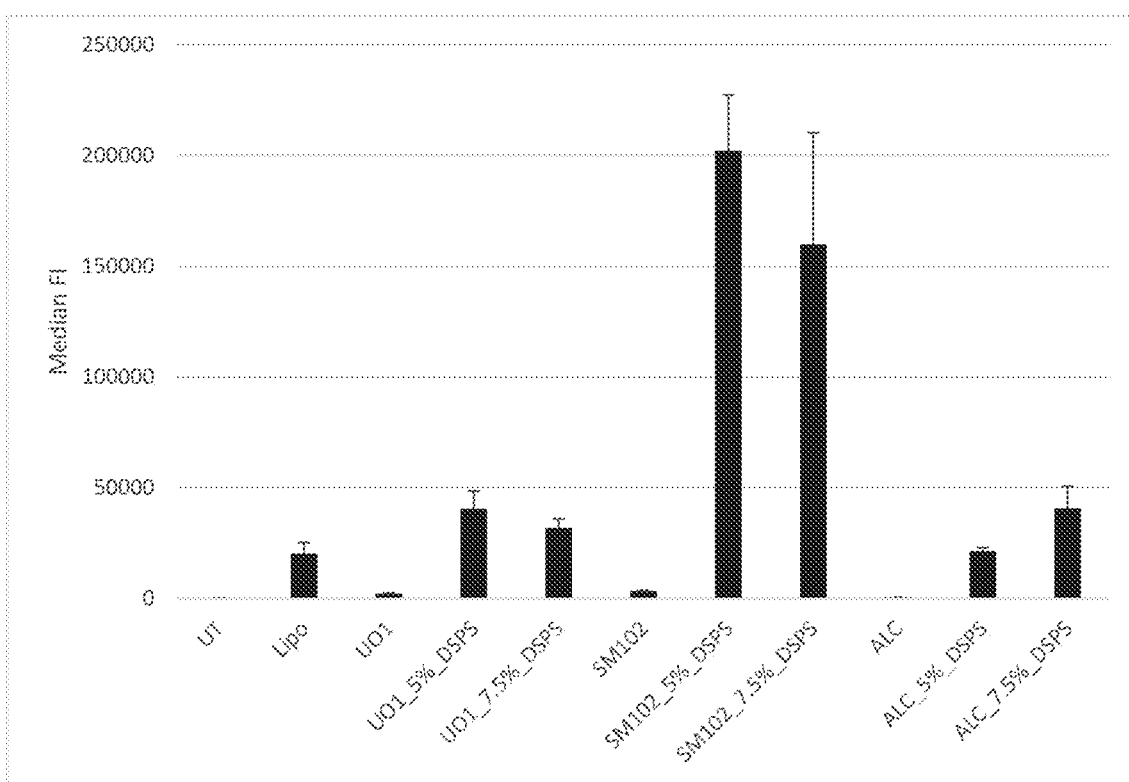

LIPID NANOPARTICLES FOR DELIVERY OF NUCLEIC ACIDS AND METHODS OF USE THEREOF

RELATED APPLICATIONS

This patent application is a continuation of PCT International Application No. PCT/US2021/060877, filed Nov. 24, 2021, which claims the benefit of and priority to U.S. Provisional Patent Application No. 63/118,534, filed on Nov. 25, 2020, each of which are incorporated herein by reference in their entireties.

REFERENCE TO SEQUENCE LISTING

This specification includes a sequence listing submitted herewith, which includes the file entitled 191016-010406_ST26.xml having the following size: 7,645 bytes which was created Jul. 26, 2022, the contents of which are incorporated by reference herein.

FIELD

The present disclosure relates to cationic ionizable lipids and lipid nanoparticles (LNP). In some embodiments, a LNP comprising one or more cationic ionizable lipid(s) is useful for delivery of a nucleic acid compound, for dendritic cell targeting or methods of using these LNP compositions as vaccines. In some embodiments, a LNP can comprise bioreducible ionizable cationic lipids or unconjugated polyolefinic ionizable cationic lipids.

BACKGROUND

Lipid nanoparticles (LNP) are used for the delivery of therapeutic nucleic acids to cells. For example, LNP pharmaceutical compositions are employed in vaccines to deliver mRNA therapeutics. LNP formulations typically include an ionizable cationic lipid (ICL). However, it is known in the art that certain ICL compounds are undesirably sensitive to oxidation during storage. Therefore, there is a need for improved ICL compounds with improved stability to oxidative degradation while in storage, while also providing desired transfection activity or potency in cells when incorporated in a LNP with a therapeutic agent such as a nucleic acid.

SNALP compositions are useful for delivery of nucleic acid therapies for various infectious diseases. Infectious diseases such as tuberculosis, HIV/AIDS, malaria, and COVID-19 represent significant challenges to human health. Mycobacteria, for example, is a genus of bacteria responsible for tuberculosis (TB). According to the World Health Organization, worldwide, TB is one of the top 10 causes of death and the leading cause of death from a single infectious agent. Despite current best efforts, there have been significant challenges in the development of effective vaccines for the prevention of many infectious diseases. New efforts in the identification of individual or combinations of antigenic peptides has helped improved the efficiency of vaccines. Nonetheless, significant opportunities remain in the engineering of adjuvants to help efficiently deliver and present these antigenic sequences to professional antigen presenting cells, like dendritic cells. mRNA coding for antigenic peptides or proteins combined with ionizable cationic lipid nanoparticles represent a particularly promising strategy in the development of a vaccine. There is a need for safe and effective therapies comprising SNALP pharmaceutical compositions for delivery of mRNA for treatment and prevention of various diseases, including vaccine compositions.

SUMMARY

In some embodiments, ionizable cationic lipids (ICLs) are provided. Cationic lipids are engineered with improved stability to oxidative degradation while in storage, while retaining high transfection activity or potency in cells. Aspects of the disclosure are based in part on the discovery that the undesired oxidation and/or degradation of ionizable lipids with polyene chains can be improved by including two or more methylene groups between a pair of alkynyl double bonds. Lipids disclosed herein comprise at least two carbon-carbon double bonds (olefins) spaced with at least two methylene or substituted methylene groups, wherein the substituted methylene is —C($R_1$)($R_2$)— wherein $R_1$ and $R_2$ are independently H, alkyl, or halogen. Lipids disclosed herein include two symmetrical polyene hydrocarbon chains each having two carbon-carbon double bonds (olefins) on either side of two, three or four methylene groups. The olefins in the lipid tails separated by at least two methylene groups renders the compounds described herein considerably less susceptible to oxidation compared to compounds separated by one methylene group, for example DLin-MC3-DMA, considered the gold standard in ionizable cationic lipid design and which was reported to have stability issues. In some embodiments, the compounds provided herein have greater than 30%, greater than 50%, greater than 75%, greater than 90%, and greater than 95% reduction in oxidation byproducts when compared to the control LNP. In some embodiments, the compounds provided herein have greater than 30%, greater than 50%, greater than 75%, greater than 90%, and greater than 95% reduction in oxidation byproducts when compared to the control LNP containing the DLin-KC2-DMA lipid.

In some embodiments, ionizable cationic lipid compositions are provided. In some aspects, the ionizable cationic lipid can comprise two polyene hydrocarbon chains, each including one or two alkenyl double bond moieties. In some aspects, the ionizable cationic lipid can comprise two polyene hydrocarbon chains, each including two or more methylene groups between two alkenyl double bond moieties. In some aspects, the ionizable cationic lipid can contain two C16 or C18 polyene hydrocarbon chains.

In some embodiments, liposomal compositions are provided comprising an ionizable cationic lipid having a pair of linear polyene C16 or C18 hydrocarbon chains each comprising an unsaturated linear ethylene, n-propylene or n-butylene between two adjacent unsaturated alkynyl double bonds in each polyene hydrocarbon chain. In some embodiments, a liposomal composition can comprise an ionizable lipid having a chemical structure consisting of a pair of 16 or 18 carbon linear polyunsaturated lipid tails covalently bound to a head group comprising a dialkyl amino group having a pKa of between 6 and 7; wherein the head group comprises a heterocyclyl or alkyl portion covalently bound to the dialkyl amino group and optionally further comprising a phosphate group; and wherein each polyunsaturated lipid tail is unsaturated except for at least two olefins separated by at least two methylene groups along the length of the lipid tail, and each lipid tail optionally comprises a single acyl group at the end covalently bound to the head group. In some embodiments, each lipid tail is identical, and each lipid tail has a total of two olefins separated only by an unsubstituted ethylene, n-propyl, or n-butyl. In some embodiments, each lipid tail further comprises an acyl group joined to an oxygen of the headgroup to form an ester.

In some embodiments, the dialkyl amino portion of the head group of the ionizable cationic lipid has a dialkyl amino chemical structure of Formula (IV-A)

Fromula IV-A

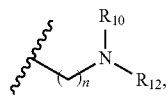

wherein n is 2, 3 or 4 in Formula (IV-A); and $R_{10}$ and $R_{12}$ in Formula (IV-A) are each independently selected from an alkyl group selected from the group consisting of: methyl, ethyl, and n-propyl, wherein the alkyl in $R_{10}$ and $R_{12}$ is optionally substituted with one or more hydroxyl. In some embodiments, $R_{10}$ and $R_{12}$ in Formula (IV-A) are each independently methyl, ethyl, —$(CH_2)(CH_2)OH$, or —$(CH_2)_2(CH_2)OH$.

In some embodiments, an ionizable cationic lipid comprises a chemical structure selected from the group consisting of:

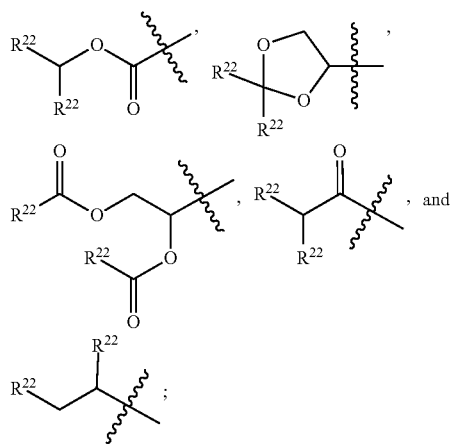

wherein $R^{22}$ is the first end of the lipid tail and

indicates attachment of the head group to the dialkyl amino chemical structure of the head group. In some embodiments, an ionizable cationic lipid comprising the chemical substructure of Formula (IV-A) further comprises an additional chemical structure selected from the group consisting of:

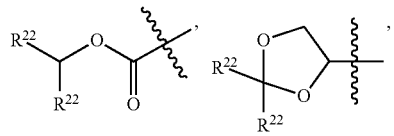

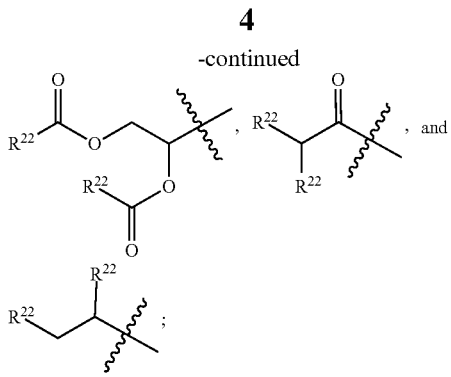

wherein $R^{22}$ is the first end of the lipid tail and

indicates attachment of the head group to the dialkyl amino chemical structure of the head group.

In some embodiments, an ionizable cationic lipid further comprises a pair of lipid tails attached to the head group, wherein each lipid tail comprises a hydrocarbon chain having the chemical structure of Formula A or Formula B:

Formula A

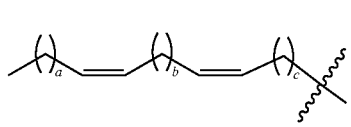

wherein a in Formula A is 1, 2, 3 or 4; b is 2, 3 or 4; and c in Formula A is 3, 4, 5, 6, or 7; or Formula B

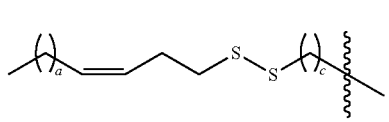

wherein a in Formula B is 5, 6 or 7; and c in Formula B is 3, 4, or 5. In some embodiments, b is 4 and the sum of a, b and c in Formula A is 10, 11, 12 or 13. In some embodiments, the ionizable cationic lipid comprises a lipid tail of Formula A or Formula B at $R^{22}$ in the chemical structure shown above. In some embodiments, the ionizable cationic lipid comprises a lipid tail of Formula A, wherein

in Formula A indicates the position of attachment at $R^{22}$ in the chemical structure shown above. In some embodiments, the ionizable cationic lipid comprises a lipid tail of Formula B, wherein

in Formula B indicates the position of attachment at $R^{22}$ in the chemical structure shown above.

In some embodiments, the ionizable cationic lipid has a chemical structure of Formula (I-A)

Formula I-A

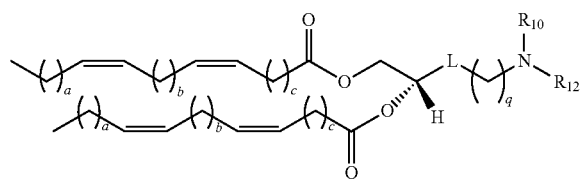

wherein
a is 1, 2, 3, 4, 5 or 6; b is 2, 3 or 4; c is 3, 4, 5, 6, or 7; and the sum of a, b and c is 10 or 12; q is 1, 2, 3 or 4; each of $R_{10}$ and $R_{12}$ is independently $(C_1-C_4)$alkyl optionally substituted with one or more hydroxyl; and L is

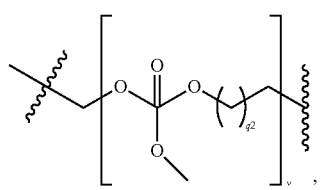

wherein v is 0 or 1; q is 1, 2 or 3 and q2 is 1 or 2. In some embodiments, q is 1, 2 or 3 when v is 0, and q is 1, 2, 3 or 4 when v is 1 in Formula I-A.

In some embodiments, v in Formula I-A is 0. In some embodiments, v in Formula I-A is 0 and q is 1, 2 or 3. In some embodiments, v in Formula I-A is 0 and q is 1 or 2. In some embodiments, the ionizable lipid is a cationic lipid selected from the group consisting of Compounds 17-19, and 23-25:

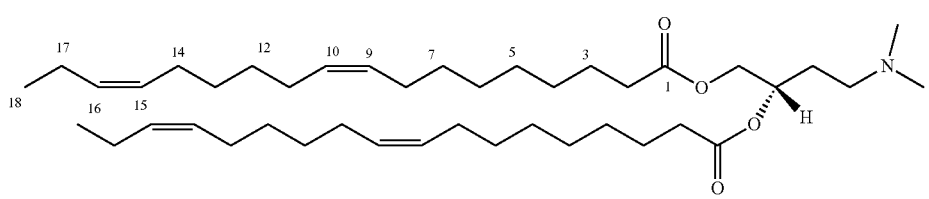

17

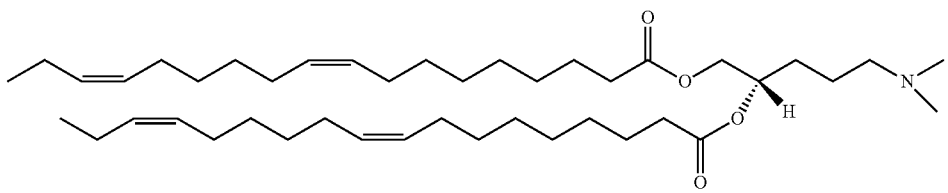

18

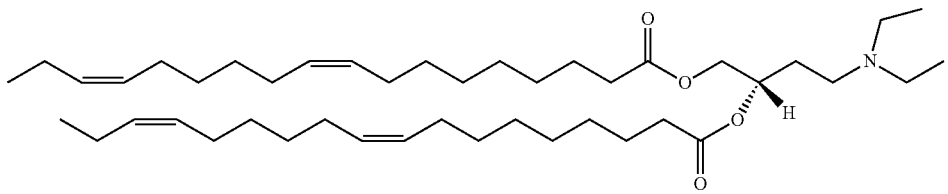

19

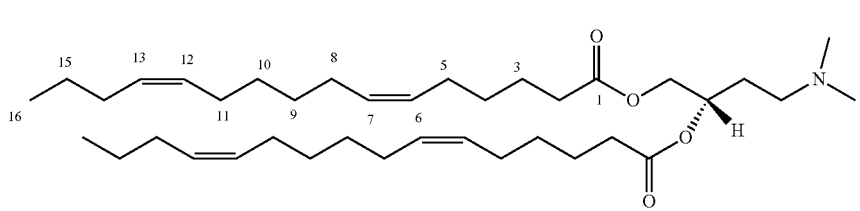

23

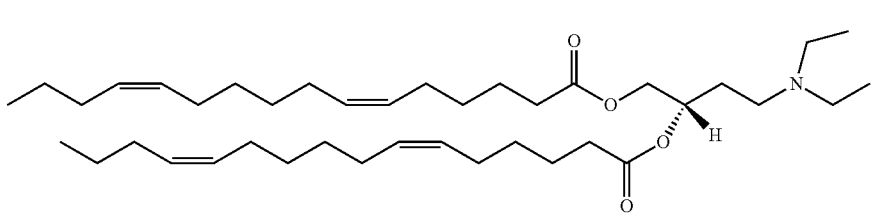

24

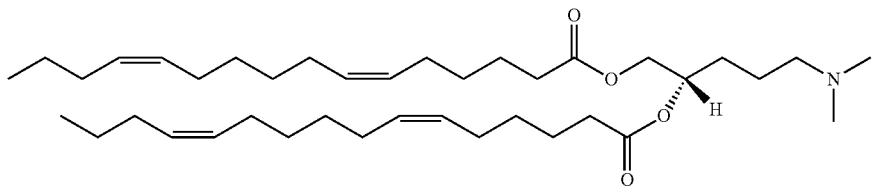
In some embodiments, the ionizable lipid is a cationic lipid selected from the group consisting of: AKG-UO-1, AKG-UO-2, AKG-UO-4, and AKG-UO-5. In some embodiments, the ionizable lipid is AKG-UO-1:
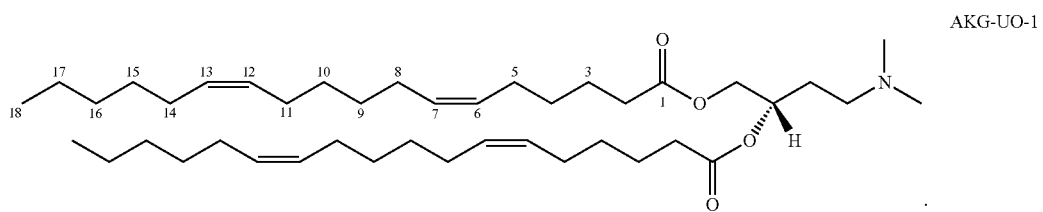 [SMILES: CCCCC/C=C\CCCC/C=C\CCCCC(=O)OC[C@H](CCN(C)C)OC(=O)CCCC/C=C\CCCC/C=C\CCCCC]
In some embodiments, the ionizable lipid is AKG-UO-1A:
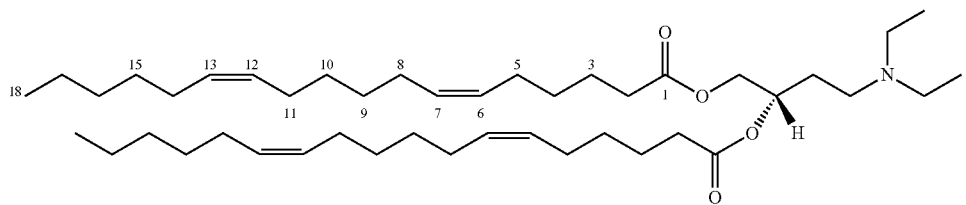 [SMILES: CCCCC/C=C\CCCC/C=C\CCCCC(=O)OC[C@H](CCN(CC)CC)OC(=O)CCCC/C=C\CCCC/C=C\CCCCC]
In some embodiments, the ionizable lipid is AKG-UO-1B:
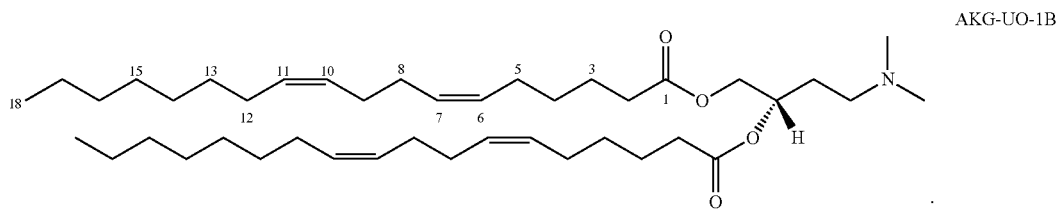 [SMILES: CCCCCCC/C=C\CC/C=C\CCCCC(=O)OC[C@H](CCN(C)C)OC(=O)CCCC/C=C\CC/C=C\CCCCCCC]
In some embodiments, the ionizable lipid is AKG-UO-2:
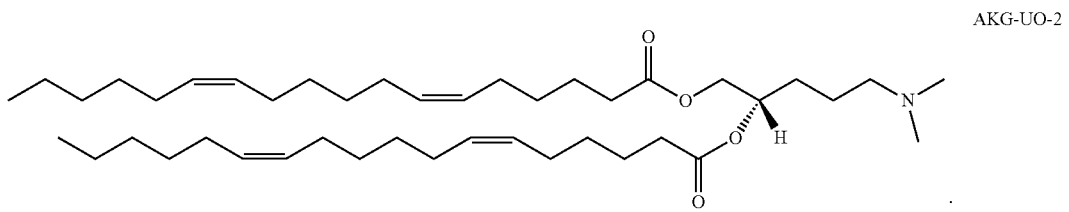 [SMILES: CCCCC/C=C\CCCC/C=C\CCCCC(=O)OC[C@H](CCCN(C)C)OC(=O)CCCC/C=C\CCCC/C=C\CCCCC]

In some embodiments, the ionizable lipid is AKG-UO-4:
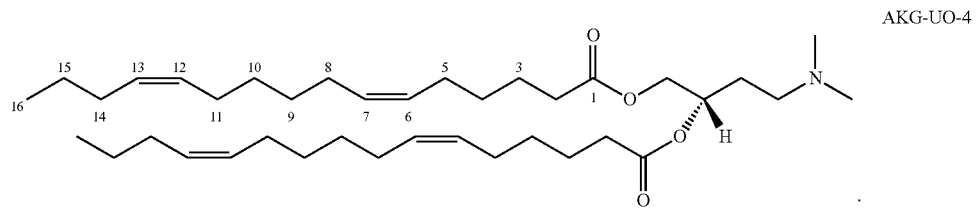 [SMILES: CCC/C=C\CCCC/C=C\CCCCC(=O)OC[C@H](CCN(C)C)OC(=O)CCCC/C=C\CCCC/C=C\CCC]
AKG-UO-4
In some embodiments, the ionizable lipid is AKG-UO-4A:
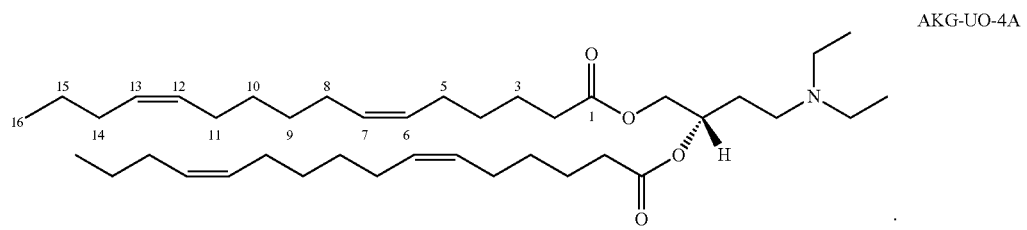 [SMILES: CCC/C=C\CCCC/C=C\CCCCC(=O)OC[C@H](CCN(CC)CC)OC(=O)CCCC/C=C\CCCC/C=C\CCC]
AKG-UO-4A
In some embodiments, the ionizable lipid is AKG-UO-5:
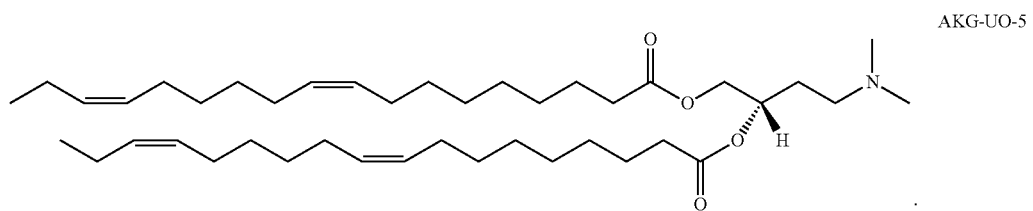 [SMILES: CC/C=C\CCCC/C=C\CCCCCCCC(=O)OC[C@H](CCN(C)C)OC(=O)CCCCCCC/C=C\CCCC/C=C\CC]
AKG-UO-5
In some embodiments, the ionizable lipid is AKG-UO-6, AKG-UO-7, AKG-UO-7, AKG-UO-8, AKG-UO-9, or AKG-UO-10:
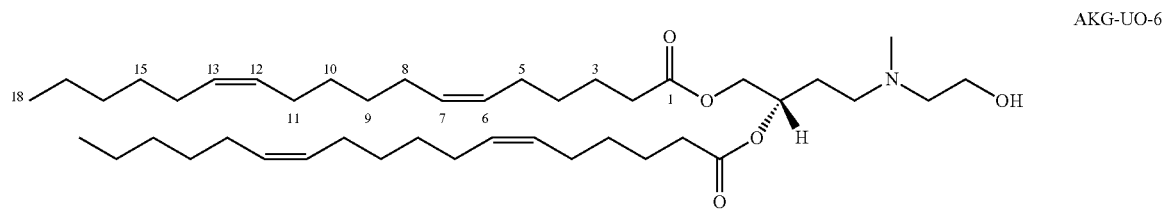
AKG-UO-6
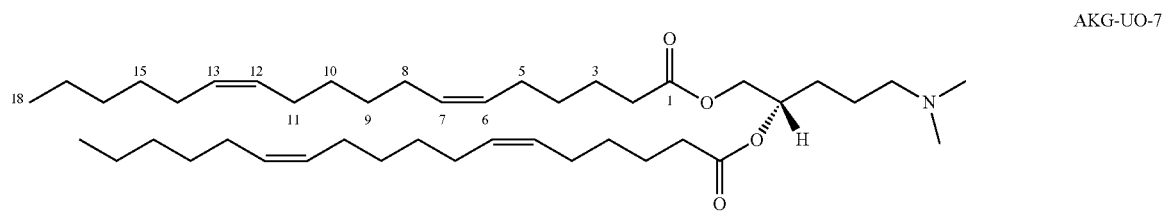
AKG-UO-7

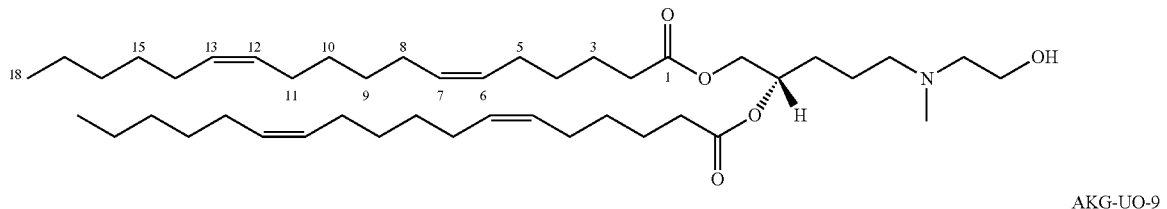

AKG-UO-8

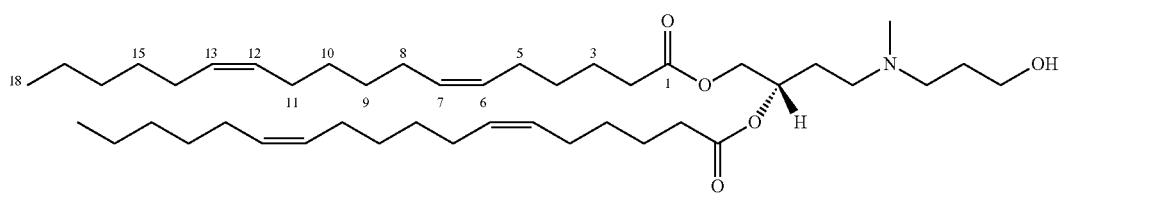

AKG-UO-9

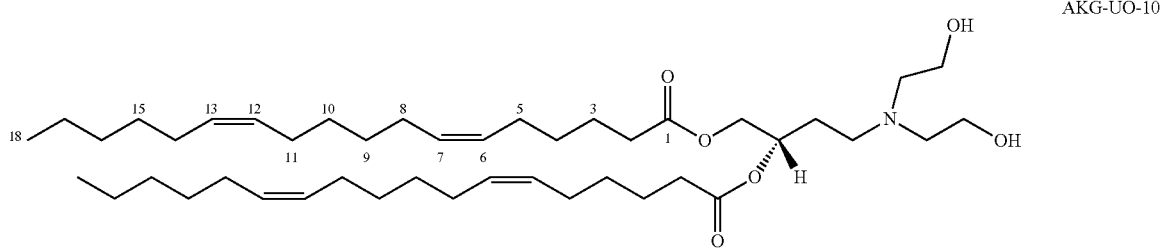

AKG-UO-10

In some embodiments, the ionizable lipid comprises a head group that includes a methylated phosphate moiety. In some embodiments, the ionizable lipid has a chemical structure of Formula I-A wherein v is 1. In some embodiments, the ionizable lipid has a chemical structure of Formula I-A wherein v is 1 and q is 3 or 4. In some embodiments, the ionizable lipid is selected from the group consisting of:

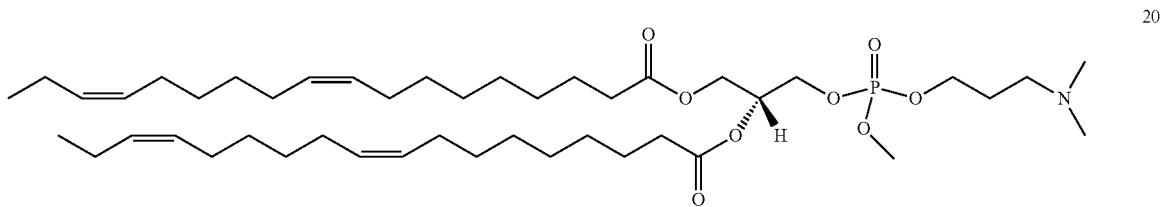

20

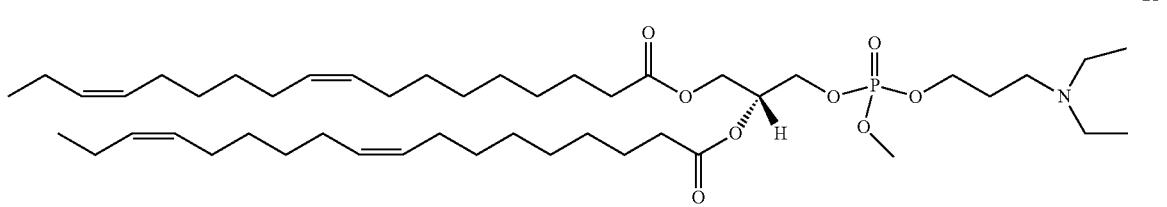

21

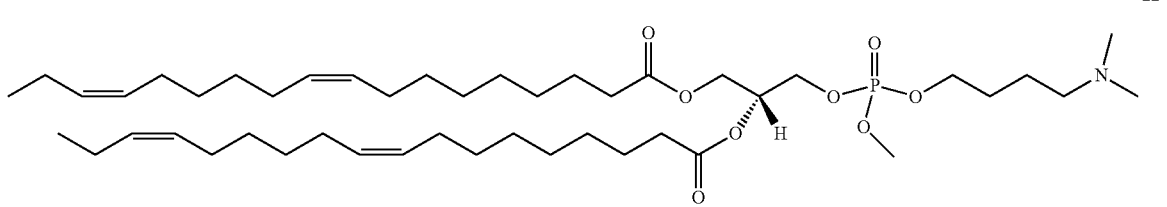

22

-continued
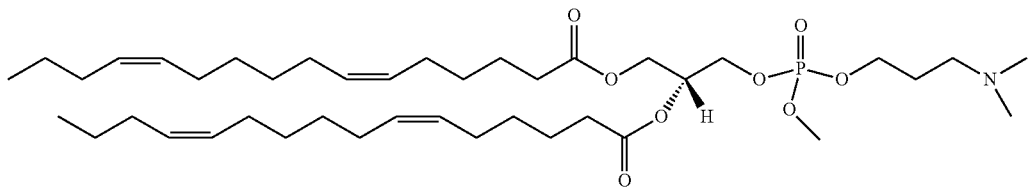
26
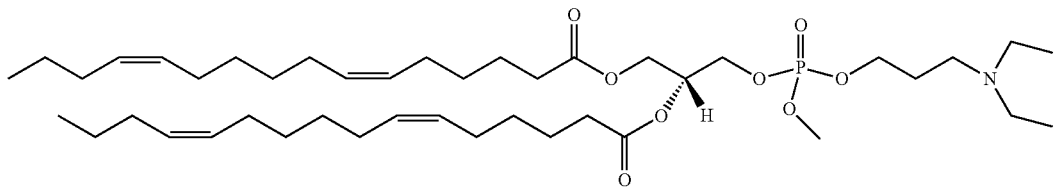
27
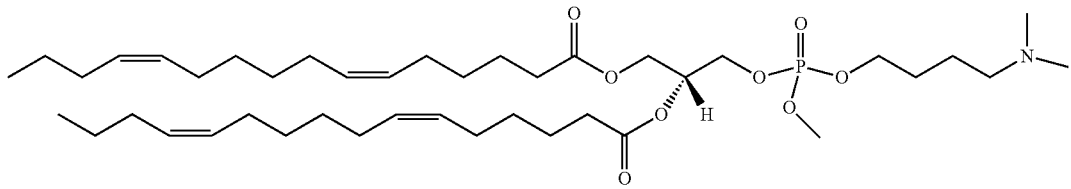
28
In some embodiments, the ionizable lipid is AKG-UO-3:
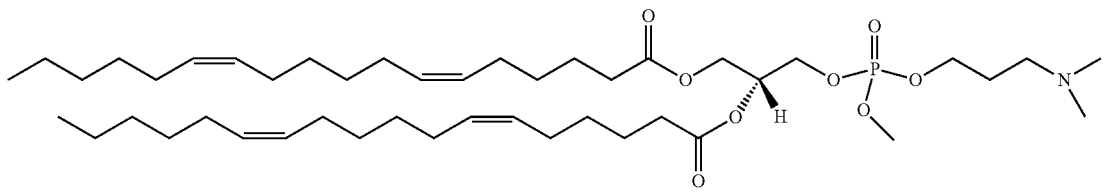
AKG-UO-3
In some embodiments, the ionizable lipid has a chemical structure of Formula II-A:
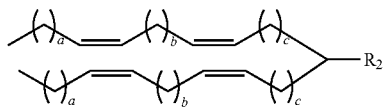
Formula (II-A)
wherein a is 1, 2, 3, 4, 5 or 6; b is 2, 3 or 4; cis 4, 5, 6, 7 or 8;
$R_2$ is
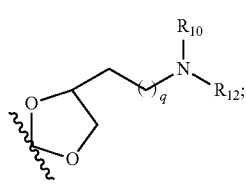
q is 1 or 2; and
each of $R_{10}$ and $R_{12}$ is independently $(C_1\text{-}C_4)$alkyl optionally substituted with one or more hydroxyl.

In some embodiments, the ionizable lipid is selected from the group consisting of Compound 1-3 and Compounds 5-8:
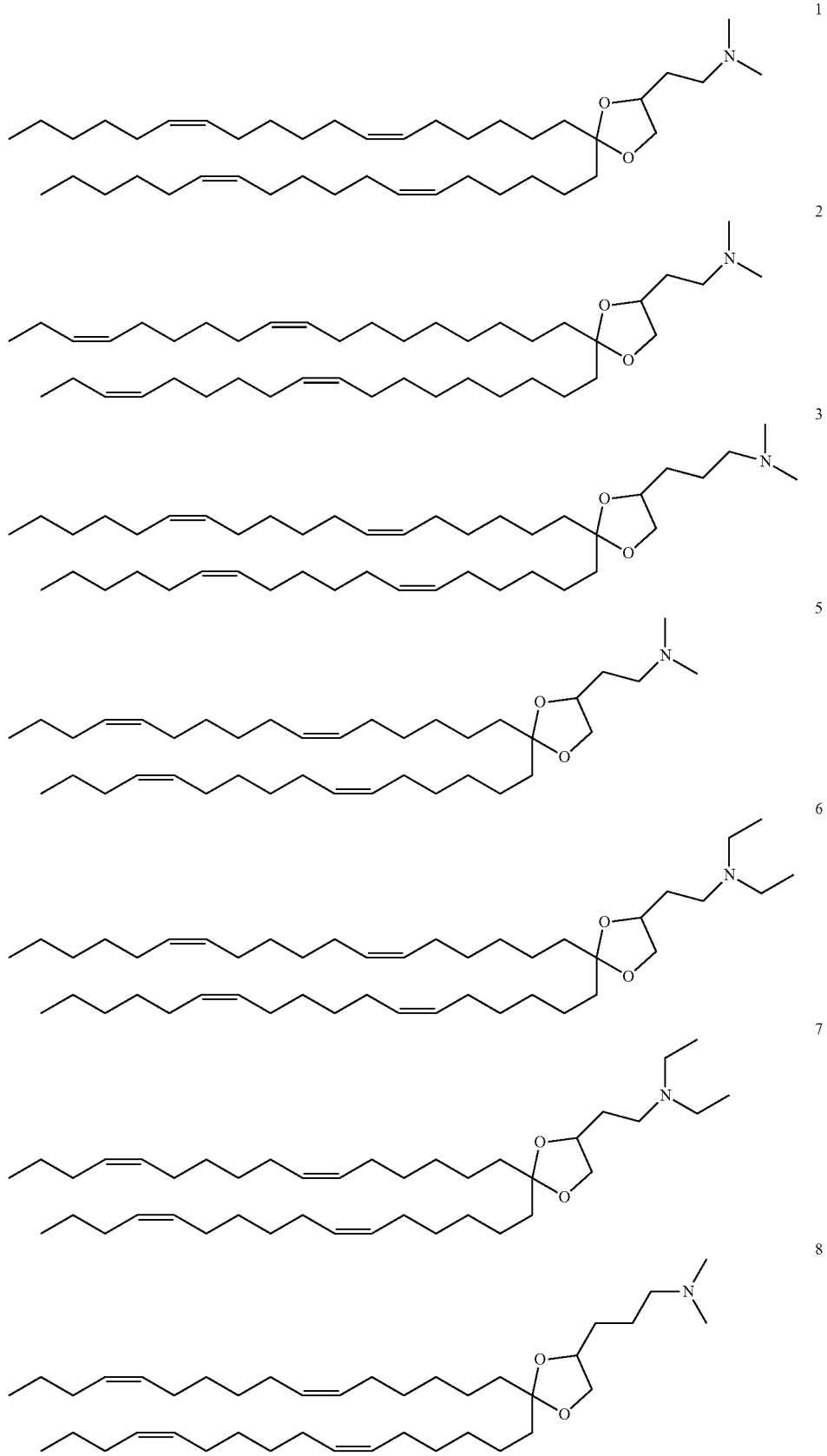

In some embodiments, the ionizable lipid is selected from the group consisting of Compound 1-8:
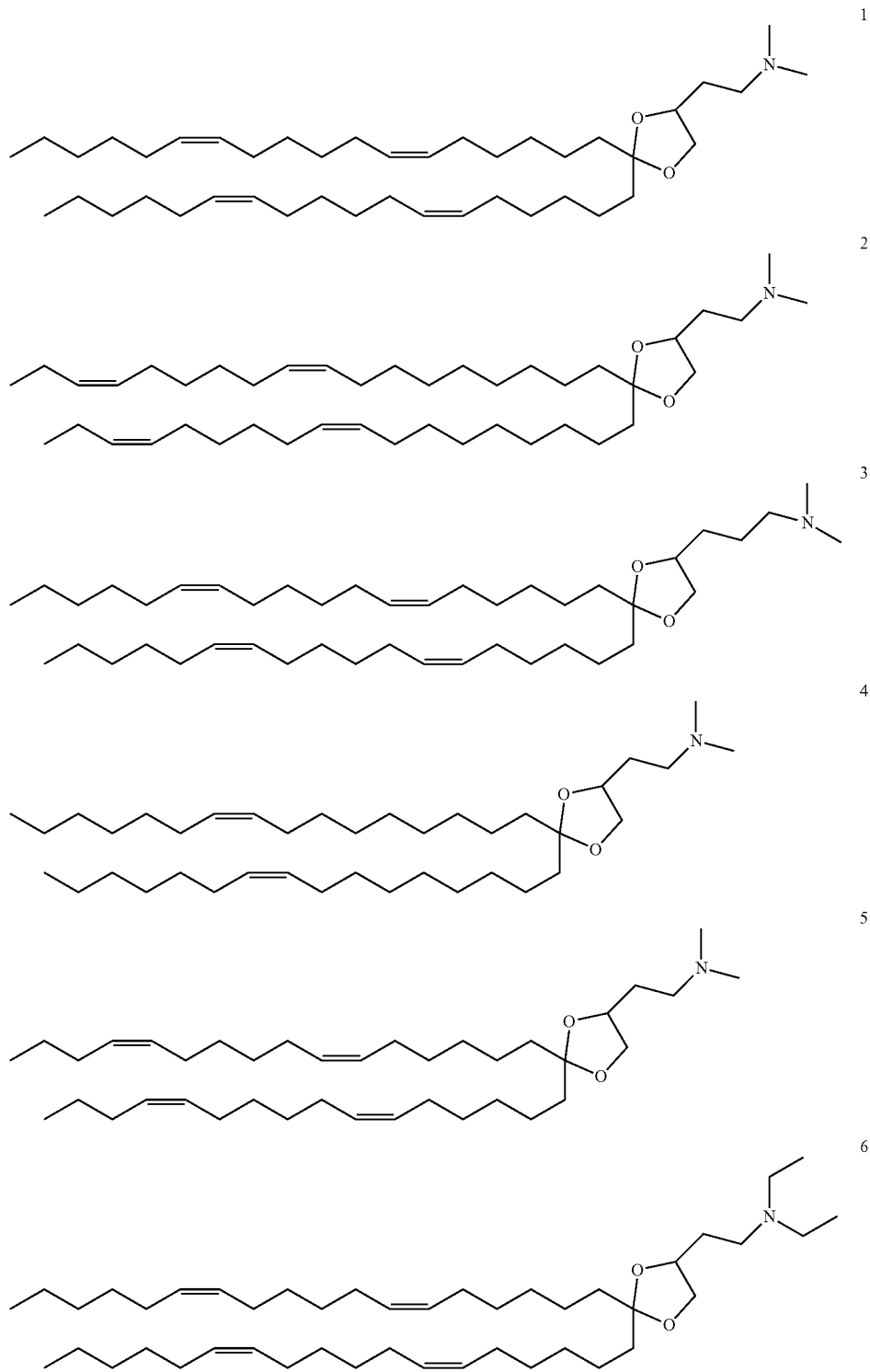

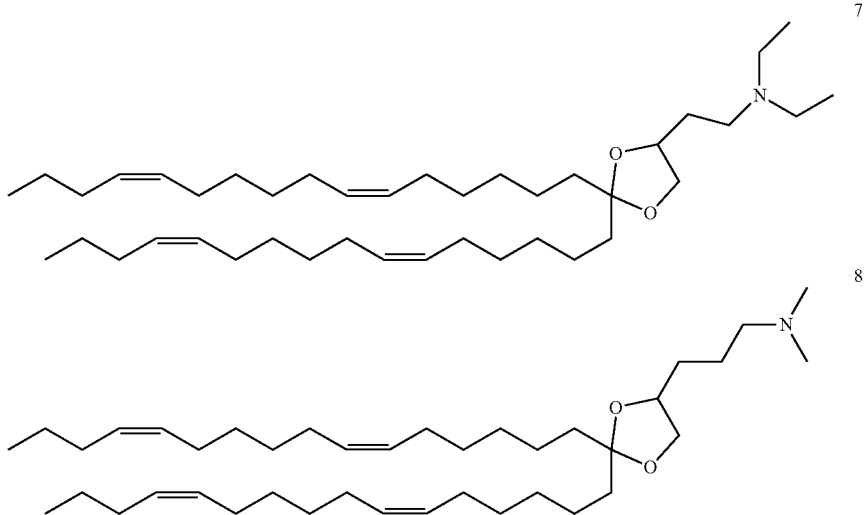
In some embodiments, the ionizable lipid has a chemical structure of Formula II-A:
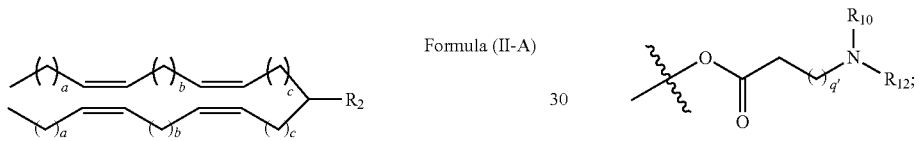
wherein a is 1, 2, 3, 4, 5 or 6; b is 2, 3 or 4; c is 4, 5, 6, 7 or 8;
$R_2$ is
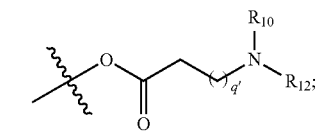
q' is 1 or 2; and
each of $R_{10}$ and $R_{12}$ is independently $(C_1$-$C_4)$alkyl optionally substituted with one or more hydroxyl.
In some embodiments, the ionizable lipid is a compound selected from the group consisting of Compounds 9-19:
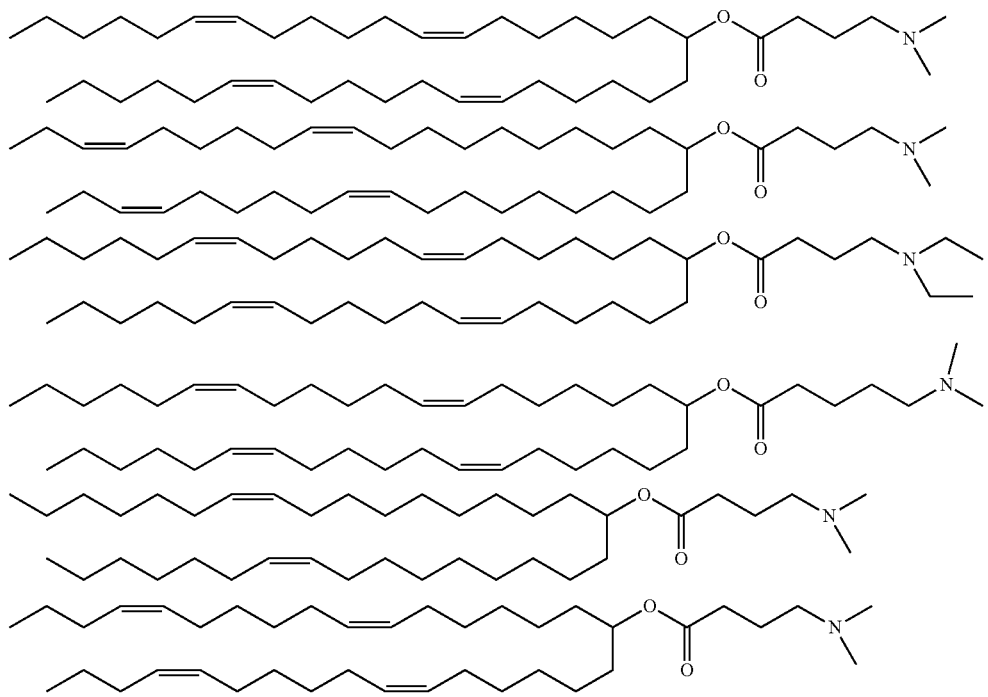

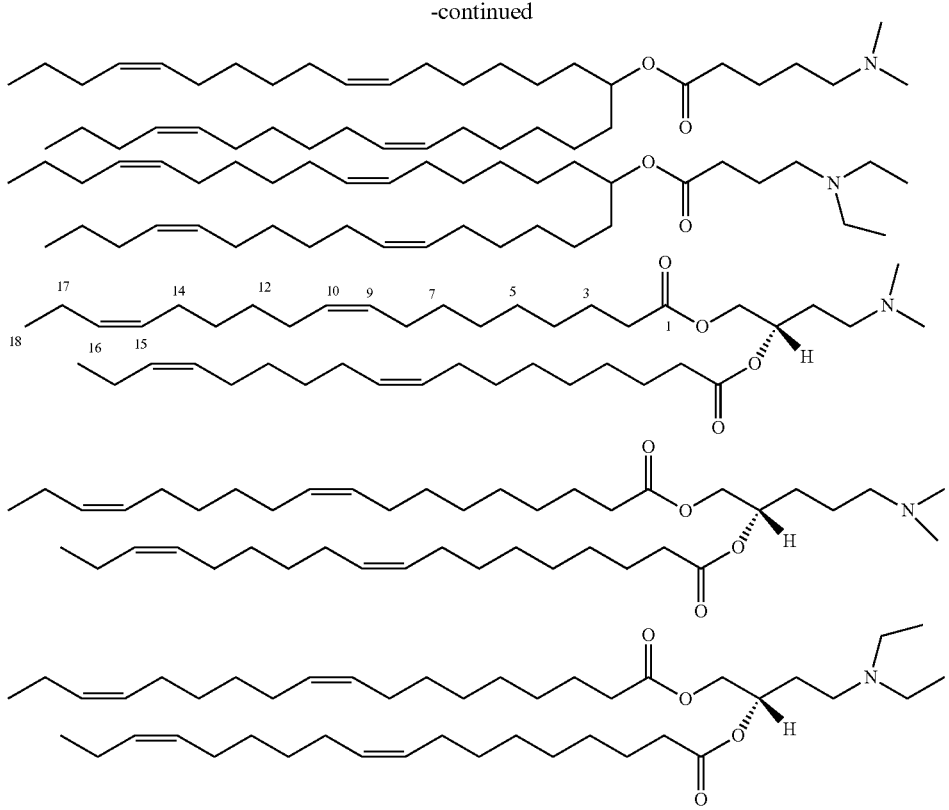

In some embodiments, the ionizable lipid has a chemical structure of Formula II-A:

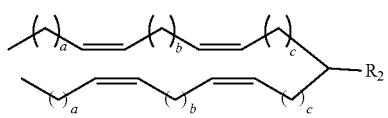

Formula (II-A)

wherein a is 1, 2, 3, 4, 5 or 6; b is 2, 3 or 4; c is 4, 5, 6, 7 or 8;
$R_2$ is

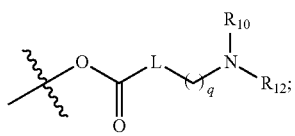

L is

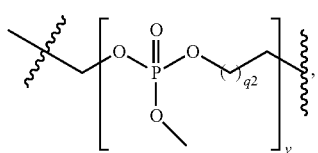

wherein v is 0 or 1; q is 1, 2, 3 or 4; and q2 is 1 or 2; and each of $R_{10}$ and $R_{12}$ is independently $(C_1$-$C_4)$alkyl optionally substituted with one or more hydroxyl. In some embodiments, q is 1, 2 or 3 when v is 0 or q is 3 or 4 when v is 1, in Formula II-A.

In some embodiments, the lipids are designed to be biodegradable, thus improving the tolerability of nanoparticles formed with them in vivo.

In some embodiments, the ionizable lipid has a chemical structure of Formula II-B:

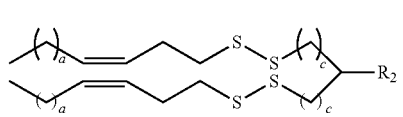

Formula (II-B)

wherein a is 5, 6 or 7; and c is 3, 4, or 5;
$R_2$ is

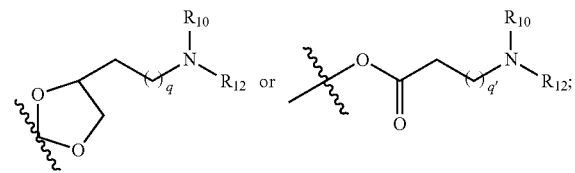

q and q' are each independently 1 or 2; and
$R_{10}$ and $R_{12}$ are each $(C_1$-$C_4)$alkyl optionally substituted with hydroxyl.

In some embodiments, the ionizable cationic lipid is a compound selected from the group consisting of Compounds 29-34:

29

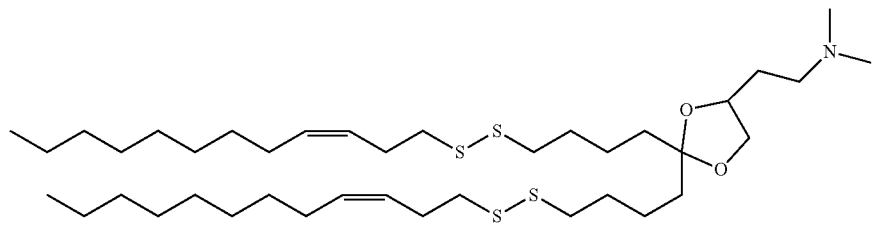

30

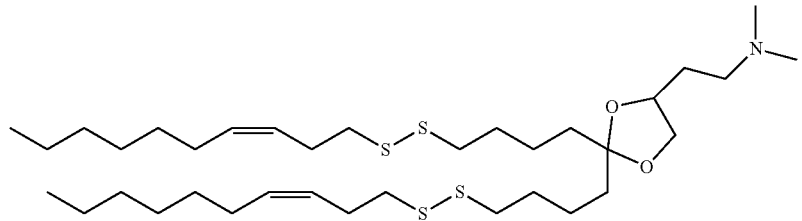

31

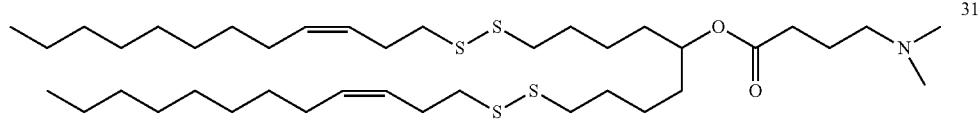

32

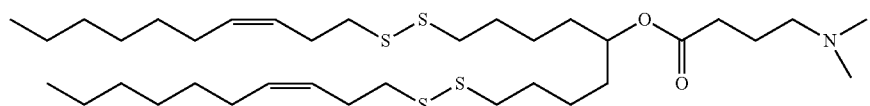

33

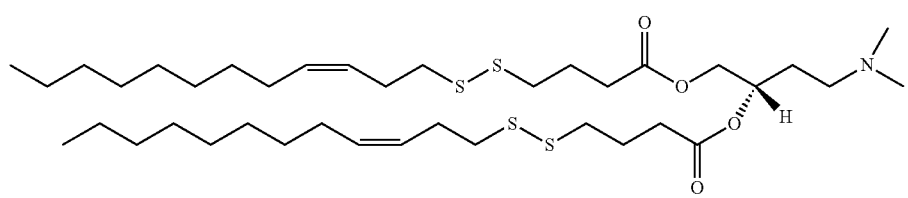

34

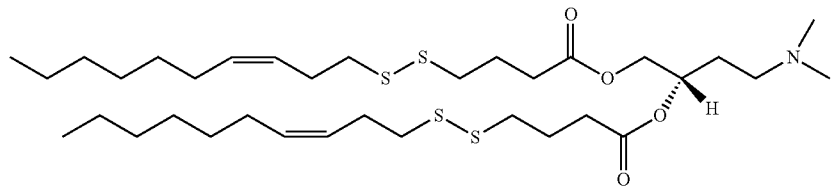

In some embodiments, the ionizable lipid is a bioreducible cationic lipid. In some embodiments, the ionizable lipid is a bioreducible cationic lipid comprising a sterol chemical structure. In some embodiments, the ionizable lipid has a chemical structure of Formula (VI-A):

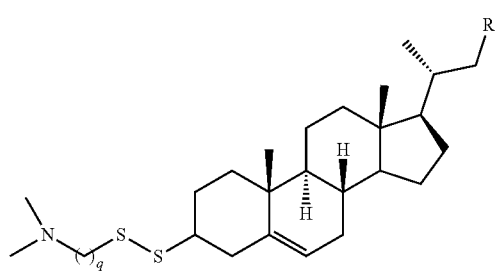

(VI-A)

or a pharmaceutically acceptable salt thereof, wherein q is 3 or 4 and $R_3$ is

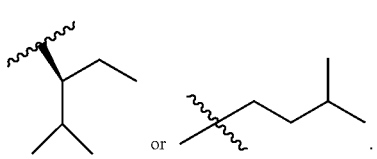

In some embodiments, the ionizable cationic lipid is selected from the group consisting of Compounds 35-38:

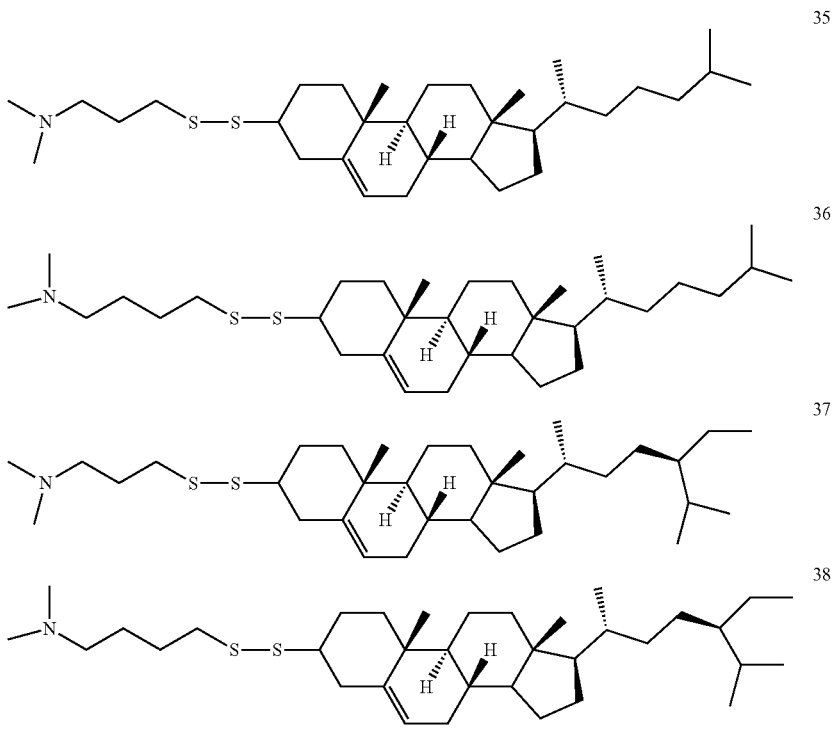

In some embodiments, a lipidic nanoparticle composition comprises lipids and nucleic acids, the lipidic nanoparticles comprising an ionizable lipid of Formula I, II, III, IV or combinations thereof or pharmaceutically acceptable salts thereof. In some embodiments, a lipidic nanoparticle composition comprises lipids and nucleic acids, the lipidic nanoparticles comprising an ionizable lipid of Formula I-A, II-A, II-B, IV-A, or VI-A or combinations thereof or pharmaceutically acceptable salts thereof. In some embodiments, a lipidic nanoparticle composition comprises lipids and nucleic acids, the lipidic nanoparticles comprising an ionizable lipid comprising a polyene hydrocarbon chain of Formula A, Formula A', Formula A'', or Formula B or combinations thereof or pharmaceutically acceptable salts thereof.

In some embodiments, the present disclosure also provides for compositions of lipid nanoparticles (LNP) for the delivery of therapeutic nucleic acids to cells. Aspects of the disclosure are based in part on the discovery that LNP compositions combining various ionizable cationic lipids with certain low amounts of a phosphatidyl-L-serine below 20 mol % of the total lipid in the composition (e.g., 2.5-10 mol % of the total lipid in the composition) surprisingly demonstrated significantly enhanced targeting of encapsulated nucleic acids.

In some embodiments, the LNP compositions comprise: (a) a nucleic acid, (b) an ionizable cationic lipid, (c) a sterol (e.g., cholesterol or a cholesterol derivative, or a phytosterol such as beta-sitosterol), (d) a phospholipid comprising phosphatidylserine (e.g., a mixture of phosphatidylserine and DSPC), and (e) a conjugated lipid (e.g., PEG-DMG). In one aspect, the LNP compositions comprise: (a) a nucleic acid, (b) an ionizable cationic lipid, (c) a sterol (e.g., cholesterol or a cholesterol derivative, or a phytosterol such as beta-sitosterol); (d) phospholipids comprising a phosphatidylserine lipid in a total amount of 1-10 mol % (e.g., 2.5-10 mol %, 3-9 mol %, 5.0-7.5 mol %) of the total lipid in the composition, and additional phospholipids (e.g., DSPC), and (e) a conjugated lipid (e.g., PEG-DMG). In one aspect, the LNP compositions comprise: (a) a nucleic acid, (b) an ionizable cationic lipid, (c) a sterol (e.g., cholesterol or a cholesterol derivative, or a phytosterol such as beta-sitosterol); (d) phospholipids comprising a phosphatidylserine lipid in a total amount of 1-10 mol % (e.g., 2.5-10 mol %, 3-9 mol %, 5.0-7.5 mol %) of the total lipid in the composition, and additional phospholipids (e.g., DSPC), and (e) a conjugated lipid (e.g., PEG-DMG) in a total amount of 0.5-4.5 mol % (e.g., 0.5-2.5 mol %, 1.5 mol %) of the total lipid in the composition. In one aspect, the LNP compositions comprise: (a) a nucleic acid, (b) an ionizable cationic lipid in a total amount of 40-65 mol % (e.g., 50 mol %) of the total lipid in the composition, (c) a sterol (e.g., cholesterol or a cholesterol derivative, or a phytosterol such as beta-sitosterol) in a total amount of 25-40 mol % (e.g., 38.5 mol %) of the total lipid in the composition; (d) phospholipids comprising a phosphatidylserine lipid in a total amount of 1-10 mol % (e.g., 2.5-10 mol %, 3-9 mol %, 5.0-7.5 mol %) of the total lipid in the composition, and additional phospholipids (e.g., DSPC), and (e) a conjugated lipid (e.g., PEG-DMG) in a total amount of 0.5-4.5 mol % (e.g., 0.5-2.5 mol %, 1.5 mol %) of the total lipid in the composition. In one aspect, the LNP compositions comprise: (a) a nucleic acid, (b) an ionizable cationic lipid in a total amount of 40-65 mol % (e.g., 50 mol %) of the total lipid in the composition, (c) a sterol (e.g., cholesterol or a cholesterol derivative, or a phytosterol such as beta-sitosterol) in a total amount of 25-40 mol % (e.g., 38.5 mol %) of the total lipid in the composition; (d) phospholipids in a total amount of 5-25 mol % of the total lipid in the composition, wherein the phospholipids comprise a phosphatidylserine lipid in a total amount of 1-10 mol % (e.g., 2.5-10 mol %, 3-9 mol %, 5.0-7.5 mol %) of the total lipid in the composition, and additional phospholipids (e.g., DSPC) (e.g., 10 mol % of the total lipid in the composition), and (e) a conjugated lipid (e.g., PEG-DMG) in a total amount of 0.5-4.5 mol % (e.g., 0.5-2.5 mol %, 1.5 mol %) of the total lipid in the composition.

In one aspect, the LNP compositions comprise: (a) a nucleic acid, (b) a ionizable cationic lipid having a pair of linear polyene C16 or C18 hydrocarbon chains each comprising an unsaturated linear ethylene, n-propylene or n-butylene between two adjacent unsaturated alkynyl double bonds in each polyene hydrocarbon chain, the ionizable cationic lipid present in the composition in a total amount of 40-65 mol % of the total lipid in the composition, (c) a sterol (e.g., cholesterol) in a total amount of 25-40 mol % of the total lipid in the composition; (d) phospholipids in a total amount of 5-25 mol % of the total lipid in the composition, the phospholipids including a phosphatidylserine lipid (e.g., phosphatidyl-L-serine lipid) in a total amount of 1-10 mol % of the total lipid in the composition, and additional phospholipids (e.g., DSPC in a total amount of 10 mol % of the total lipid in the composition), and (e) a conjugated lipid (e.g., PEG-DMG) in a total amount of 0.5-2.5 mol % of the total lipid in the composition. In one aspect, the LNP compositions comprise: (a) a mRNA nucleic acid, (b) an ionizable cationic of Formula (I-A), Formula (II-A), or Formula (II-B) when v is 0 in a total amount of 40-65 mol % of the total lipid in the composition, (c) cholesterol in a total amount of 25-40 mol % of the total lipid in the composition; (d) a L-serine phosphatidylserine lipid (e.g., DPPS or DSPS) in a total amount of 1-10 mol % (e.g., 2.5-10 mol %, 3-9 mol %, 5.0-7.5 mol %) of the total lipid in the composition, and DSPC in a total amount of 5-25 mol % of the total lipid in the composition, and (e) a conjugated lipid (e.g., PEG-DMG) in a total amount of 0.5-2.5 mol % of the total lipid in the composition. In one aspect, the LNP compositions comprise: (a) a mRNA nucleic acid, (b) an ionizable cationic of Formula (I-A) when v is 0 in a total amount of 40-65 mol % of the total lipid in the composition, (c) cholesterol in a total amount of 25-40 mol % of the total lipid in the composition; (d) a L-serine phosphatidylserine lipid (e.g., DPPS or DSPS) in a total amount of 3-9 mol % of the total lipid in the composition, and DSPC in a total amount of 5-25 mol % of the total lipid in the composition, and (e) a conjugated lipid (e.g., PEG-DMG) in a total amount of 0.5-2.5 mol % of the total lipid in the composition.

In some embodiments, a composition comprises: (a) a polyunsaturated ionizable cationic lipid; and (b) a charged phospholipid phosphatidylserine lipid In some embodiments, a composition comprises: (a) an ionizable cationic lipid of Formula IV-A; and (b) an anionic phospholipid targeting moiety selected from the group consisting of: DSPS (L-isomer), DPPS (L-isomer), DMPS (L-isomer), DOPS (L-isomer), DSPS (D-isomer), DSPG, DPPG, N-Glu-DSPE, and N-Suc-DSPE. In some embodiments, a composition comprises: (a) an ionizable cationic lipid of Formula IV-A; and (b) an anionic phospholipid targeting moiety of Formula V-A. In some embodiments, a composition comprises: (a) an ionizable cationic lipid of Formula IV-A; and (b) an anionic phospholipid targeting moiety selected from the group consisting of: DSPS (L-isomer), and DPPS (L-isomer).

In some embodiments, a composition comprises: (a) an ionizable cationic lipid of Formula IV; and (b) an anionic phospholipid targeting moiety of Formula V-A. In some embodiments, a composition comprises: (a) an ionizable cationic lipid of Formula IV; and (b) an anionic phospholipid targeting moiety selected from the group consisting of: DSPS (L-isomer), DPPS (L-isomer), DMPS (L-isomer), DOPS (L-isomer), DSPS (D-isomer), DSPG, DPPG, N-Glu-DSPE, and N-Suc-DSPE. In some embodiments, a composition comprises: (a) an ionizable cationic lipid of Formula IV; and (b) an anionic phospholipid targeting moiety of Formula V-A. In some embodiments, a composition comprises: (a) an ionizable cationic lipid of Formula IV-A; and (b) an anionic phospholipid targeting moiety selected from the group consisting of: DSPS (L-isomer), and DPPS (L-isomer).

In one aspect, the LNP compositions comprise: (a) an mRNA nucleic acid, (b) an ionizable cationic lipid selected from the group consisting of AKG-KC2-OA, AKG-KC3-OA, Dlin-KC2-DMA and Dlin-KC3-DMA in a total amount of 40-65 mol % of the total lipid in the composition, (c) cholesterol (or a derivative thereof) in a total amount of 25-40 mol % of the total lipid in the composition; (d) a mixture of two or more phospholipids in a total amount of 5-25 mol % of the total lipid in the composition, the phospholipids comprising L-serine phosphatidylserine lipid (e.g., DPPS or DSPS) in a total amount of 3-9 mol % (e.g., 5.0-7.5 mol %) of the total lipid in the composition, and (e) a conjugated lipid (e.g., PEG-DMG) in a total amount of 0.5-2.5 mol % of the total lipid in the composition.

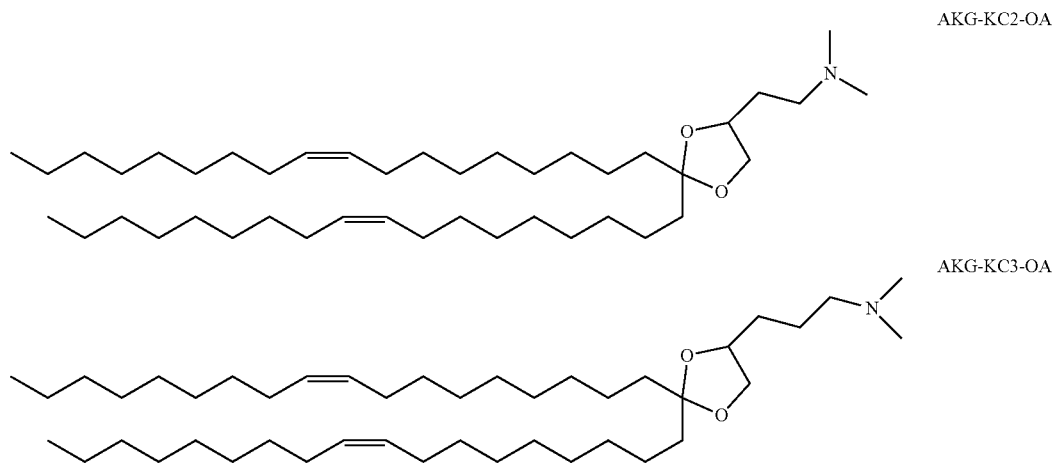

AKG-KC2-OA

AKG-KC3-OA

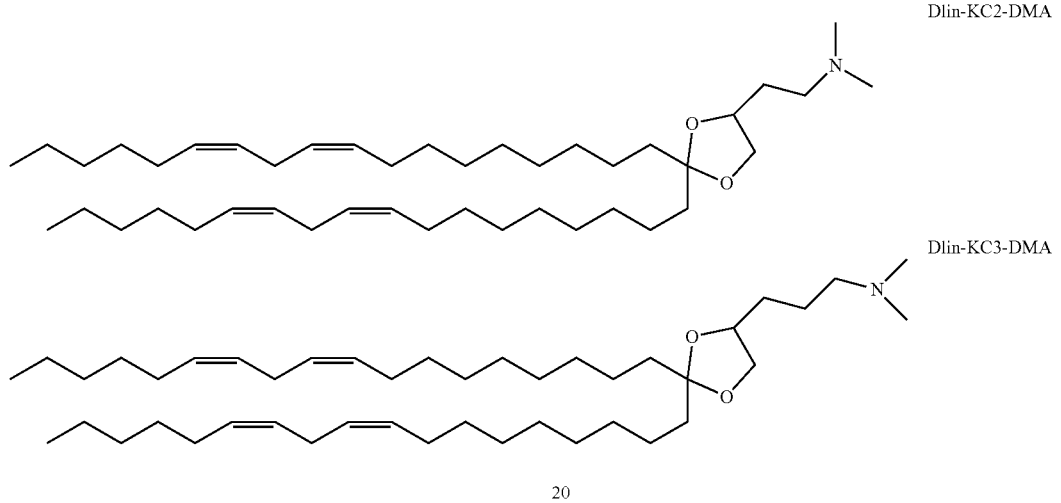

In one aspect, the nucleic acid lipid nanoparticle (LNP) composition comprises: a nucleic acid, the ionizable cationic lipid AKG-UO-1, and a (L-Serine) PS lipid in a total amount of 2.5-10 mol % of the total lipid content of the LNP composition. In some embodiments, the nucleic acid is mRNA, the PS lipid is (L-Serine) DSPS, (L-Serine) DPPS, or a mixture thereof, and the LNP composition further comprises cholesterol and a second phospholipid selected from the group consisting of: DSPC, DPPC and DOPC. The the LNP composition further comprises 0.5-1.5 mol % PEG-DMG or PEG-DSG, based on the total lipid content in the LNP composition.

In one aspect, the nucleic acid lipid nanoparticle (LNP) composition comprises: a nucleic acid, an ionizable cationic lipid selected from KC2OA, KC2, KC2-01, ALC-0315, and SM102; and a (L-Serine) PS lipid in a total amount of 2.5-10 mol % of the total lipid content of the LNP composition. In some embodiments, the LNP composition has a N/P ratio 3 to 8 (e.g. ratio of 5-7 or 5).

In one aspect, the nucleic acid lipid nanoparticle (LNP) composition comprises: a nucleic acid, an ionizable cationic lipid selected from AKG-UO-6 and AKG-UO-7; and a (L-Serine) PS lipid in a total amount of 2.5-10 mol % of the total lipid content of the LNP composition. In some embodiments, the N/P ratio 3 to 8 (e.g. ratio of 5-7 or 5 or 7).

In one aspect, the nucleic acid lipid nanoparticle (LNP) vaccine composition comprises: a mRNA nucleic acid with a N/P ratio of 3 to 8; an ALC-0315 ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

In one aspect, the nucleic acid lipid nanoparticle (LNP) vaccine composition comprises: a mRNA nucleic acid with a N/P ratio of 3 to 8; a Dlin-KC2-DMA ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

In one aspect, the lipid nanoparticle (LNP) vaccine composition comprises: a mRNA nucleic acid with a N/P ratio of 3 to 8; a KC3-OA ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and PEG-DMG in a total amount of 0-2.5 mol % of the total lipid content of the LNP composition.

In one aspect, the nucleic acid lipid nanoparticle (LNP) vaccine composition comprises: a mRNA nucleic acid with a N/P ratio of 3 to 8; an ionizable cationic lipid in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; and DSPC phospholipid in a total amount of 5-25 mol % of the total lipid content of the LNP composition; and PEG-DMG in a total amount of 0-2.5 mol % of the total lipid content of the LNP composition.

One aspect of the disclosure relates to the use of a (L-Serine) PS lipid in a LNP in a total amount of 2.5-10 mol % of the total lipid content of the LNP composition for targeting of the LNP to dendritic cells. In some embodiments, the LNP comprises mRNA. In some embodiments, the LNP further comprises cholesterol. In some embodiments, the LNP further comprises ICL. In some embodiments, the LNP further comprises one or more additional phospholipids including DSPC. In some embodiments, the LNP further comprises a conjugated lipid. In some embodiments, the LNP comprises a mRNA nucleic acid with a N/P ratio of 3 to 8; an ionizable cationic lipid (ICL) in a total amount of 40-65 mol % of the total lipid content of the LNP composition; cholesterol in a total amount of 25-40 mol % of the total lipid content of the LNP composition; a (L-Serine) PS lipid in a total amount of 2.5-10 mol % of the total lipid content of the LNP composition; DSPC phospholipid in a total amount of 5-25 mol % of the total lipid content of the LNP composition; and a conjugated lipid in a total amount of 0-2.5 mol % of the total lipid content of the LNP composition.

BRIEF DESCRIPTION OF THE DRAWINGS

FIG. 3A. Impact of DSPS inclusion from 0-2.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added. Cells were incubated with each formulation at a concentration of 1 ug mRNA/mL for 24 h. UT sample corresponds to cells where no LNPs were added. Lipofect refers to Lipofectamine treated sample.

FIG. 3B. Impact of DSPS inclusion from 0-7.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added. Cells were incubated with each formulation at a concentration of 1 ug mRNA/mL for 24 h. UT sample corresponds to cells where no LNPs were added. Lipofect refers to Lipofectamine treated sample.

FIG. 3C. Impact of DSPS inclusion from 0-7.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added. Cells were incubated with each formulation at a concentration of 0.3 ug mRNA/mL for 24 h. UT sample corresponds to where no LNPs were added.

FIG. 3D. Impact of DSPS inclusion from 0-7.5 mol % on transfection efficiency of dendritic cells (MutuDC1940) using mCherry mRNA LNPs formulated with DLin-KC2-DMA as the ionizable cationic lipid. ICL was kept at 50 mol %, cholesterol at 38.5 mol %, PEG-DMG at 1.5 mol % and the DSPS content varied. Inclusion of DSPS was made by reducing the DSPC content by the same mol % of DSPS that was added Cells were incubated with each formulation at a concentration of 0.1 ug mRNA/mL for 24 h. UT sample corresponds to cells where no LNPs were added.

FIG. 4. Transfection of murine dendritic cells (MutuDC1940) using LNPs containing various ICLs (KC2, KC2-OA, KC3-OA, and SM-102) and 5 mol % DSPS, and comparison to LNPs using Glu-DSPE or Suc-DSPE rather than DSPS. UT sample corresponds to cells where no LNPs were added.

FIG. 5. DSPS or DPPS increase mCherry LNP transfection with KC2, KC2-01, KC2-PA, KC3-01, and KC3-OA comprising ICLs. UT sample corresponds to cells where no LNPs were added.

FIG. 6A. Comparison of various chemical forms of phosphatidylserine with AKG-UO-1 containing LNPs in transfecting murine dendritic cells. UT sample corresponds to cells where no LNPs were added. Lipo refers to Lipofectamine MessengerMax (ThermoFisher) used according to manufacturer's instructions at the same dosage level as the LNPs.

FIG. 6B. Comparison of DSPS to other negatively charged phospholipids in transfecting murine dendritic cells using AKG-UO1 containing LNPs. UT sample corresponds to cells where no LNPs were added. Lipo refers to Lipofectamine MessengerMax (ThermoFisher) used according to manufacturer's instructions at the same dosage level as the LNPs.

FIG. 7. Impact of DSPS concentration in AUG-UO-1 containing LNPs on transfection of dendritic cells. UT sample corresponds to cells where no LNPs were added.

FIG. 8. Impact of PEG-DMG concentration in AUG-UO-1 containing LNPs with and without 5 mol % DSPS on transfection of dendritic cells. The Y-axis shows the % PEG used in the composition followed by the concentration of mRNA added to the cells (0.11, 0.33, or 1 µg/mL). UT sample corresponds to cells where no LNPs were added.

FIG. 9A. Oxidative degradation of lipid suspensions of ICLs with a single methylene between two olefins (KC2, KC3, and 0-11769) and those with four methylenes between the two olefins (KC2-01, KC3-01, and UO-1).

FIG. 9B. Oxidative degradation of liposomes containing 0-11769, an ICL with a single methylene between two olefins liposomes containing UO-1, an ICL with four methylenes between the two olefins.

FIG. 10A. Effect of N/P on mCherry expression of KC2-01 containing LNPs at 1 µg/ml in murine dendritic cells. UT sample corresponds to cells where no LNPs were added.

FIG. 10B. Effect of N/P on mCherry expression of KC2-01 containing LNPs at 0.33 µg/ml in murine dendritic cells. UT sample corresponds to cells where no LNPs were added.

FIG. 11. Transfection efficiency of LNPs with and without DSPS (7.5 mol %) and containing different ionizable cationic lipids. UT sample corresponds to cells where no LNPs were added.

FIG. 12. Transfection efficiency of LNP formulations containing various concentrations of DOPS (0, 10, and 25 mol % as % of total lipid) and mCherry mRNA in murine dendritic cells.

FIG. 13A. mRNA sequence of VRN-029, a SARS-COV2 spike protein generating sequence.

FIG. 13B. The effect of PEG-DMG (C14) concentration (mol %) on LNP vaccine immunogenicity. Total anti-spike antibody titers and CD4 responses from mice immunized with mRNA-LNPs using 7.5% DSPS and the ionizable lipid UO1 with increasing mol % of PEG-DMG. The middle graph shows day 34 endpoint antibody titers. The right graph shows the corresponding CD4 T cell responses.

FIG. 13C. The effect of PEG-DPPE (C16) concentration (mol %) on LNP vaccine immunogenicity. Total anti-spike antibody titers from mice immunized with mRNA-LNPs using 7.5% DSPS and the ionizable lipid UO1 with increasing mol % of PEG-DPPE. The middle graph shows day 34 endpoint antibody titers. The mol % of PEG-DPPE inversely impacted antibody levels. The right graphs shows the corresponding CD4 T cell responses.

FIG. 13D. Total anti-spike antibody titers and CD4 responses from mice immunized with mRNA-LNPs using 7.5% DSPS and the ionizable lipid KC2OA with either 1.5 mol % PEG-DMG (14C) or PEG-DSG (18C). The left graph shows day 34 endpoint antibody titers. The right graph shows the corresponding CD4 T cell responses.

FIG. 13E. Total anti-spike antibody titers and CD4 responses from mice immunized with mRNA-LNPs using 7.5% DSPS and the ionizable lipid UO1 with either 1.5 mol % PEG-DMG (14C) or PEG-DSG (18C). The left graph shows day 34 endpoint antibody titers. The right graph shows the corresponding CD4 T cell responses.

FIG. 13F. Effect of phosphatidylserine incorporation in mRNA-LNP immunogenicity. Total anti-spike antibody titers (A) and spike-specific CD4 T cell responses from mice immunized with mRNA-LNPs using various ionizable lipids and PEG-lipids plus/minus 7.5 mol % DSPS Antibody data were were log-transformed and analyzed using two-way ANOVA with a Sidak's multiple comparison test. CD4 T cell data were analyzed using a REML mixed-effects model with a Sidak's multiple comparison test.

FIG. 13G. Effect of phosphatidylserine lipid tail (DPPS vs DSPS) composition on mRNA-LNP priming of B (Panel A) and T cell (Panel B) responses. Antibody data were log-transformed prior to analysis. Data were analyzed using one-way ANOVA with a Tukey's multiple comparison test.

FIG. 14A. Comparison of the mCherry expression of KC2-01 LNPs, 7.5 mol % DSPS (D isomer) and DSPS (L isomer) at 1 μg/mL mRNA for 24 h.

FIG. 14B. Comparison of the mCherry expression of KC2-01 LNPs, 7.5 mol % DSPS (D isomer) and DSPS (L isomer) at 0.33 μg/mL mRNA for 24 h.

FIG. 15. Comparison of the mCherry expression of KC2 LNPs, with 5 and 7.5 mol % DSPS (L-isomer) to LNPs prepared with SM-102 or ALC-0315 at 1 μg/mL mRNA for 24 h. The Y-axis is mean fluorescence intensity (MFI). UT sample corresponds to cells where no LNPs were added.

FIG. 16. Comparison of the mCherry expression of UO1, UO6 and UO7 formulations alone, or with added 7.5 mol % D-isomer of DSPS, at 1 μg/mL mRNA for 24 h. UT sample corresponds to cells where no LNPs were added.

FIG. 17. Comparison of the mCherry expression of UO1, SM102, ALC-0315 formulations alone, or with added DSPS, at 1 μg/mL mRNA for 24 h. Lipo refers to Lipofectamine MessengerMax (ThermoFisher) used according to manufacturer's instructions at the same dosage level as the LNPs. UT sample corresponds to cells where no LNPs were added.

DETAILED DESCRIPTION

It is to be understood that both the foregoing general description and the following detailed description are exemplary and explanatory only and are not restrictive of the compositions and methods of the present disclosure.

Figure 1:
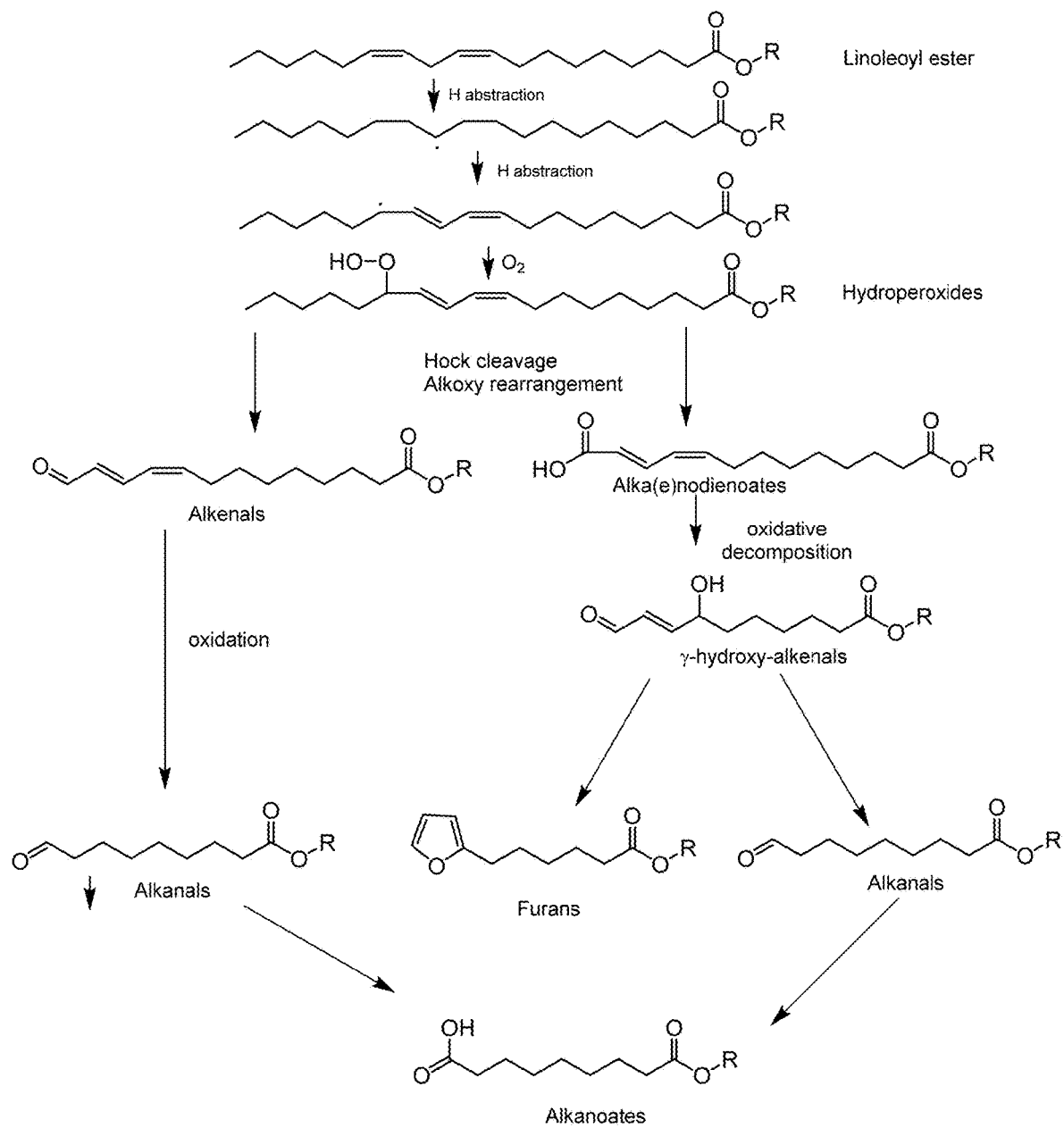
FIG. 1 is a depiction of the oxidative degradation mechanisms of lipid esters of linoleic acid containing conjugated multiple unsaturations that are particularly sensitive to oxidation.

Stabilized Nucleic Acid Lipid Particles (SNALP) are used as a vehicle for the systemic delivery of mRNA or other nucleic acid therapeutics. SNALP compositions include cationic lipids such as MC3 or KC2, comprising a protonatable tertiary amine head group joined to a pair of linear 18 carbon aliphatic chains containing a pair of carbon-carbon double bonds separated by a single methylene group (e.g., linoleic acid). However, while the structure of these hydrocarbon chains, each containing a pair of double bonds separated by a single methylene group, imparts desirable biological properties to the SNALP compositions, this chemical sub-structure also results in the undesired problem of increased sensitivity of the compound to oxidative degradation. For example, FIG. 1 is a depiction of the oxidative degradation mechanisms of lipid esters of linoleic acid containing conjugated multiple unsaturations that are particularly sensitive to oxidation. What is needed are novel cationic lipids suitable for use in a SNALP composition, but having enhanced resistance to oxidative degradation.

Disclosed herein are compounds, compositions and methods related to the treatment of bacterial infections. As used herein, the term "compound", "drug" and "active agent" are used interchangeably. Some aspects of the disclosure relate to novel ionizable lipids or bioreducible ionizable lipids. These lipids are cationic (i.e. positively charged) at acidic pH, such as encountered intracellularly following endocytosis or phagocytosis by a cell. The same lipids, and compositions containing them, are near neutral in charge when present at pH 7.4. These lipids may also have multiple olefins that are separated by at least two methylene groups present in their alkyl or acyl groups.

Some aspects of the disclosure relate to the process for the synthesis of the novel ionizable lipids.

Other aspects relate to compositions comprising lipidic nanoparticles comprising ionizable cationic lipid, the lipidic nanoparticles containing nucleic acids. In some embodiments, nucleic acids are encapsulated into the lipidic nanoparticles.

Other aspects of the disclosure relate to the use of these ionizable lipids or lipidic nanoparticles compositions comprising ionizable lipids in vaccines for the prevention of infectious diseases or cancer. In some embodiments, the infectious disease can be a bacterial or a viral infection. In some embodiments, the compositions described herein can be used to prevent infections related to tuberculosis, HIV/AIDS, malaria, or coronavirus-related infections such as COVID-19. In other embodiments, the infection is influenza, hepatitis B, hepatitis C, Dengue, human papillomavirus (HPV), norovirus, mumps, measles, Meningococcal disease, pneuomococcal disease, polio, rotovirus, respiratory syncytial virus (RSV), rubella, shingles/herpes zoster virus, tetanus, or whooping cough.

In some embodiments, the compounds and compositions described herein may promote efficient uptake and transfection of target cells, including tissue macrophages and dendritic cells. The efficient delivery nucleic acids coding for antigen specific for infectious viruses or bacteria, and subsequent presentation of that antigen to elicit the desired immune response to protect against corresponding infections is a result. In some embodiments, the nucleic acid can be a synthetic nucleic acid (e.g., engineered codon optimized mRNA) encoding an epitope of coronavirus such as SARS-CoV, MERS-CoV or SARS-CoV-2. In some embodiments the nucleic acid can be a synthetic nucleic acid (e.g. engineered codon optimized mRNA) encoding the S-protein (spike protein) or a fragment thereof of coronavirus such as SARS-CoV, MERS-CoV or SARS-CoV-2.

Definitions

For convenience, certain terms employed in the specification, examples, and appended claims are collected here. Unless defined otherwise, all technical and scientific terms used herein have the same meaning as commonly understood by one of ordinary skill in the art to which this disclosure belongs.

As used herein, the following terms and phrases are intended to have the following meanings:

The articles "a" and "an" are used herein to refer to one or to more than one (i.e., to at least one) of the grammatical object of the article. By way of example, "an element" means one element or more than one element.

As used herein the term "comprising" or "comprises" is used in reference to compositions, methods, and respective component(s) thereof, that are present in a given embodiment, yet open to the inclusion of unspecified elements.

As used herein the term "consisting essentially of" refers to those elements required for a given embodiment. The term permits the presence of additional elements that do not materially affect the basic and novel or functional characteristic(s) of that embodiment of the disclosure.

The term "consisting of" refers to compositions, methods, and respective components thereof as described herein, which are exclusive of any element not recited in that description of the embodiment.

The term "comprising" when used in the specification includes "consisting of" and "consisting essentially of".

If it is referred to "as mentioned above" or "mentioned above", "supra" within the description it is referred to any of the disclosures made within the specification in any of the preceding pages.

If it is referred to "as mentioned herein", "described herein", "provided herein," or "as mentioned in the present text," or "stated herein" within the description it is referred to any of the disclosures made within the specification in any of the preceding or subsequent pages.

As used herein, the term "about" means acceptable variations within 20%, within 10% and within 5% of the stated value. In certain embodiments, "about" can mean a variation of +/−1%, 2%, 3%, 4%, 5%, 10% or 20%.

The term "effective amount" as used herein with respect to a compound or the composition means the amount of active compound (also referred herein as active agent or drug) sufficient to cause a bactericidal or bacteriostatic effect. In one embodiment, the effective amount is a "therapeutically effective amount" meaning the amount of active compound that is sufficient alleviate the symptoms of the bacterial infection being treated.

The term "subject" (or, alternatively, "patient") as used herein refers to an animal, preferably a mammal, most preferably a human that receives either prophylactic or therapeutic treatment.

The term "administration" or "administering" as used herein includes all means of introducing the compounds or the pharmaceutical compositions to the subject in need thereof, including but not limited to, oral, intravenous, intramuscular, intraperitoneal, subcutaneous, transdermal, inhalation, buccal, ocular, sublingual, vaginal, rectal and the like. Administration of the compound or the composition is suitably parenteral. For example, the compounds or the composition can be preferentially administered intravenously, but can also be administered intraperitoneally or via inhalation like is currently used in the clinic for liposomal amikacin in the treatment of *Mycobacterium avium* (see Shirley et al., Amikacin Liposome Inhalation Suspension: A Review in *Mycobacterium avium* Complex Lung Disease. Drugs. 2019 April; 79(5):555-562)

The terms "treat," "treating," and "treatment," as used herein, refer to therapeutic or preventative measures such as those described herein.

The term "pharmaceutically acceptable salt" refers to a relatively non-toxic, inorganic or organic acid addition salt of a compound of the present disclosure which salt possesses the desired pharmacological activity.

The term "alkyl" means saturated carbon chains having from one to twenty carbon atoms which may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, and the like. Unless stated otherwise specifically in the specification, an alkyl group is optionally substituted.

The term "phosphatidylserine", with any of it's acyl chain compositions, refers to the L-isomer of serine in the headgroup unless specified in a particular example.

The term "lipid conjugate" refers to a conjugated lipid that inhibits aggregation of lipid particles. Such lipid conjugates include, but are not limited to, polysarcosine (see e.g. WO2021191265A1 which is herein incorporated by reference in its entirety for all purposes), polyamide oligomers (e.g., ATTA-lipid conjugates), PEG-lipid conjugates, such as PEG coupled to dialkyloxypropyls, PEG coupled to diacylglycerols, PEG coupled to cholesterol, PEG coupled to phosphatidylethanolamines, PEG conjugated to ceramides (see, e.g., U.S. Pat. No. 5,885,613, the disclosure of which is herein incorporated by reference in its entirety for all purposes), cationic PEG lipids, and mixtures thereof. PEG can be conjugated directly to the lipid or may be linked to the lipid via a linker moiety. Any linker moiety suitable for coupling the PEG to a lipid can be used including, e.g., non-ester containing linker moieties and ester-containing linker moieties. In preferred embodiments, non-ester containing linker moieties are used.

The abbreviations for the ionizable cationic lipids may be truncated in the Examples from that used in the Tables, For example, AKG-UO-1 or AKG-KC2-01 may be referred to as UO1 or KC2-01.

The abbreviation UT used in various studies refers to untreated samples.

The term "lipidic nanoparticle", or "LNP", refers to particles having a diameter of from about 5 to 500 nm. In some embodiments, the lipid nanoparticle comprises one or more active agents. In some embodiments, the lipid nanoparticle comprises a nucleic acid. In some embodiments, the nucleic acid is condensed in the interior of the nanoparticle with a cationic lipid, polymer, or polyvalent small molecule and an external lipid coat that interacts with the biological milieu. Due to the repulsive forces between phosphate groups, nucleic acids are naturally stiff polymers and prefer elongated configurations. In the cell, to cope with volume constraints DNA can pack itself in the appropriate solution conditions with the help of ions and other molecules. Usually, DNA condensation is defined as the collapse of extended DNA chains into compact, orderly particles containing only one or a few molecules. By binding to phosphate groups, cationic lipidic can condense DNA by neutralizing the phosphate charges and allow close packing.

In some embodiments, the active agent is encapsulated into the LNP. In some embodiments, the active agent can be an anionic compounds, for example, but not limited to DNA, RNA, natural and synthetic oligonucleotides (including antisense oligonucleotides, interfering RNA and small interfering RNA), nucleoprotein, peptide, nucleic acid, ribozyme, DNA-containing nucleoprotein, such as an intact or partially deproteinated viral particles (virions), oligomeric and polymeric anionic compounds other than DNA (for example, acid polysaccharides and glycoproteins)). In some embodiments, the active agent can be intermixed with an adjuvant.

In a LNP vaccine product, the active agent is generally contained in the interior of the LNP. In some embodiments, the active agent comprises a nucleic acid. Typically, water soluble nucleic acids are condensed with cationic lipids or polycationic polymers in the interior of the particle and the surface of the particle is enriched in neutral lipids or PEG-lipid derivatives. Additional ionizable cationic lipid may also be at the surface and respond to acidification in the environment by becoming positively charged, facilitating endosomal escape.

Ionizable lipids can have different properties or functions with respect to LNPs. Due to the pKa of the amino group, the lipid molecules can become positively charged in acidic conditions. Under these conditions, lipid molecules can electrostatically bind to the phosphate groups of the nucleic acid which allows the formation of LNPs and the entrapment of the nucleic acid. In some embodiments, the pKa can be low enough that it renders the LNP substantially neutral in surface charge in biological fluids, such as blood, which are at physiological pH values. High LNP surface charge is associated with toxicity, rapid clearance from the circulation by the fixed and free macrophages, hemolytic toxicities, including immune activation (Filion et al Biochim Biophys Acta. 1997 Oct. 23; 1329(2):345-56).

In some embodiments, pKa can be high enough that the ionizable cationic lipid can adopt a positively charged form at acidic endosomal pH values. This way, the cationic lipids can combine with endogenous endosomal anionic lipids to promote membrane lytic nonbilayer structures such as the hexagonal HII phase, resulting in more efficient intracellular delivery. In some embodiments, the pKa ranges between 6.2-6.5. For example, the pKa can be about 6.2, about 6.3, about 6.4, about 6.5. Unsaturated tails also contribute to the lipids' ability to adopt nonbilayer structures. (Jayaraman et al., Angew Chem Int Ed Engl. 2012 Aug. 20; 51(34):8529-33).

Release of nucleic acids from LNP formulations, among other characteristics such as liposomal clearance and circulation half-life, can be modified by the presence of polyethylene glycol and/or sterols (e.g. cholesterol) or other potential additives in the LNP, as well as the overall chemical structure, including pKa of any ionizable cationic lipid included as part of the formulation.

The term "bioreducible" refers to compounds that undergo accelerated degradation due to the cleavage of disulfide linkages in a reductive environment. Unlike other nucleic acid therapeutics such as siRNA, the success of mRNA-based therapies depends on the availability of a safe and efficient delivery vehicle that encapsulates the mRNA. mRNA is fragile and needs a protective coating for it to remain active until it reaches its target site. mRNA containing LNPs are a promising vaccine option for Covd-19 immunity (Jackson et al., Preliminary Report. N Engl J Med. 2020 Nov. 12; 383(20):1920-1931). The efficiency and tolerability of LNPs has been attributed to the amino lipid and unlike many biomaterial applications that may have a required service lifetime of weeks or months, functional LNP mediated delivery of mRNA occurs within hours obviating the need for persistent lipids. Indeed in applications where chronic dosing is required this will be especially important. It has been demonstrated that LNPs enter cells via endocytosis and accumulate in endolysosomal compartments. The ionizable cationic lipid (ICL) is able to effectively deliver mRNA to the cytosol after endocytosis while being susceptible to enzymatic hydrolysis in late endosomes/lysosomes by lipases or hydrolysis triggered by the reductive environment of the lysosome allowing complete biodegradation. The extracellular space is a relatively oxidative environment, while the intracellular space is a reductive one, allowing a disulfide linked molecule to remain intact in the extracellular space but be rapidly reduced once internalized (Huang et al., Mol Ther. 2005 March; 11(3): 409-17, 2005). Some embodiments, provide bioreducible disulfide linked ICL molecules (see compounds 29-36, Table 2) that are stable in LNP formulation and while in circulation but undergo cleavage in the reductive environment of the lysosome. Such compounds and compositions can facilitate rapid biological destruction of the lipids and can prevent potentially toxic accumulation of ICL lipids (as observed in rats with DLin-MC3-DMA (Sabins et al., Mol Ther. 2018 Jun. 6; 26(6):1509-1519).

The terms "encapsulation" and "entrapped," as used herein, refer to the incorporation or association of the mRNA, DNA, siRNA or other nucleic acid pharmaceutical agent in or with a lipidic nanoparticle. As used herein, the term "encapsulated" refers to complete encapsulation or partial encapsulation. A siRNA may be capable of selectively knocking down or down regulating expression of a gene of interest. For example, an siRNA could be selected to silence a gene associated with a particular disease, disorder, or condition upon administration to a subject in need thereof of a nanoparticle composition including the siRNA. A siRNA may comprise a sequence that is complementary to an mRNA sequence that encodes a gene or protein of interest.

The term "mol %" with regard to cholesterol refers to the molar amount of cholesterol relative to the sum of the molar amounts of cholesterol and non-PEGylated phospholipid expressed in percentage points. For example, "55 mol. % cholesterol" in a liposome containing cholesterol and HSPC refers to the composition of 55 mol. parts of cholesterol per 45 mol. parts of HSPC.

The term "mol %" with regard to PEG-lipid refers to the ratio of the molar amount of PEG-lipid and non-PEGylated phospholipid expressed in percentage points. For example, "5 mol. % PEG-DSPE" in a LNP containing HSPC and PEG-DSPE refers to the composition having 5 mol. parts of PEG-DSPE per 100 mol. parts of HSPC.

As used herein, the term "pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

Various aspects and embodiments are described in further detail in the following subsections.

Compounds

Provided herein are compounds, compositions and methods for the treatment or prevention of infectious diseases, including tuberculosis. According to aspects of the disclosure, the cationic lipids comprise the compounds having Formula I, II, III or IV or pharmaceutically acceptable salts thereof. According to aspects of the disclosure, the ionizable cationic lipids comprise the compounds having one or more chemical sub-structures selected from the group consisting of: Formula IV, Formula IV-A, Formula A, Formula A', Formula A'', Formula A''', and/or Formula B. In some aspects of the disclosure, the ionizable cationic lipids can comprise compounds having Formula I, Formula I-A, Formula I-A', Formula I-A'', Formula II, Formula II-A, Formula II-A', Formula II-B, Formula II-B', Formula III, or Formula III-A or pharmaceutically acceptable salts thereof. In some aspects of the disclosure, the LNP can comprise compounds having Formula V or Formula V-A or pharmaceutically acceptable salts thereof. In some aspects of the disclosure, the LNP can comprise compounds having Formula VI or Formula VI-A or pharmaceutically acceptable salts thereof. In some aspects of the disclosure, the LNP can comprise compounds having Formula VII or pharmaceutically acceptable salts thereof. In some aspects of the disclosure, the LNP can comprise compounds having Formula VIII or pharmaceutically acceptable salts thereof. According to aspects of the disclosure, the cationic lipids comprise the compounds having (a) an ionizable cationic lipid selected from a compound of Formula I, Formula I-A, Formula I-A', Formula I-A", Formula II, Formula II-A, Formula II-A', Formula II-B, Formula II-B', Formula III, or Formula III-A, or a sterol lipid of Formula VI-A, or a branched lipid of Formula VIII and (b) a sterol of Formula VI, and optionally further comprising (c) a alkylene glycol lipid of Formula VII. In some embodiments, the LNP further comprises a phospholipid of Formula V or Formula V-A. In some embodiments, the LNP further comprises an anionic phospholipid targeting moiety from Table 3.

Also provided herein are compounds, compositions and methods for the treatment or prevention of infectious diseases, including tuberculosis. According to aspects of the disclosure, the cationic lipids comprise the compounds having Formula A or pharmaceutically acceptable salts thereof. In some embodiments, the cationic lipids two fatty acyl groups as in Formula II, II, III or IV.

Disclosed herein are compounds of Formula I, Formula II, Formula III, Formula IV or pharmaceutically acceptable salts thereof that are useful in the preparation of vaccines. Also disclosed herein are compositions comprising the cationic lipids of Formula I, Formula II, Formula III, Formula IV or pharmaceutically acceptable salts thereof. In some embodiments, the vaccine is used for the prevention *Mycobacterium* infections. In some embodiments, the vaccine can be used for the prevention of tuberculosis, nontuberculous mycobacteria (NTM), nontuberculosis lung disease, leprosy, *Mycobacterium avium-intracellulare*, *Mycobacterium kansasii*, *Mycobacterium marinum*, *Mycobacterium ulcerans*, *Mycobacterium chelonae*, *Mycobacterium fortuitum*, *Mycobacterium abscessus* and other infectious diseases such as coronaviruses (COVID-19, SARS CoV2, SARS-CoV, MERS-CoV), diphtheria, ebola, flu (Influenza), hepatitis, Hib disease, HIV/AIDS, HPV (Human Papillomavirus), malaria, measles, meningococcal disease, mumps, norovirus, plague, pneumococcal disease, polio, respiratory syncytial virus (RSV), rotavirus, rubella (German Measles), shingles (Herpes Zoster), tetanus (Lockjaw), whooping cough (Pertussis) and zika.

Provided herein are compounds, compositions and methods for the treatment or prevention of infectious diseases, including tuberculosis. According to aspects of the disclosure, the cationic lipids comprise the compounds having Formula I, II, III or IV or pharmaceutically acceptable salts thereof. In some embodiments, the cationic lipids two fatty acyl groups as in Formula II, II, III or IV.

One aspect of the disclosure provides a lipid comprising one or more polyunsaturated polyene hydrocarbon chains of Formula A:

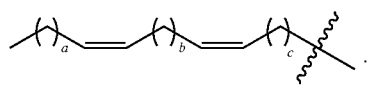

Formula A wherein a is 1, 2, 3 or 4; b is 2, 3 or 4; and c is 3, 4, 5, 6, or 7. In some aspects, an ionizable lipid can comprise two polyunsaturated polyene hydrocarbon chains where b is 4. In some aspects, an ionizable lipid can comprise two polyunsaturated polyene hydrocarbon chains of Formula A, where the sum of a, b and c is 10, 11, 12 or 13. In some aspects, an ionizable lipid can comprise two polyunsaturated polyene hydrocarbon chains of Formula A, where a is 4; b is 4; and c is 4 or 5. In some aspects, an ionizable lipid can comprise two polyunsaturated polyene hydrocarbon chains of Formula A, where a is 1, 2 or 3; b is 4; and c is 3, 4, 5, 6, or 7. In some aspects, an ionizable lipid can comprise two polyunsaturated polyene hydrocarbon chains of Formula A, where a is 5 or 6; b is 2, 3 or 4; and c is 3, 4, 5, 6, or 7. In some aspects, an ionizable lipid can comprise two polyunsaturated polyene hydrocarbon chains of Formula A, where the sum of a, b and c is 10, 11, 12 or 13. In some aspects, an ionizable lipid can comprise two polyunsaturated polyene hydrocarbon chains of Formula A, where the sum of a, b and c is 12. In some aspects, an ionizable lipid can comprise two polyunsaturated polyene hydrocarbon chains of Formula A, where b is 2 and the sum of a, b and c is 12. In some aspects, an ionizable lipid can comprise two polyunsaturated polyene hydrocarbon chains of Formula A, where b is 3 and the sum of a, b and c is 12. In some aspects, an ionizable lipid can comprise two polyunsaturated polyene hydrocarbon chains of Formula A, where b is 4 and the sum of a, b and c is 12. In some aspects, an ionizable lipid can comprise two polyunsaturated polyene hydrocarbon chains of Formula A.

One aspect of the disclosure provides a lipid comprising one or more polyunsaturated polyene hydrocarbon chains of Formula A:

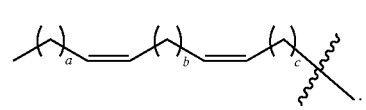

Formula A' wherein a is 1, 2 or 3; b is 2, 3 or 4; and c is 3, 4, 5, 6, or 7. In some aspects, an ionizable lipid can comprise two polyunsaturated polyene hydrocarbon chains where b is 4. In some aspects, an ionizable lipid can comprise two polyunsaturated polyene hydrocarbon chains of Formula A', where the sum of a, b and c is 10, 11, 12 or 13.

One aspect of the disclosure provides a lipid comprising one or more polyunsaturated polyene hydrocarbon chains of Formula A":

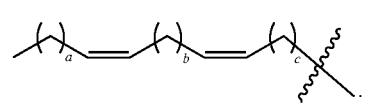

Formula A"

wherein a is 4; b is 4; and c is 4 or 5. In some aspects, an ionizable lipid can comprise two polyunsaturated polyene hydrocarbon chains of Formula A" where the sub of a, b and c is 12.

One aspect of the disclosure provides a lipid comprising one or more polyunsaturated polyene hydrocarbon chains of Formula A''':

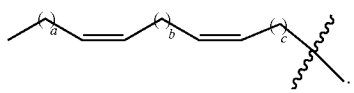

Formula A''' wherein a is 5 or 6; b is 2, 3 or 4; and c is 3, 4, 5, 6, or 7. In some aspects, an ionizable lipid can comprise two polyunsaturated polyene hydrocarbon chains of Formula A''', where the sum of a, b and c is 10, 11, 12 or 13. In some aspects, an ionizable lipid can comprise two polyunsaturated polyene hydrocarbon chains of Formula A''', where the sum of a, b and c is 12. In some aspects, an ionizable lipid can comprise two polyunsaturated polyene hydrocarbon chains of Formula A''', where b is 2 and the sum of a, b and c is 12. In some aspects, an ionizable lipid can comprise two polyunsaturated polyene hydrocarbon chains of Formula A''', where b is 3 and the sum of a, b and c is 12. In some aspects, an ionizable lipid can comprise two polyunsaturated polyene hydrocarbon chains of Formula A''', where b is 4 and the sum of a, b and c is 12. In some aspects, an ionizable lipid can comprise two polyunsaturated polyene hydrocarbon chains of Formula A'''.

One aspect of the disclosure provides a lipid comprising one or more polyunsaturated polyene hydrocarbon chains of Formula B:

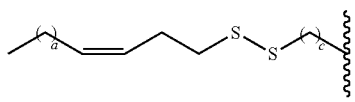

Formula B wherein a is 5, 6 or 7; and c is 3, 4, or 5. In some aspects, an ionizable lipid can comprise two polyunsaturated polyene hydrocarbon chains where b is 4. In some aspects, an ionizable lipid can comprise two polyunsaturated polyene hydrocarbon chains of Formula B, where the sum of a and c is 9, 10 or 11.

In some embodiments, an ionizable lipid comprises the chemical structure of Formula (IV-A):

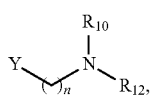

(IV-A)

or a pharmaceutically acceptable salt thereof, wherein Y is

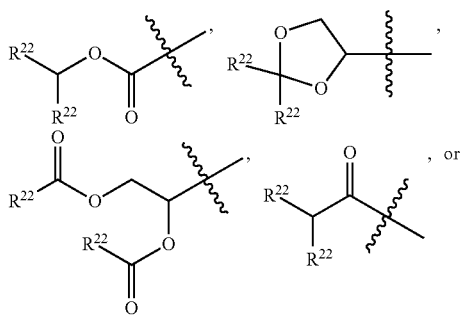

, or

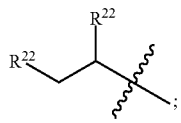

;

n is an integer 2, 3 or 4;

$R^{22}$ is a polyene hydrocarbon chain of Formula A, Formula A', Formula A'', or Formula A''' or Formula B; and each of $R_{10}$ and $R_{12}$ is independently $(C_1-C_4)$alkyl optionally substituted with hydroxyl.

In some aspects, $R^{22}$ in Formula (IV-A) is a polyene hydrorcarbon chain of Formula A. In some aspects, $R^{22}$ in Formula (IV-A) is a polyene hydrocarbon chain of Formula A'. In some aspects, $R^{22}$ in Formula (IV-A) is a polyene hydrocarbon chain of Formula A''. In some aspects, $R^{22}$ in Formula (IV-A) is a polyene hydrocarbon chain of Formula A'''. In some aspects, $R^{22}$ in Formula (IV-A) is a polyene hydrocarbon chain of Formula B.

In some aspects, $R_{10}$ and $R_{12}$ are each independently selected from methyl, ethyl, propyl, —$(CH_2)(CH_2)OH$, and —$(CH_2)_2(CH_2)OH$ in Formula (IV-A). In some aspects, $R_{10}$ and $R_{12}$ are each independently methyl in Formula (IV-A). In some aspects, $R_{10}$ and $R_{12}$ are each independently ethyl in Formula (IV-A). In some aspects, at least one of $R_{10}$ and $R_{12}$ is n-propyl optionally substituted with hydroxyl in Formula (IV-A). In some aspects, $R_{10}$ is methyl and $R_{12}$ is selected from methyl, ethyl, —$(CH_2)(CH_2)OH$, and —$(CH_2)_2(CH_2)OH$ in Formula (IV-A). In some aspects, $R_{10}$ is methyl and $R_{12}$ is selected from —$(CH_2)(CH_2)OH$, and —$(CH_2)_2(CH_2)OH$ in Formula (IV-A). In some aspects, $R_{10}$ is methyl and $R_{12}$ is selected from —$(CH_2)(CH_2)OH$, and —$(CH_2)_2(CH_2)OH$ in a compound comprising the chemical structure of Formula (IV-A). In some aspects, $R_{10}$ and $R_{12}$ are independently selected from methyl or ethyl, optionally substituted with one or more hydroxyl in Formula (IV-A). In some aspects, one or both of $R_{10}$ and $R_{12}$ in Formula (IV-A) are —$(CH_2)(CH_2)OH$, or —$(CH_2)_2(CH_2)OH$ in Formula (IV-A). In some aspects, $R_{10}$ is methyl and $R_{12}$ is methyl or ethyl substituted with hydroxyl in Formula (IV-A). In some aspects, one or both of $R_{10}$ in Formula (IV-A) is methyl and $R_{12}$ is —$(CH_2)(CH_2)OH$ in Formula (IV-A). In some aspects, one or both of $R_{10}$ in Formula (IV-A) is methyl and $R_{12}$ is —$(CH_2)_2(CH_2)OH$ in Formula (IV-A).

In some embodiments, an ionizable lipid comprises one or more polyunsaturated polyene hydrocarbon chains covalently bound to the Y portion of Formula (IV-A) wherein Y is

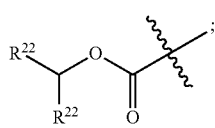

;

n is an integer 2, 3 or 4; $R^{22}$ is a polyene hydrocarbon chain of Formula A, Formula A', Formula A'', Formula A''' or Formula B; and each of $R_{10}$ and $R_{12}$ is independently $(C_1-C_4)$alkyl optionally substituted with hydroxyl. In some embodiments, an ionizable lipid comprises one or more polyunsaturated polyene hydrocarbon chains covalently bound to the Y portion of Formula (IV-A) wherein Y is

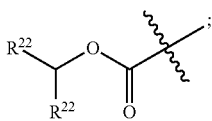

n is an integer 2, 3 or 4; $R^{22}$ is a polyene hydrocarbon chain of Formula A, Formula A', Formula A", or Formula A'''; and each of $R_{10}$ and $R_{12}$ is independently $(C_1\text{-}C_4)$alkyl optionally substituted with hydroxyl. In some embodiments, an ionizable lipid comprises one or more polyunsaturated polyene hydrocarbon chains covalently bound to the Y portion of Formula (IV-A) wherein Y is

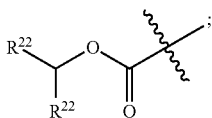

n is an integer 2, 3 or 4; $R^{22}$ is a polyene hydrocarcarbon chain of Formula B; and each of $R_{10}$ and $R_{12}$ is independently $(C_1\text{-}C_4)$alkyl optionally substituted with hydroxyl.

In some embodiments, an ionizable lipid comprises one or more polyunsaturated polyene hydrocarbon chains covalently bound to the Y portion of Formula (IV-A) wherein Y is,

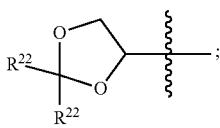

n is an integer 2, 3 or 4; $R^{22}$ is a polyene hydrocarbon chain of Formula A, Formula A', Formula A", Formula A''' or Formula B; and each of $R_{10}$ and $R_{12}$ is independently $(C_1\text{-}C_4)$alkyl optionally substituted with hydroxyl. In some embodiments, an ionizable lipid comprises one or more polyunsaturated polyene hydrocarbon chains covalently bound to the Y portion of Formula (IV-A) wherein Y is,

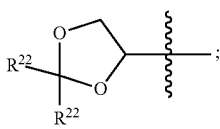

n is an integer 2, 3 or 4; $R^{22}$ is a polyene hydrocarbon chain of Formula A, Formula A', Formula A", or Formula A'''; and each of $R_{10}$ and $R_{12}$ is independently $(C_1\text{-}C_4)$alkyl optionally substituted with hydroxyl. In some embodiments, an ionizable lipid comprises one or more polyunsaturated polyene hydrocarbon chains covalently bound to the Y portion of Formula (IV-A) wherein Y is,

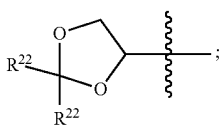

n is an integer 2, 3 or 4; $R^{22}$ is a polyene hydrocarbon chain of Formula B; and each of $R_{10}$ and $R_{12}$ is independently $(C_1\text{-}C_4)$alkyl optionally substituted with hydroxyl.

In some embodiments, an ionizable lipid comprises one or more polyunsaturated polyene hydrocarbon chains covalently bound to the Y portion of Formula (IV-A) wherein Y is

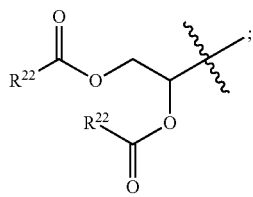

n is an integer 2, 3 or 4; $R^{22}$ is a polyene hydrocarbon chain of Formula A, Formula A', Formula A", Formula A''' or Formula B; and each of $R_{10}$ and $R_{12}$ is independently $(C_1\text{-}C_4)$alkyl optionally substituted with hydroxyl. In some embodiments, an ionizable lipid comprises one or more polyunsaturated polyene hydrocarbon chains of Formula (IV-A): or a pharmaceutically acceptable salt thereof, wherein Y is

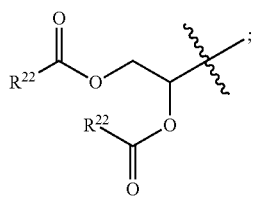

n is an integer 2, 3 or 4; $R^{22}$ is a polyene hydrocarbon chain of Formula A, Formula A', Formula A", or Formula A'''; and each of $R_{10}$ and $R_{12}$ is independently $(C_1\text{-}C_4)$alkyl optionally substituted with hydroxyl.

In some embodiments, an ionizable lipid comprises one or more polyunsaturated polyene hydrocarbon chains covalently bound to the Y portion of Formula (IV-A) wherein Y is

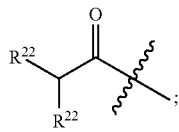

n is an integer 2, 3 or 4; $R^{22}$ is a polyene hydrocarbon chain of Formula A, Formula A', Formula A", Formula A''' or Formula B; and each of $R_{10}$ and $R_{12}$ is independently $(C_1\text{-}C_4)$alkyl optionally substituted with hydroxyl.

In some embodiments, an ionizable lipid comprises one or more polyunsaturated polyene hydrocarbon chains covalently bound to the Y portion of Formula (IV-A) wherein Y is

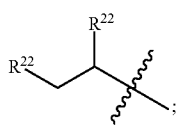

n is an integer 2, 3 or 4; $R^{22}$ is a polyene hydrocarbon chain of Formula A, Formula A', Formula A'', Formula A''' or Formula B; and each of $R_{10}$ and $R_{12}$ is independently $(C_1$-$C_4)$alkyl optionally substituted with hydroxyl.

In some embodiments, an ionizable lipid comprises one or more polyunsaturated polyene hydrocarbon chains covalently bound to the Y portion of Formula (IV):

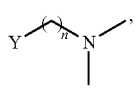

(IV)

or a pharmaceutically acceptable salt thereof, wherein Y is

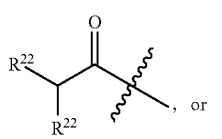

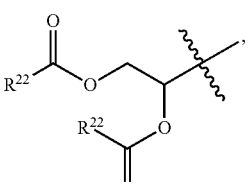

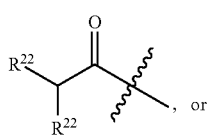

n is an integer 2, 3 or 4; and $R^{22}$ is a polyene hydrocarbon chain of Formula A, Formula A', Formula A'', Formula A''' or Formula B. In some embodiments, an ionizable lipid comprises one or more polyunsaturated polyene hydrocarbon chains covalently bound to the Y portion of Formula (IV):

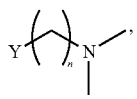

(IV)

or a pharmaceutically acceptable salt thereof, wherein Y is

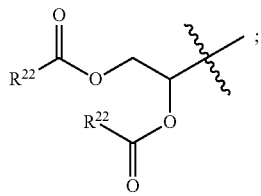

n is an integer 2, 3 or 4; and $R^{22}$ is a polyene hydrocarbon chain of Formula A. In some embodiments, an ionizable lipid comprises one or more polyunsaturated polyene hydrocarbon chains covalently bound to the Y portion of Formula (IV):

(IV)

or a pharmaceutically acceptable salt thereof, wherein Y is

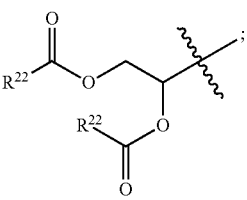

n is an integer 2; and $R^{22}$ is a polyene hydrocarbon chain of Formula A'.

One aspect of the disclosure provides a compound of Formula I or pharmaceutically acceptable salts thereof:

Formula I

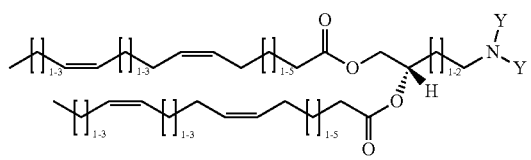

wherein Y is independently a methyl or ethyl group, wherein the two fatty acyl groups have between 16-18 carbons and contain two unconjugated olefins.

Another aspect of the disclosure provides a composition comprising ionizable lipids, the lipidic nanoparticles comprising an ionizable lipid of Formula I or pharmaceutically acceptable salts thereof Formula I

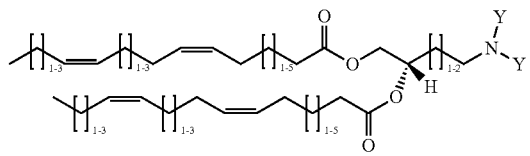

wherein Y is independently a methyl or ethyl group, wherein the two fatty acyl groups have a total of between 16-18 carbons and contain two olefins separated by two to four methylene groups.

In some embodiments, the two fatty acyl groups have 16 carbons. In some embodiments, the two fatty acyl groups have 17 carbons. In some embodiments, the two fatty acyl groups have 18 carbons.

In some embodiments, an ionizable lipid of Formula I-A is provided, or pharmaceutically acceptable salts thereof:

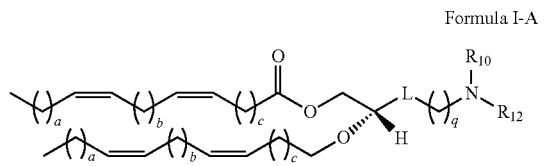

Formula I-A wherein a is 1, 2, 3, 4, 5 or 6; b is 2, 3 or 4; c is 3, 4, 5, 6, or 7; the sum of a, b and c is 10 or 12; L is

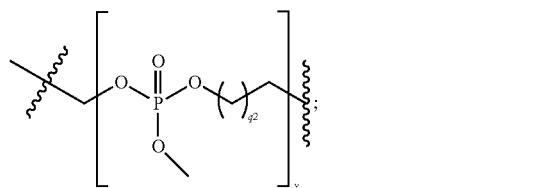

each of $R_{10}$ and $R_{12}$ is independently $(C_1-C_4)$alkyl optionally substituted with hydroxyl; v is 0 or 1; q is 1, 2, 3 or 4; and q2 is 1 or 2. In some aspects, v is 0, q is 1, 2 or 3 and the sum of a, b and c is 12 in an ionizable lipid of Formula I-A. In some aspects, v is 1, q is 3 or 4 and the sum of a, b and c is 12 in an ionizable lipid of Formula I-A. In some aspects, $R_{10}$ and $R_{12}$ are independently selected from methyl, ethyl, and propyl each optionally substituted with a single hydroxyl in an ionizable lipid of Formula I-A'. In some aspects, the sum of a, b and c is 12, and $R_{10}$ and $R_{12}$ are independently selected from methyl, ethyl, —($CH_2$)($CH_2$)OH, and —($CH_2$)$_2$($CH_2$)OH.

In some embodiments, an ionizable lipid of Formula I-A' is provided, or pharmaceutically acceptable salts thereof:

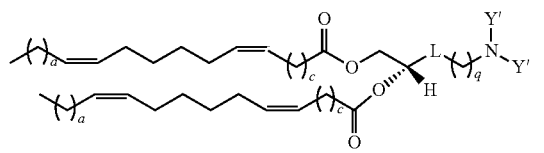

wherein a is 1, 2, or 3; c is 3, 4, 5, 6, or 7; L is

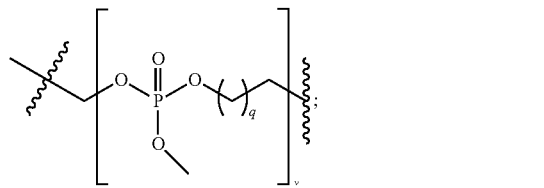

Y' is methyl or ethyl; v is 0 or 1; q is 2, 3 or 4; and q2 is 1 or 2. In some aspects, v is 0, q is 1, 2 or 3; and the sum of a and c is 6 or 8 in an ionizable lipid of Formula I-A'. In some aspects, v is 1, q is 3 or 4; and the sum of a and c is 6 or 8 in an ionizable lipid of Formula I-A'.

In some embodiments, an ionizable lipid of Formula I-A" is provided, or pharmaceutically acceptable salts thereof:

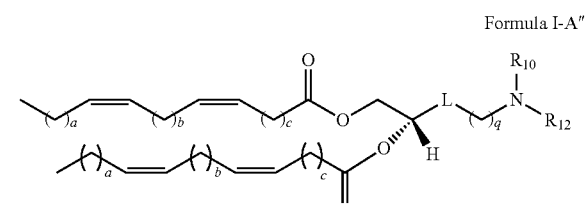

Formula I-A"

wherein a is 4, 5 or 6; b is 2, 3 or 4; c is 3, 4, 5, 6, or 7; L is

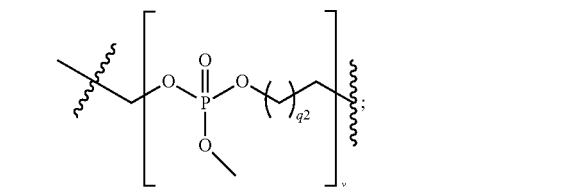

each of $R_{10}$ and $R_{12}$ is independently $(C_1-C_4)$alkyl optionally substituted with hydroxyl; v is 0 or 1; q is 1, 2, 3 or 4; and q2 is 1 or 2. In some aspects, v is 0, q is 1, 2 or 3 and the sum of a, b and c is 12 in an ionizable lipid of Formula I-A". In some aspects, v is 1, q is 3 or 4 and the sum of a, b and c is 12 in an ionizable lipid of Formula I-A". In some aspects, $R_{10}$ and $R_{12}$ are independently selected from methyl, ethyl, and propyl each optionally substituted with a single hydroxyl in an ionizable lipid of Formula I-A". In some aspects, the sum of a, b and c is 12, and $R_{10}$ and $R_{12}$ are independently selected from methyl, ethyl, —($CH_2$)($CH_2$)OH, and —($CH_2$)$_2$($CH_2$)OH.

Another aspect of the disclosure provides for a compound of Formula II or pharmaceutically acceptable salts thereof:

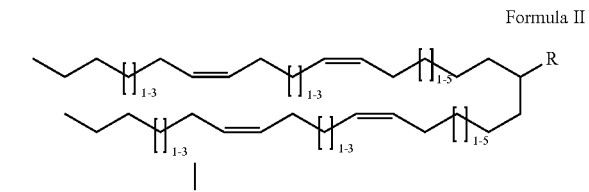

Formula II

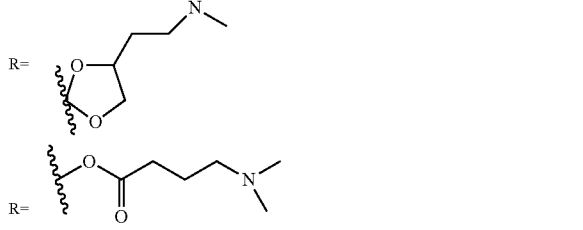

wherein R is a substituent comprising a dialkylamino group of one of the structures shown above, wherein the two fatty acyl groups are between 16-18 carbons and contain two olefins that are separated by at least two methylene groups.

In some embodiments, the two fatty acyl groups have 16 carbons. In some embodiments, the two fatty acyl groups have 17 carbons. In some embodiments, the two fatty acyl groups have 18 carbons.

Another aspect of the disclosure provides for a compound of Formula II-A or pharmaceutically acceptable salts thereof:

Formula (II-A)

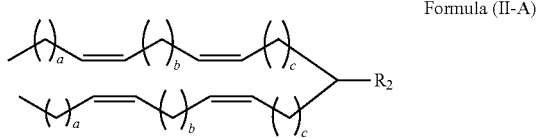

wherein a is 1, 2, 3, 4, 5 or 6; b is 2, 3 or 4; c is 4, 5, 6, 7 or 8; $R_2$ is

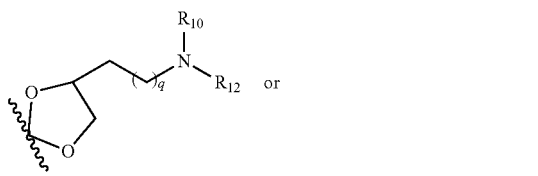

or

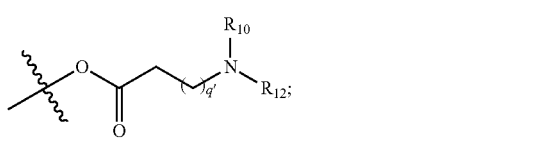

q and q' are each independently 1 or 2; and $R_{10}$ and $R_{12}$ are each methyl or ethyl. In some aspects, the sum of a, b and c is 11 or 13 in an ionizable lipid of Formula I-A. In some aspects, an ionizable lipid of Formula I-A is characterized by one or more of the following: a is 1, 2 or 3; q is 2; q' is 1; and at least one of $R_{10}$ or $R_{12}$ is ethyl. In some aspects, b is 4 in an ionizable lipid of Formula II-A. In some aspects, a is 4, b is 4 and c is 4 in an ionizable lipid of Formula II-A. In some aspects, a is 1, b is 4 and c is 8 in an ionizable lipid of Formula II-A. In some aspects, a is 2, b is 4 and c is 5 in an ionizable lipid of Formula II-A.

Another aspect of the disclosure provides for a compound of Formula II-A' or pharmaceutically acceptable salts thereof:

Formula (II-A')

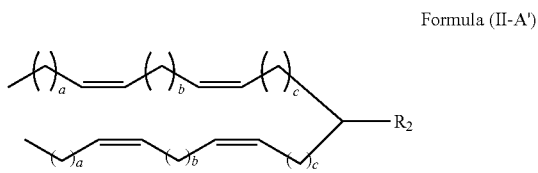

wherein a is 1, 2, or 3; b is 2, 3 or 4; c is 4, 5, 6, 7 or 8; $R_2$ is

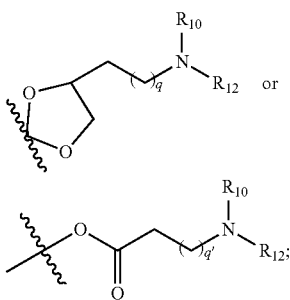

or

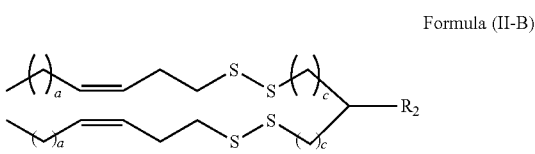

q and q' are each independently 1 or 2; and $R_{10}$ and $R_{12}$ are each methyl or ethyl. In some aspects, the sum of a, b and c is 11 or 13 in an ionizable lipid of Formula I-A'. In some aspects, an ionizable lipid of Formula I-A is characterized by one or more of the following: q is 2; q' is 1; and at least one of $R_{10}$ or $R_{12}$ is ethyl. In some aspects, b is 4 in an ionizable lipid of Formula II-A'. In some aspects, a is 4, b is 4 and c is 4 in an ionizable lipid of Formula II-A'. In some aspects, a is 1, b is 4 and c is 8 in an ionizable lipid of Formula II-A'. In some aspects, a is 2, b is 4 and c is 5 in an ionizable lipid of Formula II-A'.

Another aspect of the disclosure provides for a compound of Formula II-B or pharmaceutically acceptable salts thereof:

Formula (II-B)

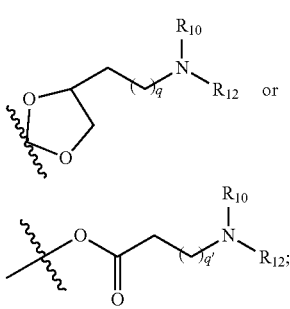

wherein a is 5, 6 or 7; and c is 3, 4, or 5; $R_2$ is

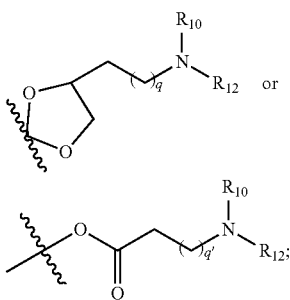

or

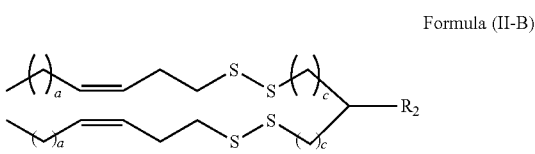

q and q' are each independently 1 or 2; and $R_{10}$ and $R_{12}$ are each methyl or ethyl. In some aspects, the sum of a and c is 9 or 11 in an ionizable lipid of Formula I-B. In some aspects, an ionizable lipid of Formula I-B is characterized by one or more of the following: q is 2; q' is 1; and at least one of $R_{10}$ or $R_{12}$ is ethyl. In some aspects, an ionizable lipid of Formula I-B is characterized by one or more of the following: q is 1; q' is 2; and $R_{10}$ and $R_{12}$ are each methyl. In some aspects, c is 4 in an ionizable lipid of Formula II-B. In some aspects, a is 5 or 7 and c is 4 in an ionizable lipid of Formula II-B. In some aspects, a is 5 and c is 4 in an ionizable lipid of Formula II-B. In some aspects, a is 7 and c is 4 in an ionizable lipid of Formula II-B.

Another aspect of the disclosure provides for a compound of Formula II-B' or pharmaceutically acceptable salts thereof:

Formula (II-B')

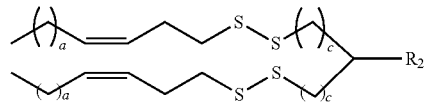

wherein a is 5, or 7; and c is 3 or 4; $R_2$ is

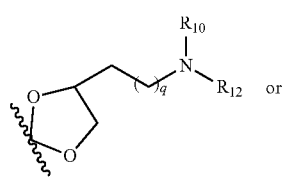

or

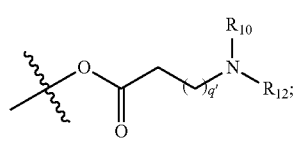

q and q' are each independently 1 or 2; and $R_{10}$ and $R_{12}$ are each methyl. In some aspects, the sum of a and c is 9 or 11 in an ionizable lipid of Formula I-B'. In some aspects, c is 4 in an ionizable lipid of Formula II-B'. In some aspects, a is 5 or 7 and c is 4 in an ionizable lipid of Formula II-B'. In some aspects, a is 5 and c is 4 in an ionizable lipid of Formula II-B. In some aspects, a is 7 and c is 4 in an ionizable lipid of Formula II-B'. In some aspects, a is 5 and c is 3 in an ionizable lipid of Formula II-B. In some aspects, a is 7 and c is 3 in an ionizable lipid of Formula II-B'.

Another aspect of the disclosure provides for a compound of Formula III or pharmaceutically acceptable salts thereof:

Formula III

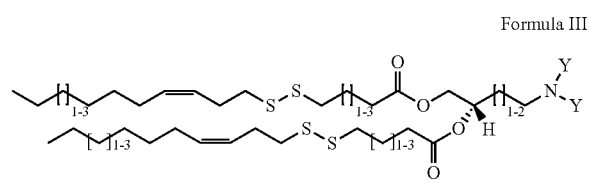

wherein Y is a methyl or ethyl group,
wherein the two fatty acyl groups are disulfide fatty acyl groups having between 16-18 carbons and containing a single olefin.

In some embodiments, the two fatty acyl groups have 16 carbons. In some embodiments, the two fatty acyl groups have 17 carbons. In some embodiments, the two fatty acyl groups have 18 carbons.

Another aspect of the disclosure provides for a compound of Formula III-A or pharmaceutically acceptable salts thereof:

Formula III-A

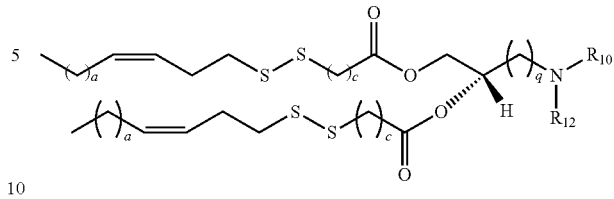

wherein a is 5, 6 or 7; c is 3, 4, or 5; q is 2 or 3 and $R_{10}$ and $R_{12}$ are methyl or ethyl. In some aspects, an ionizable lipid can comprise a compound of Formula III-A wherein a is 5 or 7. In some aspects, an ionizable lipid can comprise two polyunsaturated polyene hydrocarbon chains of Formula A, where the sum of a and c is 8, 9 or 10.

Another aspect of the disclosure provides for a compound of Formula III-A' or pharmaceutically acceptable salts thereof:

Formula III-A'

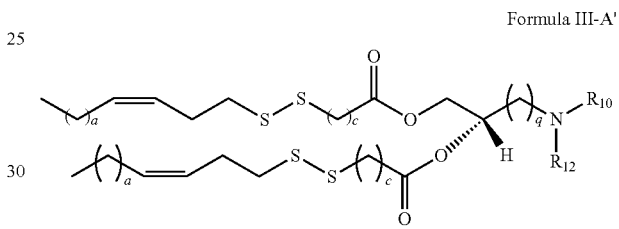

wherein a is 5 or 7; c is 3, 4, or 5; q is 2 or 3 and $R_{10}$ and $R_{12}$ are methyl or ethyl. In some aspects, an ionizable lipid can comprise two polyunsaturated polyene hydrocarbon chains where c is 3. In some aspects, an ionizable lipid can comprise two polyunsaturated polyene hydrocarbon chains of Formula where the sum of a and c is 8 or 10. In some aspects, an ionizable lipid can comprise two polyunsaturated polyene hydrocarbon chains of Formula where q is 2, and the sum of a and c is 8 or 10. In some aspects, an ionizable lipid can comprise two polyunsaturated polyene hydrocarbon chains of Formula where q is 2, $R_{10}$ and $R_{12}$ are each methyl and the sum of a and c is 8 or 10. In some aspects, an ionizable lipid can comprise two polyunsaturated polyene hydrocarbon chains of Formula where q is 2, $R_{10}$ and $R_{12}$ are each methyl and c is 3.

In some embodiments, the compound in Formula I-III has a pKa between 6 and 7. In some embodiments, a lipidic nanoparticle composition comprises lipids and nucleic acids, the lipidic nanoparticles comprising a compound of Formula I, II, III, combinations thereof or pharmaceutically acceptable salts thereof.

In some embodiments, an LNP comprises an ionizable lipid having a structure of Formula (IV):

(IV)

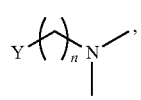

or a pharmaceutically acceptable salt thereof, wherein Y is

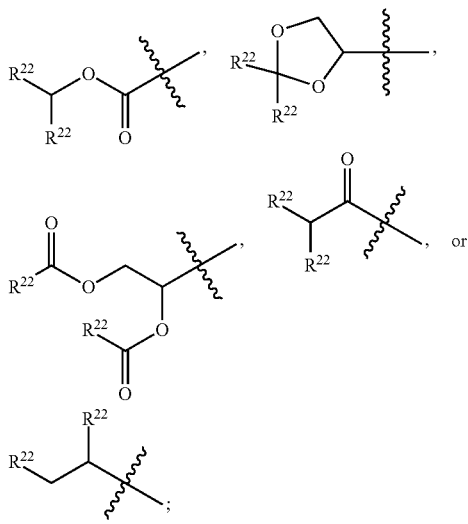

each $R^{22}$ is independently alkyl, alkenyl, alkynyl, or heteroalkyl, each of which is optionally substituted with $R^B$; each $R^B$ is independently alkyl, halo, hydroxy, amino, cycloalkyl, or heterocyclyl; n is an integer between 1 and 10 (inclusive); and 〜 denotes the attachment point.

In some embodiments, Y is

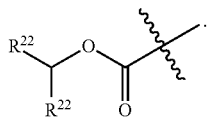

In some embodiments, the compound in Formula IV has a pKa between 6 and 7.

In some embodiments, an ionizable lipid comprises one or more polyunsaturated polyene hydrocarbon chains of Formula (IV-A):

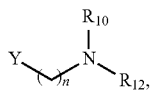

or a pharmaceutically acceptable salt thereof, wherein Y is

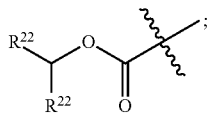

n is an integer 2, 3 or 4; $R^{22}$ is a polyene hydrocarbon chain of Formula A, Formula A', Formula A", or Formula A'''; and each of $R_{10}$ and $R_{12}$ is independently $(C_1\text{-}C_4)$alkyl optionally substituted with hydroxyl. In some aspects, $R_{10}$ and $R_{12}$ in Formula (IV-A) are independently selected from methyl, ethyl, —$(CH_2)(CH_2)OH$, and —$(CH_2)_2(CH_2)OH$.

In some embodiments, an ionizable lipid comprises one or more polyunsaturated polyene hydrocarbon chains of Formula (IV-A):

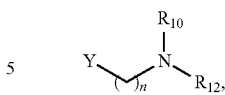
(IV-A)

or a pharmaceutically acceptable salt thereof, wherein Y is,

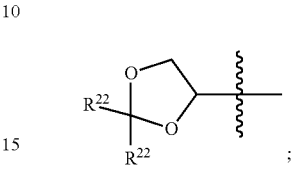

n is an integer 2, 3 or 4; $R^{22}$ is a polyene hydrocarbon chain of Formula A, Formula A', Formula A", or Formula A''', or Formula B; and each of $R_{10}$ and $R_{12}$ is independently $(C_1\text{-}C_4)$alkyl optionally substituted with hydroxyl. In some aspects, $R_{10}$ and $R_{12}$ in Formula (IV-A) are independently selected from methyl, ethyl, —$(CH_2)(CH_2)OH$, and —$(CH_2)_2(CH_2)OH$.

In some embodiments, an ionizable lipid comprises one or more polyunsaturated polyene hydrocarbon chains of Formula (IV-A):

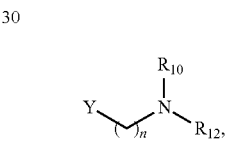
(IV-A)

or a pharmaceutically acceptable salt thereof, wherein Y is

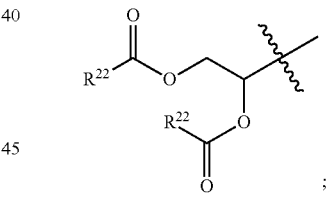

n is an integer 2, 3 or 4; $R^{22}$ is a polyene hydrocarbon chain of Formula A, Formula A', Formula A", or Formula A''', or Formula B; and each of $R_{10}$ and $R_{12}$ is independently $(C_1\text{-}C_4)$alkyl optionally substituted with hydroxyl. In some aspects, $R_{10}$ and $R_{12}$ in Formula (IV-A) are independently selected from methyl, ethyl, —$(CH_2)(CH_2)OH$, and —$(CH_2)_2(CH_2)OH$.

In some embodiments, an ionizable lipid comprises one or more polyunsaturated polyene hydrocarbon chains of Formula (IV-A):

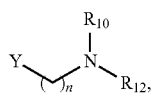
(IV-A)

or a pharmaceutically acceptable salt thereof, wherein Y is

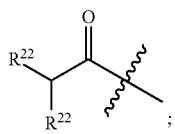
;

n is an integer 2, 3 or 4; $R^{22}$ is a polyene hydrocarcarbon chain of Formula A, Formula A', Formula A'', or Formula A''', or Formula B; and each of $R_{10}$ and $R_{12}$ is independently $(C_1\text{-}C_4)$alkyl optionally substituted with hydroxyl. In some aspects, $R_{10}$ and $R_{12}$ in Formula (IV-A) are independently selected from methyl, ethyl, —$(CH_2)(CH_2)OH$, and —$(CH_2)_2(CH_2)OH$.

In some embodiments, an ionizable lipid comprises one or more polyunsaturated polyene hydrocarbon chains of Formula (IV-A):

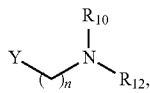
(IV-A)

or a pharmaceutically acceptable salt thereof, wherein Y is

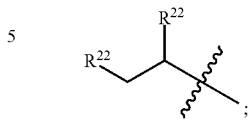
;

n is an integer 2, 3 or 4; $R^{22}$ is a polyene hydrocarcarbon chain of Formula A, Formula A', Formula A'', or Formula A''', or Formula B; and each of $R_{10}$ and $R_{12}$ is independently $(C_1\text{-}C_4)$alkyl optionally substituted with hydroxyl. In some aspects, $R_{10}$ and Ria in Formula (IV-A) are independently selected from methyl, ethyl, —$(CH_2)(CH_2)OH$, and —$(CH_2)_2(CH_2)OH$.

In some embodiments, the compounds have the structure of the compounds listed in Table 1 or Table 2.

Table 1A shows examples of cationic lipids. Table 2 shows examples of bioreducible cationic lipids.

TABLE 1A

Exemplary cationic lipids

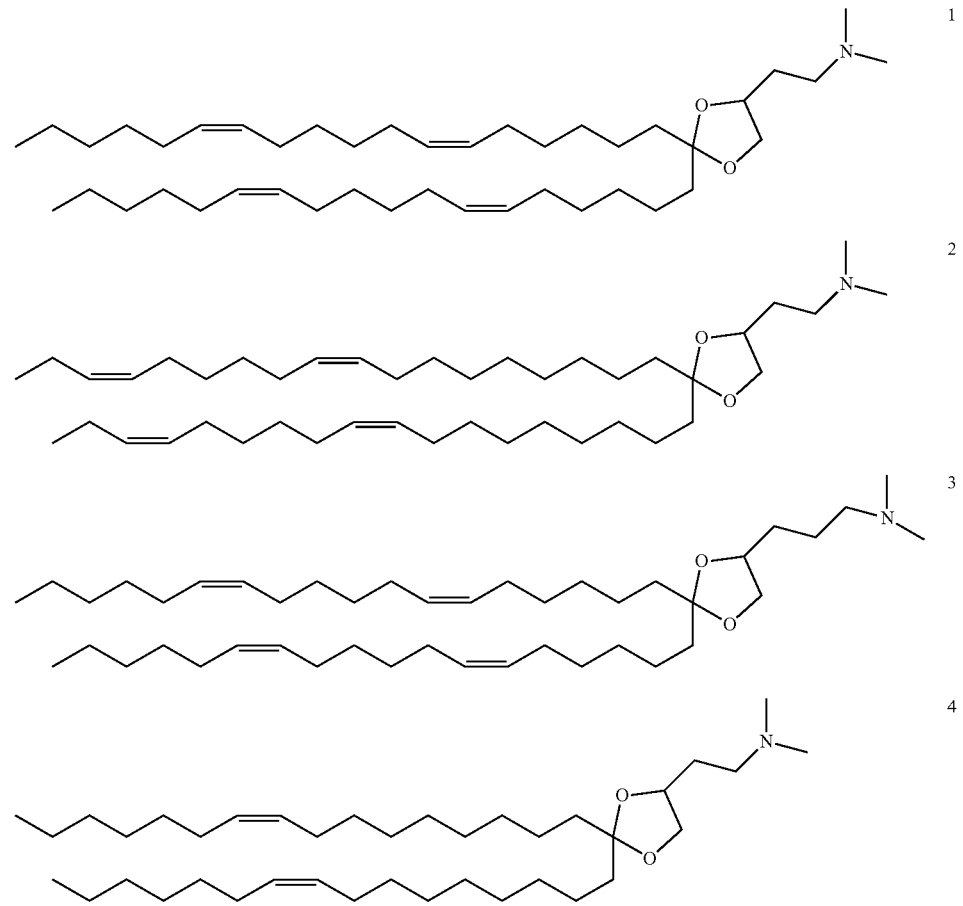

TABLE 1A-continued
Exemplary cationic lipids
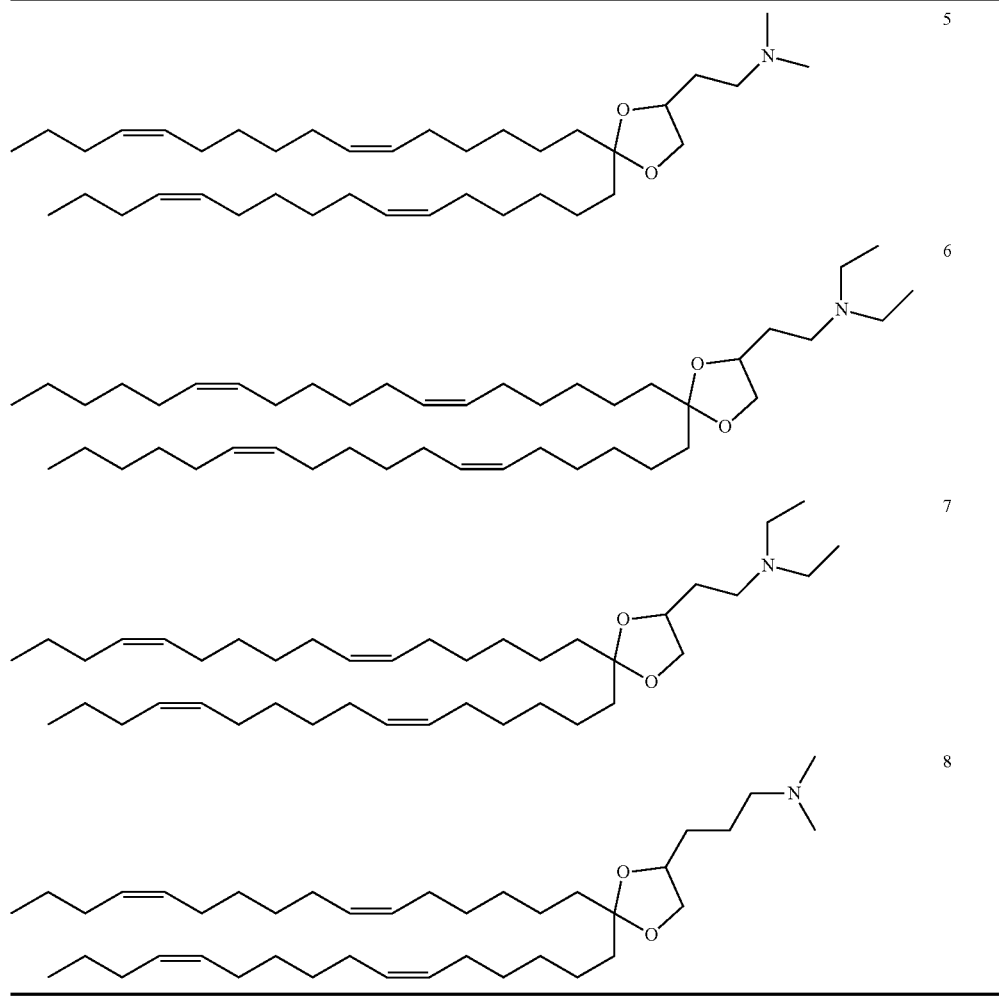
TABLE 1A
Exemplary cationic lipids (continued)
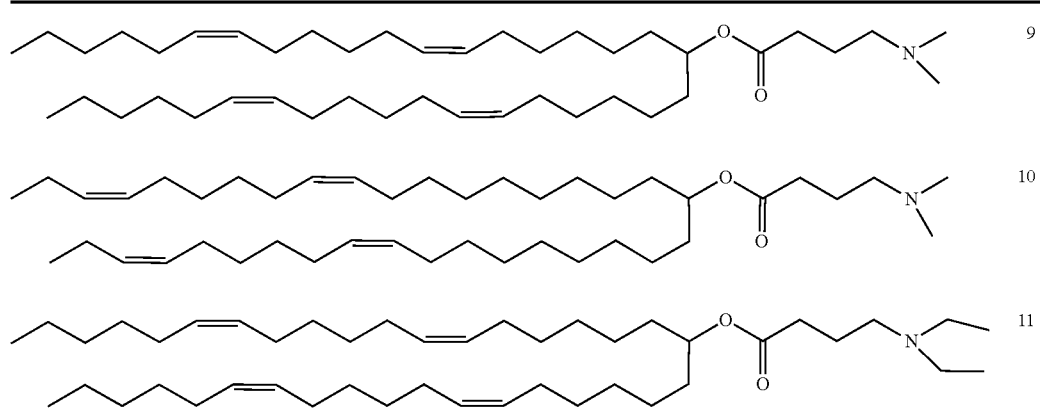

TABLE 1A-continued
Exemplary cationic lipids (continued)
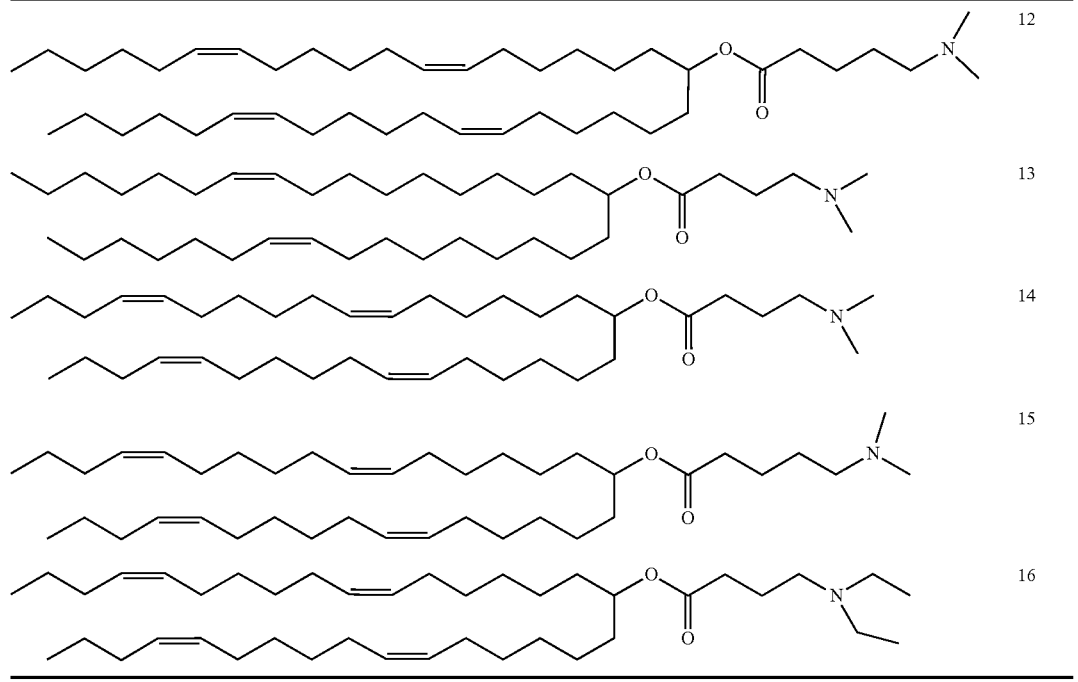
TABLE 1A
Exemplary cationic lipids (continued)
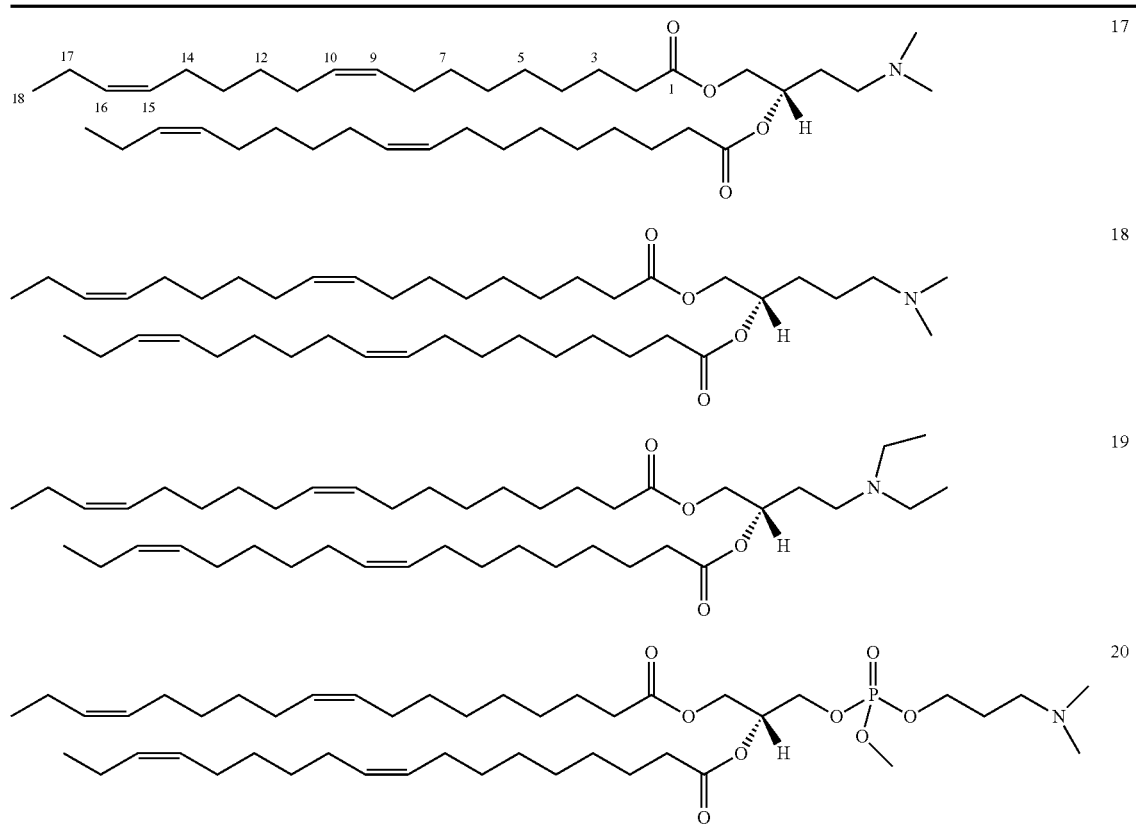

TABLE 1A-continued
Exemplary cationic lipids (continued)
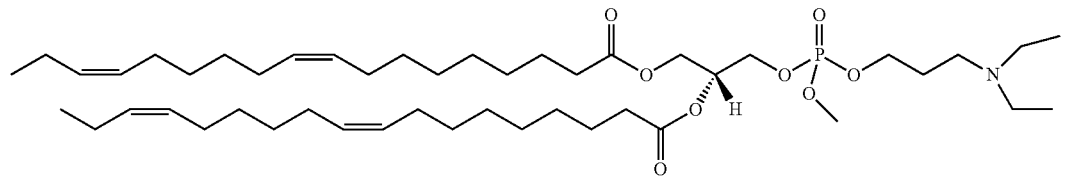 [SMILES: CC/C=C\CCCC/C=C\CCCCCCCC(=O)OC[C@H](COP(=O)(OC)OCCCN(CC)CC)OC(=O)CCCCCCC/C=C\CCCC/C=C\CC]
21
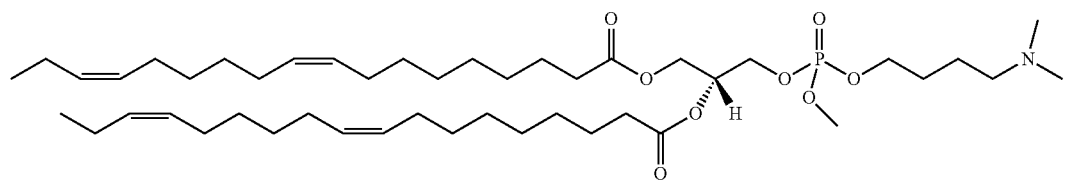 [SMILES: CC/C=C\CCCC/C=C\CCCCCCCC(=O)OC[C@H](COP(=O)(OC)OCCCCN(C)C)OC(=O)CCCCCCC/C=C\CCCC/C=C\CC]
22
20
TABLE 1A
Exemplary cationic lipids (continued)
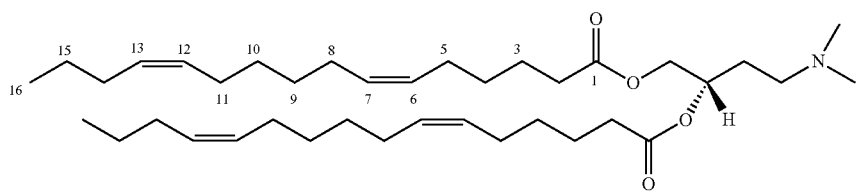 [SMILES: CCC/C=C\CCCC/C=C\CCCCC(=O)OC[C@H](CCN(C)C)OC(=O)CCCC/C=C\CCCC/C=C\CCC]
23
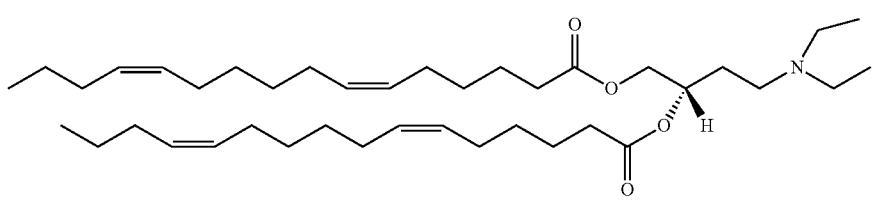 [SMILES: CCC/C=C\CCCC/C=C\CCCCC(=O)OC[C@H](CCN(CC)CC)OC(=O)CCCC/C=C\CCCC/C=C\CCC]
24
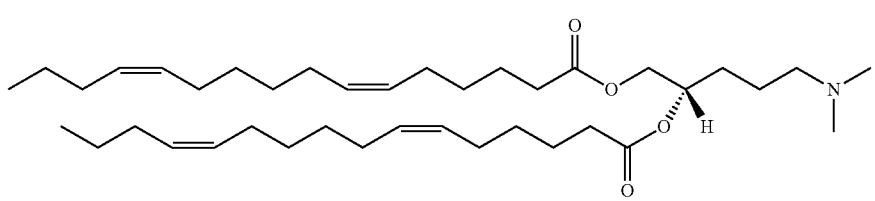 [SMILES: CCC/C=C\CCCC/C=C\CCCCC(=O)OC[C@H](CCCN(C)C)OC(=O)CCCC/C=C\CCCC/C=C\CCC]
25
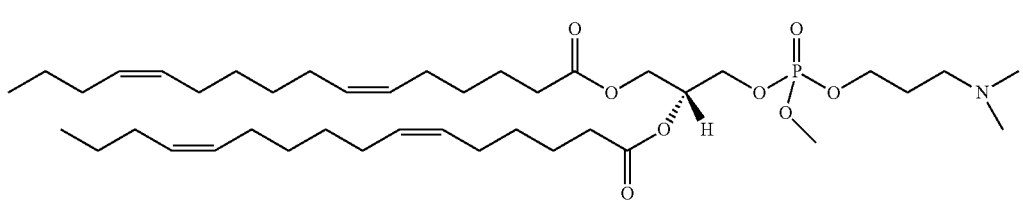 [SMILES: CCC/C=C\CCCC/C=C\CCCCC(=O)OC[C@H](COP(=O)(OC)OCCCN(C)C)OC(=O)CCCC/C=C\CCCC/C=C\CCC]
26
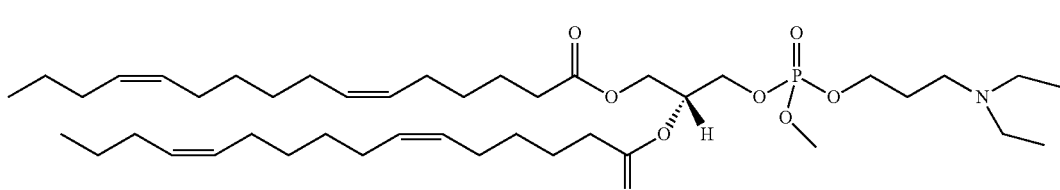
27

TABLE 1A-continued
Exemplary cationic lipids (continued)
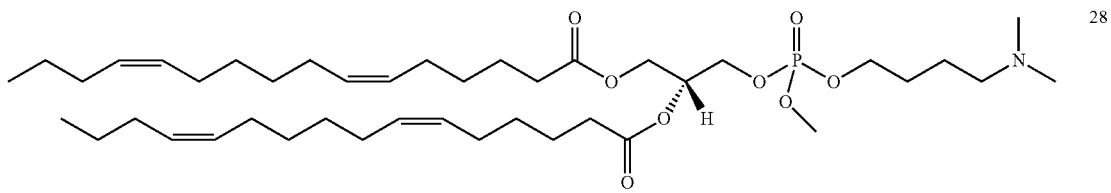
28
TABLE 1B
Additional Exemplary cationic lipids
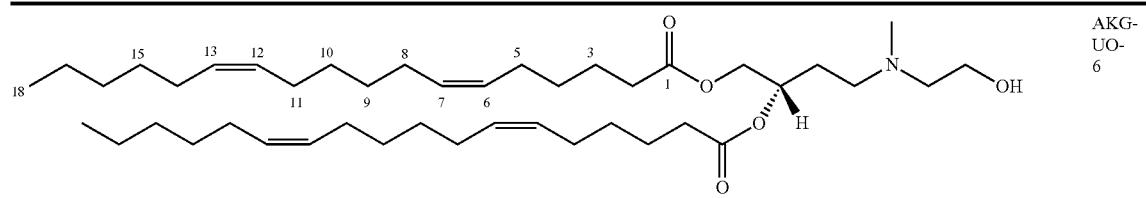
AKG-UO-6
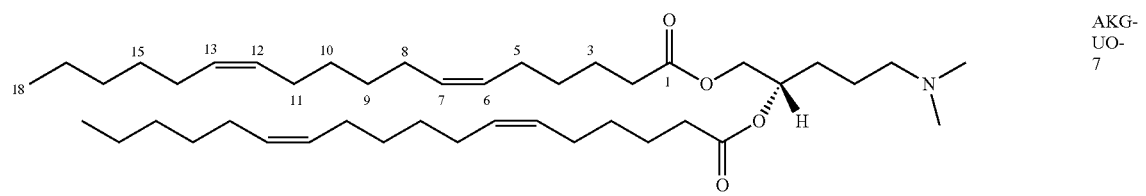
AKG-UO-7
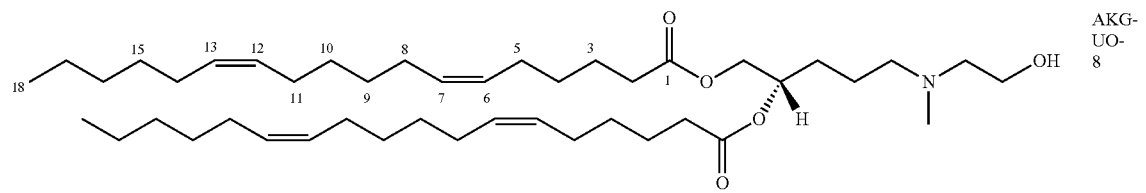
AKG-UO-8
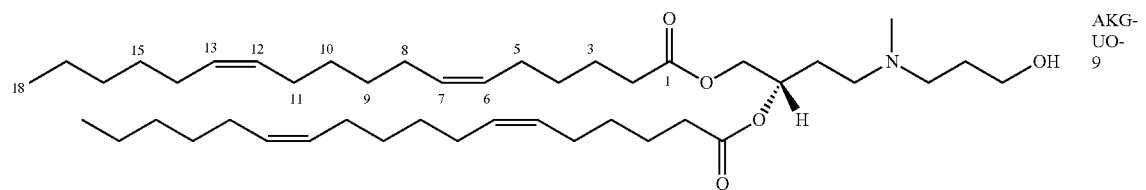
AKG-UO-9
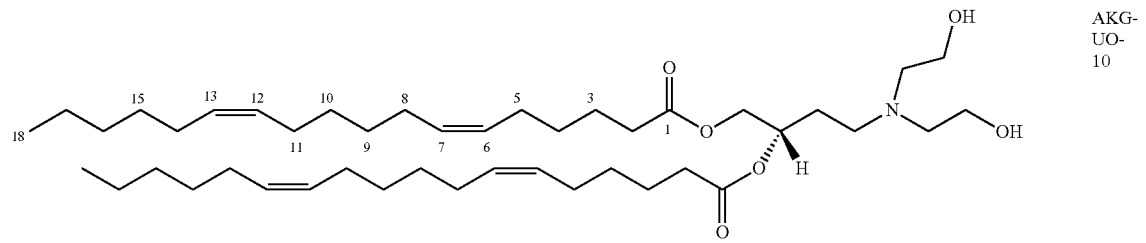
AKG-UO-10
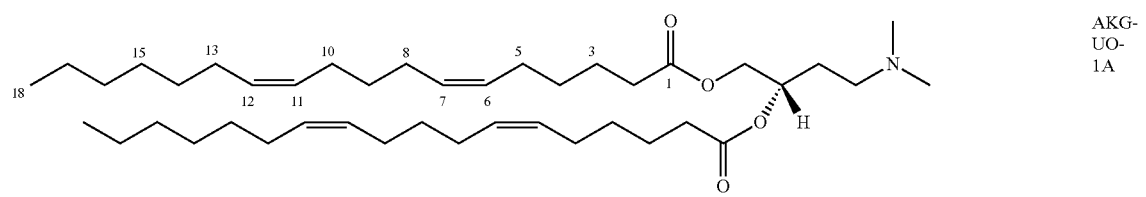
AKG-UO-1A TABLE IB-continued
Additional Exemplary cationic lipids
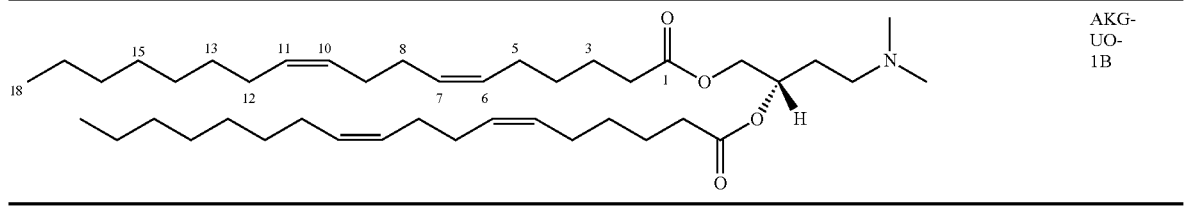
AKG-UO-1B
TABLE 2
Exemplary bioreducible cationic lipids
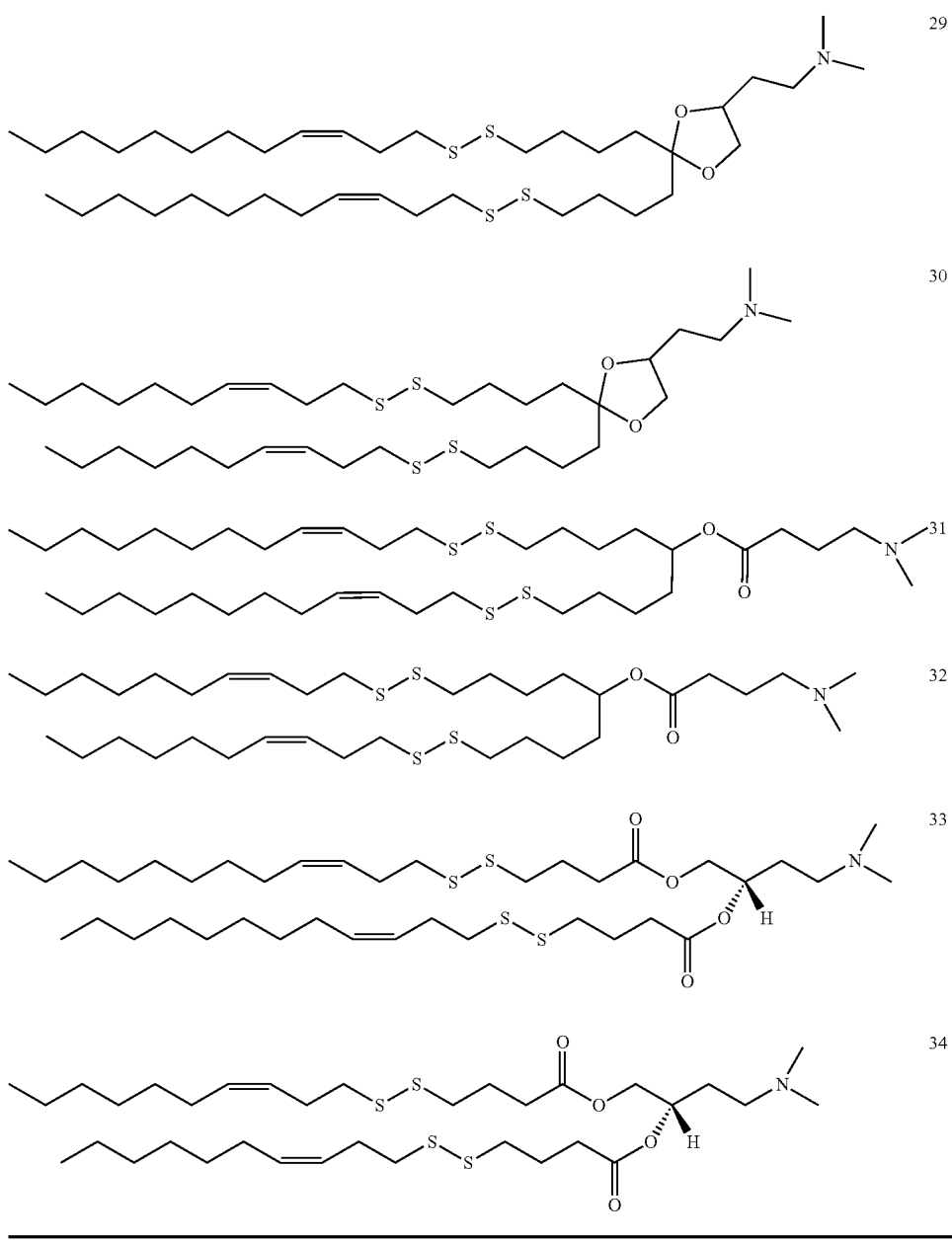

TABLE 2

Exemplary bioreducible cationic lipids (continued)

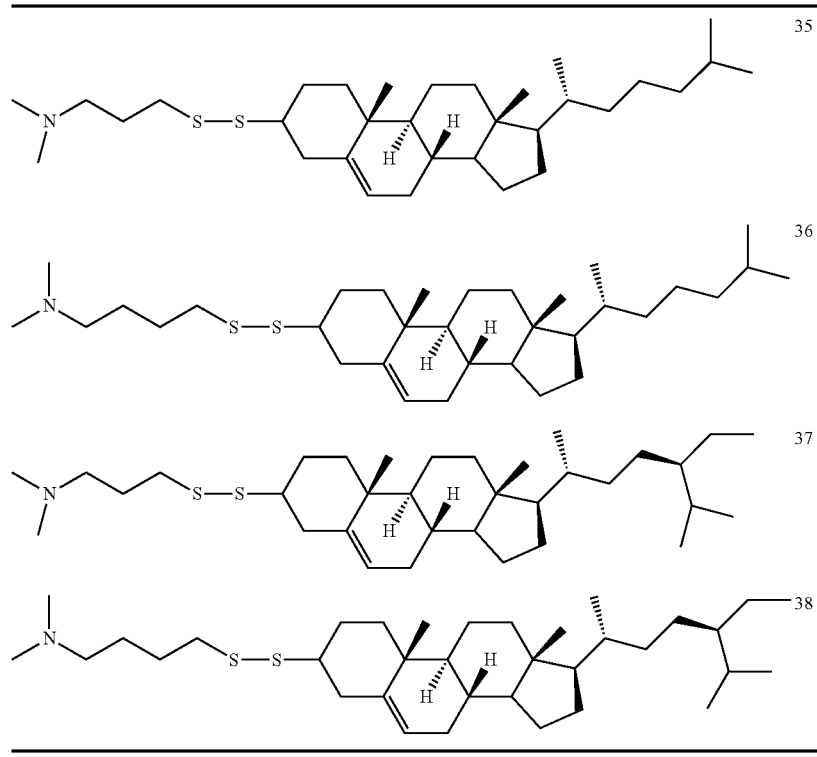

In some embodiments, the ionizable lipid encapsulate the nucleic acid. In some embodiments, the ionizable lipid encapsulate the nucleic acid in a LNP formulation. In some embodiments, the nucleic acid is a siRNA molecule. In some embodiments, the nucleic acid is a mRNA molecule. In some embodiments, the nucleic acid is a DNA molecule.

In some embodiments, compositions further comprising ligands, such as antibody conjugates, directed against cell surface receptors to target lipid nanoparticles in a highly specific manner to dendritic cells are provided. In some embodiments, the composition further comprises a targeting ligand, wherein the targeting ligand is oriented to the outside of the nanoparticle. In some embodiments, the targeting ligand is an antibody.

In some embodiments, the lipidic nanoparticles are in an aqueous medium.

In some embodiments, the nucleic acid is entrapped in the lipidic nanoparticle with a compound disclosed herein, including compounds of Formula I, II, III, IV or combinations thereof, wherein the nucleic acid is either RNA or DNA. In some embodiments, the nucleic acid is entrapped in the lipidic nanoparticle with a compound disclosed herein, including compounds of Formula I, I-A, II, II-A, II-B, III, III-A, IV, IV-A, IV-B, V, V-A, VI-A, VII, VIII or combinations thereof, wherein the nucleic acid is either RNA or DNA. In some embodiments, the nucleic acid is mRNA. In some embodiments, the nucleic acid is siRNA. In some embodiments, the nucleic acid is DNA.

In some embodiments, the lipidic nanoparticle comprises a membrane comprising phosphatidylcholine and a sterol. In some embodiments, the sterol is cholesterol. In some embodiments, the lipidic nanoparticle comprises a membrane comprising phosphatidylcholine, ionizable cationic lipid (ICL). In some embodiments, the ICL have a structure of Formula I, II, III or IV, and cholesterol, wherein the membrane separates the inside of the lipidic nanoparticles from the aqueous medium. In some embodiment, the ICL have a structure as shown in Table 1A and Table 2. In some embodiment, the ICL have a structure as shown in Table 1B.

In some embodiments, the phosphatidylcholine is distearoylphosphatidylcholine (DSPC) or hydrogenated soy phosphatidylcholine (HSPC). In some embodiments, the ionizable cationic lipid to cholesterol molar ratios is from about 65:35 to 40:60. In some embodiments, the ICL to cholesterol molar ratio is from about 60:40 to about 45:55.

In some embodiments, the phosphatidylcholine to cholesterol molar ratio is from about 1:5 to about 1:2.

In some embodiments, the membrane further comprises a polymer-conjugated lipid.

In some embodiments, the lipidic nanoparticle comprises ICL, DSPC, cholesterol and polymer-conjugated lipid in a about 49.5:10.3:39.6:2.5 molar ratio.

In some embodiments, the polymer-conjugated lipid is PEG(2000)-dimyristoylglycerol (PEG-DMG) or PEG(Mol. weight 2,000)-dimyristoylphosphatidylethanolamine (PEG-DMPE).

In some embodiments the percentage of oxidative degradation products for the ionizable lipid is less than 50% of that for a DLin-KC2-DMA or DLin-MC3-DMA control formulation.

In some embodiments, the composition is a liquid pharmaceutical formulation for parenteral administration.

In some embodiments, the composition is a liquid pharmaceutical formulation for subcutaneous, intramuscular, or intradermal administration.

In some embodiments, the composition is in the form of a lyophilized powder, that is subsequently reconstituted with aqueous medium prior to administration.

Other aspects of the disclosure relate to a method of preventing a bacterial or viral infection, the method comprising administering to a subject in need thereof an effective amount of the composition provided herein to elicit an immune response. Some embodiments provide methods of vaccinating a subject in need thereof, the method comprising administering the composition comprising a nucleic acid encoding an antigenic protein.

In some embodiments, the composition is administered subcutaneously, intramuscularly, or intradermally.

In some embodiments, the bacterial infection is *Mycobacterium tuberculosis* infection. In some embodiments, the bacterial infection is a form of nontuberculosis *Mycobacterium*.

In some embodiments, the viral infection is a coronavirus. In some embodiments, the coronavirus is SARS-CoV, MERS-CoV or SARS-CoV-2

In some embodiments, the viral infection is HIV/AIDs.

In some embodiments, the lipidic nanoparticle is administered parenterally.

In some embodiments, the lipidic nanoparticle composition is administered as part of a single injection.

The present disclosure features a lipid nanoparticle comprising nucleic acids such as DNA, mRNA, siRNA, antisense oligonucleotides, CRISPR components such as a guide RNA (gRNA or sgRNA) and a CRISPR-associated endonuclease (Cas protein) and a lipid. Exemplary lipids include ionizable cationic lipids (ICLs), phospholipids, sterol lipids, alkylene glycol lipids (e.g., polyethylene glycol lipids), sphingolipids, glycerolipids, glycerophospholipids, prenol lipids, saccharolipids, fatty acids, and polyketides. In some embodiments, the LNP comprises a single type of lipid. In some embodiments, the LNP comprises a plurality (e.g. two or more) of lipids. An LNP may comprise one or more of an ionizable cationic lipid, a phospholipid, a sterol, or an alkylene glycol lipid (e.g., a polyethylene glycol lipid).

In an embodiment, the LNP comprises an ionizable cationic lipid. As used herein "ionizable cationic lipid", "ionizable lipid" and "ICL" are used interchangeably. An ICL is a lipid that comprises an ionizable moiety capable of bearing a charge (e.g., a positive charge e.g., a cationic lipid) under certain conditions (e.g., at a certain pH range, e.g., under physiological conditions). The ionizable moiety may comprise an amine, and preferably a substituted amine. An ionizable lipid may be a cationic lipid or an anionic lipid. In addition to an ionizable moiety, an ionizable lipid may contain an alkyl or alkenyl group, e.g., greater than six carbon atoms in length (e.g., greater than about 8 carbons, 10 carbons, 12 carbons, 14 carbons, 16 carbons, 18 carbons, 20 carbons or more in length). Additional ionizable lipids that may be included in an LNP described herein are disclosed in Jayaraman et al. (*Angew. Chem. Int. Ed.* 51:8529-8533 (2012)), Semple et al. *Nature Biotechnol.* 28:172-176 (2010)), and U.S. Pat. Nos. 8,710,200 and 8,754,062, each of which is incorporated herein by reference in its entirety.

In some embodiments, an LNP comprises an ionizable lipid having a structure of Formula (IV):

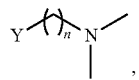
(IV)

or a pharmaceutically acceptable salt thereof, wherein Y is

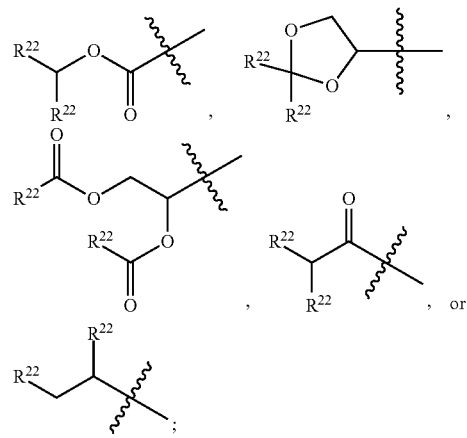

each $R^{22}$ is independently alkyl, alkenyl, alkynyl, or heteroalkyl, each of which is optionally substituted with $R^B$; each $R^B$ is independently alkyl, halo, hydroxy, amino, cycloalkyl, or heterocyclyl; n is an integer between 1 and 10 (inclusive); and ⌇ denotes the attachment point.

In some embodiments, Y is

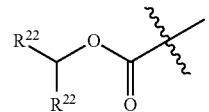

In some embodiments, an LNP comprises an ionizable lipid having a structure of Formula (IV-A), or a pharmaceutically acceptable salt thereof,

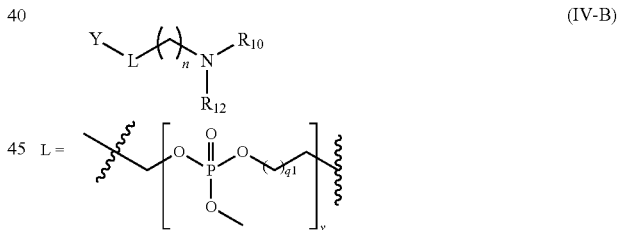
(IV-B)

wherein each of $R_{10}$ and $R_{12}$ is independently $(C_1\text{-}C_4)$alkyl optionally substituted with hydroxyl; v is 0 or 1; q1 is 1 or 2; Y is

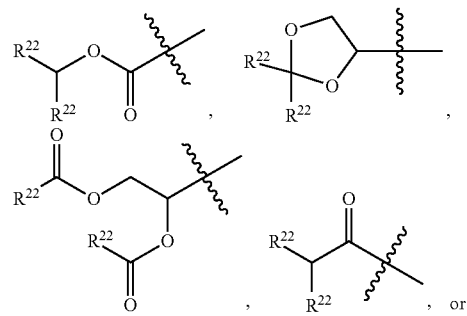

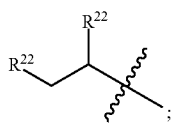

$R_{22}$ is

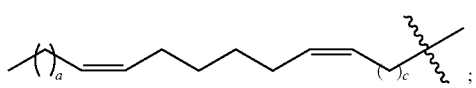

a is 1, 2, 3, 4 or 5; and c is 4, 5, 6, 7 or 8.

In some embodiments, v equals 0 for compounds of Formula (IV-B). In some embodiments, v equals 1 for compounds of Formula (IV-B). In some embodiments, v equals 1 and q1 equals 1 for compounds of Formula (IV-A). In some embodiments, v equals 1 and q1 equals 2 for compounds of Formula (IV-B).

In some embodiments, the sum of a and c is 6, 7, 8 or 9 in $R^{22}$ for compounds of Formula (IV-B). In some embodiments, the sum of a and c is 6 in $R^{22}$ for compounds of Formula (IV-B). In some embodiments, the sum of a and c is 7 in $R^{22}$ for compounds of Formula (IV-B). In some embodiments, the sum of a and c is 9 in $R^{22}$ for compounds of Formula (IV-B).

In some embodiments, v equals 0 and the sum of a and c is 6, 7, 8 or 9 in $R^{22}$ for compounds of Formula (IV-B). In some embodiments, v equals 0 and the sum of a and c is 6 in $R^{22}$ for compounds of Formula (IV-B). In some embodiments, v equals 0 and the sum of a and c is 7 in $R^{22}$ for compounds of Formula (IV-B). In some embodiments, v equals 0 and the sum of a and c is 9 in $R^{22}$ for compounds of Formula (IV-B).

In some embodiments, $R_{10}$ and $R_{12}$ are independently selected from methyl, ethyl, —(CH$_2$)(CH$_2$)OH, and —(CH$_2$)$_2$(CH$_2$)OH for compounds of Formula (IV-B). In some embodiments, $R_{10}$ and $R_{12}$ are each methyl and the sum of a and c is 6, 7, 8 or 9 in $R^{22}$ for compounds of Formula (IV-B). In some embodiments, $R_{10}$ and $R_{12}$ are each methyl, v is 0 and the sum of a and c is 6, 7, 8 or 9 in $R^{22}$ for compounds of Formula (IV-B).

In some embodiments, v equals 0 and $R^{22}$ is

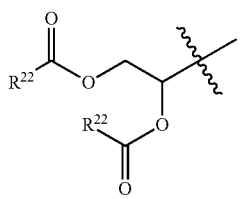

for compounds of Formula (IV-B). In some embodiments, v equals 0 and $R^{22}$ is

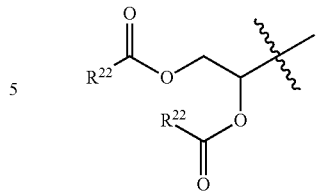

and the sum of a and c is 8 for compounds of Formula (IV-B). In some embodiments, v equals 0 and $R^{22}$ is

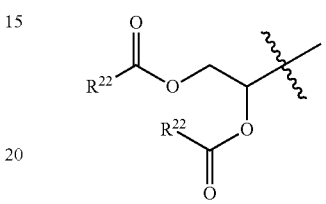

and a is 1 and c is 7 for compounds of Formula (IV-B). In some embodiments, v equals 0 and $R^{22}$ is

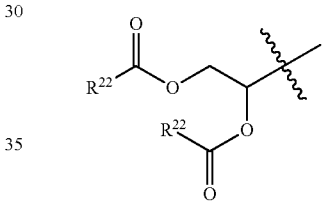

and a is 2 and c is 4 for compounds of Formula (IV-B).

In some embodiments, v equals 1 and $R^{22}$ is

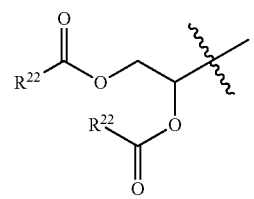

for compounds of Formula (IV-B). In some embodiments, v equals 1 and $R^{22}$ is

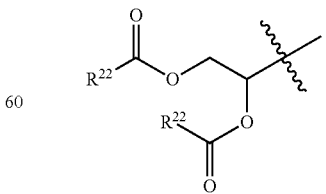

and the sum of a and c is 8 for compounds of Formula (IV-B). n some embodiments, v equals 1 and $R^{22}$ is

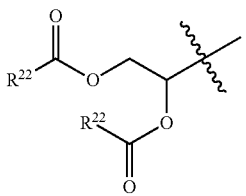

and a is 1 and c is 7 for compounds of Formula (IV-B).

In some embodiments, v equals 0 and $R^{22}$ is

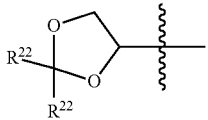

for compounds of Formula (IV-B). In some embodiments, v equals 0 and $R^{22}$ is

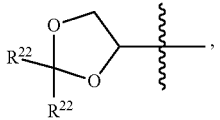, and the sum of a and c is 7 or 9 for compounds of Formula (IV-B). In some embodiments, v equals 0 and $R^{22}$ is

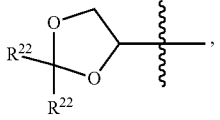, and a is 4 and c is 5 for compounds of Formula (IV-B). In some embodiments, v equals 0 and $R^{22}$ is

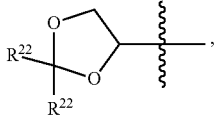, and a is 1 and c is 8 for compounds of Formula (IV-B). In some embodiments, v equals 0 and $R^{22}$ is

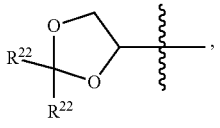, and a is 2 and c is 5 for compounds of Formula (IV-B).

In some embodiments, v equals 0 and $R^{22}$ is

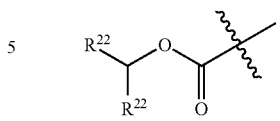

for compounds of Formula (IV-B). In some embodiments, v equals 0 and $R^{22}$ is

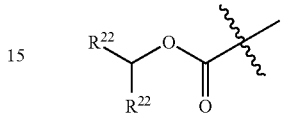

and the sum of and c is 7 or 9 for compounds of Formula (IV-B). In some embodiments, v equals 0 and $R^{22}$ is

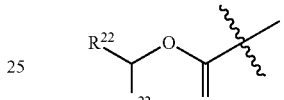

and a is 4 and c is 5 for compounds of Formula (IV-B). In some embodiments, v equals 0 and $R^{22}$ is

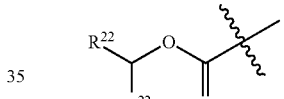

and a is 1 and c is 8 for compounds of Formula (IV-B). In some embodiments, v equals 0 and $R^{22}$ is

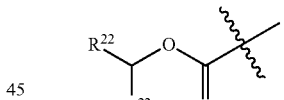

and a is 2 and c is 5 for compounds of Formula (IV-B).

An LNP may comprise an ionizable lipid at a concentration greater than about 0.1 mol %, e.g., of the total lipid content of the LNP. In an embodiment, the LNP comprises an ionizable lipid at a concentration of greater than about 1 mol %, about 2 mol %, about 4 mol %, about 8 mol %, about 20 mol %, about 40 mol %, about 50 mol %, about 60 mol %, about 80 mol %, e.g., of the total lipid content of the LNP. In an embodiment, the LNP comprises an ionizable lipid at a concentration of greater than about 20 mol %, about 40 mol %, or about 50 mol %. In an embodiment, the LNP comprises an ionizable lipid at a concentration between about 1 mol % to about 95 mol %, e.g., of the total lipid content of the LNP. In an embodiment, the LNP comprises an ionizable lipid at a concentration between about 2 mol % to about 90 mol %, about 4 mol % to about 80 mol %, about 10 mol % to about 70 mol %, about 20 mol % to about 60 mol %, about 40 mol % to about 55 mol %, e.g., of the total lipid content of the LNP. In an embodiment, the LNP comprises an ionizable lipid at a concentration between about 20 mol % to about 60 mol %. In an embodiment, the LNP comprises an ionizable lipid at a concentration between about 40 mol % to about 55 mol %.

In an embodiment, the LNP comprises a phospholipid. A phospholipid is a lipid that comprises a phosphate group and at least one alkyl, alkenyl, or heteroalkyl chain. A phospholipid may be naturally occurring or non-naturally occurring (e.g., a synthetic phospholipid). A phospholipid may comprise an amine, amide, ester, carboxyl, choline, hydroxyl, acetal, ether, carbohydrate, sterol, or a glycerol. In some embodiments, a phospholipid may comprise a phosphocholine, phosphosphingolipid, or a plasmalogen. Exemplary phospholipids include 1,2-dioleoyl-sn-glycero-3-phosphocholine (DOPC), 1,2-dipalmitoyl-sn-glycero-3-phosphocholine (DPPC), 1,2-dioleoyl-sn-glycero-3-phosphoethanolamine (DOPE), 1,2-distearoyl-sn-glycero-3-phosphocholine (DSPC), hydrogenated soy phosphatidylcholine (HSPC), 1,2-dilauroyl-sn-glycero-3-phosphocholine (DLPC), 1,2-dimyristoyl-sn-glycero-3-phosphocholine (DMPC), 1,2-distearoyl-sn-glycero-3-phosphoethanolamine (DSPE), 1-myristoyl-2-oleoyl-sn-glycero-3-phosphocholine (MOPC), 1,2-diarachidonoyl-sn-glycero-3-phosphocholine (DAPC), 1-palmitoyl-2-linoleoyl-sn-glycero-3-phosphatidylcholine (PLPC), 1-palmitoyl-2-oleoyl-glycero-3-phosphocholine (POPC), 1-stearoyl-2-myristoyl-sn-glycero-3-phosphocholine (SMPC), 1-palmitoyl-2-myristoyl-sn-glycero-3-phosphocholine (PMPC), bis(monoacylglycerol)phosphate (BMP), L-α-phosphatidylcholine, 1,2-Diheptadecanoyl-sn-glycero-3-phosphorylcholine (DHDPC), and 1-stearoyl-2-arachidonoyl-sn-glycero-3-phosphocholine (SAPC). Additional phospholipids that may be included in an LNP described herein are disclosed in Li, J. et al. (*Asian J. Pharm. Sci.* 10:81-98 (2015)), which is incorporated herein by reference in its entirety.

In some embodiments, an LNP comprises a phospholipid having a structure of Formula (V):

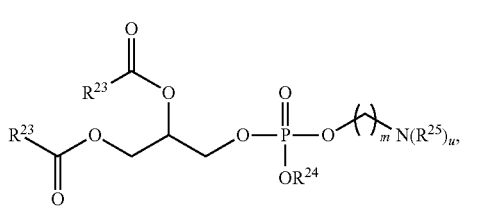

(V)

or a pharmaceutically acceptable salt thereof, wherein each $R^{23}$ is independently alkyl, alkenyl, or heteroalkyl; wherein each alkyl, alkenyl, or heteroalkyl is optionally substituted with $R^C$; each $R^{25}$ is independently hydrogen or alkyl; $R^{24}$ is absent, hydrogen, or alkyl; each $R^C$ is independently alkyl, halo, hydroxy, amino, cycloalkyl, or heterocyclyl; m is an integer between 1 and 4 (inclusive); and u is 2 or 3.

In some embodiments, each $R^{23}$ is independently alkyl (e.g., $C_2$-$C_{32}$ alkyl, $C_4$-$C_{28}$ alkyl, $C_8$-$C_{24}$ alkyl, $C_{12}$-$C_{22}$ alkyl, or $C_{16}$-$C_{20}$ alkyl). In some embodiments, each $R^{23}$ is independently alkenyl (e.g., $C_2$-$C_{32}$ alkyl, $C_4$-$C_{28}$ alkenyl, $C_8$-$C_{24}$ alkenyl, $C_{12}$-$C_{22}$ alkenyl, or $C_{16}$-$C_{20}$ alkenyl). In some embodiments, each $R^{23}$ is independently heteroalkyl (e.g., $C_4$-$C_{28}$heteroalkyl, $C_8$-$C_{24}$heteroalkyl, $C_{12}$-$C_{22}$heteroalkyl, $C_{16}$-$C_{20}$heteroalkyl). In some embodiments, each $R^{23}$ is independently $C_{16}$-$C_{20}$ alkyl. In some embodiments, each $R^{23}$ is independently $C_{17}$ alkyl. In some embodiments, each $R^{23}$ is independently heptadecyl. In some embodiments, each $R^{23}$ is the same. In some embodiments, each $R^{23}$ is different. In some embodiments, each $R^{23}$ is optionally substituted with $R^C$. In some embodiments, $R^C$ is independently alkyl, halo, hydroxy, amino, cycloalkyl, or heterocyclyl.

In some embodiments, one of $R^{25}$ is hydrogen. In some embodiments, one of $R^{25}$ is alkyl. In some embodiments, one of $R^{25}$ is methyl. In some embodiments, each $R^{25}$ is independently alkyl. In some embodiments, each $R^{25}$ is independently methyl. In some embodiments, each $R^{25}$ is independently methyl and u is 2. In some embodiments, each $R^{25}$ is independently methyl and u is 3.

In some embodiments, $R^{24}$ is absent, and the oxygen to which it is attached carries a negative charge. In some embodiments, $R^{24}$ is hydrogen.

In some embodiments, m is an integer between 1 and 10, 1 and 8, 1 and 6, 1 and 4. In some embodiments, m is 1, 2, 3, or 4. In some embodiments, m is 1. In some embodiments, m is 2. In some embodiments, m is 3.

In some embodiments, compositions comprising both a cationic ionizable lipid and an anionic phospholipid targeting moiety are provided. In some embodiments, the anionic phospholipid is a composition of Formula (V-A):

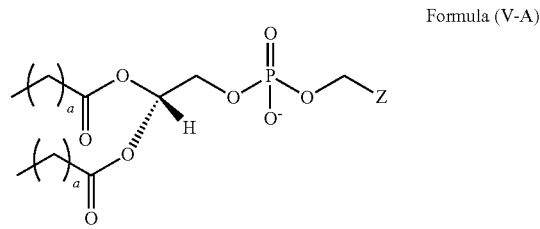

Formula (V-A)

wherein a is 14 or 16, and z is an amide, glycol, or amidyl-alkyl-carboxylic acid moiety. In some embodiments, Z is

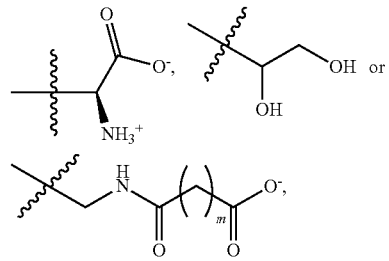

wherein m is 2 or 3. In some embodiments, the anionic phospholipid targeting moiety is selected from the group consisting of DSPS (L-isomer), DPPS (L-isomer), DMPS (L-isomer), DOPS (L-isomer), DSPS (D-isomer), DSPG, DPPG, N-Glu-DSPE, and N-Suc-DSPE.

In some embodiments, the phospholipid is 1,2-distearoyl-sn-glycero-3-phosphocholine (DSPC). In some embodiments, the phospholipid is 1,2-dioleoyl-sn-glycero-3-phosphocholine(DOPC). In some embodiments, the phospholipid is 1,2-dipalmitoyl-sn-glycero-3-phosphocholine(DPPC). In some embodiments, the phospholipid is 1,2-dioleoyl-sn-glycero-3-phosphoethanolamine (DOPE).

Incorporation of Phosphatidylserine

The LNP (e.g., as described herein) may comprise one or more of the following components: (i) Ionizable cationic lipid (ICL) containing a C16 alkyl or C16 alkenyl group or C18 alkyl or C18 alkenyl group at a concentration between about 1 mol % to about 95 mol % (or any value therebetween, e.g. about 20 mol % to about 80 mol %); (ii) A phospholipid at a concentration between 0.1 mol % to about 20 mol % (or any value there between, e.g. between about 2.5 mol % to about 10 mol %) where the phospholipid also contains C16 or C18 alkyl or alkenyl groups; (iii) cholesterol at a concentration between about 1 mol % to about 95 mol % (or any value therebetween, e.g. about 20 mol % to about 80 mol %); (iv) a phosphatidylserine (PS) or phosphatidylglycerol (PG) added to the LNP lipid formulation at a concentration between about 0.5 mol % to about 20 mol %, about 2.5 mol % to about 10 mol %, about 4 mol % to about 8 mol %, or any value therebetween of the total lipid content of the LNP, and (v) a polyethyleneglycol (PEG)-2000-containing lipid (e.g., DPG-PEG2000, DPPE-PEG2000, DMPE-PEG2000, DMG-PEG2000) at a concentration between about 0.1 mol % to about 5 mol % (or any value therebetween, e.g. between about 1 mol % to about 2.5 mol %). In an embodiment, the LNP comprises two of (i)-(v). In an embodiment, the LNP comprises three of (i)-(v). In an embodiment, the LNP comprises four of (i)-(v). In an embodiment, the LNP comprises each of (i)-(v). In some embodiments, the LNP comprises (i) and (ii). In some embodiments, the LNP comprises (i) and (iii). In some embodiments, the LNP comprises (i) and (v). In some embodiments, the LNP comprises (ii) and (iii). In some embodiments, the LNP comprises (ii) and (v). In some embodiments, the LNP comprises (iii) and (iv). In some embodiments, the LNP comprises (iii) and (v). In some embodiments, the LNP comprises (i), (ii), and (iii). In some embodiments, the LNP comprises (i), (ii), and (v). In some embodiments, the LNP comprises (ii), (iii), and (v). In some embodiments, the LNP comprises (ii), (iii), (iv) and (v). In an embodiment, the LNP consists or consists essentially of four of (i)-(v). In an embodiment, the LNP consists or consists essentially of each of (i)-(v). In some embodiments, the LNP consists or consists essentially of (i) and (ii). In some embodiments, the LNP consists or consists essentially of (i) and (iii). In some embodiments, the LNP consists or consists essentially of (i) and (v). In some embodiments, the LNP consists or consists essentially of (ii) and (iii). In some embodiments, the LNP comprises (ii) and (v). In some embodiments, the LNP consists or consists essentially of (iii) and (iv). In some embodiments, the LNP consists or consists essentially of (iii) and (v). In some embodiments, the LNP consists or consists essentially of (i), (ii), and (iii). In some embodiments, the LNP consists or consists essentially of (i), (ii), and (v). In some embodiments, the LNP comprises (ii), (iii), and (v). In some embodiments, the LNP consists or consists essentially of (ii), (iii), (iv) and (v).

An LNP may comprise a phospholipid at a concentration greater than about 0.1 mol %, e.g., of the total lipid content of the LNP. In an embodiment, the LNP comprises a phospholipid at a concentration of greater than about 0.5 mol %, about 1 mol %, about 1.5 mol %, about 2 mol %, about 3 mol %, about 4 mol %, about 5 mol %, about 6 mol %, about 8 mol %, about 10 mol %, about 12 mol %, about 15 mol %, about 20 mol %, about 50 mol %, e.g., of the total lipid content of the LNP. In an embodiment, the LNP comprises a phospholipid at a concentration of greater than about 1 mol %, about 5 mol %, or about 10 mol %. In an embodiment, the LNP comprises a phospholipid at a concentration between about 0.1 mol % to about 50 mol %, e.g., of the total lipid content of the LNP. In an embodiment, the LNP comprises a phospholipid at a concentration between about 0.5 mol % to about 40 mol %, about 1 mol % to about 30 mol %, about 5 mol % to about 25 mol %, about 10 mol % to about 20 mol %, about 10 mol % to about 15 mol %, or about 15 mol % to about 20 mol %, e.g., of the total lipid content of the LNP. In an embodiment, the LNP comprises a phospholipid at a concentration between about 5 mol % to about 25 mol %. In an embodiment, the LNP comprises a phospholipid at a concentration between about 10 mol % to 20 mol %.

In an embodiment, the LNP comprises a sterol or ionizable sterol molecule. A sterol is a lipid that comprises a polycyclic structure and an optionally a hydroxyl or ether substituent, and may be naturally occurring or non-naturally occurring (e.g., a synthetic sterol). Sterols may comprise no double bonds, a single double bond, or multiple double bonds. Sterols may further comprise an alkyl, alkenyl, halo, ester, ketone, hydroxyl, amine, polyether, carbohydrate, or cyclic moiety. Sterol may further contain a bioreducible disulfide linkage between the dialkylamino group and the polycyclic portion of the molecule (see Table 2, Compounds 35-38). An exemplary listing of sterols includes cholesterol, dehydroergosterol, ergosterol, campesterol, β-sitosterol, stigmasterol, lanosterol, dihydrolanosterol, desmosterol, brassicasterol, lathosterol, zymosterol, 7-dehydrodesmosterol, avenasterol, campestanol, lupeol, and cycloartenol. In some embodiments, the sterol comprises cholesterol, dehydroergosterol, ergosterol, campesterol, β-sitosterol, or stigmasterol. Additional sterols that may be included in an LNP described herein are disclosed in Fahy, E. et al. (*J. Lipid. Res.* 46:839-862 (2005).

Ionizable Sterols

In some embodiments, an LNP comprises a sterol having a structure of Formula (VI):

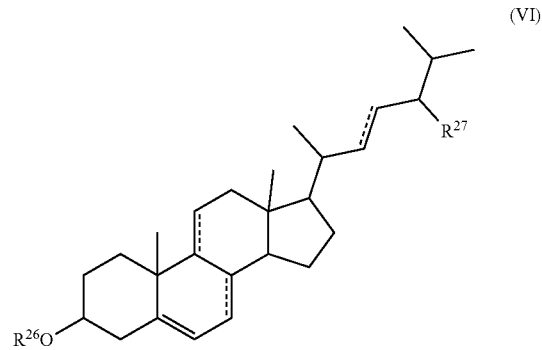

(VI)

or a pharmaceutically acceptable salt thereof, wherein $R^{26}$ is hydrogen, alkyl, heteroalkyl, or —C(O)$R^D$, $R^{27}$ is hydrogen, alkyl, or —O$R^E$; each of $R^D$ and $R^E$ is independently hydrogen, alkyl, alkenyl, heteroalkyl, cycloalkyl, heterocyclyl, aryl or heteroaryl, wherein each alkyl, alkenyl, heteroalkyl, cycloalkyl, heterocyclyl, aryl or heteroarylis optionally substituted with alkyl, halo, or carbonyl; and each "═══" is either a single or double bond, and wherein each carbon atom participating in the single or double bond is bound to 0, 1, or 2 hydrogens, valency permitting.

In some embodiments, one of "═══" is a single bond. In some embodiments, one of "═══" is a double bond. In some embodiments, two of "═══" are single bonds. In some embodiments, two of "═══" are double bonds. In some embodiments, each "═══" is a single bond. In some embodiments, each "═══" is a double bond.

In some embodiments, the sterol is cholesterol. In some embodiments, the sterol is dehydroergosterol. In some embodiments, the sterol is ergosterol. In some embodiments, the sterol is campesterol. In some embodiments, the sterol is β-sitosterol. In some embodiments, the sterol is stigmasterol. In some embodiments, the sterol is a corticosteroid. (e.g., corticosterone, hydrocortisone, cortisone, or aldosterone).

In some embodiments, an LNP comprises a sterol having a structure of Formula (VI-A):

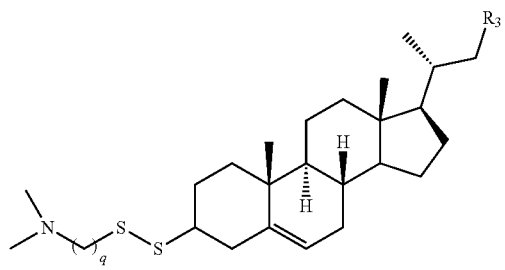

(VI-A) or a pharmaceutically acceptable salt thereof, wherein q is 3 or 4 and $R_3$ is

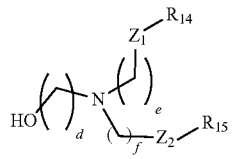

Another aspect of the disclosure provides a composition comprising an anionic phospholipid of Formula (V-A) and a branched ionizable lipid of Formula (VIII):

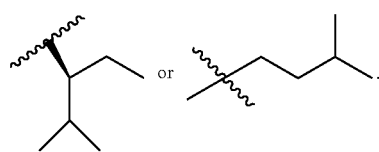

Formula VIII wherein d is 2, 3 or 4; e and f are each independently 5, 6 or 7; and $Z_1$ and $Z_2$ are each independently —O—C(O)— or —C(O)—O—; and $R_{14}$ and $R_{15}$ are each independently linear or branched $(C_{10}\text{-}C_{20})$alkyl. In some aspects, $R_{14}$ and $R_{15}$ in Formula VII are each a C14 or C16 branched alkyl. In some aspects, $R_{14}$ is a $C_{11}$ linear alkyl and $R_{15}$ is a $C_{14}$ or $C_{16}$ branched alkyl. In some aspects, $R_{14}$ in Formula VII is a $C_{11}$ linear alkyl and $R_{15}$ is a $C_{14}$ or $C_{16}$ linear alkyl. In some aspects, $R_{14}$ and/or $R_{15}$ in Formula VII are each independently

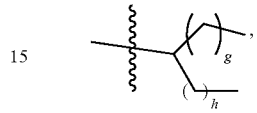

where g and h are each independently 5, 6, or 7. In some aspects, $R_{14}$ and $R_{15}$ in Formula VII are each independently

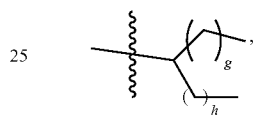

where g and h are both the same and are 5, 6, or 7. In some aspects, $R_{14}$ in Formula VII is a linear $C_{11}$ alkyl and $R_{15}$ in Formula VII is

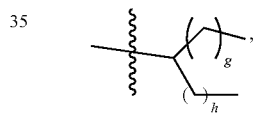

where g and h are both the same and are 5, 6, or 7.

In some embodiments, the ionizable lipid can be a branched ionizable lipid selected from ALC-0315 and SM-102:

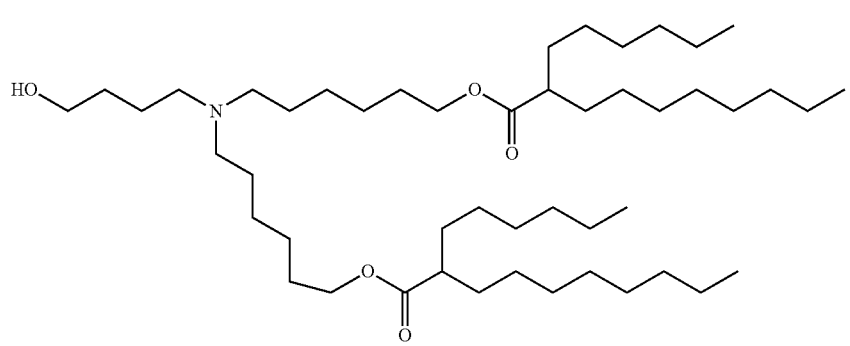

ALC-0315

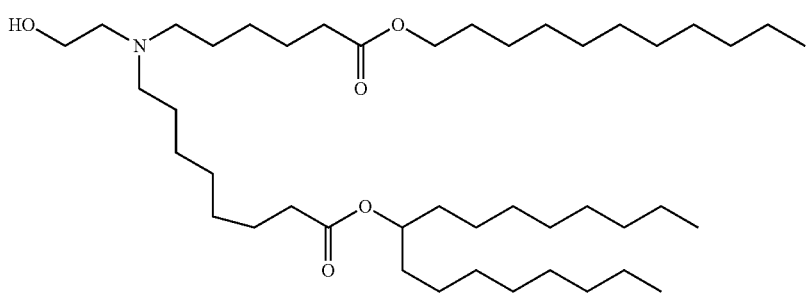

S-M-102

An LNP may comprise a sterol at a concentration greater than about 0.1 mol %, e.g., of the total lipid content of the LNP. In an embodiment, the LNP comprises a sterol at a concentration greater than about 0.5 mol %, about 1 mol %, about 5 mol %, about 10 mol %, about 15 mol %, about 20 mol %, about 25 mol %, about 35 mol %, about 40 mol %, about 45 mol %, about 50 mol %, about 55 mol %, about 60 mol %, about 65 mol %, or about 70 mol %, e.g., of the total lipid content of the LNP. In an embodiment, the LNP comprises a sterol at a concentration greater than about 10 mol %, about 15 mol %, about 20 mol %, or about 25 mol %. In an embodiment, the LNP comprises a sterol at a concentration between about 1 mol % to about 95 mol %, e.g., of the total lipid content of the LNP. In an embodiment, the LNP comprises a sterol at a concentration between about 5 mol % to about 90 mol %, about 10 mol % to about 85 mol %, about 20 mol % to about 80 mol %, about 20 mol % to about 60 mol %, about 20 mol % to about 50 mol %, or about 20 mol % to 40 mol %, e.g., of the total lipid content of the LNP. In an embodiment, the LNP comprises a sterol at a concentration between about 20 mol % to about 50 mol %. In an embodiment, the LNP comprises a sterol at a concentration between about 30 mol % to about 60 mol %.

In some embodiments, the LNP comprises an alkylene glycol-containing lipid. An alkylene glycol-containing lipid is a lipid that comprises at least one alkylene glycol moiety, for example, a methylene glycol or an ethylene glycol moiety. In some embodiments, the alkylene glycol-containing lipid comprises a polyethylene glycol (PEG). An alkylene glycol-containing lipid may be a PEG-containing lipid. Polymer-conjugated lipids may include poly(ethylene glycol)-conjugated (pegylated)phospholipids (PEG-lipids) such as PEG(Mol. weight 2,000) methoxy-poly(ethylene glycol)-1,2-distearoyl-sn-glycerol (PEG-DSG), PEG(Mol. weight 2,000) methoxy-poly(ethylene glycol)-1,2-palmitoyl-sn-glycerol (PEG-DPG), PEG(Mol. weight 2,000) 1,2-distearoyl-sn-glycero-3-phosphoethanolamine-N-[methoxy(polyethylene glycol)-2000] (PEG-DSPE) or N-palmitoyl-sphingosine-1-{succinyl[methoxy(polyethylene glycol) 2000]} (PEG-ceramide). The molecular weight of the PEG portion in the PEG-lipid component can also vary from 500-10,000 g/mol, from 1,500-6000 g/mol, but is preferably about 2,000 MW. Other polymers used for conjugation to lipid anchors may include poly(2-methyl-2-oxazoline) (PMOZ), poly(2-ethyl-2-oxazoline) (PEOZ), poly-N-vinylpyrrolidone (PVP), polyglycerol, poly(hydroxyethyl L-asparagine) (PHEA), and poly(hydroxyethyl L-glutamine) (PHEG).

A PEG-containing lipid may further comprise an amine, amide, ester, carboxyl, phosphate, choline, hydroxyl, acetal, ether, heterocycle, or carbohydrate. PEG-containing lipids may comprise at least one alkyl or alkenyl group, e.g., greater than six carbon atoms in length (e.g., greater than about 8 carbons, 10 carbons, 12 carbons, 14 carbons, 16 carbons, 18 carbons, 20 carbons or more in length), e.g., in addition to a PEG moiety. In an embodiment, a PEG-containing lipid comprises a PEG moiety comprising at least 20 PEG monomers, e.g., at least 30 PEG monomers, 40 PEG monomers, 45 PEG monomers, 50 PEG monomers, 100 PEG monomers, 200 PEG monomers, 300 PEG monomers, 500 PEG monomers, 1000 PEG monomers, or 2000 PEG monomers. Exemplary PEG-containing lipids include PEG-DMG (e.g., DMG-PEG2k), PEG-c-DMG, PEG-DSG, PEG-DPG, PEG-DSPE, PEG-DMPE, PEG-DPPE, PEG-DOPE, and PEG-DLPE. In some embodiments, the PEG-lipids include PEG-DMG (e.g., DMG-PEG2k), PEG-c-DMG, PEG-DSG, and PEG-DPG. Additional PEG-lipids that may be included in an LNP described herein are disclosed in Fahy, E. et al. (*J. Lipid. Res.* 46:839-862 (2005) which is incorporated herein by reference in its entirety.

In some embodiments, an LNP comprises an alkylene glycol-containing lipid having a structure of Formula (VII):

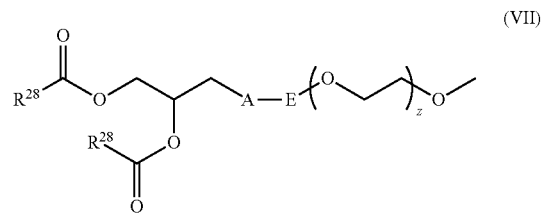

(VII)

or a pharmaceutically acceptable salt thereof, wherein each $R^{28}$ is independently alkyl, alkenyl, or heteroalkyl, each of which is optionally substituted with $R^F$; A is absent, O, $CH_2$, C(O), or NH; E is absent, alkyl, or heteroalkyl, wherein alkyl or heteroalkyl is optionally substituted with carbonyl; each $R^F$ is independently alkyl, halo, hydroxy, amino, cycloalkyl, or heterocyclyl; and z is an integer between 10 and 200 (inclusive).

In some embodiments, each $R^{28}$ is independently alkyl. In some embodiments, each $R^{28}$ is independently heteroalkyl. In some embodiments, each $R^{28}$ is independently alkenyl.

In some embodiments, A is O or NH. In some embodiments, A is $CH_2$. In some embodiments, A is carbonyl. In some embodiments, A is absent.

In some embodiments, E is alkyl. In some embodiments, E is heteroalkyl. In some embodiments, both A and E are not absent. In some embodiments, A is absent. In some embodiments, E is absent. In some embodiments, either one of A or E is absent. In some embodiments, both A and E are independently absent.

In some embodiments, z is an integer between 10 and 200 (e.g., between 20 and 180, between 20 and 160, between 20 and 120, between 20 and 100, between 40 and 80, between 40 and 60, between 40 and 50). In some embodiments, z is 45.

In some embodiments, the PEG-lipid is PEG-DMG (e.g., DMG-PEG2k). In some embodiments, the PEG-lipid is α-(3'-{[1,2-di(myristyloxy)propanoxy]carbonylamino}propyl)-ω-methoxy, polyoxyethylene (PEG-c-DMG). In some embodiments, the PEG-lipid is PEG-DSG. In some embodiments, the PEG-lipid is PEG-DPG.

An LNP may comprise an alkylene glycol-containing lipid at a concentration greater than about 0.1 mol %, e.g., of the total lipid content of the LNP. In an embodiment, the LNP comprises an alkylene glycol-containing lipid at a concentration of greater than about 0.5 mol %, about 1 mol %, about 1.5 mol %, about 2 mol %, about 3 mol %, about 4 mol %, about 5 mol %, about 6 mol %, about 8 mol %, about 10 mol %, about 12 mol %, about 15 mol %, about 20 mol %, about 50 mol %, e.g., of the total lipid content of the LNP. In an embodiment, the LNP comprises an alkylene glycol-containing lipid at a concentration of greater than about 1 mol %, about 4 mol %, or about 6 mol %. In an embodiment, the LNP comprises an alkylene glycol-containing lipid at a concentration between about 0.1 mol % to about 50 mol %, e.g., of the total lipid content of the LNP. In an embodiment, the LNP comprises an alkylene glycol-containing lipid at a concentration between about 0.5 mol % to about 40 mol %, about 1 mol % to about 35 mol %, about 1.5 mol % to about 30 mol %, about 2 mol % to about 25 mol %, about 2.5 mol % to about 20%, about 3 mol % to about 15 mol %, about 3.5 mol % to about 10 mol %, or about 4 mol % to 9 mol %, e.g., of the total lipid content of the LNP. In an embodiment, the LNP comprises an alkylene glycol-containing lipid at a concentration between about 3.5 mol % to about 10 mol %. In an embodiment, the LNP comprises an alkylene glycol-containing lipid at a concentration between about 4 mol % to 9 mol %.

In some embodiments, the LNP comprises at least two types of lipids. In an embodiment, the LNP comprises two of an ionizable lipid, a phospholipid, a sterol, and an alkylene glycol-containing lipid. In some embodiments, the LNP comprises at least three types of lipids. In an embodiment, the LNP comprises three of an ionizable lipid, a phospholipid, a sterol, and an alkylene glycol-containing lipid. In some embodiments, the LNP comprises at least four types of lipids. In an embodiment, the LNP comprises each of an ionizable lipid, a phospholipid, a sterol, and an alkylene glycol-containing lipid.

The LNP (e.g., as described herein) may comprise one or more of the following components: (i) an ionizable cationic lipid at a concentration between about 1 mol % to about 95 mol % (e.g. about 20 mol % to about 80 mol %); (ii) a phospholipid at a concentration between 0.1 mol % to about 50 mol % (e.g. between about 2.5 mol % to about 20 mol %); (iii) a sterol at a concentration between about 1 mol % to about 95 mol % (e.g. about 20 mol % to about 80 mol %); and (iv) a PEG-containing lipid at a concentration between about 0.1 mol % to about 50 mol % (e.g. between about 2.5 mol % to about 20 mol %). In an embodiment, the LNP comprises one of (i)-(iv). In an embodiment, the LNP comprises two of (i)-(iv). In an embodiment, the LNP comprises three of (i)-(iv). In an embodiment, the LNP comprises each of (i)-(iv). In some embodiments, the LNP comprises (i) and (ii). In some embodiments, the LNP comprises (i) and (iii). In some embodiments, the LNP comprises (i) and (iv). In some embodiments, the LNP comprises (ii) and (iii). In some embodiments, the LNP comprises (ii) and (iv). In some embodiments, the LNP comprises (iii) and (iv). In some embodiments, the LNP comprises (i), (ii), and (iii). In some embodiments, the LNP comprises (i), (ii), and (iv). In some embodiments, the LNP comprises (ii), (iii), and (iv).

The LNP (e.g., as described herein) may comprise one or more of the following components: (i) Ionizable cationic lipid (ICL) at a concentration between about 1 mol % to about 95 mol % (e.g. about 20 mol % to about 80 mol %); (ii) DSPC at a concentration between 0.1 mol % to about 50 mol % (e.g. between about 2.5 mol % to about 20 mol %); (iii) cholesterol at a concentration between about 1 mol % to about 95 mol % (e.g. about 20 mol % to about 80 mol %); and (iv) DMG-PEG2k at a concentration between about 0.1 mol % to about 50 mol % (e.g. between about 2.5 mol % to about 20 mol %). In an embodiment, the LNP comprises two of (i)-(iv). In an embodiment, the LNP comprises three of (i)-(iv). In an embodiment, the LNP comprises each of (i)-(iv). In some embodiments, the LNP comprises (i) and (ii). In some embodiments, the LNP comprises (i) and (iii). In some embodiments, the LNP comprises (i) and (iv). In some embodiments, the LNP comprises (ii) and (iii). In some embodiments, the LNP comprises (ii) and (iv). In some embodiments, the LNP comprises (iii) and (iv). In some embodiments, the LNP comprises (iii) and (iv). In some embodiments, the LNP comprises (i), (ii), and (iii). In some embodiments, the LNP comprises (i), (ii), and (iv). In some embodiments, the LNP comprises (ii), (iii), and (iv).

In an embodiment, the LNP comprises a ratio of ionizable lipid to phospholipid of about 50:1 to about 1:1 (e.g., 40:1, 32:3, 6:1, 7:1, 5:1, 24:5, 26:5, 10:3, 15:2, 16:7, 18:1, 3:1, 3:2, or 1:1). In an embodiment, the LNP comprises a ratio of ionizable lipid to phospholipid of about 15:2. In an embodiment, the LNP comprises a ratio of ionizable lipid to phospholipid of about 5:1. In an embodiment, the LNP comprises a ratio of ionizable lipid to a sterol of about 10:1 to about 1:10 (e.g., 9:1, 8:1, 8:7, 7:1, 7:5, 7:3, 6:1, 6:5, 5:1, 5:3, 4:1, 4:3, 3:1, 2:1, 1:1, 1:2, 1:3, 3:4, 1:4, 3:5, 1:5, 4:5, 1:6, 5:6, 7:6, 7:8, or 8:9). In an embodiment, the LNP comprises a ratio of ionizable lipid to an alkylene-containing lipid of about 1:10 to about 10:1 (e.g., 1:9, 1:8, 7:8, 7:1, 7:5, 7:3, 6:1, 6:5, 5:1, 5:3, 4:1, 4:3, 3:1, 2:1, 1:1, 1:2, 1:3, 3:4, 1:4, 3:5, 1:5, 4:5, 1:6, 5:6, 7:6, 7:8, or 8:9). In an embodiment, the LNP comprises a ratio of phospholipid to an alkylene-containing lipid of about 10:1 to about 1:10 (e.g., 9:1, 8:1, 8:7, 7:1, 7:5, 7:3, 6:1, 6:5, 5:1, 5:3, 4:1, 4:3, 3:1, 2:1, 1:1, 1:2, 1:3, 3:4, 1:4, 3:5, 1:5, 4:5, 1:6, 5:6, 7:6, 7:8, or 8:9). In an embodiment, the LNP comprises a ratio of a sterol to an alkylene-containing lipid of about 50:1 to about 1:1 (e.g., 40:1, 32:3, 6:1, 7:1, 5:1, 24:1, 22:1, 20:1, 22:5, 24:5, 26:5, 10:3, 15:2, 16:7, 18:1, 3:1, 3:2, or 1:1).

In an embodiment, a LNP (e.g., described herein) comprises two of an ionizable lipid, a phospholipid, a sterol, and an alkylene glycol-containing lipid (e.g., PEG-containing lipid). In another embodiment, a LNP (e.g., described herein) comprises three of an ionizable lipid, a phospholipid, a sterol, and an alkylene glycol-containing lipid (e.g., PEG-containing lipid). In an embodiment LNP (e.g., described herein) comprises each of an ionizable lipid, a phospholipid, a sterol, and an alkylene glycol-containing lipid (e.g., PEG-containing lipid).

In some embodiments, an LNP described herein has a diameter between 5 and 500 nm, e.g., between 10 and 400 nm, 20 and 350 nm, 25 and 325 nm, 30 and 300 nm, 50 and 250 nm, 60 and 200 nm, 75 and 190 nm, 80 and 180 nm, 100 and 200 nm, 200 and 300 nm, and 150 and 250 nm. The diameter of an LNP may be determined by any method known in the art, for example, dynamic light scattering, transmission electron microscopy (TEM) or scanning electron microscopy (SEM). In some embodiments, an LNP has a diameter between 50 and 100 nm, between 70 and 100 nm, and between 80 and 100 nm. In an embodiment, an LNP has a diameter of about 90 nm. In some embodiments, an LNP described herein has a diameter greater than about 30 nm. In some embodiments, an LNP has a diameter greater than about 35 nm, about 40 nm, about 45 nm, about 50 nm, about 60 nm, about 70 nm, about 80 nm, about 90 nm, about 100 nm, about 120 nm, about 140 nm, about 160 nm, about 180 nm, about 200 nm, about 225 nm, about 250 nm, about 275 nm or about 300 nm. In an embodiment, an LNP has a diameter greater than about 70 nm. In an embodiment, an LNP has a diameter greater than about 90 nm. In an embodiment, an LNP has a diameter greater than about 180 nm.

In some embodiments, a plurality of LNPs described herein has an average diameter ranging from about 40 nm to about 180 nm. In some embodiments, a plurality of LNPs described herein has an average diameter from about 50 nm to about 150 nm. In some embodiments, a plurality of LNPs described herein has an average diameter from about 50 nm to about 120 nm. In some embodiments, a plurality of LNPs described herein has an average diameter from about 60 nm to about 120 nm. In some embodiments, a plurality of LNPs has an average diameter of about 40 nm, about 45 nm, about 50 nm, about 60 nm, about 70 nm, about 80 nm, about 90 nm, about 100 nm, about 120 nm, about 140 nm, about 160 nm, about 180 nm In some embodiments, a nanoparticle or plurality of nanoparticles described herein has an average neutral to negative surface charge of less than −100 mv, for example, less than −90 mv, −80 mv, −70 mv, −60 mv, −50 mv, −40 mv, −30 mv, and −20 mv. In some embodiments, a nanoparticle or plurality of nanoparticles has a neutral to negative surface charge of between −100 mv and 100 mv, between −75 mv to 0, or between −50 mv and −10 mv.

In some embodiments, at least 5% (e.g., at least 10%, at least 15%, at least 20%, at least 25%, at least 30%, at least 40%, at least 50%, at least 60%, at least 70%, at least 80%, at least 90%, at least 95%, or at least 99%) of the nanoparticles of a plurality of nanoparticles have an average neutral to negative surface charge of less than −100 mv. In some embodiments, a nanoparticle or plurality of nanoparticles has an average surface charge of between −20 mv to +20, between −10 mv and +10 mv, or between −5 mv and +5 mv at pH 7.4. LNPs that are neutral in charge have improved pharmacokinetics and biological performance compared to cationic LNPs.

Making Lipid Nanoparticles (LNPs)

The method of making an LNP can comprise mixing a first solution with a second solution. Mixing can be achieved using standard liquid mixing techniques, such as propellor mixing, vortexing solutions or preferably through microfluidic mixing or high efficiency T-mixing. In some embodiments, the first solution comprises a lipid or a plurality of lipids and a nucleic acid, where all components are solubilized, in water/solvent system. The solvent may be any water miscible solvent (e.g., ethanol, methanol, isopropanol, acetonitrile, dimethylformamide, dimethylsulfoxide, dioxane or tetrahydrofuran). In some embodiments, the first solution comprises a small percentage of water or pH buffered water. The first solution may comprise up to at least 60% by volume of water, e.g., up to at least about 0.05%, 0.1%, 0.5%, 1%, 2%, 3%, 4%, 5%, 10%, 15%, 20%, 25%, 30%, 35%, 40%, 45%, 50%, 55% or 60% by volume of water. In an embodiment, the first solution comprises between about 0.05% and 60% by volume of water, e.g., between about 0.05% and 50%, about 0.05% and 40%, or about 5% and 20% by volume of water.

In some embodiments, the first solution comprises a single type of lipid, for example, an ionizable lipid, a phospholipid, a sterol, or a PEG-containing lipid. In some embodiments, the first solution comprises a plurality of lipids. In some embodiments, the plurality comprises an ionizable lipid, a phospholipid, a sterol, or a PEG-containing lipid. In some embodiments, the plurality of lipids comprise cholesterol, 1,2-distearoyl-sn-glycero-3-phosphocholine (DSPC), 1,2-dimyristoyl-rac-glycero-3-methylpolyoxyethylene2000 (DMG-PEG2k) or α-(3'-{[1,2-di(myristyloxy)propanoxy] carbonylamino}propyl)-ω-methoxy, polyoxyethylene (PEG2000-C-DMG), and an ionizable lipid. The plurality of lipids may exist in any ratio. In an embodiment, the plurality of lipids comprises an ionizable lipid or sterol, a phospholipid, a sterol, a PEG-containing lipid of the above lipids or a combination thereof in a particular ratio (e.g., a ratio described herein).

In some embodiments, the second solution is water. In some embodiments, the second solution is an aqueous buffer with a pH between 3-6 (e.g., a pH of about 3, about 4, about 5, or about 6). The second solution may comprise a load component, e.g., a nucleic acid (e.g., mRNA). The second solution may comprise a small percentage of water-miscible organic solvent. The second solution may comprise up to at least 60% by volume of at least one water miscible organic solvent, e.g., up to at least about 0.05%, 0.1%, 0.5%, 1%, 2%, 3%, 4%, 5%, 6%, 7%, 8%, 9%, 10%, 15%, 20%, 25%, 30%, 35%, 40%, 45%, 50%, 55%, 60% or any percent therebetween by volume of at least one organic solvent (e.g., a water miscible organic solvent). In an embodiment, the second solution comprises between about 0.05% and 60% by volume of organic solvent, e.g., between about 0.05% and 50%, about 0.05% and 40%, or about 5% and 20% by volume of organic solvent (e.g., a water miscible organic solvent). The aqueous buffer solution can be an aqueous solution of citrate buffer. In some embodiments, the aqueous buffer solution is a citrate buffer solution with a pH between 4-6 (e.g., a pH of about 4, about 5, or about 6). In an embodiment, the aqueous buffer solution is a citrate buffer solution with a pH of about 6.

In some embodiments, the solution comprising a mixture of the first and second solutions comprising the LNP suspension can be diluted. In some embodiments, the pH of the solution comprising a mixture of the first and second solutions comprising the LNP suspension can be adjusted. Dilution or adjustment of the pH of the LNP suspension can be achieved with the addition of water, acid, base or aqueous buffer. In some embodiments, no dilution or adjustment of the pH of the LNP suspension is carried out. In some embodiments, both dilution and adjustment of the pH of the LNP suspension is carried out.

In some embodiments, excess reagents, solvents, unencapsulated nucleic acid maybe removed from the LNP suspension by tangential flow filtration (TFF) (e.g., diafiltration). The organic solvent (e.g., ethanol) and buffer may also be removed from the LNP suspension with TFF. In some embodiments, the LNP suspension is subjected to dialysis and not TFF. In some embodiments, the LNP suspension is subjected to TFF and not dialysis. In some embodiments, the LNP suspension is subjected to both dialysis and TFF.

In one aspect, the present disclosure features a method comprising treating a sample of LNPs comprising nucleic acid, with a fluid comprising a detergent (e.g., Triton X-100, or anionic detergents (such as, but not limited to, sodium dodecyl sulfate (SDS), or non-ionic detergent, such as but not limited to β-octylglucoside, or Zwittergent 3-14) for a period of time suitable to degrade the lipid layer and thereby release the encapsulated and/or entrapped nucleic acid(s). In an embodiment, the method further comprises analyzing the sample for the presence, absence, and/or amount of the released nucleic acid(s).

LNP Comprising Ligands

Some aspects of the disclosure relate to LNP comprising a ligand (also referred herein as targeting ligand) having a binding specificity for a cell surface antigen, wherein the binding of the ligand to the antigen induces the internalization of the ligand. Some embodiments relate to compositions comprising LNP comprising a ligand as described herein.

In some embodiment, the targeting ligand is coupled to a lipid conjugate. For example, the lipid conjugate can be a hydrophilic polymer-lipid conjugate such as, but not limited to, PEG(2000)-DSPE or PEG(2000)-DSG. Coupling can be achieved by a variety of chemistries know in the art (for example, see Bioconjugates Techniques (Greg T. Hermanson), 3rd Edition, 2013, Elsevier). In some embodiment, the targeting ligand is coupled to the lipid conjugate through a linker. The linker molecule generally contains a hydrophilic polymer chain, such as PEG-terminally linked to a lipid domain (phospholipid or sterol) and contains a thiol-reactive functional group such as a maleimide at the terminus. The linkers comprising PEG spacers of size, phosphatidylethanolamine (PE) lipid anchors of various hydrocarbon chain length, and terminal maleimide or iodoacetate groups are currently commercially available from Avanti Polar Lipids (Alabama, USA) and NOF Corporation (Japan). One such strategy commonly used is to couple protein to a thiol-reactive lipopolymer linker, such as 1,2-distearoyl-sn-glycero-3-phosphoethanolamine-N-[maleimide(polyethylene glycol)-2000 (Mal-PEG-DSPE). Preferably, the protein of interest is engineered to contain one cysteine in the C-terminus to ensure a single-point conjugation. Alternatively, F(ab)$_2$ or Fab' can be enzymatically generated from IgGs and by reduction of disulfide bonds with a reducing agent such as dithiothreitol (DTT), mercaptoethylamine, (tris(2-carboxyethyl)phosphine) TCEP-HCL generate reactive cysteine thiol groups to couple to Mal-PEG-DSPE. The reaction of Mal-PEG-DSPE with reduced cysteine takes place in aqueous buffer at pH 5.5-7.5, for example pH 5.5, 6, 6.5, 7, 7.5, and preferably pH 6.0. The reaction is typically complete within 4 hours. A small amount of cysteine or mercaptoethanol is added to react with unreacted maleimide groups and quenches the coupling reaction. Although it is not necessary to remove unconjugated protein prior to the subsequent membrane insertion step it is useful to purify the conjugate for the purposes of storage and allow more precise characterization. Due to the large size of the lipopolymer micelles (equivalent molecular weight 850 kDa; Nellis et al., 2005a), size exclusion chromatography (SEC) is a convenient way to do so. Characterization of such protein-conjugates is achieved by a variety of techniques. For example, the purity is determined by SEC, molecular weight is quantitated by sodium dodecyl sulphate-polyacrylamide gel electrophoresis (SDS-PAGE), protein melting points by differential scanning calorimetry (DSC), isoelectric point determination by capillary electrophoresis and target binding affinity by surface plasmon resonance (BIAcore) and biolayer interferometry (ForteBio).

Examples of targeting ligands may be antibodies or antibody fragments against cell surface receptors, including the Her2 receptor, epidermal growth factor receptor (EGFR) receptor, Ephrin A2 receptor, CLEC9A receptor, DEC205 receptor, CLEC4A receptor, XCR1 receptor, CD141 receptor, HLA-DR receptor, transferrin receptor type 1, transferrin receptor type 2, VEGF receptor, PDGF receptor, integrin, NGF receptor, CD19, CD20, CD22, CD33, CD43, CD38, CD56, CD69, prostate specific membrane antigen (PSMA) or a variety of other cell surface receptors, or glycoconjugates, proteoglycans, glycoproteins, and glycolipids such as the glycoconjugate N-acetylgalactosamine (GalNAc) ligand which binds the asialoglycoprotein receptor (ASGPR), or small molecule conjugates such as folate-PEG-DSPE which targets the folate receptor.

In one embodiment, the targeting ligand is an anti-DEC205 antibody. DEC-205 (CD205) is a type I cell surface protein expressed primarily by dendritic cells (DC). It is found on interdigitating DC in T cell areas of lymphoid tissues, bone marrow-derived DC, Langerhan's cells, and at low levels on macrophages and T cell and is significantly up-regulated during the maturation of DC. Expression of DEC-205 is positively correlated with that of CD8a, both being found at high levels on lymphoid DC and at low levels on myeloid DC. DEC-205 is also expressed at moderate levels by B cells and is up-regulated during the pre-B cell to B cell transition. Recombinant anti-human DEC205 antibody is commercially available from Creative Biolabs.

In one embodiment, antigen specific targeting on LNPs is achieved by preparing ligand-targeted LNP by co-incubation of LNP with targeting ligand-lipid conjugate. The targeting ligand-lipid conjugate may be prepared prior to LNP preparation (see Nellis et al. Biotechnol Prog. 2005 January-February; 21(1):205-20).

In one embodiment, LNPs are co-incubated with antibody or fragment-PEG-phospholipid micelles or other ligand-conjugate and heated at 37° C. overnight to promote antibody conjugate insertion into the LNP outer membrane (Nellis et al. Biotechnol Prog. 2005 January-February; 21(1):221-32). In another aspect, insertion can be achieved by heating at elevated temperatures for shorter time periods, for example 0.5-8h at 37° C., or preferably 0.5-2h at 37° C. Micellar insertion can be quenched by lowering the temperature quickly by putting the LNPs on ice after which they can be stored in the refrigerator at 4° C. The total amount of lipid conjugate added can be between 0.02%-2% of total lipid, or preferably 0.1%-1%, or preferably 0.1%-0.5% total lipid. The incorporation efficiency of antibody-lipid conjugate can be measured by SDS-PAGE after LNP dissociation by SDS or other detergents by comparison to a standard curve of the same protein (Nellis et al. Biotechnol Prog. 2005 January-February; 21(1):205-20). The insertion efficiency of other targeting ligands can be measured by ultra high performance liquid chromatography equipped with evaporative light scattering detector (UPLC-ELSD) (Gauthier et al., J Mol Sci. 2019 Nov. 12; 20(22):5669).

Figure 2:
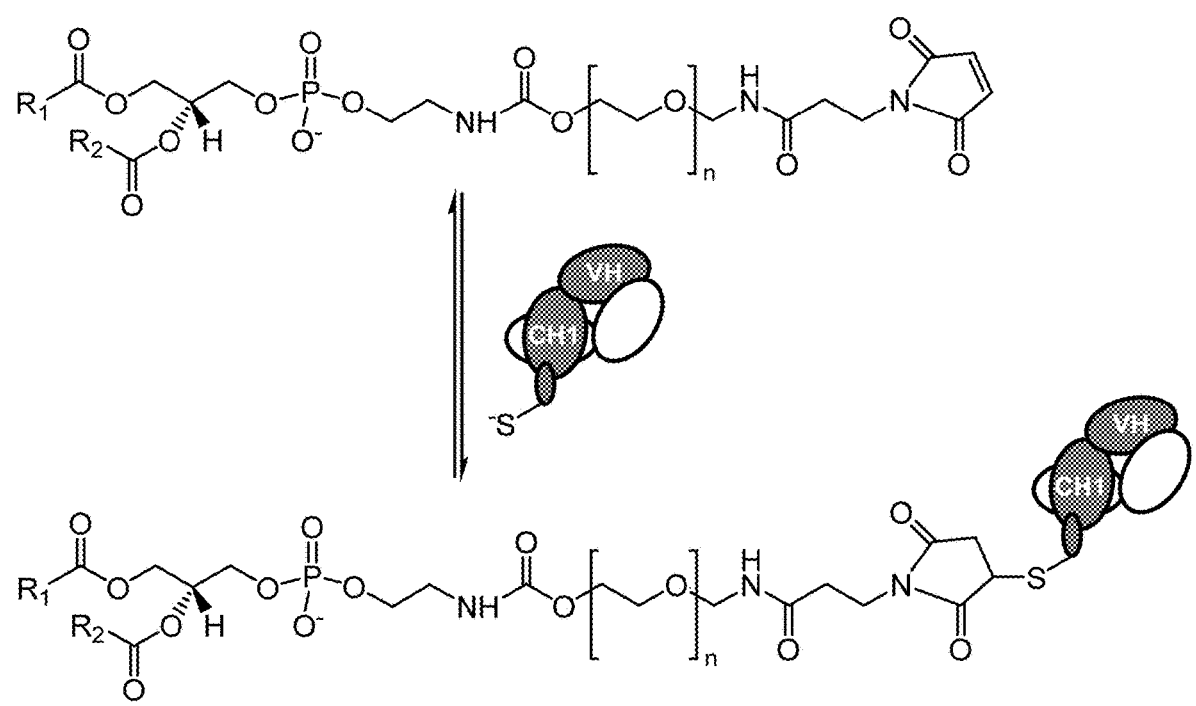
FIG. 2 shows the reaction of the reduced c-terminal cysteine of a Fab' antibody fragment with a maleimide terminated-poly(ethylene glycol) 2000 derivatized distearoylphosphatidylethanolamine. R1 and R2 are stearic acid. The final antibody lipopolymer conjugate is an intermediate that is subsequently inserted into the outer lipid layer of lipidic nanoparticle to make it actively targeted.

FIG. 2 shows the reaction of the reduced c-terminal cysteine of a Fab' antibody fragment with a maleimide terminated-poly(ethylene glycol) 2000 derivatized distearoylphosphatidylethanolamine. R1 and R2 are stearic acid. The final antibody lipopolymer conjugate is an intermediate that is subsequently inserted into the outer lipid layer of lipidic nanoparticle to make it actively targeted.

LNP targeting can also accomplished by adding lipids to the formulation. For example, phosphatidylserine is known to redistribute to the external surface of the plasma membrane during apoptosis and is a molecular cue for phagocytotic cell attraction (Fadok et al. Curr Biol. 2003 Aug. 19; 13(16):R655-7). Phosphatidylserine (PS) and phosphatidylglycerol (PG) are recognized by dendritic cells and can induce uptake and activation of dendritic cells LNP targeting can also accomplished by adding certain anionic phospholipids to the formulation (Table 3). For example, phosphatidylserine is known to redistribute to the external surface of the plasma membrane during apoptosis and is a molecular cue for phagocytotic cell attraction (Fadok et al. Curr Biol. 2003 Aug. 19; 13(16):R655-7). Phosphatidylserine (PS) and phosphatidylglycerol (PG) are recognized by dendritic cells and can induce uptake and activation of dendritic cells (Caronni et al., Nat Comm. 2021 Apr. 14; 12: 2237-2253; Ischihashi et al., PLOS One 2013). Although anionic phospholipids have been used previously in the context of liposomes, their inclusion in lipidic nanoparticles that include condensed nucleic acids is unexpected since anionic headgroups may compete for binding sites of the ionizable cationic lipids with the phosphate backbone of mRNA, may inhibit intracellular escape by altering the surface charge, or may result in aggregation of LNPs during formation or storage.

TABLE 3

Anionic Phospholipid Targeting Moieties

[Chemical structure] DSPS (L-isomer)

[Chemical structure] DPPS (L-isomer)

[Chemical structure] DMPS (L-isomer)

[Chemical structure] DOPS (L-isomer)

[Chemical structure] DSPS (D-isomer)

[Chemical structure] DSPG

[Chemical structure] DPPG

TABLE 3-continued

Anionic Phospholipid Targeting Moieties

N-Glu-DSPE

N-Suc-DSPE

In one embodiment, the anionic targeting ligands are selected from the group, phosphatidylserine (PS), phoshatidylglycerol (PG), N-glutaryl-phosphatidylethanolamine (N-glu-PE), or N-succinyl-phosphatidylethanolamine (N-Suc-PE). In one embodiment, the anionic phospholipid used is phosphatidylserine. In another embodiment, the phosphatidylserine contains the L-isomer of serine. In another embodiment, the acyl chains for the phosphatidylserine are fully saturated, such as the case for dimyristoylphosphatidyl-L-serine (DMPS), dipalmitoylphosphatidyl-L-serine (DPPS), or distearoylphosphatidyl-L-serine (DSPS). In a preferred embodiment, the PS used is the L-isomer of either DPPS or DSPS. The phosphatidylserine may also contain an asymmetric acyl chain composition, for example where one acyl chain is stearic acid and another is palmitic acid.

In one embodiment, PS or PG are added to the LNP lipid formulation at a concentration between about 0.1 mol % to about 20 mol %, about 0.1 mol % to about 10 mol %, about 0.1 mol % to about 5 mol %, about 0.5 mol % to about 20 mol %, about 0.5 mol % to about 10 mol %, about 0.5 mol % to about 5 mol %, about 1 mol % to about 20 mol %, about 1 mol % to about 10 mol %, or about 1 mol % to about 5 mol %, of the total lipid content of the LNP. In one embodiment, the PS is added to the LNP lipid formulation at a concentration between about 1 mol % to about 20 mol %, about 2.5 mol % to about 10 mol %, about 3 mol % to about 9 mol %, or about 4 mol % to about 8 mol %, of the total lipid content of the LNP.

In one embodiment the PS lipid is included in the LNP composition comprising ionizable cationic lipids known in the art, including DODAP, AKG-OA-DM2, O-11769, DLin-MC3-DMA, DLin-KC2-DMA, DLin-KC3-DMA, ALC-0315, and SM-102.

In another embodiment the PS lipid is included in the LNP composition comprising ICLs of Formula I, II, III, combinations thereof or pharmaceutically salts thereof. In another embodiment the PS lipid is included in the LNP composition using N/P ratios between 3 and 8, between 4 and 7, or between 5 and 6.

In some aspects, a method of delivering a nucleic acid to a cell is provided, the method comprising: contacting the cell with a composition comprising an LNP comprising a ligand (also referred herein as targeting ligand) having a binding specificity for a cell surface antigen, wherein the binding of the ligand to the antigen induces the internalization of the ligand. In some embodiments, the targeting ligand can be, but is not limited to, an internalizing antibody, or a fragment thereof, a small molecule conjugates or glycoconjugates. In some embodiments, the binding of the targeting ligand to a specific cell surface antigen induces the internalization of the LNP with the targeting ligand attached by a cell expressing at least 100,000 or at least 1,000,000 molecules of the antigen when contacted and incubated with the cell under internalizing conditions.

TABLE 4

Exemplary dialkyl and branched ionizable cationic lipids

DODAP

AKG-OA-DMS

TABLE 4-continued
Exemplary dialkyl and branched ionizable cationic lipids
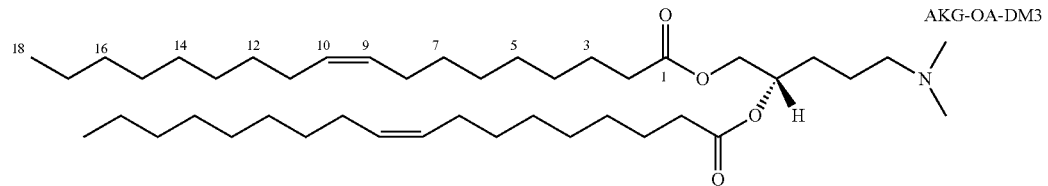
AKG-OA-DM3
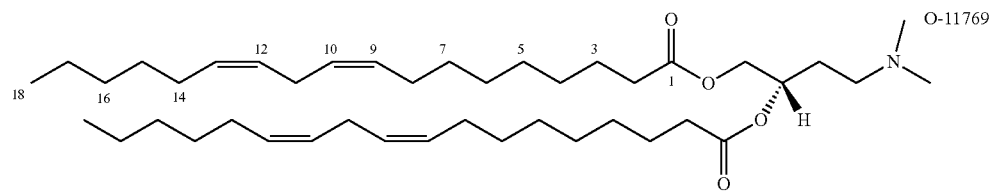
O-11769
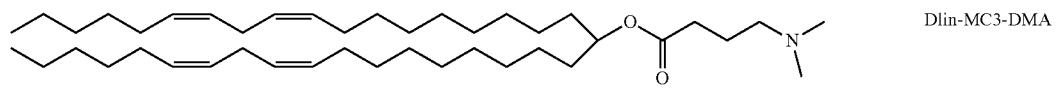
Dlin-MC3-DMA
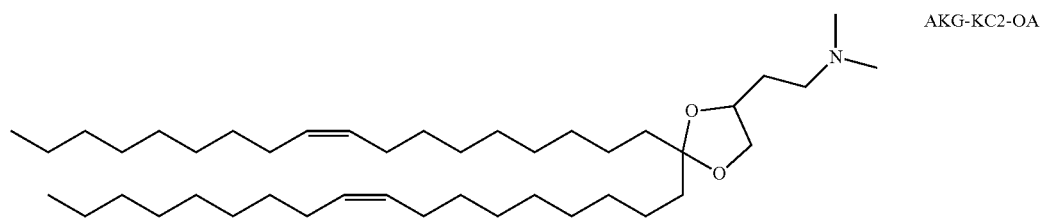
AKG-KC2-OA
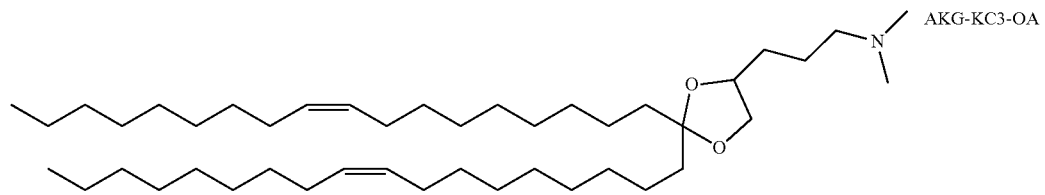
AKG-KC3-OA
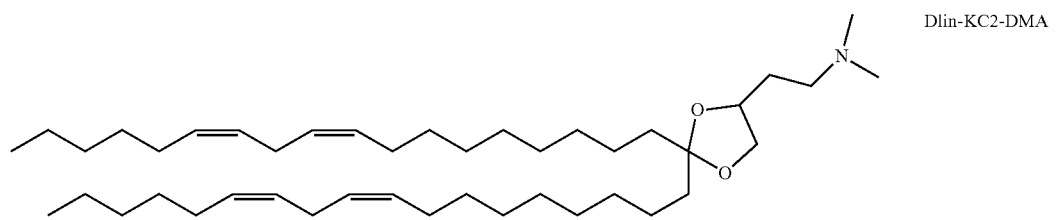
Dlin-KC2-DMA
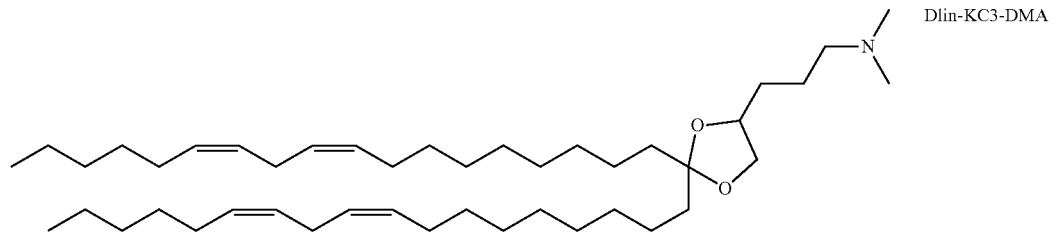
Dlin-KC3-DMA TABLE 4-continued Exemplary dialkyl and branched ionizable cationic lipids

ALC-0315

SM-102

Compositions

In some embodiments, a lipidic nanoparticle composition comprises lipids and nucleic acids, the lipidic nanoparticles comprising a compound of Formula I, II, III, combinations thereof or pharmaceutically acceptable salts thereof.

In some embodiments, an LNP comprises an ionizable lipid having a structure of Formula (IV).

In some embodiments, the composition further comprises a pharmaceutical excipient.

In some embodiments, the lipidic nanoparticles are in an aqueous medium.

In some embodiments, the nucleic acid is entrapped in the lipidic nanoparticle with a compound of Formula I, II, III, IV or combinations thereof, wherein the nucleic acid is either RNA or DNA. In some embodiments, the nucleic acid is mRNA. In some embodiments, the nucleic acid is siRNA. In some embodiments, the nucleic acid is DNA.

In some embodiments, the lipidic nanoparticle comprises a membrane comprising phosphatidylcholine and a sterol. In some embodiments, the sterol is cholesterol. In some embodiments, the lipidic nanoparticle comprises a membrane comprising phosphatidylcholine, ionizable cationic lipid (ICL). In some embodiments, the ICL have a structure of Formula I, II, III or IV, and cholesterol, wherein the membrane separates the inside of the lipidic nanoparticles from the aqueous medium. In some embodiment, the ICL have a structure as shown in Table 1A and Table 2. In some embodiment, the ICL have a structure as shown in Table 1B. In some embodiments, the phosphatidylcholine is distearoylphosphatidylcholine (DSPC) or hydrogenated soy phosphatidylcholine (HSPC). In some embodiments, the ionizable cationic lipid to cholesterol molar ratios is from about 65:35 to 40:60. In some embodiments, the ICL to cholesterol molar ratio is from about 60:40 to about 45:55.

In some embodiments, the phosphatidylcholine to cholesterol molar ratio is from about 1:5 to about 1:2.

In some embodiments, the membrane further comprises a polymer-conjugated lipid.

In some embodiments, the lipidic nanoparticle comprises ICL, DSPC, cholesterol and polymer-conjugated lipid in a about 49.5:10.3:39.6:2.5 molar ratio.

In some embodiments, the polymer-conjugated lipid is PEG(2000)-dimyristoylglycerol (PEG-DMG) or PEG(Mol. weight 2,000)-dimyristoylphosphatidylethanolamine (PEG-DMPE).

The compositions of this disclosure may be administered by various routes, for example, to effect systemic delivery via intravenous, parenteral, intraperitoneal, or topical routes. The compositions may be administered intravenously, subcutaneously, or intraperitoneally to a subject. In some embodiments, the disclosure provides methods for in vivo delivery of nucleic acids to a subject.

In some embodiments, the composition is a liquid pharmaceutical formulation for parenteral administration.

In some embodiments, the composition is a liquid pharmaceutical formulation for subcutaneous, intramuscular, or intradermal administration.

In some embodiments, the composition is in the form of a lyophilized powder, that is subsequently reconstituted with aqueous medium prior to administration.

Methods of Use

Targeting of Dendritic Cells

Dendritic cells (DCs) are specialized antigen-presenting cells that play a central role in initiating and regulating adaptive immunity. Owing to their potent antigen (Ag) presentation capacity and ability to generate distinct T-cell responses, efficient and specific delivery of Ags to DCs is the cornerstone for generating Ag-specific effector and memory cells against tumors or pathogens.

Dendritic cells can be generated from human blood monocytes by adding granulocyte-macrophage colony-stimulating factor (GM-CSF), IL-4, and IFN-gamma to differentiate monocyte-derived DC in vitro. Cells in culture exhibit both dendritic and veiled morphologies, the former being adherent, and the latter suspended. Phenotypically, they are CD1a−/dim, CD11a+, CD11b++, CD11c+, CD14dim/−, CD16a−/dim, CD18+, CD32dim/−, CD33+, CD40+, CD45R0+, CD50+, CD54+, CD64−/dim, CD68+, CD71+, CD80dim, CD86+/++, MHC class I++/, HLA−DR++/, HLA−DP+, and HLA−DQ (Geiseler et al. Dev Immunol. 1998; 6(1-2):25-39).

Alternatively, human primary blood dendritic cell lines have been developed and are commercially available from Creative Biolabs.

CD8+ T cells can produce IL2, IFN-γ, and TNF, cytokines that are known to have critical functions during *Mycobacterium tuberculosis* infection. Importantly, CD8+ T cells have cytolytic functions to kill *Mycobacterium tuberculosis*-infected cells via granule-mediated function (via perforin, granzymes, and granulysin) or Fas-Fas ligand interaction to induce apoptosis. In humans, CD8+ T cell can produce granulysin, which can kill *Mycobacterium tuberculosis* directly. Therefore, it is anticipated that antigen generating mRNA LNPs delivered to DC will stimulate a CD8+ T cell response to fight against *Mycobacterium tuberculosis* infection.

CD8+ T cells are able to recognize *M. tuberculosis* specific antigens (as peptides) presented by classical and non-classical MHC molecules. Classically restricted CD8+ T cells have been identified that recognize antigens presented by antigen presenting cells in the context of classical MHC Ia (HLA-A, -B, -C) molecules. Non-classically restricted CD8+ T cells include those CD8+ T cells that are capable of recognizing Mg antigen in the context of HLA-E molecules (non-MHC 1a), glycolipids associated with group 1 CD1 molecules and MHC I-related molecules (MR1) such as mucosal associated invariant T cells (MAIT). Finally, γδ T cells represent a separate population of CD8 (and CD4) T cells that have both innate and adaptive functions in response to *Mycobacterium tuberculosis* infection. CD8+ T cells have been shown to play direct functions in response to *Mycobacterium tuberculosis* infection but they also play important roles in orchestrating many different functions in the overall host immune response (e.g., interaction to provide optimal CD4 T cell function)

In one embodiment, LNPs can be added to cultured human dendritic cells at an appropriate concentration, (e.g. 1-5 μg/mL mRNA). After some time to allow for cellular uptake and antigen expression, human T cells (HemaCare) can be added, and the cell culture media is sampled at various times for INF-γ by Elisa (R&D Systems, DIF50C). Alternatively, the cells can be analyzed by flow cytometry for CD8+ marker or intracellular INFγ production (PE anti-human IFN-γ antibody, Biolegend).

In one embodiment, LNPs can be administered into a subject at a dose of 0.01-5 mg/kg mRNA by any route of administration outlined above. According to some embodiments, a proportion of LNPs are taken up DC cells, while most will accumulate in the liver and spleen. The DC cells can express the antigenic peptide, process it for MHC I presentation and travel to the lymph node for presentation to naïve T cells inducing an education of memory T-cells towards the antigen.

In one embodiment, LNPs that have been modified with a targeting ligand such as anti-DEC205-PEG-DSPE can be administered into a subject at a dose of 0.01-5 mg/kg mRNA. According to some embodiments, a higher proportion of LNPs can be taken up DC cells, allowing for increased production of antigenic peptide compared to non-targeted LNP and a more efficient vaccination against the pathogen. Additional targeting ligands for dendritic cells include, but are not limited to, CLEC9A, CLEC4A, XCR1, CD141, and HLD-DR. For example, assessing the CD8+ reactivity to the in vivo produced antigen could be accomplished by measuring INFγ plasma levels by species specific IFN-gamma Quantikine ELISA Kits from R&D Systems.

In some embodiments, LNP compositions provide desirable pharmacokinetic properties such as extended plasma half-life and stable encapsulation of mRNA. The plasma half-life can be measured as the percentage of the injected dose (ID) remaining in blood after 6 or 24 hours following injection intravenously in immunocompetent mice. The stability of the encapsulation of mRNA over 24 hours in plasma can be determined by changes in the mRNA-to-lipid ratio (mRNA/L ratio) following iv administration in mice. In some embodiments, the percentage of encapsulated mRNA remaining in blood is greater than 20%, preferably greater than 30%, and most preferably greater than 40% of the injected dose at 6 hours. The percent retained in blood after 24 h is preferably greater than 10%, and more preferably greater than 20% of the injected dose.

Disclosed herein are methods for preventing mycobacteria infection, such as *Mycobacterium tuberculosis*, or gram positive bacteria, such as methicillin-resistant *Staphylococcus aureus* (MRSA). Additional mycobacteria and gram positive bacteria include, but are not limited to, *Mycobacterium avium* complex, *Mycobacterium leprae, Mycobacterium gordonae, Mycobacterium abscessus, Mycobacterium abscessus, Mycobacterium mucogenicum, streptococci, vancomycin*-resistant enterococci (VRE), *Staphylococcus pneumoniae, Enterococcus faecium, Streptococcus agalactiae, Streptococcus pneumoniae, Streptococcus pyogenes*, the *viridans* group streptococci, *Listeria monocytogenes, Nocardia*, and *Corynebacterium.*

Administration of a vaccine for inducing a second immune response may provide MHC class II-presented epitopes that are capable of eliciting a CD4+ helper T cell response against cells expressing antigens from which the MHC presented epitopes are derived. Alternatively or additionally, administration of a vaccine for inducing a second immune response may provide MHC class I-presented epitopes that are capable of eliciting a CD8+ T cell response against cells expressing antigens from which the MHC presented epitopes are derived. Furthermore, administration of a vaccine for inducing a second immune response may provide one or more neo-epitopes (including known neo epitopes) as well as one or more epitopes not containing cancer specific somatic mutations but being expressed by cancer cells and preferably inducing an immune response against cancer cells, preferably a cancer specific immune response. In one embodiment, administration of a vaccine for inducing a second immune response provides neo—epitopes that are MHC class II—presented epitopes and/or are capable of eliciting a CD4+ helper T cell response against cells expressing antigens from which the MHC presented epitopes are derived as well as epitopes not containing cancer—specific somatic mutations that are MHC class I—presented epitopes and/or are capable of eliciting a CD8+ T cell response against cells expressing antigens from which the MHC presented epitopes are derived. In one embodiment, the epitopes do not contain cancer—specific somatic mutations.

A "cellular immune response", a "cellular response", a "cellular response against an antigen" or a similar term is meant to include a cellular response directed to cells characterized by presentation of an antigen with class I or class II MHC. The cellular response relates to cells called T cells or T-lymphocytes which act as either "helper cells" or "killer cells". The helper T cells (also termed CD4+T cells) play a central role by regulating the immune response and the killer cells (also termed cytotoxic T cells, cytolytic T cells, CD8+T cells or CTLS) kill diseased cells such as cancer cells, preventing the production of more diseased cells. In preferred embodiments, the present disclosure involves the stimulation of an anti Mycobacterium tuberculosis CTL response against the Mycobacterium expressing one or more expressed antigens and preferably presenting such expressed antigens with class I MHC.

An "antigen" according to the disclosure covers any substance that will elicit an immune response. In particular, an "antigen" relates to any substance, preferably a peptide or protein, that reacts specifically with antibodies or T-lymphocytes (T cells). As used herein, the term "antigen" comprises any molecule which comprises at least one epitope. Preferably, an antigen in the context of the present disclosure is a molecule which, optionally after processing, induces an immune reaction, which is preferably specific for the antigen (including cells expressing the antigen). According to the present disclosure, any suitable antigen may be used, which is a candidate for an immune reaction, wherein the immune reaction is preferably a cellular immune reaction. In the context of the embodiments of the present disclosure, the antigen is preferably presented by a cell, preferably by an antigen presenting cell which includes a diseased cell, in particular a cancer cell, in the context of MHC molecules, which results in an immune reaction against the antigen. An antigen is preferably a product which corresponds to or is derived from a naturally occurring antigen. Such naturally occurring antigens may include tumor antigens.

As used herein, an "antigen peptide" relates to a portion or fragment of an antigen which is capable of stimulating an immune response, preferably a cellular response against the antigen or cells characterized by expression of the antigen and preferably by presentation of the antigen such as diseased cells, in particular cancer cells. Preferably, an antigen peptide is capable of stimulating a cellular response against a cell characterized by presentation of an antigen with class I MHC and preferably is capable of stimulating an antigen-responsive cytotoxic T-lymphocyte (CTL). Preferably, the antigen peptides according to the disclosure are MHC class I and/or class II presented peptides or can be processed to produce MHC class I and/or class II presented peptides. Preferably, the antigen peptides comprise an amino acid sequence substantially corresponding to the amino acid sequence of a fragment of an antigen. Preferably, said fragment of an antigen is an MHC class I and/or class II presented peptide. Preferably, an antigen peptide according to the disclosure comprises an amino acid sequence substantially corresponding to the amino acid sequence of such fragment and is processed to produce such fragment, i.e., an MHC class I and/or class II presented peptide derived from an antigen. If a peptide is to be presented directly, i.e., without processing, in particular without cleavage, it has a length which is suitable for binding to an MHC molecule, in particular a class I MHC molecule, and preferably is 7-20 amino acids in length, more preferably 7-12 amino acids in length, more preferably 8-11 amino acids in length, in particular 9 or 10 amino acids in length.

The main types of professional antigen-presenting cells are dendritic cells, which have the broadest range of antigen presentation, and are probably the most important antigen-presenting cells, macrophages, B-cells, and certain activated epithelial cells. Dendritic cells (DCs) are leukocyte populations that present antigens captured in peripheral tissues to T cells via both MHC class II and I antigen presentation pathways. It is well known that dendritic cells are potent inducers of immune responses and the activation of these cells is a critical step for the induction of antitumoral immunity. Dendritic cells are conveniently categorized as "immature" and "mature" cells, which can be used as a simple way to discriminate between two well characterized phenotypes.

However, this nomenclature should not be construed to exclude all possible intermediate stages of differentiation. Immature dendritic cells are characterized as anti gen presenting cells with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g. CD54 and CD11) and costimulatory molecules (e.g., CD40, CD80, CD86 and 4-1 BB). Dendritic cell maturation is referred to as the status of dendritic cell activation at which such antigen—presenting dendritic cells lead to T cell priming, while presentation by immature dendritic cells results in tolerance. Dendritic cell maturation is chiefly caused by biomolecules with microbial features detected by innate receptors (bacterial DNA, viral RNA, endotoxin, etc.), pro-inflammatory cytokines (TNF, IL-1, IFNs), ligation of CD40 on the dendritic cell surface by CD4OL, and substances released from cells undergoing stressful cell death. The dendritic cells can be derived by culturing bone marrow cells in vitro with cytokines, such as granulocyte-macrophage colony-stimulating factor (GM CSF) and tumor necrosis factor alpha. Non-professional antigen-presenting cells do not constitutively express the MHC class II proteins required for interaction with naive T cells; these are expressed only upon stimulation of the non-professional antigen-presenting cells by certain cytokines such as IFNγ. "Antigen presenting cells" can be loaded with MHC class I presented peptides by transducing the cells with nucleic acid, preferably mRNA, encoding a peptide or polypeptide comprising the peptide to be presented, e.g. a nucleic acid encoding the antigen.

In some embodiments, a pharmaceutical composition comprising a gene delivery vehicle that targets a dendritic or other antigen presenting cell may be administered to a patient, resulting in transfection that occurs in vivo. As used herein, a "nucleic acid" is a deoxyribonucleic acid (DNA) or ribonucleic acid (RNA), more preferably RNA, most preferably in vitro transcribed RNA (IVT RNA) or synthetic RNA. Nucleic acids include according to the disclosure genomic DNA, cDNA, mRNA, recombinantly produced and chemically synthesized molecules. According to the disclosure, a nucleic acid may be present as a single-stranded or double-stranded and linear or covalently circularly closed molecule. A nucleic acid can, according to the disclosure, be isolated. The term "isolated nucleic acid" means, according to the disclosure, that the nucleic acid (i) was amplified in vitro, for example via polymerase chain reaction (PCR), (ii) was produced recombinantly by cloning, (iii) was purified, for example, by cleavage and separation by gel electrophoresis, or (iv) was synthesized, for example, by chemical synthesis. A nucleic can be employed for introduction into, i.e. transfection of cells, in particular, in the form of RNA which can be prepared by in vitro transcription from a DNA template. The RNA can moreover be modified before application by stabilizing sequences, capping, and polyadenylation.

As used herein, the term "RNA" relates to a molecule which comprises ribonucleotide residues and preferably being entirely or substantially composed of ribonucleotide residues. "Ribonucleotide" relates to a nucleotide with a hydroxyl group at the 2'-position of a B-D-ribofuranosyl group. The term "RNA" comprises double-stranded RNA, single-stranded RNA, isolated RNA such as partially or completely purified RNA, essentially pure RNA, synthetic RNA, and recombinantly generated RNA such as modified RNA which differs from naturally occurring RNA by addition, deletion, substitution and/or alteration of one or more nucleotides. Such alterations can include addition of non-nucleotide material, such as to the end (s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogs or analogs of naturally-occurring RNA.

As used herein, the term "RNA" includes and preferably relates to "mRNA". The term "mRNA" means "messenger-RNA" and relates to a "transcript" which is generated by using a DNA template and encodes a peptide or polypeptide. Typically, an mRNA comprises a 5'-UTR, a protein coding region, and a 3'-UTR. mRNA only possesses limited half-life in cells and in vitro. In the context of the present disclosure, mRNA may be generated by in vitro transcription from a DNA template. The term "modification" in the context of the RNA used in the present disclosure includes any modification of an RNA which is not naturally present in said RNA. In one embodiment of the disclosure, the RNA used according to the disclosure does not have uncapped 5'-triphosphates. Removal of such uncapped 5'-triphosphates can be achieved by treating RNA with a phosphatase. The RNA according to the disclosure may have modified ribonucleotides in order to increase its stability and/or decrease cytotoxicity. For example, in one embodiment, in the RNA used according to the disclosure 5-methylcytidine is substituted partially or completely, preferably completely, for cytidine. Alternatively or additionally, in one embodiment, in the RNA used according to the disclosure pseudouridine is substituted partially or completely, preferably completely, for uridine.

In one embodiment, the term "modification" relates to providing an RNA with a 5-cap or 5'-cap analog. The term "5-cap" refers to a cap structure found on the 5'-end of an mRNA molecule and generally consists of a guanosine nucleotide connected to the mRNA via an unusual 5' to 5 triphosphate linkage. In one embodiment, this guanosine is methylated at the 7-position. The term "conventional 5'-cap" refers to a naturally occurring RNA 5'-cap, preferably to the 7-methylguanosine cap (m'G). as used herein, the term "5'-cap" includes a 5'-cap analog that resembles the RNA cap structure and is modified to possess the ability to stabilize RNA and/or enhance translation of RNA if attached thereto, preferably in vivo and/or in a cell.

According to the disclosure, the stability and translation efficiency of RNA may be modified as required. For example, RNA may be stabilized and its translation increased by one or more modifications having a stabilizing effects and/or increasing translation efficiency of RNA. Such modifications are described, for example, in PCT/EP2006/009448 incorporated herein by reference. In order to increase expression of the RNA used according to the present disclosure, it may be modified within the coding region, i.e. the sequence encoding the expressed peptide or protein, preferably without altering the sequence of the expressed peptide or protein, so as to increase the GC content to increase mRNA stability and to perform a codon optimization and, thus, enhance translation in cells.

Aspects of the disclosure relate to a method of preventing a bacterial or viral infection, the method comprising administering to a subject in need thereof an effective amount of the composition provided herein to elicit an immune response.

Aspects of the disclosure provide methods of vaccinating a subject comprising administering to the subject a single dosage of the compositions described herein comprising a nucleic acid (e.g. mRNA) encoding an polypeptide in an effective amount to vaccinate the subject. In some embodiments, the nucleic acid is formulated within a cationic lipidic nanoparticle. In some embodiments, the lipidic nanoparticle composition is administered as a single injection.

In some embodiments, the bacterial infection is *Mycobacterium tuberculosis* infection.

In some embodiments, the viral infection is a coronavirus. In some embodiments, the coronavirus is SARS-CoV, MERS-CoV or SARS-CoV-2

In some embodiments, the viral infection is HIV/AIDS.

In some embodiments, the lipidic nanoparticle is administered parenterally.

In general, administration to a patient by intradermal injection is possible. However, injection may also be carried out intranodally into a lymph node (Maloy et al. (2001), Proc Natl Acad Sci USA 98:3299-3033). The resulting cells present the complex of interest and are recognized by autologous cytotoxic T lymphocytes which then propagate.

In some embodiments, the compositions is administered by inhalation. In some embodiments, the composition is formulated as nasal spray, and/or aerosol Actual dosage levels of the active agents in the pharmaceutical compositions disclosed herein may be varied so as to obtain an amount of the active agent which is effective to achieve the desired therapeutic response for a particular patient, composition, and mode of administration, without being toxic to the patient.

"Parenteral" as used herein in the context of administration means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The phrases "parenteral administration" and "administered parenterally" as used herein refer to modes of administration other than enteral (i.e., via the digestive tract) and topical administration, usually by injection or infusion, and includes, without limitation, intravenous, intramuscular, intraarterial, intrathecal, intracapsular, intraorbital, intracardiac, intradermal, intraperitoneal, transtracheal, subcutaneous, subcuticular, intraarticular, inhalation, subcapsular, subarachnoid, respiratory mucosal, intraspinal, epidural and intrasternal injection and infusion. Intravenous injection and infusion are often (but not exclusively) used for liposomal drug administration.

Dosage regimens can be adjusted to provide the optimum desired response (e.g., a therapeutic response). For example, one or more doses may be administered over time or the dose may be proportionally reduced or increased as indicated by the exigencies of the therapeutic situation.

In some embodiments, the dose comprises between 0.01 to 5 mg/kg of nucleic acid. In some embodiments, the dose comprises between 0.01 to 5 mg/kg of mRNA. In some embodiments, the dose comprises between 0.01 to 3 mg/kg of nucleic acid. In some embodiments, the dose comprises between 0.01 to 3 mg/kg of mRNA. In some embodiments, the dose comprises between 0.01 to 1 mg/kg of nucleic acid. In some embodiments, the dose comprises between 0.01 to 1 mg/kg of mRNA. In some embodiments, the dose comprises between 0.01 to 0.5 mg/kg of nucleic acid. In some embodiments, the dose comprises between 0.01 to 0.5 mg/kg of mRNA. In some embodiments, the dose comprises between 0.01 to 1 mg/kg of mRNA. In some embodiments, the dose comprises between 0.01 to 0.1 mg/kg of nucleic acid. In some embodiments, the dose comprises between 0.01 to 0.05 mg/kg of mRNA. In some embodiments, the dose comprises between 0.01 to 0.1 mg/kg of nucleic acid. In some embodiments, the dose comprises between 0.01 to 0.05 mg/kg of mRNA.

The dosage of the compounds and/or of their pharmaceutically acceptable salts or the LNPs comprising the compounds and/or of their pharmaceutically acceptable salts may vary within wide limits and should naturally be adjusted, in each particular case, to the individual conditions and to the pathogenic agent to be controlled.

ADDITIONAL EMBODIMENTS

1. A compound of Formula I or pharmaceutically acceptable salts thereof
2. A compound of Formula II or pharmaceutically acceptable salts thereof
3. A compound of Formula III or pharmaceutically acceptable salts thereof.
4. A compound of Formula IV or pharmaceutically acceptable salts thereof.
5. A compound having a structure as in Table 1A.
6. A compound having a structure as in Table 2, wherein the compound is bioreducible.
7. The compound of anyone of embodiments 1-6 above, wherein the compound has a pKa between 6 and 7.
8. A lipidic nanoparticle composition comprising a ionizable lipid of Formula I or pharmaceutically acceptable salts thereof, and a nucleic acid.
9. A lipidic nanoparticle composition comprising a ionizable lipid of Formula II or pharmaceutically acceptable salts thereof, and a nucleic acid.
10. A lipidic nanoparticle composition comprising a ionizable lipid of Formula III or pharmaceutically acceptable salts thereof, and a nucleic acid.
11. A lipidic nanoparticle composition comprising a ionizable lipid of Formula IV or pharmaceutically acceptable salts thereof, and a nucleic acid.
12. The composition of any one of embodiments 8-11 above, wherein the ionizable lipid encapsulate the nucleic acid.
13. The composition of any one of embodiments 8-11, wherein the nucleic acid is a siRNA.
14. The composition of any one of embodiments 8-11, wherein the nucleic acid is a DNA.
15. The composition of any one of embodiments 8-11, wherein the nucleic acid is a mRNA.
16. The composition of any one of embodiments 8-11, further comprising a sterol, phosphatidylcholine, or combinations thereof
17. The composition of embodiment 16, wherein the sterol is cholesterol.
18. The composition of embodiment 17, wherein the ionizable lipid to cholesterol molar ratios is from about 65:35 to about 40:60.
19. The composition of embodiment 17, wherein the ionizable lipid to cholesterol molar ratios is from about 60:40 to about 45:55.
20. The composition of embodiment 17, wherein the phosphatidylcholine to cholesterol molar ratio is from about 1:5 to about 1:2.
21. The composition of embodiment 17, further comprising a polymer-conjugated lipid.
22. The composition of embodiment 21, wherein the polymer-conjugated lipid comprises PEG(2000)-dimyristoylglycerol (PEG-DMG) or PEG(Mol. weight 2,000)-dimyristoylphosphatidylethanolamine (PEG-DMPE).
23. The composition of any one of embodiments 8-11, further comprising a targeting ligand, wherein the targeting ligand is oriented to the outside of the nanoparticle.
24. The composition of embodiment 23, wherein the targeting ligand is an antibody.
25. The composition of any one of embodiments 8-11, wherein the composition is a liquid pharmaceutical formulation.
26. The composition of any one of embodiments 8-11, wherein the percentage of oxidative degradation products for the ionizable lipid is less than 50% of that for a DLin-KC2-DMA or DLin-MC3-DMA control formulation.
27. A method of preventing a bacterial or viral infection, the method comprising administering to a subject in need thereof an effective amount of the composition of any one of embodiments 9-26, and a pharmaceutical excipient, wherein administration elicits an immune response.
28. The method of embodiment 27, wherein the composition is administered for subcutaneously, intramuscularly, or intradermally.
29. The method of embodiment 27, wherein the bacterial infection is *Mycobacterium tuberculosis* infection.
30. The method of embodiment 27, wherein the viral infection is a SARS-CoV, MERS-CoV or SARS-CoV-2 infection.
31. The method of embodiment 27, wherein the viral infection is a HIV infection.
32. The method of embodiment 27, wherein the infection is a form of nontuberculosis *Mycobacterium*.
33. A lipid nanoparticle (LNP) composition comprising an ionizable lipid having a chemical structure consisting of a pair of 16 or 18 carbon linear polyunsaturated lipid tails covalently bound to a head group comprising a dialkyl amino group having a pKa of between 6 and 7;
    the head group comprising a heterocyclyl or alkyl portion covalently bound to the dialkyl amino group and optionally further comprising a phosphate group;
    each polyunsaturated lipid tail being unsaturated except for the at least two olefins separated by at least two methylene groups along the length of the lipid tail, and optionally comprising a single acyl group at the end covalently bound to the head group.
34. The composition of embodiment 33, wherein each lipid tail is identical, and each lipid tail has a total of two olefins separated only by an unsubstituted ethylene, n-propyl, or n-butyl.
35. The composition of embodiment 34, wherein each lipid tail further comprises an acyl group joined to an oxygen of the headgroup to form an ester.

36. The composition of embodiment 34, wherein each lipid tail has the chemical structure of Formula A or Formula B:

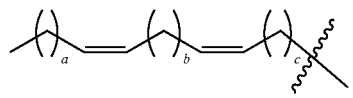

Formula A wherein a in Formula A is 1, 2, 3 or 4; b is 2, 3 or 4; and c in Formula A is 3, 4, 5, 6, 7; or

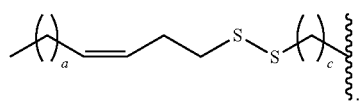

wherein a in Formula B is 5, 6 or 7; and c in Formula B is 3, 4, or 5.

37. The composition of embodiment 36, wherein b is 4.

38. The composition of embodiment 36, wherein the ionizable lipid comprises a chemical structure selected from the group consisting of:

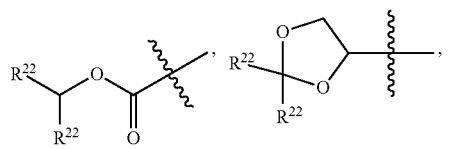

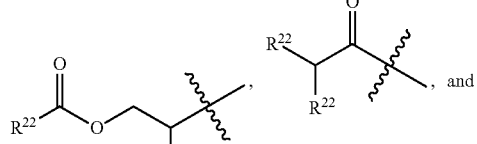, and

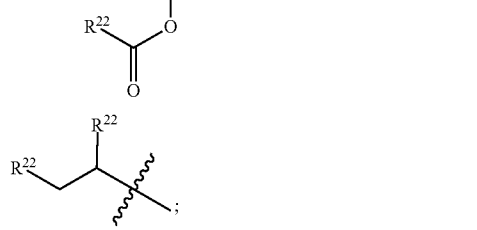

wherein $R^{22}$ is the first end of the lipid tail and

indicates attachment of the head group to the dialkyl amino portion of the head group.

39. The composition of embodiment 38, wherein the dialkyl amino portion of the head group has a chemical structure of Formula (IV-A)

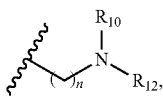

Formula IV-A wherein n is 2, 3 or 4 in Formula (IV-A); and $R_{10}$ and $R_{12}$ in Formula (IV-A) are each independently selected from an alkyl group selected from the group consisting of: methyl, ethyl, and propyl, wherein the alkyl in $R_{10}$ and $R_{12}$ is optionally substituted with one or more hydroxyl.

40. The composition of embodiment 39, wherein $R_{10}$ and $R_{12}$ in Formula (IV-A) are each independently methyl, ethyl, —$(CH_2)(CH_2)OH$, or —$(CH_2)_2(CH_2)OH$.

41. The composition of embodiment 33, wherein the ionizable lipid has a chemical structure of Formula (I-A)

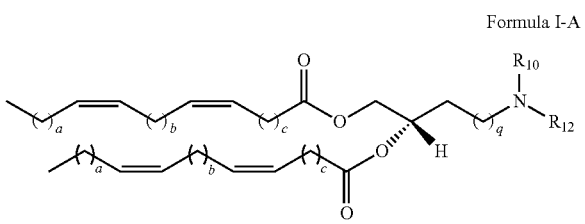

Formula I-A wherein a is 1, 2, 3, 4, 5 or 6; b is 2, 3 or 4; cis 3, 4, 5, 6, or 7; and the sum of a, b and c is 10 or 12;

each of $R_{10}$ and $R_{12}$ is independently $(C_1$-$C_4)$alkyl optionally substituted with one or more hydroxyl; and L is

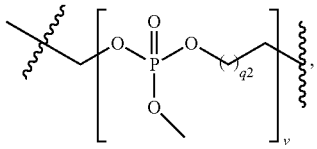

wherein v is 0 or 1; and q2 is 1 or 2.

42. The composition of embodiment 41, wherein v is 0.

43. The composition of embodiment 41, wherein v is 1.

44. The composition of embodiment 33, wherein the ionizable lipid has a chemical structure of Formula II-A:

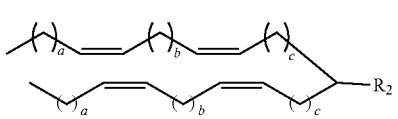

Formula (II-A)

wherein a is 1, 2, 3, 4, 5 or 6; b is 2, 3 or 4; cis 4, 5, 6, 7 or 8;

$R_2$ is

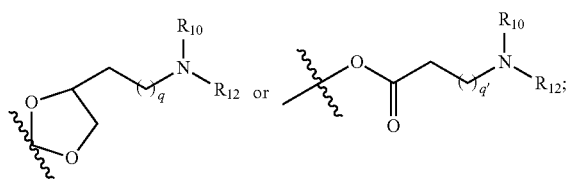

q and q' are each independently 1 or 2; and
$R_{10}$ and $R_{12}$ are each ($C_1$-$C_4$)alkyl optionally substituted with hydroxyl.

45. The composition of embodiment 33, wherein the ionizable lipid has a chemical structure of Formula II-A:

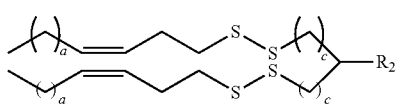

Formula (II-B)

wherein a is 5, 6 or 7; and c is 3, 4, or 5;
$R_2$ is

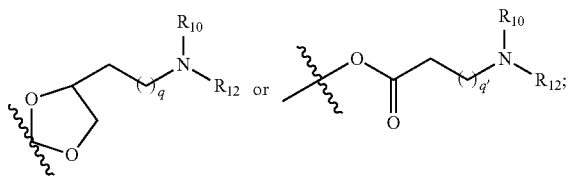

q and q' are each independently 1 or 2; and
$R_{10}$ and $R_{ig}$ are each ($C_1$-$C_4$)alkyl optionally substituted with hydroxyl.

EXAMPLES

While this disclosure has been described in relation to certain embodiments, and many details have been set forth for purposes of illustration, it will be apparent to those skilled in the art that this disclosure includes additional embodiments, and that some of the details described herein may be varied considerably without departing from this disclosure. This disclosure includes such additional embodiments, modifications and equivalents. In particular, this disclosure includes any combination of the features, terms, or elements of the various illustrative components and examples.

Unless explicitly indicated otherwise, the isomer form of the phosphatidylserine lipids used in the Examples is phosphatidyl-L-serine.

Certain examples are provided below to illustrate various embodiments of the embodiments disclosed herein. One of ordinary skill in the art will recognize that the various embodiments disclosed herein are not limited to these specific illustrative examples.

Example 1A: Synthesis of Ionizable Lipids

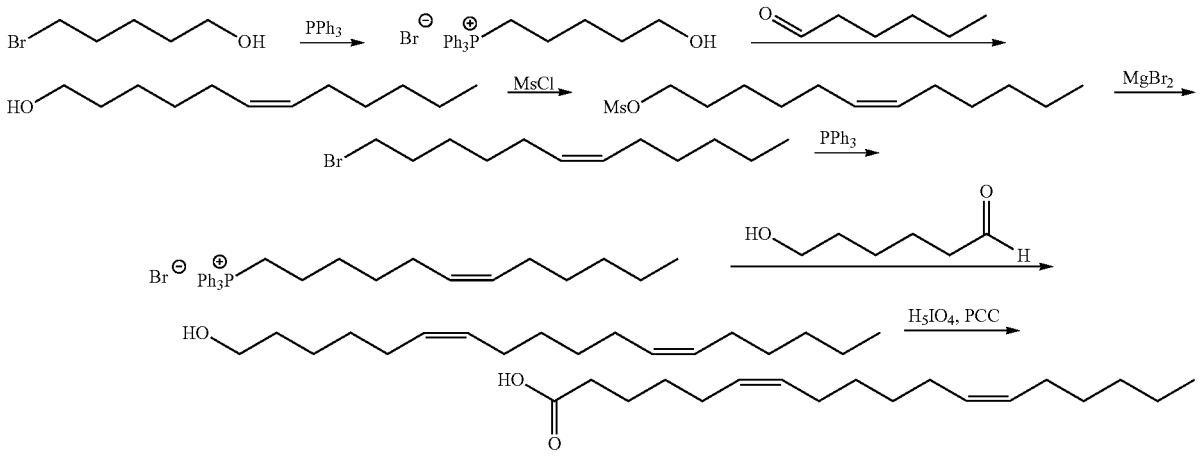

Scheme 1 Synthesis of acid intermediates for AKG-UO-1 to AKG-UO-3

For AKG-UO-1, AKG-UO-2, and AKG-UO-3

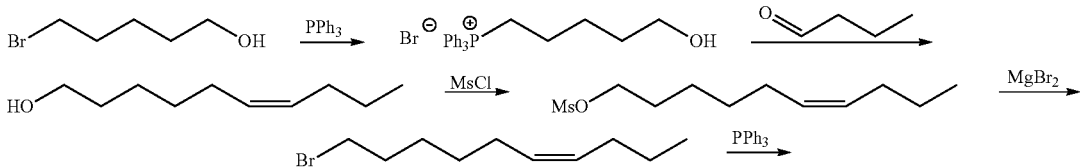

-continued

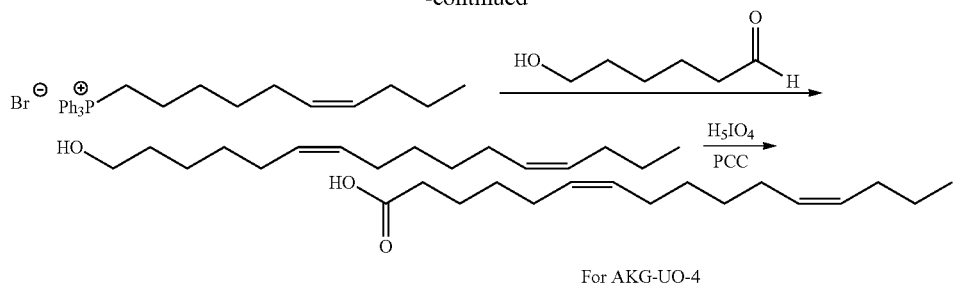

For AKG-UO-4

The acid intermediates (6Z,12Z)-6,12-octadecadienoic acid and (6Z,12Z)-6,12-hexadecadienoic acid were prepared by a general synthesis, shown in
(S)-4-(dimethylamino)butane-1,2-diyl (6Z,6'Z,12Z,12'Z)-bis(octadeca-6,12-dienoate) (AKG-UO-1, O-11956)
(S)-4-(diethylamino)butane-1,2-diyl (6Z,6'Z,12Z,12'Z)-bis(octadeca-6,12-dienoate) (AKG-UO-1A, O-11955)
(S)-4-(dimethylamino)butane-1,2-diyl (6Z,6'Z,12Z,12'Z)-bis(hexadeca-6,12-dienoate, AKG-UO-4, O-12401)
(S)-4-(diethylamino)butane-1,2-diyl (6Z,6'Z,12Z,12'Z)-bis(hexadeca-6,12-dienoate, AKG-UO-4A, O-12402)
(S)-4-(dimethylamino)butane-1,2-diyl (6Z,6'Z,11Z,11'Z)-bis(octadeca-6,11-dienoate)(AKG-UO-1a)

Scheme 7

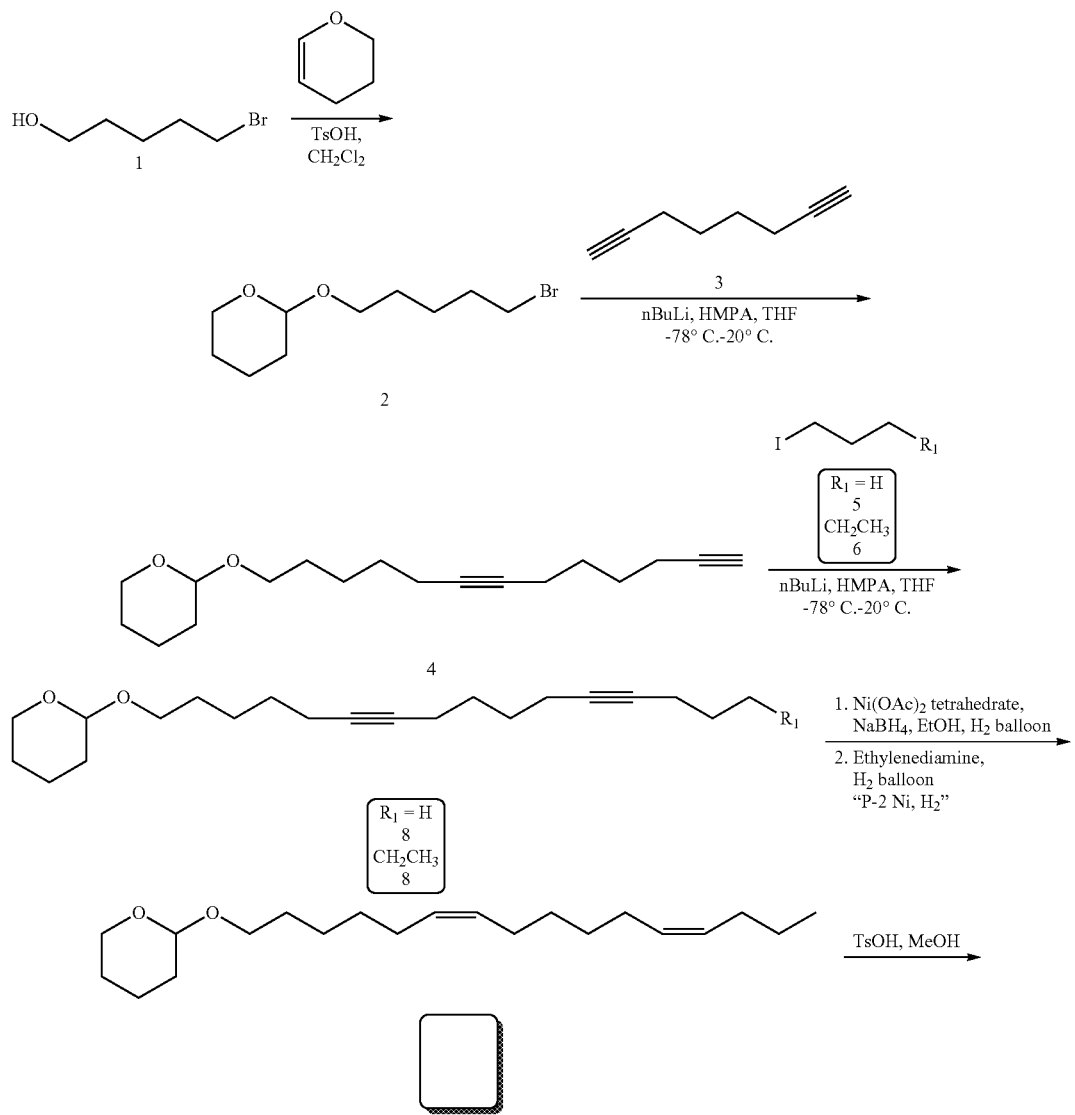

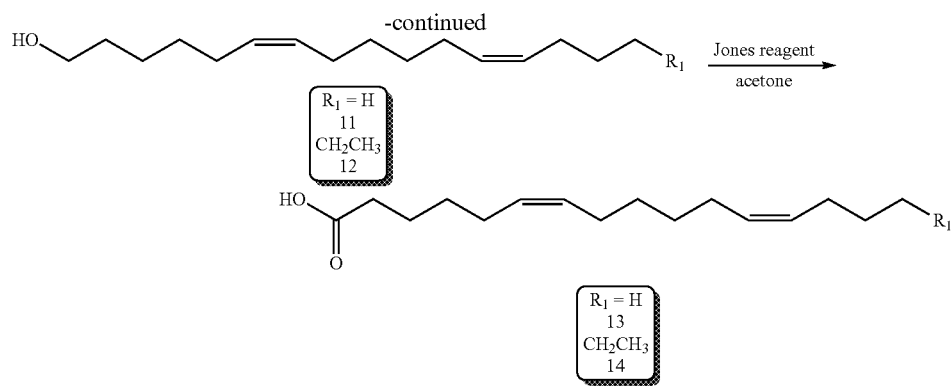
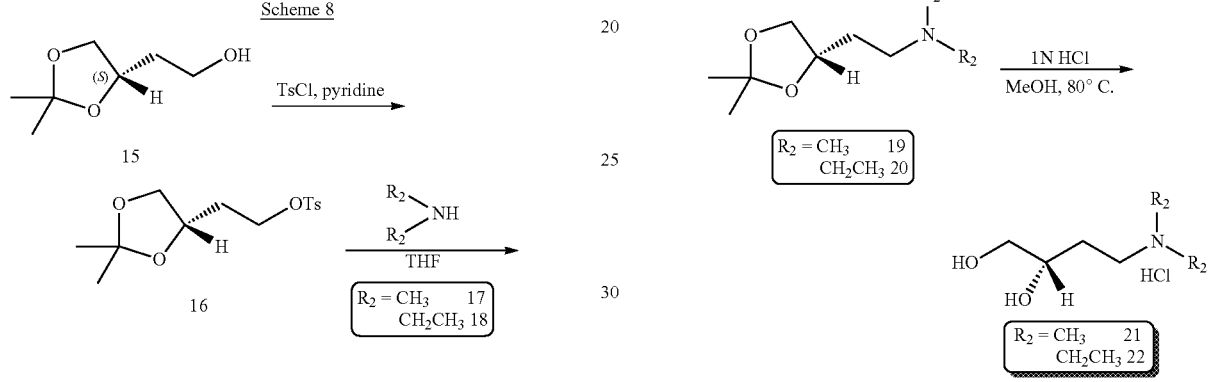
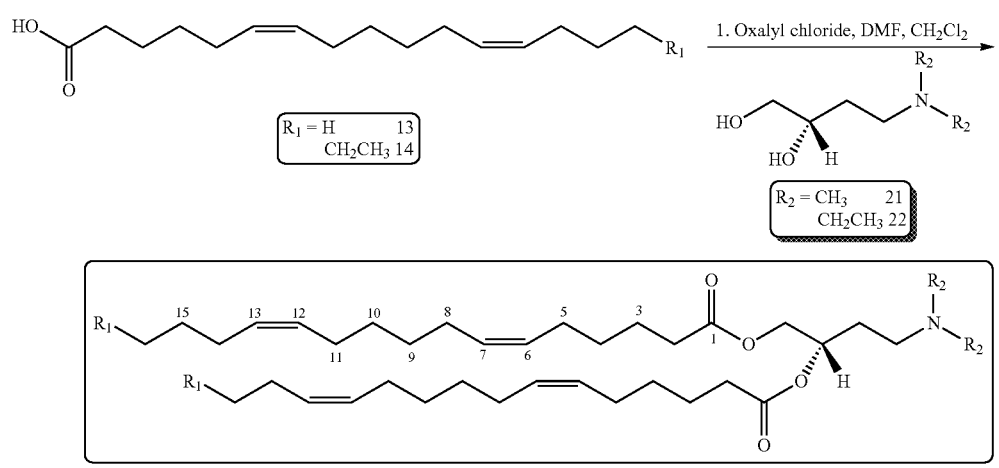
| Compounds | R₁ | R₂ |
|---|---|---|
| AKG-UO-1 | CH₂CH₃ | CH₃ |
| AKG-UO-1A | CH₂CH₃ | CH₂CH₃ |
| AKG-UO-4 | H | CH₃ |
| AKG-UO-4A | H | CH₂CH₃ |

EXPERIMENTAL PROCEDURE

Synthesis of 2-((5-bromopentyl)oxy)tetrahydro-2H-pyran 2

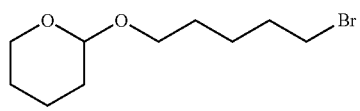

2

To a solution of 5-bromo-1-pentanol 1 (3.6 g, 21.6 mmol) in dichloromethane (100 mL) and pyridinium p-toluene sulfonate (40 mg, 0.16 mmol) at 0° C. was added 3,4-dihydro-2H-pyran (6.54 mL, 71.8 mmol). The resulting solution was stirred at room temperature for one hour then quenched with water. The mixture was extracted with ethyl acetate (2×100 mL). The combined organics were washed with brine then dried over magnesium sulfate, filtered, and the filtrate concentrated under vacuum to give a crude oil. The crude oil was purified by chromatography on silica using 5-10% ethyl acetate in n-hexane as eluant to give 2-((5-bromopentyl)oxy)tetrahydro-2H-pyran, 2 (4.5 g, 83%) as a clear oil.

1H NMR (300 MHz, CDCl3): δ ppm 4.55-4.54 (d, J=4.3 Hz, 1H), 3.92-3.72 (m, 2H), 3.42-3.38 (m, 3H), 1.88-1.55 (m, 3H), 1.52-1.50 (m, 10H).

Synthesis of 2-(trideca-6,12-diyn-1-yloxy)tetrahydro-2H-pyran 4

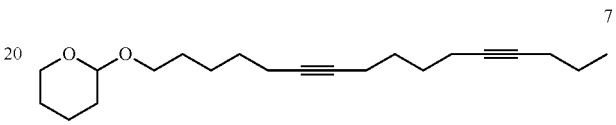

4

To a solution of 1,7-Octadiyne 3 (6 mL, 45.4 mmol) and hexamethylphosphoramide (16 mL, 90.8 mmol) in tetrahydrofuran (100 mL) at −78° C. was added [2.5 M n-butyllithium in n-hexane] (18 mL, 45.4 mmol) dropwise. Upon completion of addition, the solution was stirred at −78° C. for one hour then warmed to −20° C. for an additional hour. The resulting solution was cooled once again to −78° C. whereupon a solution of 2-((5-bromopentyl)oxy)tetrahydro-2H-pyran, 2 (5.67 g, 22.7 mmol) in tetrahydrofuran (10 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil weighing 9 g. The crude oil was purified by chromatography on silica using 5-10% ethyl acetate in n-hexane as eluant to give 2-(trideca-6,12-diyn-1-yloxy)tetrahydro-2H-pyran, 4 (4.5 g, 72%) as a clear oil.

1H NMR (300 MHz, d6.DMSO): δ ppm 4.54-4.53 (m, 1H), 3.72-3.61 (m, 1H), 3.60-3.58 (m, 1H), 3.43-3.33 (m, 1H), 3.32-3.29 (m, 1H), 2.77-2.75 (t, J=5.8 Hz, 1H), 2.16-2.13 (m, 6H), 1.55-1.41 (m, 16H).

Representative Procedure for Alkylation of Alkynes

Synthesis of 2-(hexadeca-6,12-diyn-1-yloxy) tetrahydro-2H-pyran 7

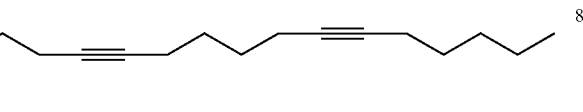

7

To a solution of 2-(trideca-6,12-diyn-1-yloxy) tetrahydro-2H-pyran, 4 (7.14 g, 25.86 mmol) and hexamethylphosphoramide (18 mL, 103.4 mmol) in tetrahydrofuran (100 mL) at −78° C. was added [2.5 M n-butyllithium in n-hexane] (41.3 mL, 103.4 mmol) dropwise. Upon completion of addition, the solution was stirred at −78° C. for one hour then warmed to −20° C. for an additional hour. The resulting solution was cooled once again to −78° C. whereupon a solution of 1-iodopropane 5 (9.9 mL, 103.4 mmol) in tetrahydrofuran (20 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil weighing 9 g. The crude oil was purified by chromatography on silica using 5% ethyl acetate in n-hexane as eluant to give 2-(hexadeca-6,12-diyn-1-yloxy)tetrahydro-2H-pyran, 7 (5.9 g, 72%) as a clear oil.

$^{1H}$ NMR (300 MHz, CDCl3): 4.57-4.55 (m, 1H), 3.86-3.74 (m, 1H), 3.73-3.71 (m, 1H), 3.50-3.39 (m, 1H), 3.37-3.36 (m, 1H), 2.16-2.11 (m, 8H), 1.59-1.56 (m, 2H), 1.55-1.47 (m, 16H), 0.98-0.93 (t, J=1.6 Hz, 3H).

2-(octadeca-6,12-diyn-1-yloxy)tetrahydro-2H-pyran 8

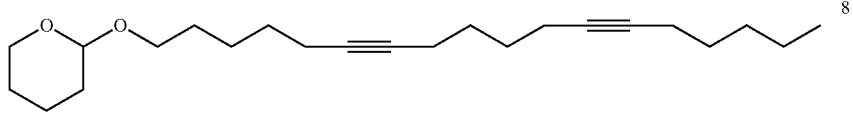 [SMILES: CCCCCC#CCCCCC#CCCCCCOC1CCCCO1]

8

1H NMR (300 MHz, CDCl3): 4.57-4.55 (m, 1H), 3.85-3.74 (m, 1H), 3.73-3.70 (m, 1H), 3.50-3.38 (m, 1H), 3.36-3.35 (m, 1H), 2.23-2.12 (m, 8H), 1.61-1.54 (m, 2H), 1.53-1.48 (m, 16H), 1.47-1.46 (m, 4H), 0.90-0.85 (t, J=1.6 Hz, 3H).

Representative Procedure for Reduction of Alkynes to Alkenes Using "P-2 Ni"

Synthesis of 2-(((6Z,12Z)-hexadeca-6,12-dien-1-yl)oxy)tetrahydro-2H-pyran 9

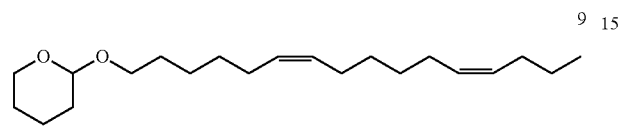

9

To a solution of Sodium borohydride (0.56 g, 14.8 mmol) in ethanol (80 mL) under hydrogen blanket at 0° C. was added Nickel (II) acetate tetrahydrate (3.22 g, 12.98 mmol). Upon completion of addition, the reaction was evacuated under vacuum and flushed with hydrogen. After 10 minutes of stirring, ethylenediamine (3.7 mL, 65.6 mmol), and a solution of 2-(hexadeca-6,12-diyn-1-yloxy)tetrahydro-2H-pyran, 7 (5.9 g, 18.55 mmol) in ethanol (10 mL) was added. The reaction was stirred at room temperature under a hydrogen balloon for 4 hours. After 4 hours, the reaction mixture was evacuated of hydrogen and then flushed with nitrogen. The crude mixture was filtered over celite, and the filtrate concentrated under vacuum to give a crude oil weighing 4 g. The crude oil was purified by chromatography on silica using 5-10% diethyl ether in n-hexane as eluant to give 2-(((6Z,12Z)-hexadeca-6,12-dien-1-yl)oxy)tetrahydro-2H-pyran, 9 (4.67 g, 78% yield) as a clear oil.

1H NMR (300 MHz, CDCl3): 5.35-5.34 (m, 4H), 4.58-4.55 (m, 1H), 3.86-3.74 (m, 1H), 3.73-3.71 (m, 1H), 3.51-3.39 (m, 1H), 3.36-3.35 (m, 1H), 2.03-1.98 (m, 8H), 1.57-1.39 (m, 2H), 1.38-1.36 (m, 6H), 1.35-1.32 (m, 10H), 0.91-0.86 (t, J=1.6 Hz, 3H).

$^{13C}$ NMR (300 MHz, CDCl3): 129.98, 129.85, 98.93, 77.53, 77.10, 76.68, 67.72, 62.43, 30.86, 29.71, 29.70, 29.45, 29.46, 29.44, 27.20, 27.19, 26.01, 25.59, 22.98, 19.78, 13.91.

2-(((6Z,12Z)-octadeca-6,12-dien-1-yl)oxy)tetrahydro-2H-pyran 10

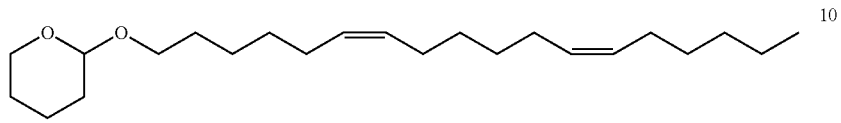 [SMILES: CCCCC/C=C\CCCC/C=C\CCCCCOC1CCCCO1]

10

1H NMR (300 MHz, CDCl3): 5.39-5.29 (m, 4H), 4.58-4.55 (m, 1H), 3.86-3.76 (m, 1H), 3.74-3.68 (m, 1H), 3.51-3.41 (m, 1H), 3.39-3.36 (m, 1H), 2.14-1.97 (m, 8H), 1.56-1.38 (m, 2H), 1.37-1.35 (m, 6H), 1.34-1.28 (m, 14H), 0.93-0.85 (t, J=1.6 Hz, 3H).

13C NMR (300 MHz, CDCl3): 130.13, 129.97, 129.84, 129.71, 98.93, 77.53, 77.10, 76.68, 67.71, 62.42, 31.62, 30.86, 29.72, 29.71, 29.47, 29.46, 27.27, 27.18, 26.01, 25.59, 22.67, 19.78, 14.18.

Representative Procedure for Deprotection of Tetrahydropyranyl Ether (THP)

Synthesis of (6Z,12Z)-hexadeca-6,12-dien-1-ol 11

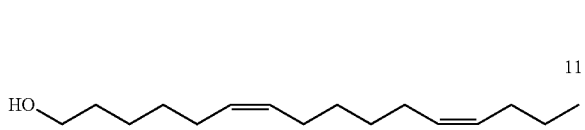

11

To a solution of 2-(((6Z,12Z)-hexadeca-6,12-dien-1-yl)oxy)tetrahydro-2H-pyran, 9 (4.67 g, 14.5 mmol) in methanol (20 mL) was added p-Toluenesulfonic acid monohydrate (300 mg, 1.58 mmol) at room temperature. The resulting solution was stirred at room temperature for 3 hours then quenched with water. The mixture was extracted with ethyl acetate (2×50 mL). The combined organics were washed with water then dried over magnesium sulfate, filtered and the filtrate concentrated under vacuum to give a crude oil weighing 4 g. The crude oil was purified by chromatography on silica using 5-10% diethyl ether in n-hexane as eluant to give (6Z,12Z)-hexadeca-6,12-dien-1-ol, 11 (2.5 g, 72%) as a clear oil.

1H NMR (300 MHz, CDCl3): 5.34-5.33 (m, 4H), 3.65-3.61 (m, 2H), 2.02-2.00 (m, 8H), 1.36-1.34 (m, 2H), 1.34-1.25 (m, 10H), 0.89-0.86 (t, J=0.82 Hz, 3H).

(6Z,12Z)-octadeca-6,12-dien-1-ol 12

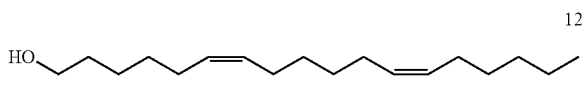 [SMILES: CCCCC/C=C\CCCC/C=C\CCCCCO]

12

1H NMR (300 MHz, CDCl3): 5.36-5.33 (m, 4H), 3.65-3.61 (m, 2H), 2.02-2.01 (m, 8H), 1.36-1.35 (m, 2H), 1.34-1.25 (m, 14H), 0.88-0.85 (t, J=0.76 Hz, 3H).

Representative Procedure for Oxidation of Alcohol to Carboxylic Acid Using Jones Reagent Synthesis of (6Z,12Z)-hexadeca-6,12-dienoic Acid 13

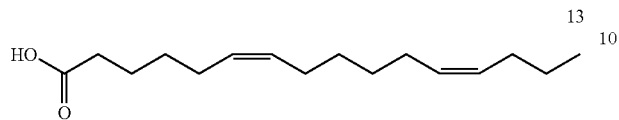

A mixture of (6Z,12Z)-hexadeca-6,12-dien-1-ol, 11 (2.5 g, 10.5 mmol) and Jones Reagent [2M in sulfuric acid], (10.5 mL, 21 mmol) in acetone (20 mL) at 0° C. was stirred for 2 hours. The mixture was quenched with water and extracted with ethyl acetate (2×100 mL). The combined organics were dried over magnesium sulfate, filtered and the filtrate concentrated under vacuum to give a crude oil. The crude oil was purified by chromatography on silica using 20% ethyl acetate in n-hexane as eluant to give (6Z,12Z)-hexadeca-6, 12-dienoic acid, 13 (1.7 g, 68%) as a clear oil.

1H NMR (300 MHz, CDCl3): 5.35-5.33 (m, 4H), 2.37-2.32 (t, 2H), 2.06-1.98 (m, 8H), 1.64-1.39 (m, 2H), 1.37-1.32 (m, 8H), 0.91-0.87 (t, J=0.91 Hz, 3H).

(6Z,12Z)-octadeca-6,12-dienoic Acid 14

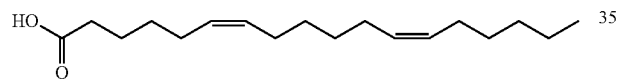

1H NMR (300 MHz, CDCl3): 5.36-5.32 (m, 4H), 2.35-2.33 (t, 2H), 2.06-2.01 (m, 8H), 1.64-1.42 (m, 2H), 1.34-1.28 (m, 12H), 0.90-0.85 (t, 3H).

Synthesis of (S)-2-(2,2-dimethyl-1,3-dioxolan-4-yl) ethyl 4-methylbenzenesulfonate 16

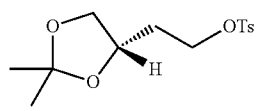

To a mixture of (S)-2-(2,2-dimethyl-1,3-dioxolan-4-yl) ethan-1-ol 15 (25 g, 171.1 mmol) in pyridine (30 mL) at 0° C. was added p-Toluenesulfonylchloride (35.8 g, 188.2 mmol) and DMAP (140 mg, 1.14 mmol) and the reaction was stirred at room temperature overnight. The mixture was diluted with CH2Cl2 (500 mL), washed with sat. NH4Cl, water and Brine. The organic layer was dried over anhydrous Na2SO4. The solvent was evaporated, and the crude residue used for the next step without purification. (43.8 g, 85%).

1H NMR (300 MHz, CDCl3): δ ppm 7.77 (d, J=8.2 Hz, 2H), 7.34 (d, J=8.1 Hz, 2H), 4.15-4.01 (m, 3H), 3.65-3.47 (m, 2H), 2.43 (s, 3H), 1.82-1.62 (m, 2H), 1.32 (s, 3H), 1.27 (s, 3H).

Representative Procedure for Di-Alkylamine Substitution

Synthesis of (S)-2-(2,2-dimethyl-1,3-dioxolan-4-yl)-N,N-dimethylethan-1-amine 19

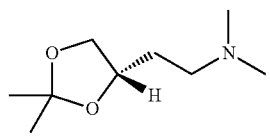

A mixture of (S)-2-(2,2-dimethyl-1,3-dioxolan-4-yl)ethyl 4-methylbenzenesulfonate 16 (10 g, 33.3 mmol) and dimethylamine solution 17 (166 mL, 333.3 mmol) (2M in THF) was stirred at room temperature for 2 days. The mixture was concentrated, and the crude residue was diluted with CH2Cl2 (500 mL), washed with sat. NaHCO3, water and Brine. The organic layer was dried over anhydrous Na2SO4. The solvent was evaporated, and the crude residue was purified by flash chromatography (SiO2:CH2Cl2=100% to 10% of MeOH in CH2Cl2 with 1% NH4OH) and colorless oil product 19 was obtained (2.1 g, 37%).

1H NMR (300 MHz, CDCl3): δ ppm 4.15-4.01 (m, 2H), 3.52 (dd, J=7.4, 7.4 Hz, 1H), 2.41-2.23 (m, 2H), 2.21 (s, 6H), 1.82-1.62 (m, 2H), 1.39 (s, 3H), 1.33 (s, 3H).

MS (APCI+): 174.1 (M+1)

(S)-2-(2,2-diethyl-1,3-dioxolan-4-yl)-N,N-dimethyl-ethan-1-amine 20

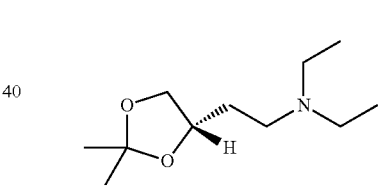

1H NMR (300 MHz, CDCl3): δ ppm 4.15-4.01 (m, 2H), 3.48 (dd, J=7.4, 7.4 Hz, 1H), 2.48-2.43 (m, 6H), 1.82-1.62 (m, 2H), 1.36 (s, 3H), 1.27 (s, 3H), 0.97 (t, J=7.2 Hz, 6H).

MS (APCI+): 202.2 (M+1)

Representative Procedure for Ketal Hydrolysis

Synthesis of (S)-4-(dimethylamino)butane-1,2-diol hydrochloride Salt 21

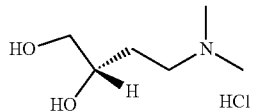

To a mixture of (S)-2-(2,2-dimethyl-1,3-dioxolan-4-yl)-N,N-dimethylethan-1-amine 19 (2 g, 11.54 mmol) in MeOH (10 mL) was added 1N HCl aqueous solution (17 mL, 17.3 mmol) and the reaction was heated at 80° C. for 45 min. TLC (Rf=0.1, 10% MeOH in CH2Cl2 with 1% NH4OH) showed the completion of reaction. After concentration of the reaction mixture, the crude residue was dissolved in water (5 mL) and lyophilized overnight. Sticky syrup product 21 was obtained (2.1 g, quant.) as HCl salt.

1H NMR (300 MHz, D2O): δ ppm 3.77-3.72 (m, 1H), 3.54-3.46 (m, 2H), 3.29-3.22 (m, 2H), 2.85 (s, 6H), 1.92-1.79 (m, 2H).

MS (APCI+): 134.1 (M+1)

(S)-4-(diethylamino)butane-1,2-diol hydrochloride Salt 22

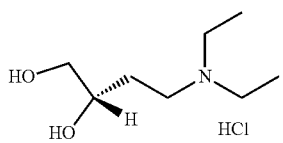

1H NMR (300 MHz, D2O): δ ppm 3.77-3.72 (m, 1H), 3.54-3.46 (m, 2H), 3.22-3.15 (m, 6H), 1.92-1.74 (m, 2H), 1.24 (t, J=7.4 Hz, 6H).

MS (APCI+): 162.1 (M+1)

Representative Procedure for Di-Esterification

Synthesis of (S)-4-(dimethylamino)butane-1,2-diyl (6Z,6'Z,12Z,12'Z)-bis(octadeca-6,12-dienoate) AKG-UO-1 (O-11956)

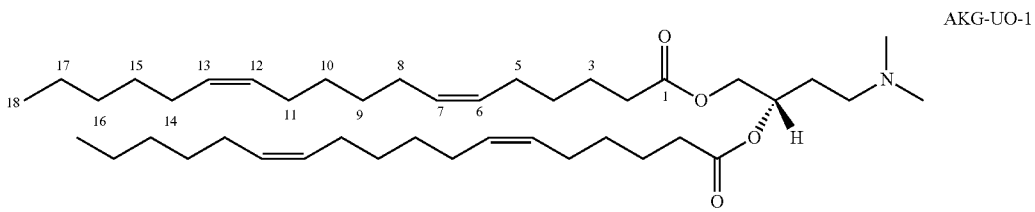 [SMILES: CCCCC/C=C\CCCC/C=C\CCCCC(=O)OC[C@H](CCN(C)C)OC(=O)CCCC/C=C\CCCC/C=C\CCCCC]

Oxalyl chloride (0.33 mL, 3.9 mmol) was added dropwise to a solution of (6Z,12Z)-octadeca-6,12-dienoic acid, 14 (0.36 g, 1.3 mmol) in dichloromethane/DMF (15 mLs, 25 mL) at 0° C. and allowed reaction to warm to room temperature and stir for one hour. After one hour, the reaction was concentrated under vacuum to dryness. The residue was re-dissolved in dichloromethane (10 mL) and added to a mixture of N,N-Diisopropylethylamine (2.3 mL, 10 mmol), 4-Dimethylaminopyridine (317 mg, 2.6 mmol), and (S)-4-(dimethylamino)butane-1,2-diol hydrochloride, 21 (101 mg, 0.6 mmol). The resulting solution was allowed to stir for 24 hours. After 24 hours, the reaction was cooled to 0 C and quenched with water (10 mL). The reaction mixture was extracted with dichloromethane (2×100 mL) and the organics were washed with water and brine (2×100 mL). The organic layer was dried over magnesium sulfate, filtered, and the filtrate concentrated under vacuum to give a crude oil. The crude oil was purified by chromatography on silica using 2% methanol in dichloromethane as eluant to give (S)-4-(dimethylamino)butane-1,2-diyl (6Z,6'Z,12Z,12'Z)-bis(octadeca-6,12-dienoate), AKG-UO-1, (0.12 g, 30%) as a yellow oil.

1H NMR (300 MHz, CDCl3): 5.40-5.29 (m, 8H), 5.14-5.12 (m, 1H), 4.25 (dd, J=11.8, 3.3 Hz, 1H), 4.05 (dd, J=12.1, 6.3 Hz, 1H), 2.32-2.26 (m, 6H), 2.20 (s, 6H), 2.06-1.99 (m, 16H), 1.78-1.70 (m, 2H), 1.65-1.58 (m, 4H), 1.42-1.25 (m, 24H), 0.90-0.85 (m, 6H).

MS (APCI+): 658.5 (M+1)

(S)-4-(diethylamino)butane-1,2-diyl (6Z,6'Z,12Z,12'Z)-bis(octadeca-6,12-dienoate) AKG-UO-1A
(O-11955)
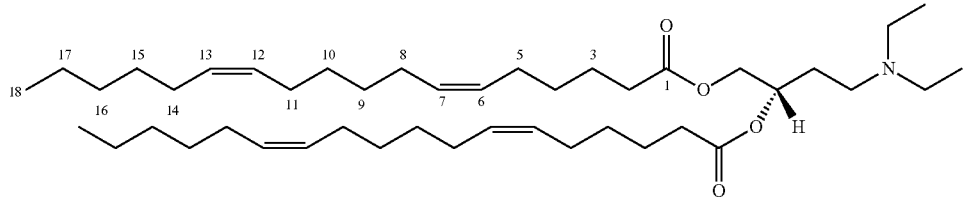
1H NMR (300 MHz, CDCl3): 5.37-5.29 (m, 8H), 5.12-5.10 (m, 1H), 4.25 (dd, J=12.1, 3.6 Hz, 1H), 4.05 (dd, J=11.8, 6.3 Hz, 1H), 2.52-2.42 (m, 6H), 2.29 (t, J=7.4 Hz, 4H)), 2.06-1.99 (m, 16H), 1.78-1.70 (m, 2H), 1.64-1.59 (m, 4H), 1.41-1.19 (m, 24H), 0.99 (t, J=7.1 Hz, 6H), 0.96-0.87 (m, 6H).
MS (APCI+): 686.6 (M+1)
(S)-4-(dimethylamino)butane-1,2-diyl (6Z,6'Z,12Z,12'Z)-bis(hexadeca-6,12-dienoate) AKG-UO-4
(O-12401)
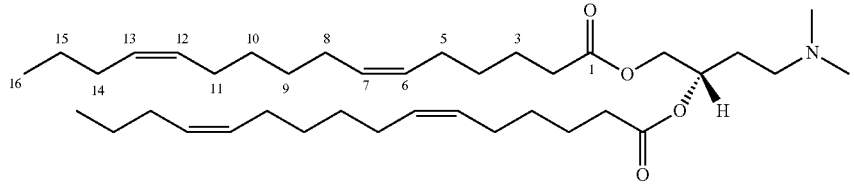
1H NMR (300 MHz, CDCl3): 5.39-5.29 (m, 8H), 5.13-5.12 (m, 1H), 4.24 (dd, J=11.8, 3.3 Hz, 1H), 4.05 (dd, J=11.8, 6.3 Hz, 1H), 2.32-2.27 (m, 6H), 2.19 (s, 6H), 2.01-1.99 (m, 16H), 1.75-1.72 (m, 2H), 1.65-1.58 (m, 4H), 1.36-1.31 (m, 16H), 0.91-0.86 (m, 6H).
MS (APCI+): 602.5 (M+1)
Synthesis of (S)-4-(diethylamino)butane-1,2-diyl (6Z,6'Z,12Z,12'Z)-bis(hexadeca-6,12-dienoate) AKG-UO-4A (O-12402)
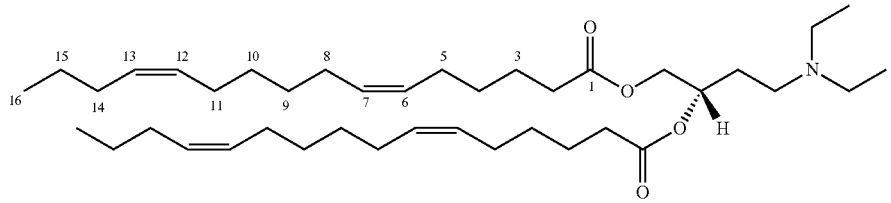

1H NMR (300 MHz, CDCl3): 5.40-5.29 (m, 8H), 5.12-5.11 (m, 1H), 4.25 (dd, J=11.8, 3.3 Hz, 1H), 4.05 (dd, J=11.8, 6.3 Hz, 1H), 2.54-2.43 (m, 6H), 2.29 (t, J=7.4 Hz, 4H), 2.11-1.96 (m, 16H), 1.74-1.65 (m, 2H), 1.65-1.59 (m, 4H), 1.39-1.31 (m, 16H), 0.99 (t, J=7.1 Hz, 6H), 0.91-0.89 (m, 6H).

MS (APCI+): 630.5 (M+1), involving i) an initial Witting reaction of triphenyl phosphonium ylide, prepared from 5-bromo pentanol, and the corresponding aldehyde, ii) conversion of the terminal alcohol to bromide by mesylation and substitution, iii) repeating the sequence of ylide synthesis and Witting reaction, and finally iv) periodic acid oxidation of the terminal alcohol. The resulting acid intermediates were utilized in the synthesis of AKG-UO-1 to AKG-UO-4, vide infra.

Scheme 2 Synthesis of acid intermediate for AKG-UO-5

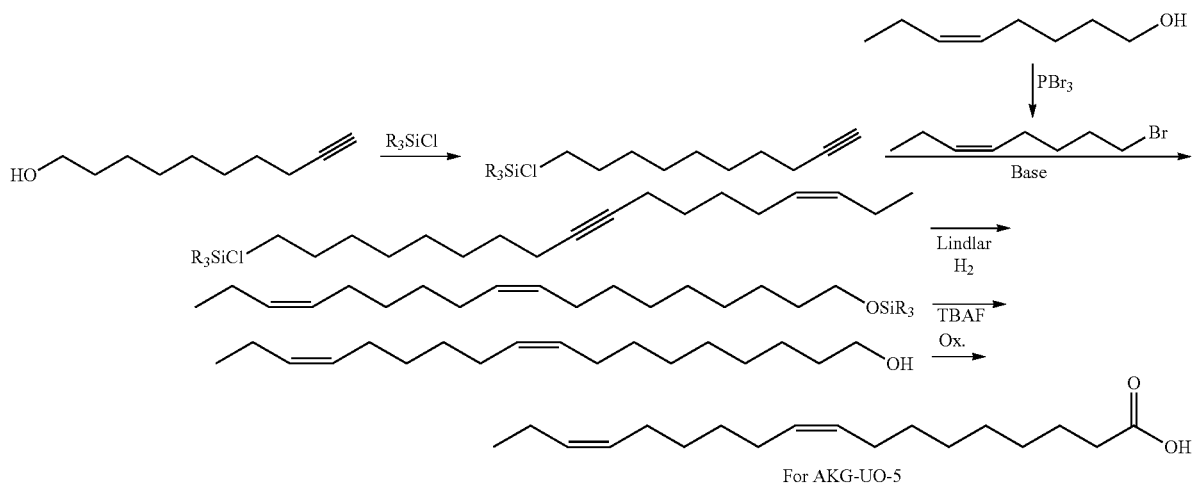

The acid intermediate (9Z,15Z)-9,15-octadecadienoic acid used in the synthesis of AKG-UO-5 was prepared by a general synthesis shown in Scheme 2, involving i) alkylation of silyl protected 10-hydroxy-1-decyne with (5Z)-1-bromo-5-octene, ii) catalytic hydrogenation of the alkyne to a cis-alkene, iii) removal of silyl protection on the alcohol, and finally iv) oxidation of the terminal alcohol to the desired acid.

Scheme 3 Synthesis of acid intermediates for AKG-BDG-01 and AKG-BDG-02

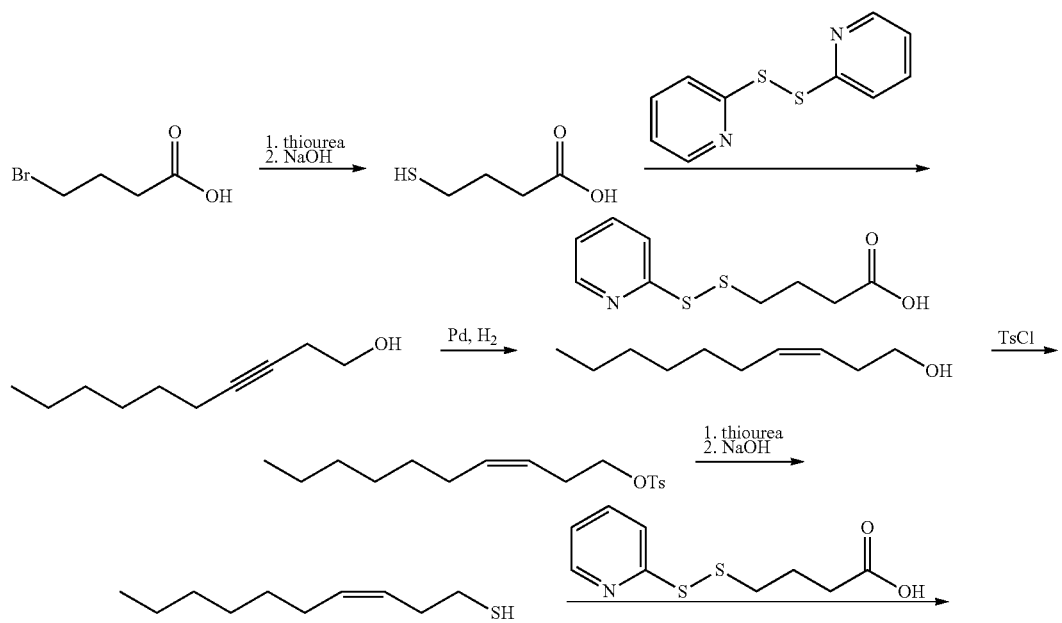

-continued
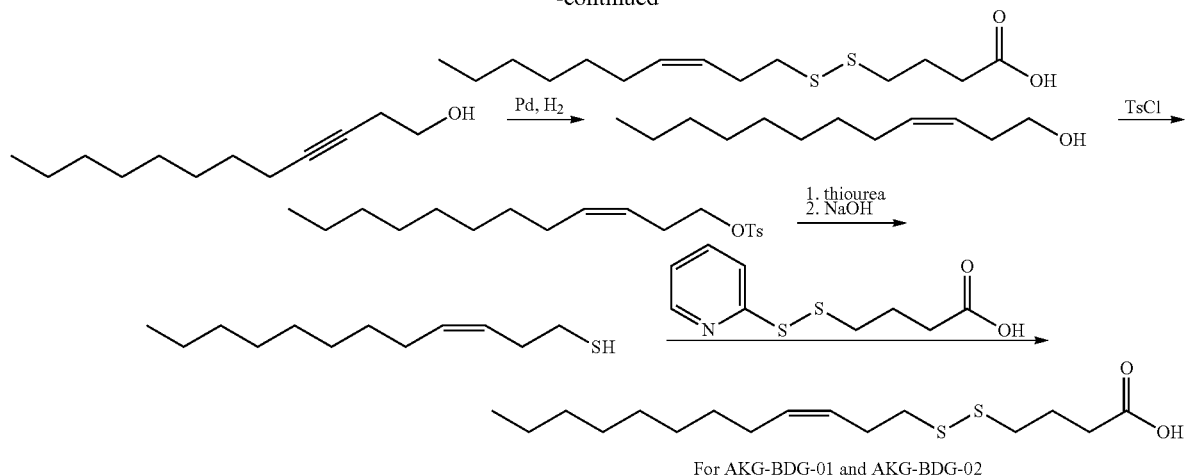
Synthesis of two disulfide acid intermediates used in the synthesis of AKG-BDG-1 and AKG-BDG-2 is shown in
Synthesis of (S)-4-(dimethylamino)butane-1,2-diyl (6Z,6'Z,11Z,11'Z)-bis(octadeca-6,11-dienoate) (AKG-UO-1a)
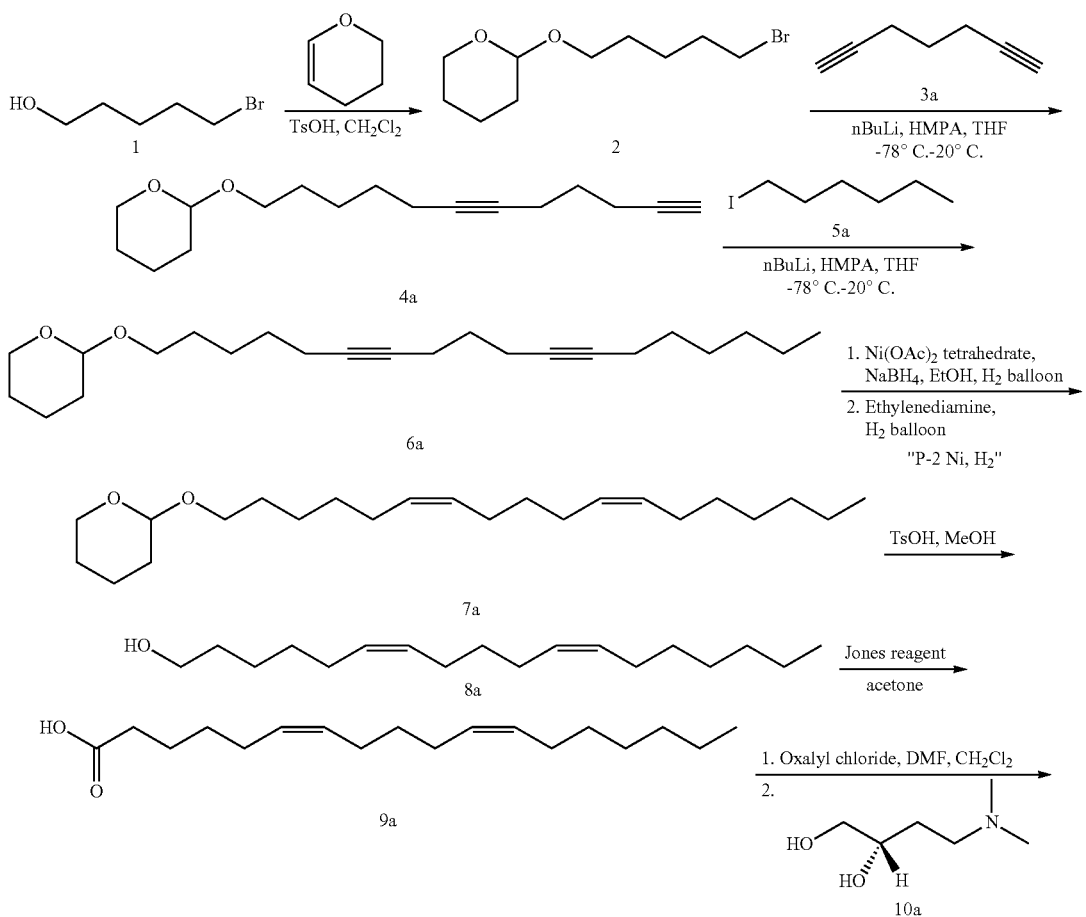

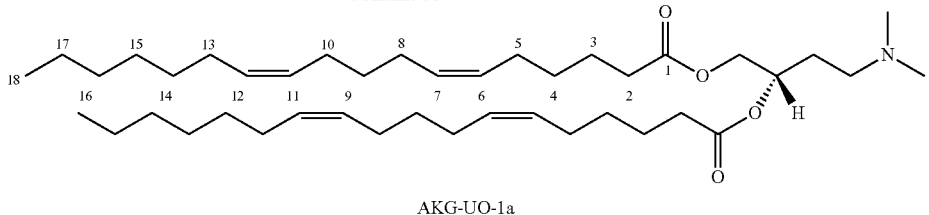

AKG-UO-1a

Experimental Procedure

Synthesis of 2-((5-bromopentyl)oxy)tetrahydro-2H-pyran 2

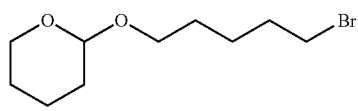

To a solution of 5-bromo-1-pentanol 1 (3.6 g, 21.6 mmol) in dichloromethane (100 mL) and pyridinium p-toluene sulfonate (40 mg, 0.16 mmol) at 0° C. was added 3,4-dihydro-2H-pyran (6.54 mL, 71.8 mmol). The resulting solution was stirred at room temperature for one hour then quenched with water. The mixture was extracted with ethyl acetate (2×100 mL). The combined organics were washed with brine then dried over magnesium sulfate, filtered, and the filtrate concentrated under vacuum to give a crude oil. The crude oil was purified by chromatography on silica using 5-10% ethyl acetate in n-hexane as eluant to give 2-((5-bromopentyl)oxy)tetrahydro-2H-pyran, 2 (4.5 g, 83%) as a clear oil.

$^{1H}$ NMR (300 MHz, CDCl3): δ ppm 4.55-4.54 (d, J=4.3 Hz, 1H), 3.92-3.72 (m, 2H), 3.42-3.38 (m, 3H), 1.88-1.55 (m, 3H), 1.52-1.50 (m, 10H).

Synthesis of 2-(dodeca-6,11-diyn-1-yloxy)tetrahydro-2H-pyran 4a

To a solution of 1,6-heptadiyne 3a (5 g, 54.3 mmol) and hexamethylphosphoramide (19 mL, 108 mmol) in tetrahydrofuran (100 mL) at −78° C. was added [2.5 M n-butyllithium in n-hexane] (21.7 mL, 54.3 mmol) dropwise. Upon completion of addition, the solution was stirred at −78° C. for one hour then warmed to −20° C. for an additional hour. The resulting solution was cooled once again to −78° C. whereupon a solution of 2-((5-bromopentyl)oxy)tetrahydro-2H-pyran, 2 (6.8 g, 27.1 mmol) in tetrahydrofuran (10 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil. The crude oil was purified by chromatography on silica using 5-10% ethyl acetate in n-hexane as eluant to give 2-(dodeca-6,11-diyn-1-yloxy)tetrahydro-2H-pyran, 4a (4.1 g, 58%) as a clear oil.

1H NMR (300 MHz, CDCl3): δ ppm 4.57-4.56 (m, 1H), 3.96-3.82 (m, 1H), 3.77-3.69 (m, 1H), 3.50-3.41 (m, 1H), 3.39-3.34 (m, 1H), 2.29-2.25 (m, 4H), 2.15-2.12 (m, 2H), 1.95-1.94 (t, J=5.8 Hz, 1H), 1.73-1.43 (m, 14H).

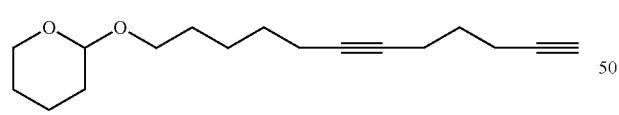

Synthesis of 2-(octadeca-6,11-diyn-1-yloxy)tetrahydro-2H-pyran 6a

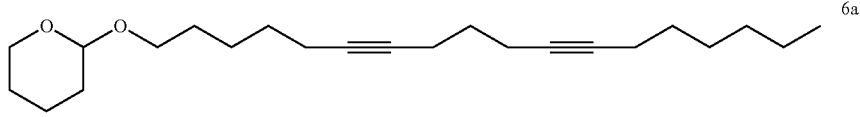 [SMILES: CCCCCCC#CCCCC#CCCCCCOC1CCCCO1]

To a solution of 2-(dodeca-6,11-diyn-1-yloxy)tetrahydro-2H-pyran, 4a (4.1 g, 15.64 mmol) and hexamethylphosphoramide (11 mL, 62.6 mmol) in tetrahydrofuran (100 mL) at −78° C. was added [2.5 M n-butyllithium in n-hexane] (12.5 mL, 31.3 mmol) dropwise. Upon completion of addition, the solution was stirred at −78° C. for one hour then warmed to −20° C. for an additional hour. The resulting solution was cooled once again to −78° C. whereupon a solution of 1-iodohexane 5a (9.5 mL, 62.6 mmol) in tetrahydrofuran (20 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil. The crude oil was purified by chromatography on silica using 5% ethyl acetate in n-hexane as eluant to give 2-(octadeca-6,11-diyn-1-yloxy)tetrahydro-2H-pyran, 6a (3.1 g, 57%) as a clear oil. $^{1H}$ NMR (300 MHz, CDCl3): 4.58-4.55 (m, 1H), 3.86-3.82 (m, 1H), 3.77-3.69 (m, 1H), 3.51-3.47 (m, 1H), 3.41-3.34 (m, 1H), 2.26-2.21 (m, 6H), 2.14-2.12 (m, 6H), 1.66-1.26 (m, 18H), 0.93-0.85 (t, J=6.5 Hz, 3H).

To a solution of Sodium borohydride (0.27 g, 14.8 mmol) in ethanol (50 mL) under hydrogen blanket at 0° C. was added Nickel (II) acetate tetrahydrate (1.55 g, 6.25 mmol). Upon completion of addition, the reaction was evacuated under vacuum and flushed with hydrogen. After 10 minutes of stirring, ethylenediamine (1.8 mL, 26.8 mmol), and a solution of 2-(octadeca-6,11-diyn-1-yloxy)tetrahydro-2H-pyran, 6a (3.1 g, 8.93 mmol) in ethanol (10 mL) was added. The reaction was stirred at room temperature under a hydrogen balloon for 4 hours. After 4 hours, the reaction mixture was evacuated of hydrogen and then flushed with nitrogen. The crude mixture was filtered over celite, and the filtrate concentrated under vacuum to give a crude oil weighing 4 g. The crude oil was purified by chromatography on silica using 5-10% diethyl ether in n-hexane as eluant to give 2-(((6Z,11Z)-octadeca-6,11-dien-1-yl)oxy)tetrahydro-2H-pyran, 7a (2.86 g, 92% yield) as a clear oil.

1H NMR (300 MHz, CDCl3): 5.4-5.34 (m, 4H), 4.58-4.55 (m, 1H), 3.86-3.82 (m, 1H), 3.74-3.68 (m, 1H), 3.51-3.49 (m, 1H), 3.41-3.36 (m, 1H), 2.06-1.99 (m, 6H), 1.83-1.67 (m, 2H), 1.59-1.51 (m, 6H), 1.48-1.32 (m, 16H), 0.92-0.85 (t, J=6.6 Hz, 3H).

Synthesis of (6Z,11Z)-octadeca-6,11-dien-1-ol 8a

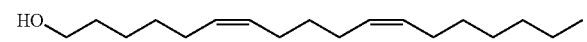

8a

Procedure previously described.

1H NMR (300 MHz, CDCl3): 5.37-5.33 (m, 4H), 3.65-3.61 (m, 1H), 2.06-1.99 (m, 6H), 1.56-1.41 (m, 4H), 1.38-1.27 (m, 14H), 0.88-0.85 (t, J=6.6 Hz, 3H).

Synthesis of (6Z,11Z)-octadeca-6,11-dienoic Acid 9a

9a

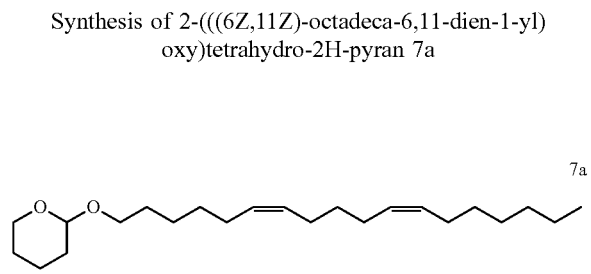

Synthesis of 2-(((6Z,11Z)-octadeca-6,11-dien-1-yl)oxy)tetrahydro-2H-pyran 7a

7a

Procedure previously described.

1H NMR (300 MHz, CDCl3): 5.38-5.33 (m, 4H), 2.37-2.33 (t, J=5.6 Hz, 2H), 2.06-1.99 (m, 6H), 1.67-1.59 (m, 2H), 1.41-1.25 (m, 14H), 0.89-0.85 (t, J=6.6 Hz, 3H).

Synthesis of (S)-4-(dimethylamino)butane-1,2-diyl (6Z,6'Z,11Z,11'Z)-bis(octadeca-6,11-dienoate) (AKG-UO-1a)

AKG-UO-1a

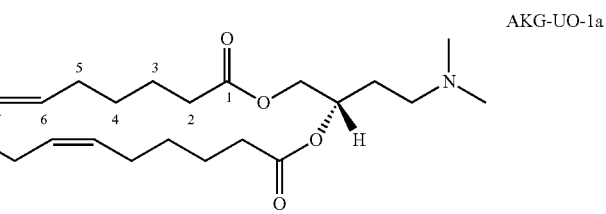

Procedure previously described.

1H NMR (300 MHz, CDCl3): 5.39-5.29 (m, 8H), 5.14-5.12 (m, 1H), 4.25 (dd, J=11.8, 3.3 Hz, 1H), 4.06 (dd, J=11.8, 6.3 Hz, 1H), 2.32-2.28 (m, 6H), 2.20 (s, 6H), 2.03-2.01 (m, 16H), 1.74-1.64 (m, 2H), 1.62-1.60 (m, 6H), 1.38-1.27 (m, 22H), 0.89-0.85 (m, 6H).

MS (APCI+): 658.5 (M+1)

A general synthesis of acid intermediate for AKG-BDG-1 involves i) synthesis of 4-mercapto butyric acid from 4-bromo butyric acid, ii) reaction of 4-mercapto butyric acid with DPS resulting in 4-(2-pyridinyldisulfanyl)butanoic acid iii) catalytic hydrogenation of 3-decyn-1-ol to a cis-alkene, iv) tosylation of the primary alcohol, v) displacement of the tosyl group using thiourea resulting in a terminal thiol, and finally vi) coupling of the terminal thiol with 4-(2-pyridinyldisulfanyl)butanoic acid prepared in step ii above, resulting in the disulfide containing acid intermediate. Following a similar synthetic sequence starting from 3-dodecyn-1-ol yielded the second acid intermediate used in the synthesis of AKG-BDG-2.

Scheme 4 Synthesis of AKG-UO-1, AKG-UO-4, AKG-UO-5, AKG-BDG-1 and AKG-BDG-2

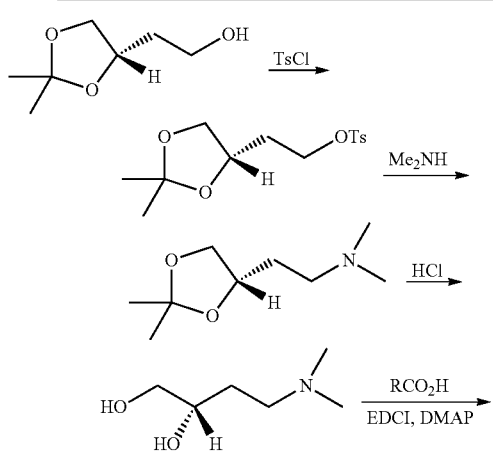

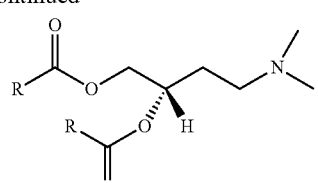

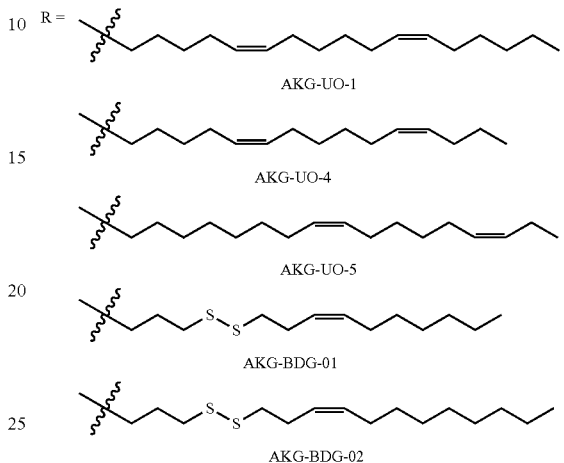

AKG-UO-1

AKG-UO-4

AKG-UO-5

AKG-BDG-01

AKG-BDG-02

A general synthesis of lipids AKG-UO-1, AKG-UO-4, AKG-UO-5, AKG-BDG-1 and AKG-BDG-2 shown in Scheme 4, involves the following steps: i) tosylation of the primary alcohol of the commercially available chiral dioxolane ii) displacement of the tosyl group using dimethylamine resulting in a tertiary amine, iii) acid catalyzed deprotection of the diol, and finally iv) esterification of the diol with the corresponding acid intermediates synthesized according to Schemes 1-3. AKG-UO-2 is prepared following a similar synthetic sequence starting from a different dioxolane and a corresponding acid intermediate, as shown in Scheme 5 below.

Scheme 5 Synthesis of AKG-UO-2

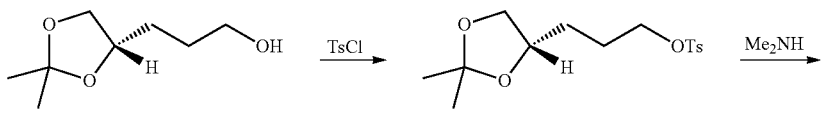

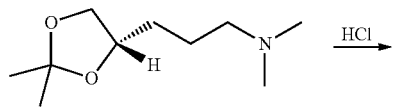

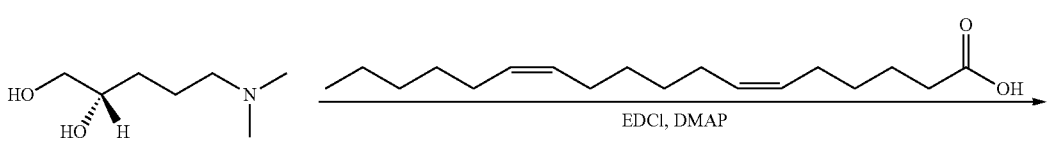

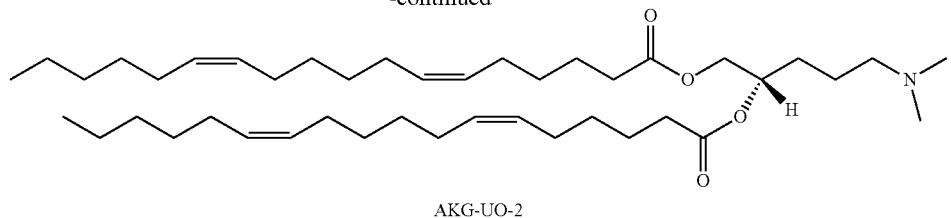

AKG-UO-2

A general synthesis of trialkyl phosphate containing lipid AKG-UO-3 shown in Scheme 6, involves the following steps: i) reaction of primary alcohol of a commercially available chiral dioxolane with methyl dichlorophosphite resulting in the corresponding dialkyl chlorophosphite ii) displacement of the chloride in dialkyl chlorophosphite by treating it with 3-bromo propanol, resulting in the corresponding trialkyl phosphite iii) acid catalyzed deprotection of the diol iv) esterification of the diol with the corresponding acid intermediate synthesized according to Scheme 1, and finally v) displacement of the bromide group using dimethylamine resulting in a tertiary amine.

Scheme 6 Synthesis of AKG-UO-3

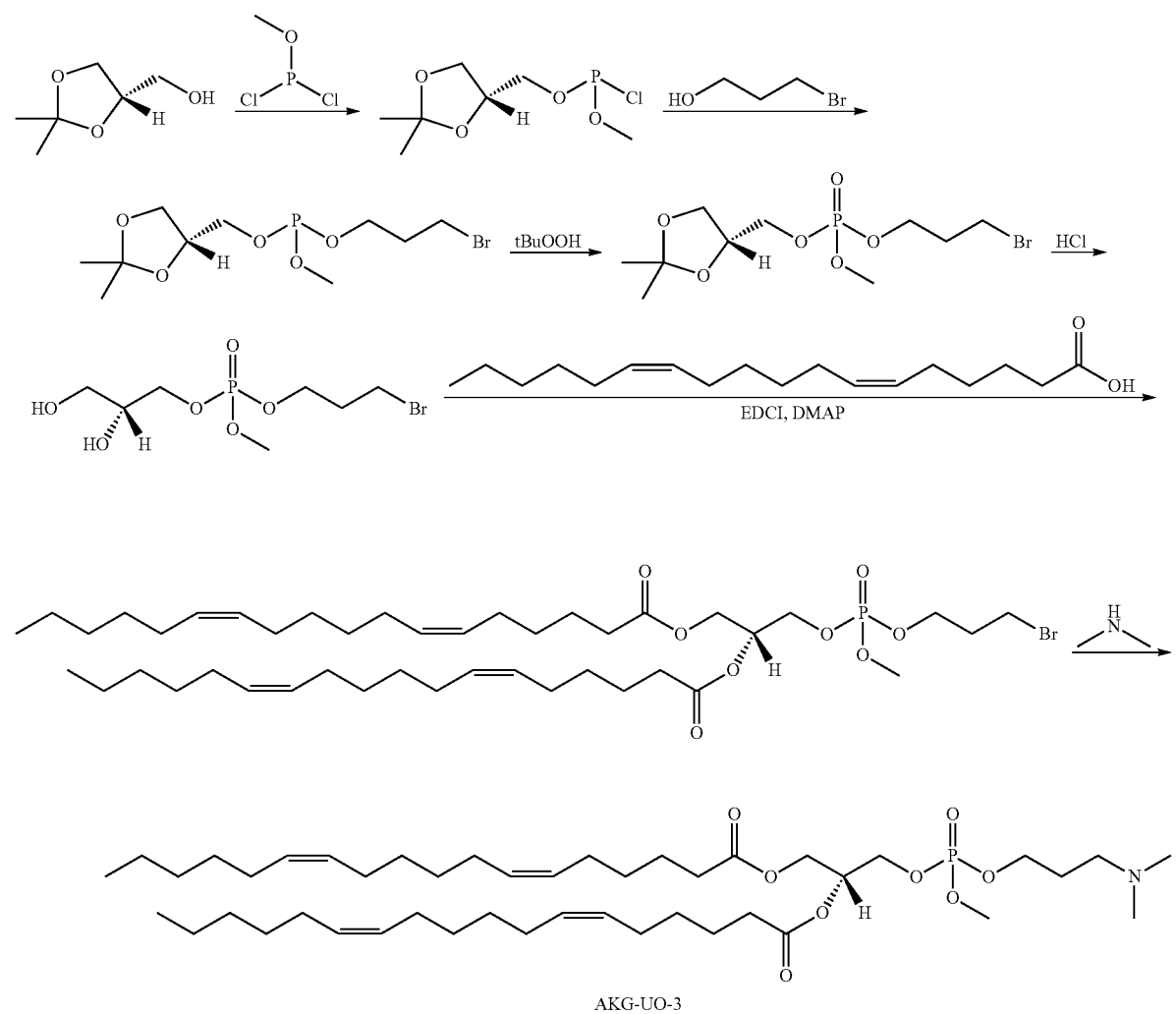

AKG-UO-3

Alternatively, acid intermediates having two methylene groups between double bond positions in the hydrocarbon chain are synthesized as described in Caballeira et al., Chem. Phys. Lipids, vol. 100, p. 33-40, 1999, or as described by D'yakonov et al. (D'yakonov et al., Med. Chem. Res., 2016, vol. 25, p. 30-39; D'yakonov et al., Chem. Commun. 2013, vol. 49, p 8401-8403; D'yakonov et al., 2020, Phytochem. Rev.).

(S)-4-(dimethylamino)butane-1,2-diyl (6Z,6'Z,12Z,12'Z)-bis(octadeca-6,12-dienoate) (AKG-UO-1, O-11956)

(S)-4-(diethylamino)butane-1,2-diyl (6Z,6'Z,12Z,12'Z)-bis(octadeca-6,12-dienoate) (AKG-UO-1A, O-11955)

(S)-4-(dimethylamino)butane-1,2-diyl (6Z,6'Z,12Z,12'Z)-bis(hexadeca-6,12-dienoate, AKG-UO-4, O-12401)

(S)-4-(diethylamino)butane-1,2-diyl (6Z,6'Z,12Z,12'Z)-bis(hexadeca-6,12-dienoate, AKG-UO-4A, O-12402)

(S)-4-(dimethylamino)butane-1,2-diyl (6Z,6'Z,11Z,11'Z)-bis(octadeca-6,11-dienoate)(AKG-UO-1a)

Scheme 7

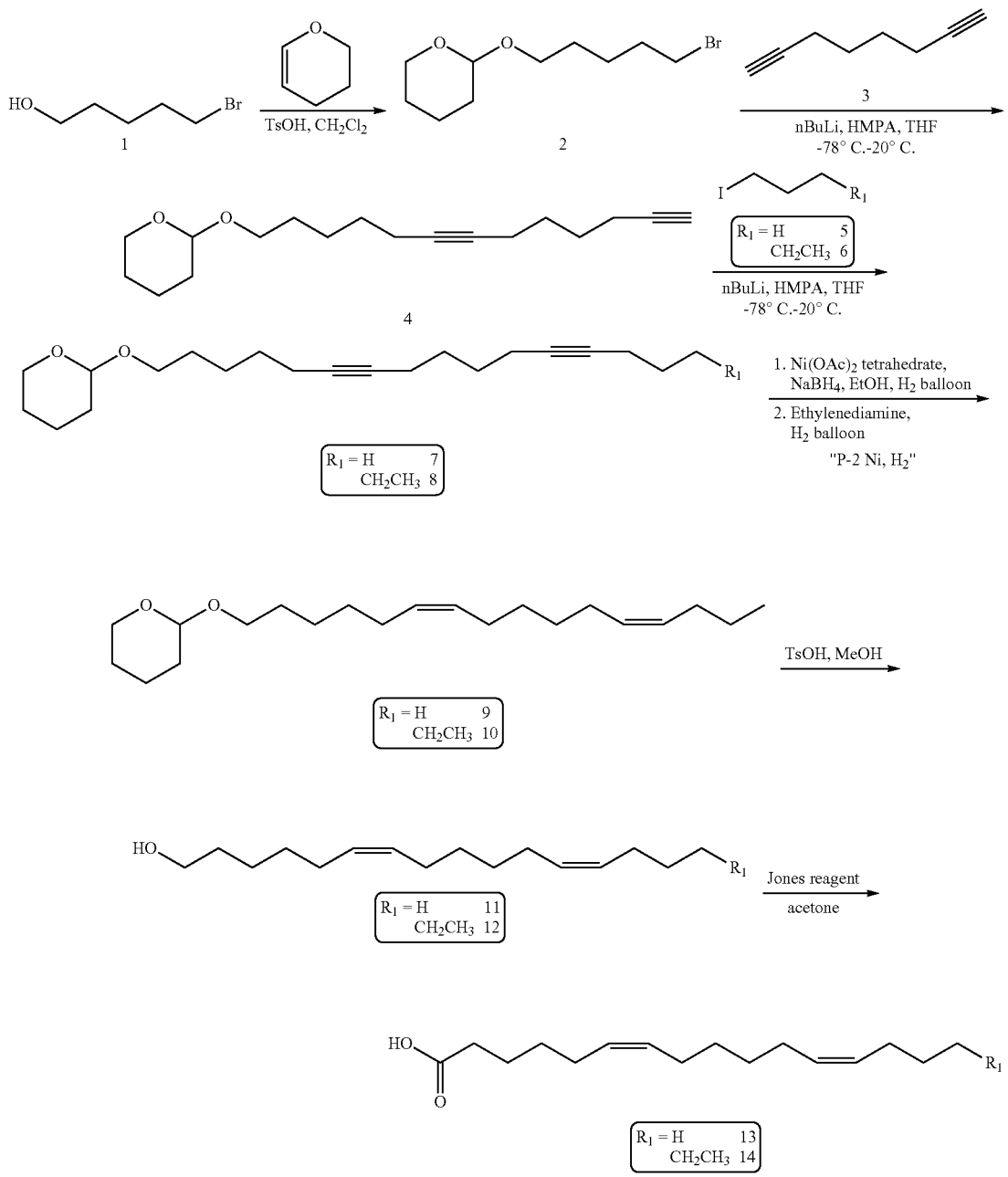

Scheme 8

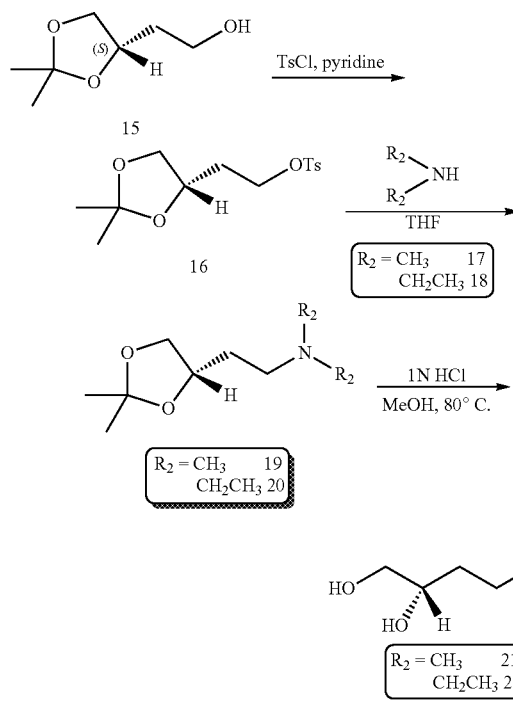

Experimental Procedure

Synthesis of 2-((5-bromopentyl)oxy)tetrahydro-2H-pyran 2

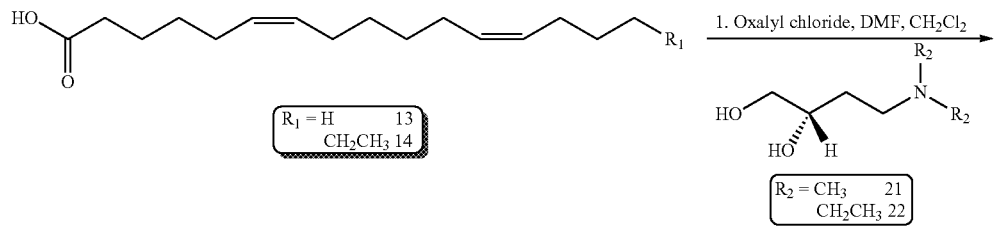

To a solution of 5-bromo-1-pentanol 1 (3.6 g, 21.6 mmol) in dichloromethane (100 mL) and pyridinium p-toluene sulfonate (40 mg, 0.16 mmol) at 0° C. was added 3,4-dihydro-2H-pyran (6.54 mL, 71.8 mmol). The resulting solution was stirred at room temperature for one hour then quenched with water. The mixture was extracted with ethyl acetate (2×100 mL). The combined organics were washed with brine then dried over magnesium sulfate, filtered, and the filtrate concentrated under vacuum to give a crude oil. The crude oil was purified by chromatography on silica using 5-10% ethyl acetate in n-hexane as eluant to give 2-((5-bromopentyl)oxy)tetrahydro-2H-pyran, 2 (4.5 g, 83%) as a clear oil.

1H NMR (300 MHz, CDCl3): δ ppm 4.55-4.54 (d, J=4.3 Hz, 1H), 3.92-3.72 (m, 2H), 3.42-3.38 (m, 3H), 1.88-1.55 (m, 3H), 1.52-1.50 (m, 10H).

Scheme 9

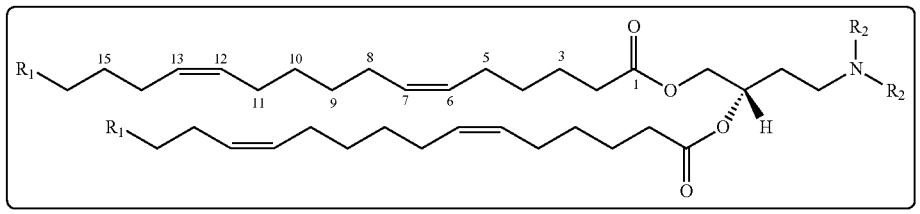

| Compounds | $R_1$ | $R_2$ |
|---|---|---|
| AKG-UO-1 | $CH_2CH_3$ | $CH_3$ |
| AKG-UO-1A | $CH_2CH_3$ | $CH_2CH_3$ |
| AKG-UO-4 | H | $CH_3$ |
| AKG-UO-4A | H | $CH_2CH_3$ |

Synthesis of 2-(trideca-6,12-diyn-1-yloxy)tetrahydro-2H-pyran 4

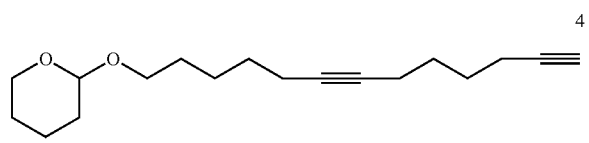 [SMILES: C#CCCCCC#CCCCCCOC1CCCCO1]

4

To a solution of 1,7-Octadiyne 3 (6 mL, 45.4 mmol) and hexamethylphosphoramide (16 mL, 90.8 mmol) in tetrahydrofuran (100 mL) at −78° C. was added [2.5 M n-butyllithium in n-hexane] (18 mL, 45.4 mmol) dropwise. Upon completion of addition, the solution was stirred at −78° C. for one hour then warmed to −20° C. for an additional hour. The resulting solution was cooled once again to −78° C. whereupon a solution of 2-((5-bromopentyl)oxy)tetrahydro-2H-pyran, 2 (5.67 g, 22.7 mmol) in tetrahydrofuran (10 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil weighing 9 g. The crude oil was purified by chromatography on silica using 5-10% ethyl acetate in n-hexane as eluant to give 2-(trideca-6,12-diyn-1-yloxy)tetrahydro-2H-pyran, 4 (4.5 g, 72%) as a clear oil.

1H NMR (300 MHz, d6.DMSO): δ ppm 4.544.53 (m, 1H), 3.72-3.61 (m, 1H), 3.60-3.58 (m, 1H), 3.43-3.33 (m, 1H), 3.32-3.29 (m, 1H), 2.77-2.75 (t, J=5.8 Hz, 1H), 2.16-2.13 (m, 6H), 1.55-1.41 (m, 16H).

Representative Procedure for Alkylation of Alkynes

Synthesis of 2-(hexadeca-6,12-diyn-1-yloxy)tetrahydro-2H-pyran 7

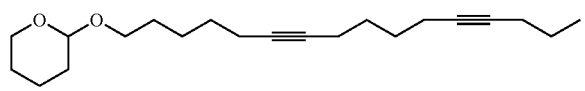

7

To a solution of 2-(trideca-6,12-diyn-1-yloxy) tetrahydro-2H-pyran, 4 (7.14 g, 25.86 mmol) and hexamethylphosphoramide (18 mL, 103.4 mmol) in tetrahydrofuran (100 mL) at −78° C. was added [2.5 M n-butyllithium in n-hexane] (41.3 mL, 103.4 mmol) dropwise. Upon completion of addition, the solution was stirred at −78° C. for one hour then warmed to −20° C. for an additional hour. The resulting solution was cooled once again to −78° C. whereupon a solution of 1-iodopropane 5 (9.9 mL, 103.4 mmol) in tetrahydrofuran (20 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil weighing 9 g. The crude oil was purified by chromatography on silica using 5% ethyl acetate in n-hexane as eluant to give 2-(hexadeca-6,12-diyn-1-yloxy)tetrahydro-2H-pyran, 7 (5.9 g, 72%) as a clear oil.

$^{1H}$ NMR (300 MHz, CDCl3): 4.57-4.55 (m, 1H), 3.86-3.74 (m, 1H), 3.73-3.71 (m, 1H), 3.50-3.39 (m, 1H), 3.37-3.36 (m, 1H), 2.16-2.11 (m, 8H), 1.59-1.56 (m, 2H), 1.55-1.47 (m, 16H), 0.98-0.93 (t, J=1.6 Hz, 3H).

2-(octadeca-6,12-diyn-1-yloxy)tetrahydro-2H-pyran 8

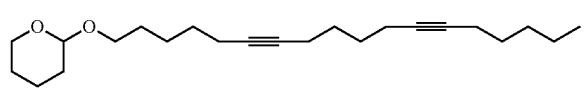

8

1H NMR (300 MHz, CDCl3): 4.57-4.55 (m, 1H), 3.85-3.74 (m, 1H), 3.73-3.70 (m, 1H), 3.50-3.38 (m, 1H), 3.36-3.35 (m, 1H), 2.23-2.12 (m, 8H), 1.61-1.54 (m, 2H), 1.53-1.48 (m, 16H), 1.47-1.46 (m, 4H), 0.90-0.85 (t, J=1.6 Hz, 3H).

Representative Procedure for Reduction of Alkynes to Alkenes Using "P-2 Ni"

Synthesis of 2-(((6Z,12Z)-hexadeca-6,12-dien-1-yl)oxy)tetrahydro-2H-pyran 9

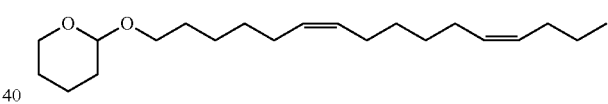

9

To a solution of Sodium borohydride (0.56 g, 14.8 mmol) in ethanol (80 mL) under hydrogen blanket at 0° C. was added Nickel (II) acetate tetrahydrate (3.22 g, 12.98 mmol). Upon completion of addition, the reaction was evacuated under vacuum and flushed with hydrogen. After 10 minutes of stirring, ethylenediamine (3.7 mL, 65.6 mmol), and a solution of 2-(hexadeca-6,12-diyn-1-yloxy)tetrahydro-2H-pyran, 7 (5.9 g, 18.55 mmol) in ethanol (10 mL) was added. The reaction was stirred at room temperature under a hydrogen balloon for 4 hours. After 4 hours, the reaction mixture was evacuated of hydrogen and then flushed with nitrogen. The crude mixture was filtered over celite, and the filtrate concentrated under vacuum to give a crude oil weighing 4 g. The crude oil was purified by chromatography on silica using 5-10% diethyl ether in n-hexane as eluant to give 2-(((6Z,12Z)-hexadeca-6,12-dien-1-yl)oxy)tetrahydro-2H-pyran, 9 (4.67 g, 78% yield) as a clear oil.

1H NMR (300 MHz, CDCl3): 5.35-5.34 (m, 4H), 4.58-4.55 (m, 1H), 3.86-3.74 (m, 1H), 3.73-3.71 (m, 1H), 3.51-3.39 (m, 1H), 3.36-3.35 (m, 1H), 2.03-1.98 (m, 8H), 1.57-1.39 (m, 2H), 1.38-1.36 (m, 6H), 1.35-1.32 (m, 10H), 0.91-0.86 (t, J=1.6 Hz, 3H).

$^{13C}$ NMR (300 MHz, CDCl3): 129.98, 129.85, 98.93, 77.53, 77.10, 76.68, 67.72, 62.43, 30.86, 29.71, 29.70, 29.45, 29.46, 29.44, 27.20, 27.19, 26.01, 25.59, 22.98, 19.78, 13.91.

2-(((6Z,12Z)-octadeca-6,12-dien-1-yl)oxy)tetrahydro-2H-pyran 10

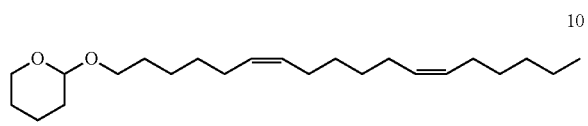 [SMILES: CCCCC/C=C\CCCC/C=C\CCCCCOC1CCCCO1]

10

1H NMR (300 MHz, CDCl3): 5.39-5.29 (m, 4H), 4.58-4.55 (m, 1H), 3.86-3.76 (m, 1H), 3.74-3.68 (m, 1H), 3.51-3.41 (m, 1H), 3.39-3.36 (m, 1H), 2.14-1.97 (m, 8H), 1.56-1.38 (m, 2H), 1.37-1.35 (m, 6H), 1.34-1.28 (m, 14H), 0.93-0.85 (t, J=1.6 Hz, 3H).

13C NMR (300 MHz, CDCl3): 130.13, 129.97, 129.84, 129.71, 98.93, 77.53, 77.10, 76.68, 67.71, 62.42, 31.62, 30.86, 29.72, 29.71, 29.47, 29.46, 27.27, 27.18, 26.01, 25.59, 22.67, 19.78, 14.18.

Representative Procedure for Deprotection of Tetrahydropyranyl Ether (THP)

Synthesis of (6Z,12Z)-hexadeca-6,12-dien-1-ol 11

11

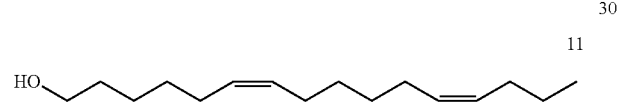

To a solution of 2-(((6Z,12Z)-hexadeca-6,12-dien-1-yl)oxy)tetrahydro-2H-pyran, 9 (4.67 g, 14.5 mmol) in methanol (20 mL) was added p-Toluenesulfonic acid monohydrate (300 mg, 1.58 mmol) at room temperature. The resulting solution was stirred at room temperature for 3 hours then quenched with water. The mixture was extracted with ethyl acetate (2×50 mL). The combined organics were washed with water then dried over magnesium sulfate, filtered and the filtrate concentrated under vacuum to give a crude oil weighing 4 g. The crude oil was purified by chromatography on silica using 5-10% diethyl ether in n-hexane as eluant to give (6Z,12Z)-hexadeca-6,12-dien-1-ol, 11 (2.5 g, 72%) as a clear oil.

1H NMR (300 MHz, CDCl3): 5.34-5.33 (m, 4H), 3.65-3.61 (m, 2H), 2.02-2.00 (m, 8H), 1.36-1.34 (m, 2H), 1.34-1.25 (m, 10H), 0.89-0.86 (t, J=0.82 Hz, 3H).

(6Z,12Z)-octadeca-6,12-dien-1-ol 12

12

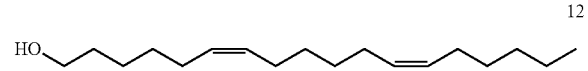 [SMILES: CCCCC/C=C\CCCC/C=C\CCCCCO]

1H NMR (300 MHz, CDCl3): 5.36-5.33 (m, 4H), 3.65-3.61 (m, 2H), 2.02-2.01 (m, 8H), 1.36-1.35 (m, 2H), 1.34-1.25 (m, 14H), 0.88-0.85 (t, J=0.76 Hz, 3H).

Representative Procedure for Oxidation of Alcohol to Carboxylic Acid Using Jones Reagent

Synthesis of (6Z,12Z)-Hexadeca-6,12-Dienoic Acid 13

13

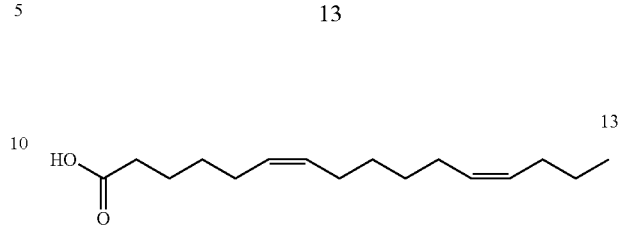

A mixture of (6Z,12Z)-hexadeca-6,12-dien-1-ol, 11 (2.5 g, 10.5 mmol) and Jones Reagent [2M in sulfuric acid], (10.5 mL, 21 mmol) in acetone (20 mL) at 0° C. was stirred for 2 hours. The mixture was quenched with water and extracted with ethyl acetate (2×100 mL). The combined organics were dried over magnesium sulfate, filtered and the filtrate concentrated under vacuum to give a crude oil. The crude oil was purified by chromatography on silica using 20% ethyl acetate in n-hexane as eluant to give (6Z,12Z)-hexadeca-6,12-dienoic acid, 13 (1.7 g, 68%) as a clear oil.

1H NMR (300 MHz, CDCl3): 5.35-5.33 (m, 4H), 2.37-2.32 (t, 2H), 2.06-1.98 (m, 8H), 1.64-1.39 (m, 2H), 1.37-1.32 (m, 8H), 0.91-0.87 (t, J=0.91 Hz, 3H).

(6Z,12Z)-octadeca-6,12-dienoic Acid 14

14

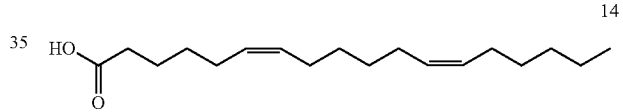

1H NMR (300 MHz, CDCl3): 5.36-5.32 (m, 4H), 2.35-2.33 (t, 2H), 2.06-2.01 (m, 8H), 1.64-1.42 (m, 2H), 1.34-1.28 (m, 12H), 0.90-0.85 (t, 3H).

Synthesis of (S)-2-(2,2-dimethyl-1,3-dioxolan-4-yl)ethyl 4-methylbenzenesulfonate 16

16

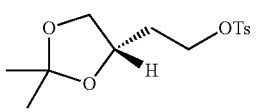

To a mixture of (S)-2-(2,2-dimethyl-1,3-dioxolan-4-yl)ethan-1-ol 15 (25 g, 171.1 mmol) in pyridine (30 mL) at 0° C. was added p-Toluenesulfonylchloride (35.8 g, 188.2 mmol) and DMAP (140 mg, 1.14 mmol) and the reaction was stirred at room temperature overnight. The mixture was diluted with CH2Cl2 (500 mL), washed with sat. NH4Cl, water and Brine. The organic layer was dried over anhydrous Na2SO4. The solvent was evaporated, and the crude residue used for the next step without purification. (43.8 g, 85%).

1H NMR (300 MHz, CDCl3): δ ppm 7.77 (d, J=8.2 Hz, 2H), 7.34 (d, J=8.1 Hz, 2H), 4.15-4.01 (m, 3H), 3.65-3.47 (m, 2H), 2.43 (s, 3H), 1.82-1.62 (m, 2H), 1.32 (s, 3H), 1.27 (s, 3H).

Representative Procedure for Di-Alkylamine Substitution

Synthesis of (S)-2-(2,2-dimethyl-1,3-dioxolan-4-yl)-N,N-dimethylethan-1-amine 19

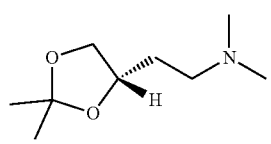

19

A mixture of (S)-2-(2,2-dimethyl-1,3-dioxolan-4-yl)ethyl 4-methylbenzenesulfonate 16 (10 g, 33.3 mmol) and dimethylamine solution 17 (166 mL, 333.3 mmol) (2M in THF) was stirred at room temperature for 2 days. The mixture was concentrated, and the crude residue was diluted with CH2Cl2 (500 mL), washed with sat. NaHCO₃, water and Brine. The organic layer was dried over anhydrous Na2SO4. The solvent was evaporated, and the crude residue was purified by flash chromatography (SiO2:CH2Cl2=100% to 10% of MeOH in CH2Cl2 with 1% NH4OH) and colorless oil product 19 was obtained (2.1 g, 37%).

1H NMR (300 MHz, CDCl3): δ ppm 4.15-4.01 (m, 2H), 3.52 (dd, J=7.4, 7.4 Hz, 1H), 2.41-2.23 (m, 2H), 2.21 (s, 6H), 1.82-1.62 (m, 2H), 1.39 (s, 3H), 1.33 (s, 3H).

MS (APCI+): 174.1 (M+1)

(S)-2-(2,2-diethyl-1,3-dioxolan-4-yl)-N,N-dimethyl-ethan-1-amine 20

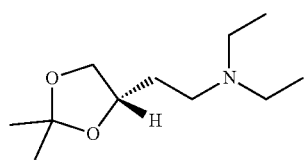

20

1H NMR (300 MHz, CDCl3): δ ppm 4.15-4.01 (m, 2H), 3.48 (dd, J=7.4, 7.4 Hz, 1H), 2.48-2.43 (m, 6H), 1.82-1.62 (m, 2H), 1.36 (s, 3H), 1.27 (s, 3H), 0.97 (t, J=7.2 Hz, 6H).

MS (APCI+): 202.2 (M+1)

Representative Procedure for Ketal Hydrolysis

Synthesis of (S1-4-(dimethylamino)butane-1,2-diol hydrochloride Salt 21

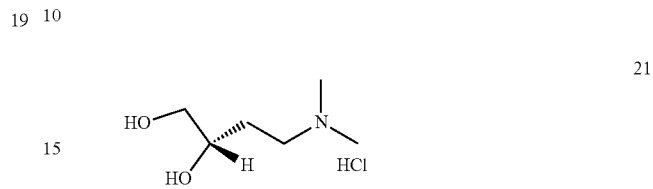

21

To a mixture of (S)-2-(2,2-dimethyl-1,3-dioxolan-4-yl)-N,N-dimethylethan-1-amine 19 (2 g, 11.54 mmol) in MeOH (10 mL) was added 1N HCl aqueous solution (17 mL, 17.3 mmol) and the reaction was heated at 80° C. for 45 min. TLC (Rf=0.1, 10% MeOH in CH2Cl2 with 1% NH4OH) showed the completion of reaction. After concentration of the reaction mixture, the crude residue was dissolved in water (5 mL) and lyophilized overnight. Sticky syrup product 21 was obtained (2.1 g, quant.) as HCl salt.

1H NMR (300 MHz, D2O): δ ppm 3.77-3.72 (m, 1H), 3.54-3.46 (m, 2H), 3.29-3.22 (m, 2H), 2.85 (s, 6H), 1.92-1.79 (m, 2H).

MS (APCI+): 134.1 (M+1)

(S)-4-(diethylamino)butane-1,2-diol hydrochloride Salt 22

22

1H NMR (300 MHz, D2O): δ ppm 3.77-3.72 (m, 1H), 3.54-3.46 (m, 2H), 3.22-3.15 (m, 6H), 1.92-1.74 (m, 2H), 1.24 (t, J=7.4 Hz, 6H).

MS (APCI+): 162.1 (M+1)

Representative Procedure for Di-Esterification

Synthesis of (S)-4-(dimethylamino)butane-1,2-diyl (6Z,6'Z,12Z,12'Z)-bis(octadeca-6,12-dienoate) AKG-UO-1 (O-11956)

AKG-UO-1

Oxalyl chloride (0.33 mL, 3.9 mmol) was added dropwise to a solution of (6Z,12Z)-octadeca-6,12-dienoic acid, 14 (0.36 g, 1.3 mmol) in dichloromethane/DMF (15 mLs, 25 mL) at 0° C. and allowed reaction to warm to room temperature and stir for one hour. After one hour, the reaction was concentrated under vacuum to dryness. The residue was re-dissolved in dichloromethane (10 mL) and added to a mixture of N,N-Diisopropylethylamine (2.3 mL, 10 mmol), 4-Dimethylaminopyridine (317 mg, 2.6 mmol), and (S)-4-(dimethylamino)butane-1,2-diol hydrochloride, 21 (101 mg, 0.6 mmol). The resulting solution was allowed to stir for 24 hours. After 24 hours, the reaction was cooled to 0 C and quenched with water (10 mL). The reaction mixture was extracted with dichloromethane (2×100 mL) and the organics were washed with water and brine (2×100 mL). The organic layer was dried over magnesium sulfate, filtered, and the filtrate concentrated under vacuum to give a crude oil. The crude oil was purified by chromatography on silica using 2% methanol in dichloromethane as eluant to give (S)-4-(dimethylamino)butane-1,2-diyl (6Z,6'Z,12Z, 12'Z)-bis(octadeca-6,12-dienoate), AKG-UO-1, (0.12 g, 30%) as a yellow oil.

1H NMR (300 MHz, CDCl3): 5.40-5.29 (m, 8H), 5.14-5.12 (m, 1H), 4.25 (dd, J=11.8, 3.3 Hz, 1H), 4.05 (dd, J=12.1, 6.3 Hz, 1H), 2.32-2.26 (m, 6H), 2.20 (s, 6H), 2.06-1.99 (m, 16H), 1.78-1.70 (m, 2H), 1.65-1.58 (m, 4H), 1.42-1.25 (m, 24H), 0.90-0.85 (m, 6H).

MS (APCI+): 658.5 (M+1)

(S)-4-(diethylamino)butane-1,2-diyl (6Z,6'Z,12Z, 12'Z)-bis(octadeca-6,12-dienoate) AKG-UO-1A (O-11955)

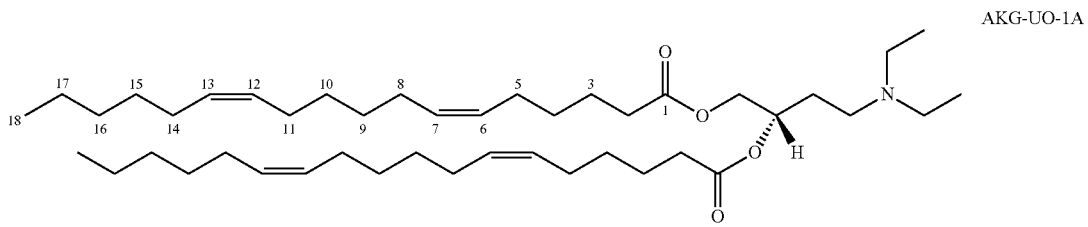 [SMILES: CCCCC/C=C\CCCC/C=C\CCCCC(=O)OC[C@H](CCN(CC)CC)OC(=O)CCCC/C=C\CCCC/C=C\CCCCC]

1H NMR (300 MHz, CDCl3): 5.37-5.29 (m, 8H), 5.12-5.10 (m, 1H), 4.25 (dd, J=12.1, 3.6 Hz, 1H), 4.05 (dd, J=11.8, 6.3 Hz, 1H), 2.52-2.42 (m, 6H), 2.29 (t, J=7.4 Hz, 4H)), 2.06-1.99 (m, 16H), 1.78-1.70 (m, 2H), 1.64-1.59 (m, 4H), 1.41-1.19 (m, 24H), 0.99 (t, J=7.1 Hz, 6H), 0.96-0.87 (m, 6H).

MS (APCI+): 686.6 (M+1)

(S)-4-(dimethylamino)butane-1,2-diyl (6Z,6'Z,12Z, 12'Z)-bis(hexadeca-6,12-dienoate) AKG-UO-4 (O-12401)

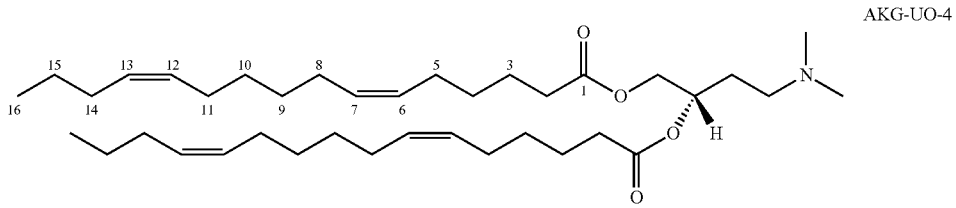 [SMILES: CCC/C=C\CCCC/C=C\CCCCC(=O)OC[C@H](CCN(C)C)OC(=O)CCCC/C=C\CCCC/C=C\CCC]

1H NMR (300 MHz, CDCl3): 5.39-5.29 (m, 8H), 5.13-5.12 (m, 1H), 4.24 (dd, J=11.8, 3.3 Hz, 1H), 4.05 (dd, J=11.8, 6.3 Hz, 1H), 2.32-2.27 (m, 6H), 2.19 (s, 6H), 2.01-1.99 (m, 16H), 1.75-1.72 (m, 2H), 1.65-1.58 (m, 4H), 1.36-1.31 (m, 16H), 0.91-0.86 (m, 6H).

MS (APCI+): 602.5 (M+1)

Synthesis of (S)-4-(diethylamino)butane-1,2-diyl (6Z,6'Z,12Z,12'Z)-bis(hexadeca-6,12-dienoate) AKG-UO-4A (O-12402)

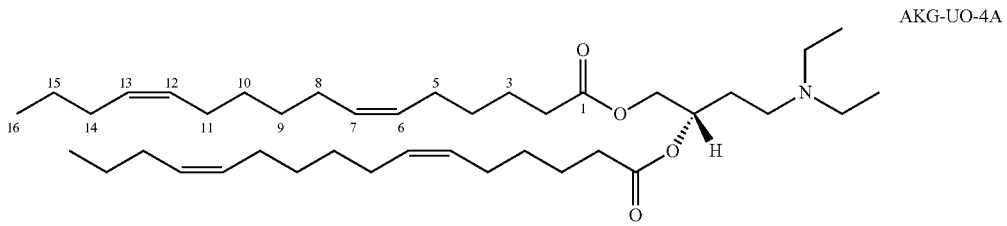 [SMILES: CCC/C=C\CCCC/C=C\CCCCC(=O)OC[C@H](CCN(CC)CC)OC(=O)CCCC/C=C\CCCC/C=C\CCC]

1H NMR (300 MHz, CDCl3): 5.40-5.29 (m, 8H), 5.12-5.11 (m, 1H), 4.25 (dd, J=11.8, 3.3 Hz, 1H), 4.05 (dd, J=11.8, 6.3 Hz, 1H), 2.54-2.43 (m, 6H), 2.29 (t, J=7.4 Hz, 4H), 2.11-1.96 (m, 16H), 1.74-1.65 (m, 2H), 1.65-1.59 (m, 4H), 1.39-1.31 (m, 16H), 0.99 (t, J=7.1 Hz, 6H), 0.91-0.89 (m, 6H).

MS (APCI+): 630.5 (M+1), and finally v) displacement of the bromide group using dimethylamine resulting in a tertiary amine.

vol. 25, p. 30-39; D'yakonov et al., Chem. Commun. 2013, vol. 49, p 8401-8403; D'yakonov et al., 2020, Phytochem. Rev.).

Example 1B: Synthesis of Ionizable Lipids (S)-4-(dimethylamino)butane-1,2-diyl (6Z,6'Z,12Z,12'Z)-bis(octadeca-6,12-dienoate) (AKG-UO-1, O-11956)

Scheme 7 Synthesis of AKG-UO-3

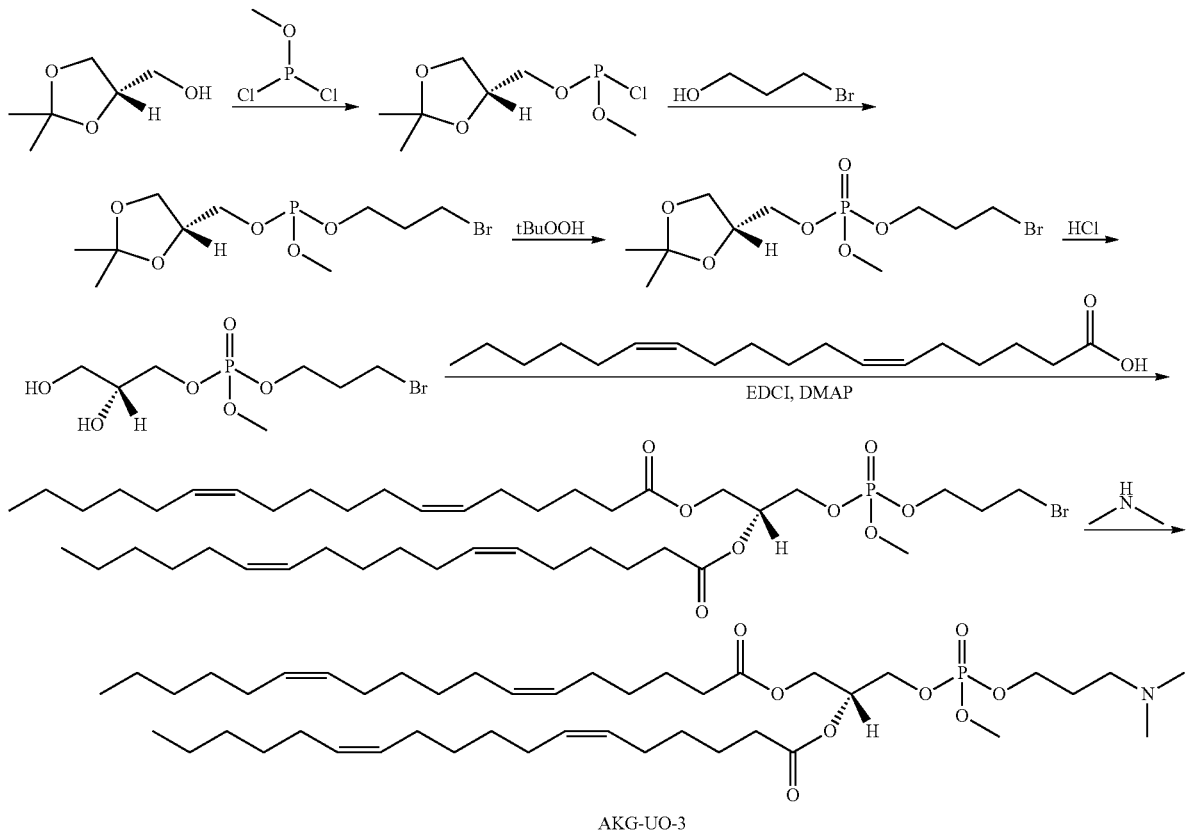

AKG-UO-3

Alternatively, acid intermediates having two methylene groups between double bond positions in the hydrocarbon chain are synthesized as described in Caballeira et al., Chem. Phys. Lipids, vol. 100, p. 33-40, 1999, or as described by D'yakonov et al. (D'yakonov et al., Med. Chem. Res., 2016, (S)-4-(diethylamino)butane-1,2-diyl (6Z,6'Z,12Z,12'Z)-bis(octadeca-6,12-dienoate) (AKG-UO-1A, O-11955)

(S)-4-(dimethylamino)butane-1,2-diyl (6Z,6'Z,12Z,12'Z)-bis(hexadeca-6,12-dienoate, AKG-UO-4, O-12401)

(S)-4-(diethylamino)butane-1,2-diyl (6Z,6'Z,12Z,12'Z)-bis(hexadeca-6,12-dienoate, AKG-UO-4A, O-12402)
(S)-4-(dimethylamino)butane-1,2-diyl (6Z,6'Z,11Z,11'Z)-bis(octadeca-6,11-dienoate)(AKG-UO-1a)
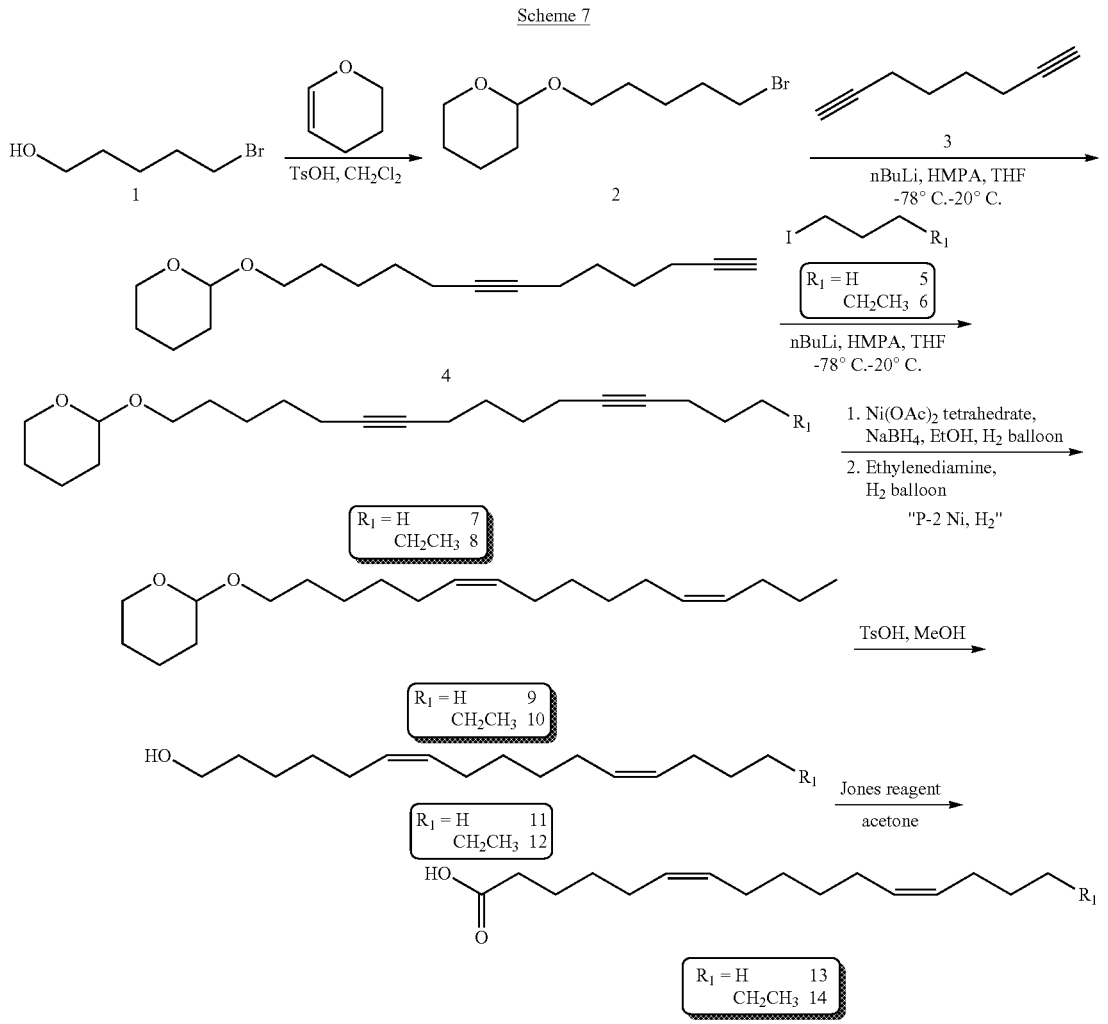
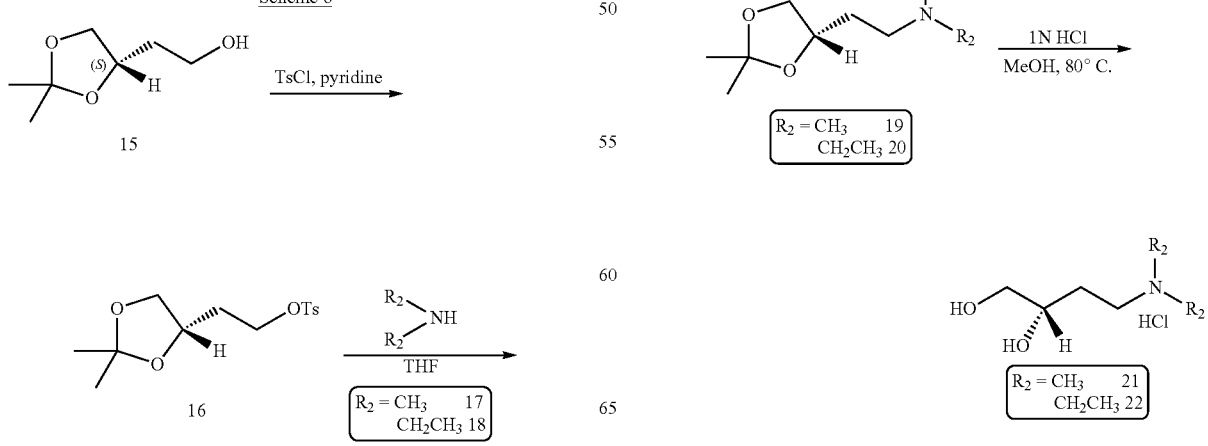

Scheme 9

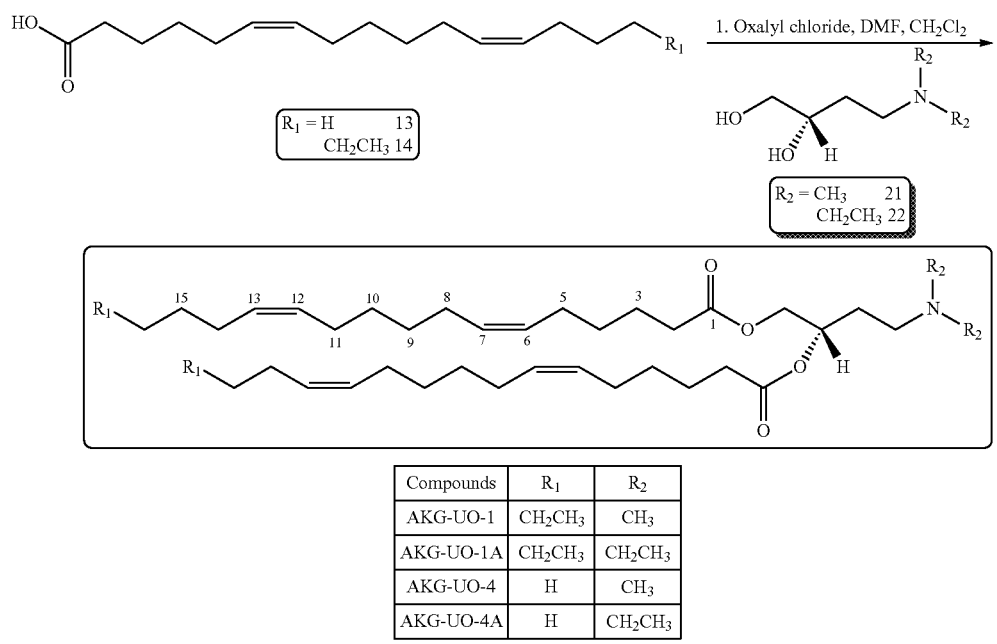

| Compounds | R₁ | R₂ |
|---|---|---|
| AKG-UO-1 | CH₂CH₃ | CH₃ |
| AKG-UO-1A | CH₂CH₃ | CH₂CH₃ |
| AKG-UO-4 | H | CH₃ |
| AKG-UO-4A | H | CH₂CH₃ |

EXPERIMENTAL PROCEDURE

Synthesis of 2-((5-bromopentyl)oxy)tetrahydro-2H-pyran 2

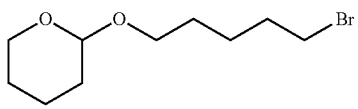

To a solution of 5-bromo-1-pentanol 1 (3.6 g, 21.6 mmol) in dichloromethane (100 mL) and pyridinium p-toluene sulfonate (40 mg, 0.16 mmol) at 0° C. was added 3,4-dihydro-2H-pyran (6.54 mL, 71.8 mmol). The resulting solution was stirred at room temperature for one hour then quenched with water. The mixture was extracted with ethyl acetate (2×100 mL). The combined organics were washed with brine then dried over magnesium sulfate, filtered, and the filtrate concentrated under vacuum to give a crude oil. The crude oil was purified by chromatography on silica using 5-10% ethyl acetate in n-hexane as eluant to give 2-((5-bromopentyl)oxy)tetrahydro-2H-pyran, 2 (4.5 g, 83%) as a clear oil.

$^1$H NMR (300 MHz, CDCl₃): δ ppm 4.55-4.54 (d, J=4.3 Hz, 1H), 3.92-3.72 (m, 2H), 3.42-3.38 (m, 3H), 1.88-1.55 (m, 3H), 1.52-1.50 (m, 10H).

Synthesis of 2-(trideca-6,12-diyn-1-yloxy)tetrahydro-2H-pyran 4

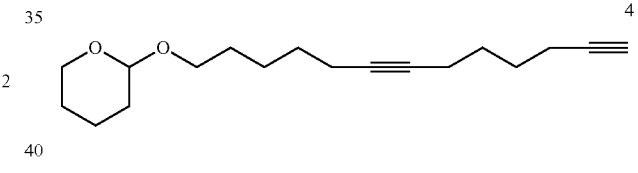

To a solution of 1,7-Octadiyne 3 (6 mL, 45.4 mmol) and hexamethylphosphoramide (16 mL, 90.8 mmol) in tetrahydrofuran (100 mL) at −78° C. was added [2.5 M n-butyllithium in n-hexane] (18 mL, 45.4 mmol) dropwise. Upon completion of addition, the solution was stirred at −78° C. for one hour then warmed to −20° C. for an additional hour. The resulting solution was cooled once again to −78° C. whereupon a solution of 2-((5-bromopentyl)oxy)tetrahydro-2H-pyran, 2 (5.67 g, 22.7 mmol) in tetrahydrofuran (10 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil weighing 9 g. The crude oil was purified by chromatography on silica using 5-10% ethyl acetate in n-hexane as eluant to give 2-(trideca-6,12-diyn-1-yloxy) tetrahydro-2H-pyran, 4 (4.5 g, 72%) as a clear oil.

$^1$H NMR (300 MHz, d$^6$·DMSO): δ ppm 4.544.53 (m, 1H), 3.72-3.61 (m, 1H), 3.60-3.58 (m, 1H), 3.43-3.33 (m, 1H), 3.32-3.29 (m, 1H), 2.77-2.75 (t, J=5.8 Hz, 1H), 2.16-2.13 (m, 6H), 1.55-1.41 (m, 16H).

Representative Procedure for Alkylation of Alkynes

Synthesis of 2-(hexadeca-6,12-diyn-1-yloxy)tetrahydro-2H-pyran 7

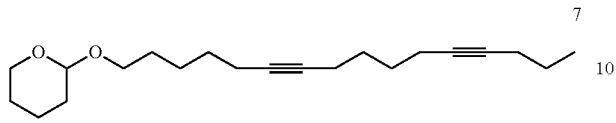

7

To a solution of 2-(trideca-6,12-diyn-1-yloxy) tetrahydro-2H-pyran, 4 (7.14 g, 25.86 mmol) and hexamethylphosphoramide (18 mL, 103.4 mmol) in tetrahydrofuran (100 mL) at −78° C. was added [2.5 M n-butyllithium in n-hexane] (41.3 mL, 103.4 mmol) dropwise. Upon completion of addition, the solution was stirred at −78° C. for one hour then warmed to −20° C. for an additional hour. The resulting solution was cooled once again to −78° C. whereupon a solution of 1-iodopropane 5 (9.9 mL, 103.4 mmol) in tetrahydrofuran (20 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil weighing 9 g. The crude oil was purified by chromatography on silica using 5% ethyl acetate in n-hexane as eluant to give 2-(hexadeca-6,12-diyn-1-yloxy)tetrahydro-2H-pyran, 7 (5.9 g, 72%) as a clear oil.

$^1$H NMR (300 MHz, CDCl$_3$): 4.57-4.55 (m, 1H), 3.86-3.74 (m, 1H), 3.73-3.71 (m, 1H), 3.50-3.39 (m, 1H), 3.37-3.36 (m, 1H), 2.16-2.11 (m, 8H), 1.59-1.56 (m, 2H), 1.55-1.47 (m, 16H), 0.98-0.93 (t, J=1.6 Hz, 3H).

2-(octadeca-6,12-diyn-1-yloxy)tetrahydro-2H-pyran 8

$^1$H NMR (300 MHz, CDCl$_3$): 4.57-4.55 (m, 1H), 3.85-3.74 (m, 1H), 3.73-3.70 (m, 1H), 3.50-3.38 (m, 1H), 3.36-3.35 (m, 1H), 2.23-2.12 (m, 8H), 1.61-1.54 (m, 2H), 1.53-1.48 (m, 16H), 1.47-1.46 (m, 4H), 0.90-0.85 (t, J=1.6 Hz, 3H).

Representative Procedure for Reduction of Alkynes to Alkenes Using "P-2 Ni"

Synthesis of 2-(((6Z,12Z)-hexadeca-6,12-dien-1-yl)oxy)tetrahydro-2H-pyran 9

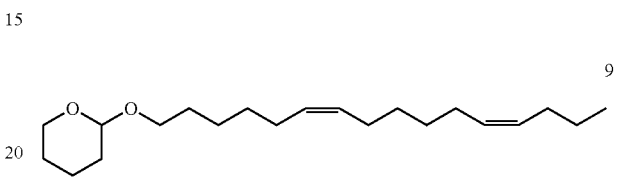

9

To a solution of Sodium borohydride (0.56 g, 14.8 mmol) in ethanol (80 mL) under hydrogen blanket at 0° C. was added Nickel (II) acetate tetrahydrate (3.22 g, 12.98 mmol). Upon completion of addition, the reaction was evacuated under vacuum and flushed with hydrogen. After 10 minutes of stirring, ethylenediamine (3.7 mL, 65.6 mmol), and a solution of 2-(hexadeca-6,12-diyn-1-yloxy)tetrahydro-2H-pyran, 7 (5.9 g, 18.55 mmol) in ethanol (10 mL) was added. The reaction was stirred at room temperature under a hydrogen balloon for 4 hours. After 4 hours, the reaction mixture was evacuated of hydrogen and then flushed with nitrogen. The crude mixture was filtered over celite, and the filtrate concentrated under vacuum to give a crude oil weighing 4 g. The crude oil was purified by chromatography on silica using 5-10% diethyl ether in n-hexane as eluant to give 2-(((6Z,12Z)-hexadeca-6,12-dien-1-yl)oxy)tetrahydro-2H-pyran, 9 (4.67 g, 78% yield) as a clear oil.

$^1$H NMR (300 MHz, CDCl$_3$): 5.35-5.34 (m, 4H), 4.58-4.55 (m, 1H), 3.86-3.74 (m, 1H), 3.73-3.71 (m, 1H), 3.51-3.39 (m, 1H), 3.36-3.35 (m, 1H), 2.03-1.98 (m, 8H), 1.57-1.39 (m, 2H), 1.38-1.36 (m, 6H), 1.35-1.32 (m, 10H), 0.91-0.86 (t, J=1.6 Hz, 3H).

$^{13}$C NMR (300 MHz, CDCl$_3$): 129.98, 129.85, 98.93, 77.53, 77.10, 76.68, 67.72, 62.43, 30.86, 29.71, 29.70, 29.45, 29.46, 29.44, 27.20, 27.19, 26.01, 25.59, 22.98, 19.78, 13.91.

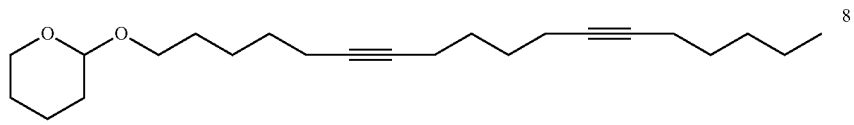

8

2-(((6Z,12Z)-octadeca-6,12-dien-1-yl)oxy)tetra-
hydro-2H-pyran 10

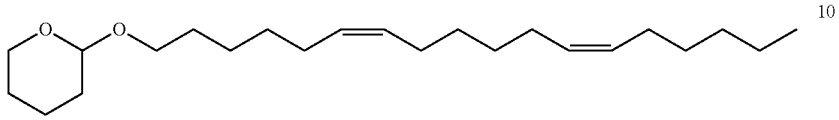 [SMILES: CCCCC/C=C\CCCC/C=C\CCCCCOC1CCCCO1]

¹H NMR (300 MHz, CDCl₃): 5.39-5.29 (m, 4H), 4.58-4.55 (m, 1H), 3.86-3.76 (m, 1H), 3.74-3.68 (m, 1H), 3.51-3.41 (m, 1H), 3.39-3.36 (m, 1H), 2.14-1.97 (m, 8H), 1.56-1.38 (m, 2H), 1.37-1.35 (m, 6H), 1.34-1.28 (m, 14H), 0.93-0.85 (t, J=1.6 Hz, 3H).

¹³C NMR (300 MHz, CDCl₃): 130.13, 129.97, 129.84, 129.71, 98.93, 77.53, 77.10, 76.68, 67.71, 62.42, 31.62, 30.86, 29.72, 29.71, 29.47, 29.46, 27.27, 27.18, 26.01, 25.59, 22.67, 19.78, 14.18.

Representative Procedure for Deprotection of
Tetrahydropyranyl Ether (THP)

Synthesis of (6Z,12Z)-hexadeca-6,12-dien-1-ol 11

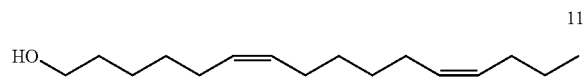

To a solution of 2-(((6Z,12Z)-hexadeca-6,12-dien-1-yl)oxy)tetrahydro-2H-pyran, 9 (4.67 g, 14.5 mmol) in methanol (20 mL) was added p-Toluenesulfonic acid monohydrate (300 mg, 1.58 mmol) at room temperature. The resulting solution was stirred at room temperature for 3 hours then quenched with water. The mixture was extracted with ethyl acetate (2×50 mL). The combined organics were washed with water then dried over magnesium sulfate, filtered and the filtrate concentrated under vacuum to give a crude oil weighing 4 g. The crude oil was purified by chromatography on silica using 5-10% diethyl ether in n-hexane as eluant to give (6Z,12Z)-hexadeca-6,12-dien-1-ol, 11 (2.5 g, 72%) as a clear oil.

¹H NMR (300 MHz, CDCl₃): 5.34-5.33 (m, 4H), 3.65-3.61 (m, 2H), 2.02-2.00 (m, 8H), 1.36-1.34 (m, 2H), 1.34-1.25 (m, 10H), 0.89-0.86 (t, J=0.82 Hz, 3H).

(6Z,12Z)-octadeca-6,12-dien-1-ol 12

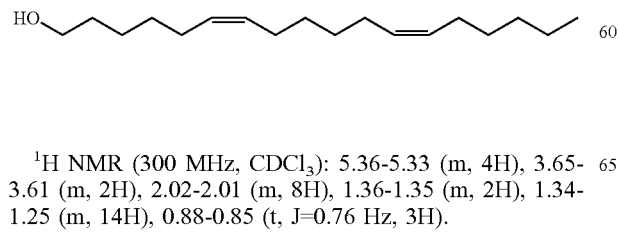

¹H NMR (300 MHz, CDCl₃): 5.36-5.33 (m, 4H), 3.65-3.61 (m, 2H), 2.02-2.01 (m, 8H), 1.36-1.35 (m, 2H), 1.34-1.25 (m, 14H), 0.88-0.85 (t, J=0.76 Hz, 3H).

Representative Procedure for Oxidation of Alcohol
to Carboxylic Acid Using Jones Reagent Synthesis of (6Z,12Z)-hexadeca-6,12-dienoic Acid
13

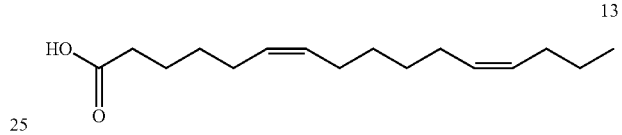

A mixture of (6Z,12Z)-hexadeca-6,12-dien-1-ol, 11 (2.5 g, 10.5 mmol) and Jones Reagent [2M in sulfuric acid], (10.5 mL, 21 mmol) in acetone (20 mL) at 0° C. was stirred for 2 hours. The mixture was quenched with water and extracted with ethyl acetate (2×100 mL). The combined organics were dried over magnesium sulfate, filtered and the filtrate concentrated under vacuum to give a crude oil. The crude oil was purified by chromatography on silica using 20% ethyl acetate in n-hexane as eluant to give (6Z,12Z)-hexadeca-6,12-dienoic acid, 13 (1.7 g, 68%) as a clear oil.

¹H NMR (300 MHz, CDCl₃): 5.35-5.33 (m, 4H), 2.37-2.32 (t, 2H), 2.06-1.98 (m, 8H), 1.64-1.39 (m, 2H), 1.37-1.32 (m, 8H), 0.91-0.87 (t, J=0.91 Hz, 3H).

(6Z,12Z)-octadeca-6,12-dienoic Acid 14

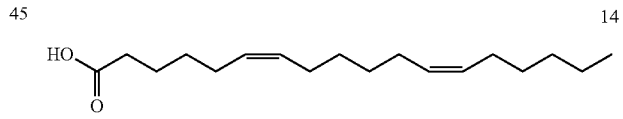

¹H NMR (300 MHz, CDCl₃): 5.36-5.32 (m, 4H), 2.35-2.33 (t, 2H), 2.06-2.01 (m, 8H), 1.64-1.42 (m, 2H), 1.34-1.28 (m, 12H), 0.90-0.85 (t, 3H).

Synthesis of (S)-2-(2,2-dimethyl-1,3-dioxolan-4-yl)
ethyl 4-methylbenzenesulfonate 16

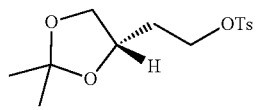

To a mixture of (S)-2-(2,2-dimethyl-1,3-dioxolan-4-yl)
ethan-1-ol 15 (25 g, 171.1 mmol) in pyridine (30 mL) at 0°

C. was added p-Toluenesulfonylchloride (35.8 g, 188.2 mmol) and DMAP (140 mg, 1.14 mmol) and the reaction was stirred at room temperature overnight. The mixture was diluted with CH$_2$Cl$_2$ (500 mL), washed with sat. NH4Cl, water and Brine. The organic layer was dried over anhydrous Na$_2$SO$_4$. The solvent was evaporated, and the crude residue used for the next step without purification. (43.8 g, 85%).

$^1$H NMR (300 MHz, CDCl$_3$): δ ppm 7.77 (d, J=8.2 Hz, 2H), 7.34 (d, J=8.1 Hz, 2H), 4.15-4.01 (m, 3H), 3.65-3.47 (m, 2H), 2.43 (s, 3H), 1.82-1.62 (m, 2H), 1.32 (s, 3H), 1.27 (s, 3H).

Representative Procedure for Di-Alkylamine Substitution

Synthesis of (S)-2-(2,2-dimethyl-1,3-dioxolan-4-yl)-N,N-dimethylethan-1-amine 19

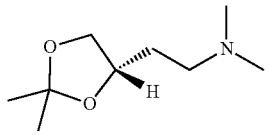

19

A mixture of (S)-2-(2,2-dimethyl-1,3-dioxolan-4-yl)ethyl 4-methylbenzenesulfonate 16 (10 g, 33.3 mmol) and dimethylamine solution 17 (166 mL, 333.3 mmol) (2M in THF) was stirred at room temperature for 2 days. The mixture was concentrated, and the crude residue was diluted with CH$_2$Cl$_2$ (500 mL), washed with sat. NaHCO$_3$, water and Brine. The organic layer was dried over anhydrous Na$_2$SO$_4$. The solvent was evaporated, and the crude residue was purified by flash chromatography (SiO$_2$:CH$_2$Cl$_2$=100% to 10% of MeOH in CH$_2$Cl$_2$ with 1% NH$_4$OH) and colorless oil product 19 was obtained (2.1 g, 37%).

$^1$H NMR (300 MHz, CDCl$_3$): δ ppm 4.15-4.01 (m, 2H), 3.52 (dd, J=7.4, 7.4 Hz, 1H), 2.41-2.23 (m, 2H), 2.21 (s, 6H), 1.82-1.62 (m, 2H), 1.39 (s, 3H), 1.33 (s, 3H).

MS (APCI$^+$): 174.1 (M+1)

(S)-2-(2,2-diethyl-1,3-dioxolan-4-yl)-N,N-dimethyl-ethan-1-amine 20

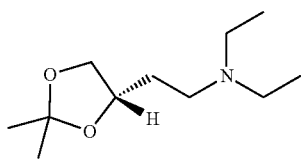

20

$^1$H NMR (300 MHz, CDCl$_3$): δ ppm 4.15-4.01 (m, 2H), 3.48 (dd, J=7.4, 7.4 Hz, 1H), 2.48-2.43 (m, 6H), 1.82-1.62 (m, 2H), 1.36 (s, 3H), 1.27 (s, 3H), 0.97 (t, J=7.2 Hz, 6H).

MS (APCI$^+$): 202.2 (M+1)

Representative Procedure for Ketal Hydrolysis

Synthesis of (S)-4-(dimethylamino)butane-1,2-diol hydrochloride Salt 21

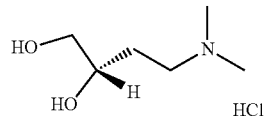

21

To a mixture of (S)-2-(2,2-dimethyl-1,3-dioxolan-4-yl)-N,N-dimethylethan-1-amine 19 (2 g, 11.54 mmol) in MeOH (10 mL) was added 1N HCl aqueous solution (17 mL, 17.3 mmol) and the reaction was heated at 80° C. for 45 min. TLC (Rf=0.1, 10% MeOH in CH$_2$Cl$_2$ with 1% NH$_4$OH) showed the completion of reaction. After concentration of the reaction mixture, the crude residue was dissolved in water (5 mL) and lyophilized overnight. Sticky syrup product 21 was obtained (2.1 g, quant.) as HCl salt.

$^1$H NMR (300 MHz, D$_2$O): δ ppm 3.77-3.72 (m, 1H), 3.54-3.46 (m, 2H), 3.29-3.22 (m, 2H), 2.85 (s, 6H), 1.92-1.79 (m, 2H).

MS (APCI$^+$): 134.1 (M+1)

(S)-4-(diethylamino)butane-1,2-diol hydrochloride Salt 22

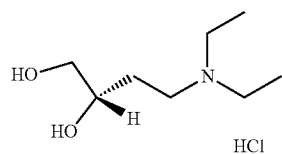

22

$^1$H NMR (300 MHz, D$_2$O): δ ppm 3.77-3.72 (m, 1H), 3.54-3.46 (m, 2H), 3.22-3.15 (m, 6H), 1.92-1.74 (m, 2H), 1.24 (t, J=7.4 Hz, 6H).

MS (APCI$^+$): 162.1 (M+1)

Representative Procedure for Di-Esterification

Synthesis of (S)-4-(dimethylamino)butane-1,2-diyl (6Z,6′Z,12Z,12′Z)-bis(octadeca-6,12-dienoate) AKG-UO-1 (O-11956)

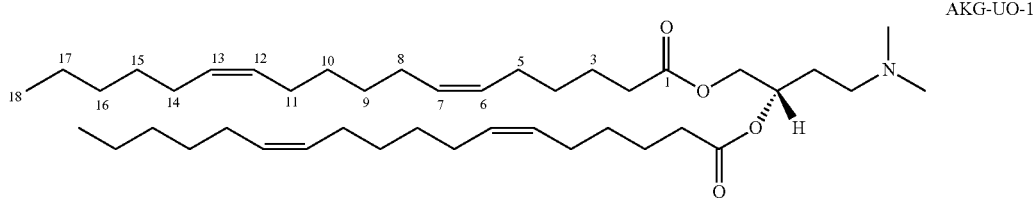 [SMILES: CCCCC/C=C\CCCC/C=C\CCCCC(=O)OC[C@H](CCN(C)C)OC(=O)CCCC/C=C\CCCC/C=C\CCCCC]

AKG-UO-1

Oxalyl chloride (0.33 mL, 3.9 mmol) was added dropwise to a solution of (6Z,12Z)-octadeca-6,12-dienoic acid, 14 (0.36 g, 1.3 mmol) in dichloromethane/DMF (15 mLs, 25 µL) at 0° C. and allowed reaction to warm to room temperature and stir for one hour. After one hour, the reaction was concentrated under vacuum to dryness. The residue was re-dissolved in dichloromethane (10 mL) and added to a mixture of N,N-Diisopropylethylamine (2.3 mL, 10 mmol), 4-Dimethylaminopyridine (317 mg, 2.6 mmol), and (S)-4-(dimethylamino)butane-1,2-diol hydrochloride, 21 (101 mg, 0.6 mmol). The resulting solution was allowed to stir for 24 hours. After 24 hours, the reaction was cooled to 0 C and quenched with water (10 mL). The reaction mixture was extracted with dichloromethane (2×100 mL) and the organics were washed with water and brine (2×100 mL). The organic layer was dried over magnesium sulfate, filtered, and the filtrate concentrated under vacuum to give a crude oil. The crude oil was purified by chromatography on silica using 2% methanol in dichloromethane as eluant to give (S)-4-(dimethylamino)butane-1,2-diyl (6Z,6'Z,12Z,12'Z)-bis(octadeca-6,12-dienoate), AKG-UO-1, (0.12 g, 30%) as a yellow oil.

$^1$H NMR (300 MHz, CDCl$_3$): 5.40-5.29 (m, 8H), 5.14-5.12 (m, 1H), 4.25 (dd, J=11.8, 3.3 Hz, 1H), 4.05 (dd, J=12.1, 6.3 Hz, 1H), 2.32-2.26 (m, 6H), 2.20 (s, 6H), 2.06-1.99 (m, 16H), 1.78-1.70 (m, 2H), 1.65-1.58 (m, 4H), 1.42-1.25 (m, 24H), 0.90-0.85 (m, 6H).

MS (APCI$^+$): 658.5 (M+1)

(S)-4-(diethylamino)butane-1,2-diyl (6Z,6'Z,12Z,12'Z)-bis(octadeca-6,12-dienoate) AKG-UO-1A
(O-11955)

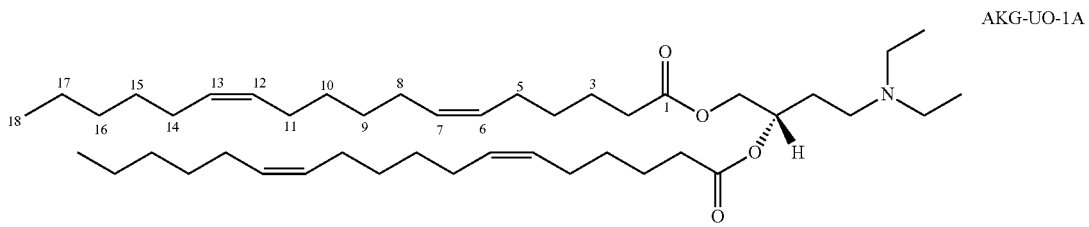 [SMILES: CCCCC/C=C\CCCC/C=C\CCCCC(=O)OC[C@H](CCN(CC)CC)OC(=O)CCCC/C=C\CCCC/C=C\CCCCC]

$^1$H NMR (300 MHz, CDCl$_3$): 5.37-5.29 (m, 8H), 5.12-5.10 (m, 1H), 4.25 (dd, J=12.1, 3.6 Hz, 1H), 4.05 (dd, J=11.8, 6.3 Hz, 1H), 2.52-2.42 (m, 6H), 2.29 (t, J=7.4 Hz, 4H)), 2.06-1.99 (m, 16H), 1.78-1.70 (m, 2H), 1.64-1.59 (m, 4H), 1.41-1.19 (m, 24H), 0.99 (t, J=7.1 Hz, 6H), 0.96-0.87 (m, 6H).

MS (APCI$^+$): 686.6 (M+1)

(S)-4-(dimethylamino)butane-1,2-diyl (6Z,6'Z,12Z,12'Z)-bis(hexadeca-6,12-dienoate) AKG-UO-4
(O-12401)

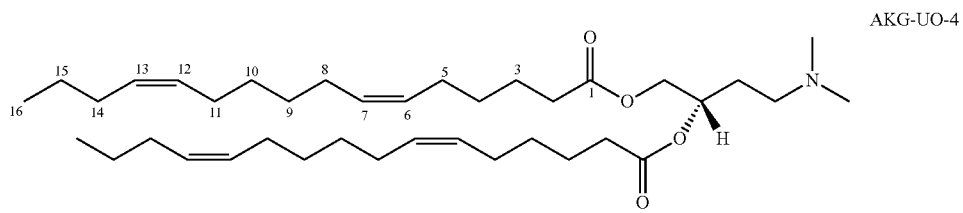 [SMILES: CCC/C=C\CCCC/C=C\CCCCC(=O)OC[C@H](CCN(C)C)OC(=O)CCCC/C=C\CCCC/C=C\CCC]

$^1$H NMR (300 MHz, CDCl$_3$): 5.39-5.29 (m, 8H), 5.13-5.12 (m, 1H), 4.24 (dd, J=11.8, 3.3 Hz, 1H), 4.05 (dd, J=11.8, 6.3 Hz, 1H), 2.32-2.27 (m, 6H), 2.19 (s, 6H), 2.01-1.99 (m, 16H), 1.75-1.72 (m, 2H), 1.65-1.58 (m, 4H), 1.36-1.31 (m, 16H), 0.91-0.86 (m, 6H).

MS (APCI$^+$): 602.5 (M+1)

Synthesis of (S)-4-(diethylamino)butane-1,2-diyl (6Z,6'Z,12Z,12'Z)-bis(hexadeca-6,12-dienoate) AKG-UO-4A (O-12402)
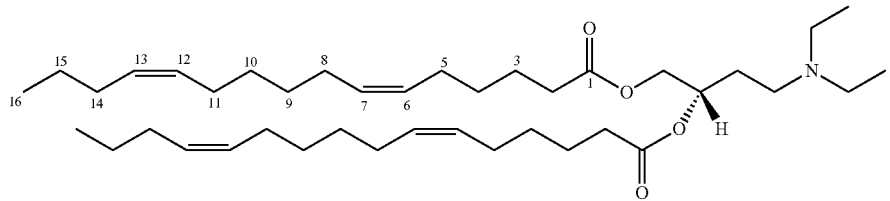
$^1$H NMR (300 MHz, CDCl$_3$): 5.40-5.29 (m, 8H), 5.12-5.11 (m, 1H), 4.25 (dd, J=11.8, 3.3 Hz, 1H), 4.05 (dd, J=11.8, 6.3 Hz, 1H), 2.54-2.43 (m, 6H), 2.29 (t, J=7.4 Hz, 4H), 2.11-1.96 (m, 16H), 1.74-1.65 (m, 2H), 1.65-1.59 (m, 4H), 1.39-1.31 (m, 16H), 0.99 (t, J=7.1 Hz, 6H), 0.91-0.89 (m, 6H).
MS (APCI$^+$): 630.5 (M+1)
Synthesis of (S)-4-(dimethylamino)butane-1,2-diyl (6Z,6'Z,11Z,11'Z)-bis(octadeca-6,11-dienoate) (AKG-UO-1a)
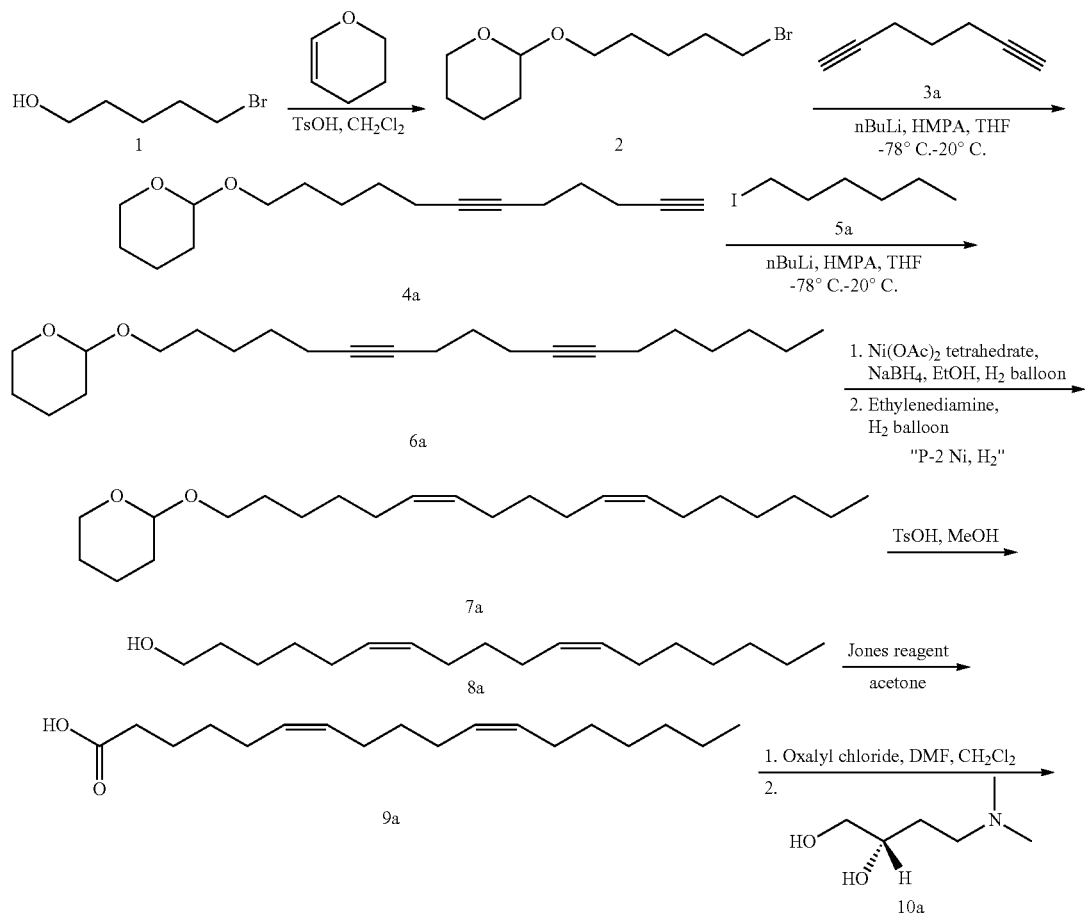

-continued

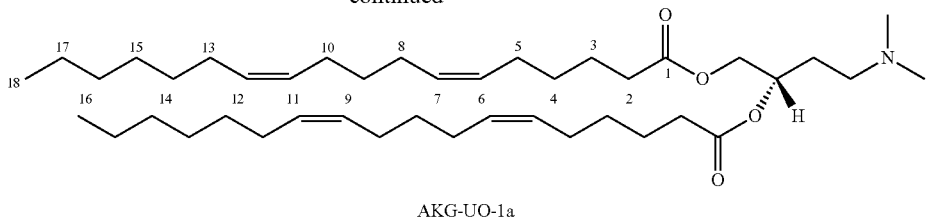

AKG-UO-1a

Experimental Procedure

Synthesis of 2-((5-bromopentyl)oxy)tetrahydro-2H-pyran 2

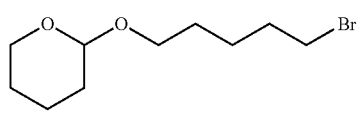

2

To a solution of 5-bromo-1-pentanol 1 (3.6 g, 21.6 mmol) in dichloromethane (100 mL) and pyridinium p-toluene sulfonate (40 mg, 0.16 mmol) at 0° C. was added 3,4-dihydro-2H-pyran (6.54 mL, 71.8 mmol). The resulting solution was stirred at room temperature for one hour then quenched with water. The mixture was extracted with ethyl acetate (2×100 mL). The combined organics were washed with brine then dried over magnesium sulfate, filtered, and the filtrate concentrated under vacuum to give a crude oil. The crude oil was purified by chromatography on silica using 5-10% ethyl acetate in n-hexane as eluant to give 2-((5-bromopentyl)oxy)tetrahydro-2H-pyran, 2 (4.5 g, 83%) as a clear oil.

$^1$H NMR (300 MHz, CDCl$_3$): δ ppm 4.55-4.54 (d, J=4.3 Hz, 1H), 3.92-3.72 (m, 2H), 3.42-3.38 (m, 3H), 1.88-1.55 (m, 3H), 1.52-1.50 (m, 10H).

Synthesis of 2-(dodeca-6,11-diyn-1-yloxy)tetrahydro-2H-pyran 4a

To a solution of 1,6-heptadiyne 3a (5 g, 54.3 mmol) and hexamethylphosphoramide (19 mL, 108 mmol) in tetrahydrofuran (100 mL) at −78° C. was added [2.5 M n-butyl-lithium in n-hexane] (21.7 mL, 54.3 mmol) dropwise. Upon completion of addition, the solution was stirred at −78° C. for one hour then warmed to −20° C. for an additional hour. The resulting solution was cooled once again to −78° C. whereupon a solution of 2-((5-bromopentyl)oxy)tetrahydro-2H-pyran, 2 (6.8 g, 27.1 mmol) in tetrahydrofuran (10 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil. The crude oil was purified by chromatography on silica using 5-10% ethyl acetate in n-hexane as eluant to give 2-(dodeca-6,11-diyn-1-yloxy)tetrahydro-2H-pyran, 4a (4.1 g, 58%) as a clear oil.

$^1$H NMR (300 MHz, CDCl$_3$): δ ppm 4.57-4.56 (m, 1H), 3.96-3.82 (m, 1H), 3.77-3.69 (m, 1H), 3.50-3.41 (m, 1H), 3.39-3.34 (m, 1H), 2.29-2.25 (m, 4H), 2.15-2.12 (m, 2H), 1.95-1.94 (t, J=5.8 Hz, 1H), 1.73-1.43 (m, 14H).

4a

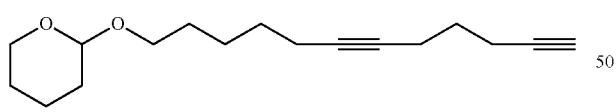

Synthesis of 2-(octadeca-6,11-diyn-1-yloxy)tetrahydro-2H-pyran 6a

6a

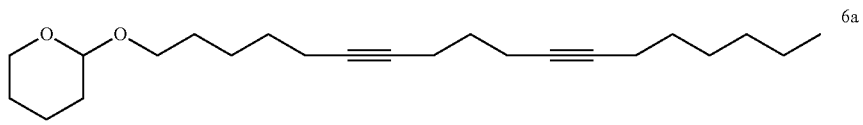

To a solution of 2-(dodeca-6,11-diyn-1-yloxy)tetrahydro-2H-pyran, 4a (4.1 g, 15.64 mmol) and hexamethylphosphoramide (11 mL, 62.6 mmol) in tetrahydrofuran (100 mL) at −78° C. was added [2.5 M n-butyllithium in n-hexane] (12.5 mL, 31.3 mmol) dropwise. Upon completion of addition, the solution was stirred at −78° C. for one hour then warmed to −20° C. for an additional hour. The resulting solution was cooled once again to −78° C. whereupon a solution of 1-iodohexane 5a (9.5 mL, 62.6 mmol) in tetrahydrofuran (20 mL) was added. The resulting solution was allowed to warm to room temperature and stirred for 12 hours. After 12 hours, the reaction was cooled to 0° C. and quenched with water (100 mL). The reaction mixture was then concentrated under vacuum to remove tetrahydrofuran and then diluted with n-hexane. The organics were washed with water and brine (2×100 mL). The organic layer was dried over magnesium sulfate, filtered, and the filtrate concentrated under vacuum to give a crude oil. The crude oil was purified by chromatography on silica using 5% ethyl acetate in n-hexane as eluant to give 2-(octadeca-6,11-diyn-1-yloxy)tetrahydro-2H-pyran, 6a (3.1 g, 57%) as a clear oil.

$^1$H NMR (300 MHz, CDCl$_3$): 4.58-4.55 (m, 1H), 3.86-3.82 (m, 1H), 3.77-3.69 (m, 1H), 3.51-3.47 (m, 1H), 3.41-3.34 (m, 1H), 2.26-2.21 (m, 6H), 2.14-2.12 (m, 6H), 1.66-1.26 (m, 18H), 0.93-0.85 (t, J=6.5 Hz, 3H).

Synthesis of 2-(((6Z,11Z)-octadeca-6,11-dien-1-yl)oxy)tetrahydro-2H-pyran 7a

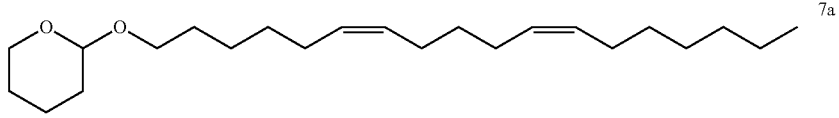 [SMILES: CCCCCC/C=C\CCC/C=C\CCCCCOC1CCCCO1]

To a solution of Sodium borohydride (0.27 g, 14.8 mmol) in ethanol (50 mL) under hydrogen blanket at 0° C. was added Nickel (II) acetate tetrahydrate (1.55 g, 6.25 mmol). Upon completion of addition, the reaction was evacuated under vacuum and flushed with hydrogen. After 10 minutes of stirring, ethylenediamine (1.8 mL, 26.8 mmol), and a solution of 2-(octadeca-6,11-diyn-1-yloxy)tetrahydro-2H-pyran, 6a (3.1 g, 8.93 mmol) in ethanol (10 mL) was added. The reaction was stirred at room temperature under a hydrogen balloon for 4 hours. After 4 hours, the reaction mixture was evacuated of hydrogen and then flushed with nitrogen. The crude mixture was filtered over celite, and the filtrate concentrated under vacuum to give a crude oil weighing 4 g. The crude oil was purified by chromatography on silica using 5-10% diethyl ether in n-hexane as eluant to give 2-(((6Z,11Z)-octadeca-6,11-dien-1-yl)oxy)tetrahydro-2H-pyran, 7a (2.86 g, 92% yield) as a clear oil.

$^1$H NMR (300 MHz, CDCl$_3$): 5.4-5.34 (m, 4H), 4.58-4.55 (m, 1H), 3.86-3.82 (m, 1H), 3.74-3.68 (m, 1H), 3.51-3.49 (m, 1H), 3.41-3.36 (m, 1H), 2.06-1.99 (m, 6H), 1.83-1.67 (m, 2H), 1.59-1.51 (m, 6H), 1.48-1.32 (m, 16H), 0.92-0.85 (t, J=6.6 Hz, 3H).

Synthesis of (6Z,11Z)-octadeca-6,11-dien-1-ol 8a

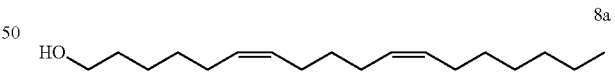

Procedure previously described.

$^1$H NMR (300 MHz, CDCl$_3$): 5.37-5.33 (m, 4H), 3.65-3.61 (m, 1H), 2.06-1.99 (m, 6H), 1.56-1.41 (m, 4H), 1.38-1.27 (m, 14H), 0.88-0.85 (t, J=6.6 Hz, 3H).

Synthesis of (6Z,11Z)-octadeca-6,11-dienoic Acid 9a

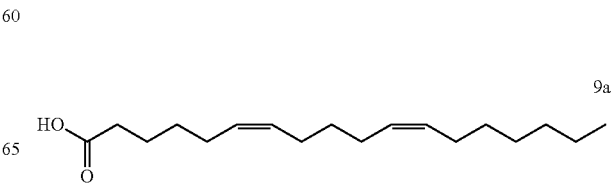

Procedure previously described.

¹H NMR (300 MHz, CDCl₃): 5.38-5.33 (m, 4H), 2.37-2.33 (t, J=5.6 Hz, 2H), 2.06-1.99 (m, 6H), 1.67-1.59 (m, 2H), 1.41-1.25 (m, 14H), 0.89-0.85 (t, J=6.6 Hz, 3H).

Synthesis of (S)-4-(dimethylamino)butane-1,2-diyl (6Z,6'Z,11Z,11'Z)-bis(octadeca-6,11-dienoate) (AKG-UO-1a)

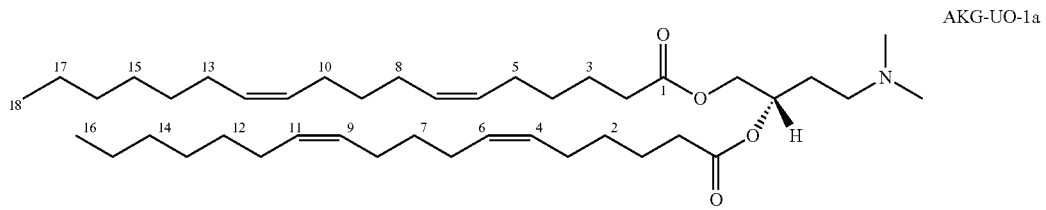 [SMILES: CCCCCC/C=C\CCC/C=C\CCCCC(=O)OC[C@H](CCN(C)C)OC(=O)CCCC/C=C\CCC/C=C\CCCCCC]

AKG-UO-1a

Procedure previously described.

¹H NMR (300 MHz, CDCl₃): 5.39-5.29 (m, 8H), 5.14-5.12 (m, 1H), 4.25 (dd, J=11.8, 3.3 Hz, 1H), 4.06 (dd, J=11.8, 6.3 Hz, 1H), 2.32-2.28 (m, 6H), 2.20 (s, 6H), 2.03-2.01 (m, 16H), 1.74-1.64 (m, 2H), 1.62-1.60 (m, 6H), 1.38-1.27 (m, 22H), 0.89-0.85 (m, 6H).

MS (APCI⁺): 658.5 (M+1)

Example 1C. Synthesis of KC-01 Series of Ionizable Lipids

Synthesis of 2-((S)-2,2-di((6Z,12Z)-octadeca-6,12-dien-1-yl)-1,3-dioxolan-4-yl)-N,N-dimethylethan-1-amine (AKG-KC2-01, O-12095)

3-((S)-2,2-di((6Z,12Z)-octadeca-6,12-dien-1-yl)-1,3-dioxolan-4-yl)-N,N-dimethylpropan-1-amine (AKG-KC3-01, O-12096)

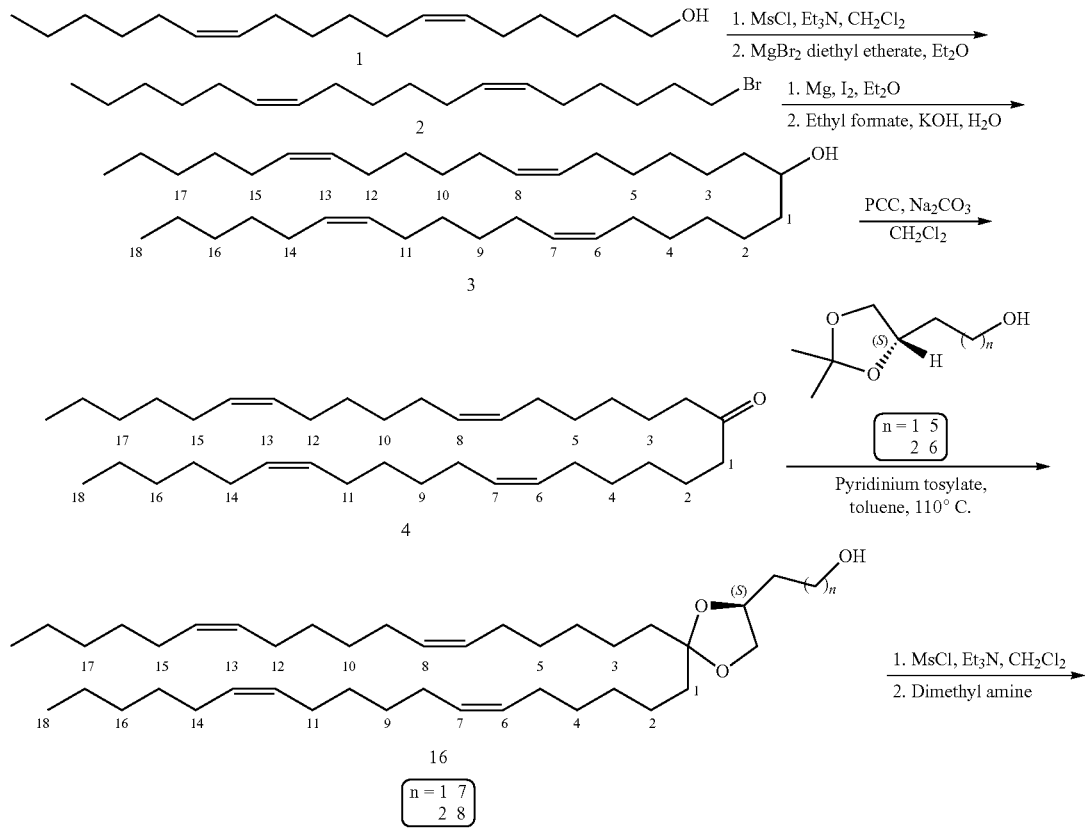

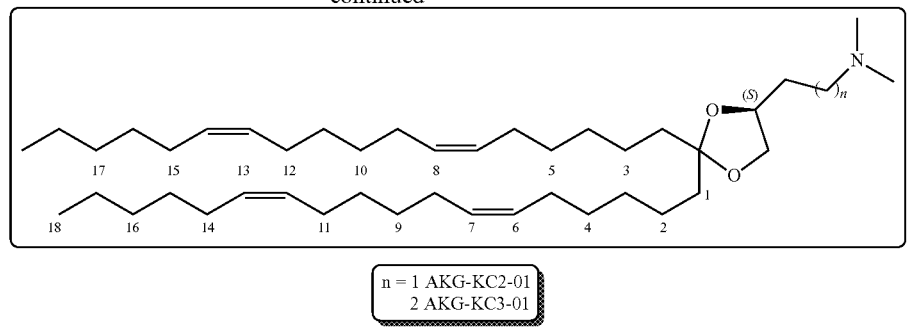

n = 1 AKG-KC2-01
2 AKG-KC3-01

Synthesis of (6Z,12Z)-1-bromooctadeca-6,12-diene, 2

Synthesis of (6Z,12Z,25Z,31Z)-heptatriaconta-6,12,25,31-tetraen-19-ol, 3

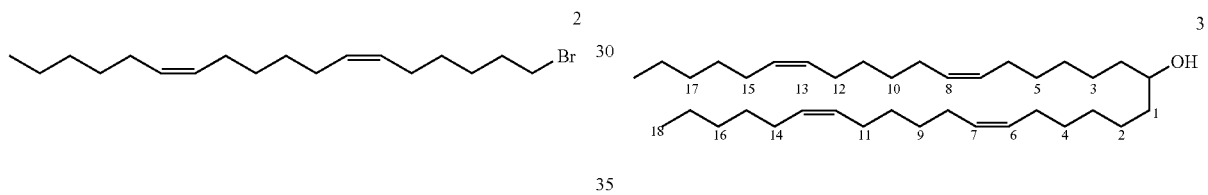

To a solution of (6Z,12Z)-octadeca-6,12-dien-1-ol, 1 (3.6 g, 13.7 mmol) in dichloromethane (50 mL) at 0° C. was added methane sulfonyl chloride (1.26 mL, 16.4 mmol) and triethylamine (3.6 mL, 20.5 mmol). The resulting solution was warmed to room temperature and stirred for 2 hours. The mixture was quenched with water and extracted with dichloromethane (2×100 mL). The combined organics were washed with brine then dried over magnesium sulfate then filtered. The filtrate was concentrated under vacuum to give a crude oil. The resulting oil was dissolved in diethyl ether (50 mL), added to a stirring slurry of magnesium bromide ethyl etherate (7 g, 27.4 mmol) in diethyl ether (50 mL) at OC. The mixture was warmed to room temperature and stirred for 2 hours. The reaction mixture was quenched with water and extracted with ethyl acetate (2×100 mL). The combined organics were washed with brine then dried over magnesium sulfate then filtered. The filtrate was concentrated under vacuum to give a crude oil. The crude oil was purified by chromatography on silica using 5-10% ethyl acetate in n-hexane as eluant to give (6Z,12Z)-1-bromooctadeca-6,12-diene, 3 (2.9 g, 8.89 mmol, 65%) as a yellow oil. $^1$H NMR (300 MHz, CDCl$_3$): 5.36-5.33 (m, 4H), 3.42-3.37 (t, J=7.5 Hz, 2H), 2.04-1.97 (m, 8H), 1.83-1.83 (m, 2H), 1.37-1.28 (m, 14H), 0.90-0.86 (t, J=6.6 Hz, 3H).

A solution of (6Z,12Z)-1-bromooctadeca-6,12-diene, 2 (2 g, 6.08 mmol) in ether (10 mL) was added to a mixture of magnesium turnings (162 mg, 6.69 mmol) and iodine in ether (2 mL) under argon at room temperature. The mixture stirred at room temperature for 90 minutes (magnesium turnings consumed) whereupon ethyl formate (0.24 mL, 3.04 mmol) was added. After stirring for one hour at room temperature, the reaction was quenched with 1N HCl solution. The mixture was extracted with ethyl acetate (2×100 mL) and the combined organics washed with water then brine. The organics were dried under magnesium sulfate, filtered, and the filtrate concentrated under vacuum to give a crude oil. The resulting oil was dissolved in ethanol (10 mL) and added to a solution of potassium hydroxide (260 mg) in water (3 mL). After stirring for 12 hours, the mixture pH was adjusted 4 with 2N HCl. The aqueous solution was extracted with dichloromethane (2×) and combined. The organics were washed with brine then dried under magnesium sulfate and filtered. The filtrate was concentrated under vacuum to give a crude oil. Purification of the crude oil on silica using 10-30% ethyl acetate in n-hexane as eluant to give (6Z,12Z,25Z,31Z)-heptatriaconta-6,12,25,31-tetraen-19-ol, 3 (0.29 g, 0.55 mmol, 18%) as a clear oil.
$^1$H NMR (300 MHz, CDCl$_3$): 5.36-5.32 (m, 8H), 3.57 (bs, 1H), 3.33-3.32, (m, 2H), 2.13-1.97 (m, 16H), 1.36-1.29 (m, 34H), 0.90-0.86 (t, J=6.6 Hz, 6H).

Synthesis of (6Z,12Z,25Z,31Z)-heptatriaconta-6,12,25,31-tetraen-19-one, 4

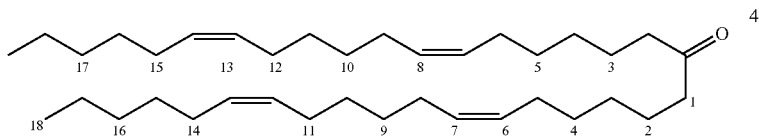

To a mixture of (6Z,12Z,25Z,31Z)-heptatriaconta-6,12,25,31-tetraen-19-ol, 3 (0.29 g, 0.55 mmol) and sodium carbonate (3 mg, 0.03 mmol) in dichloromethane was added pyridinium chlorochromate (236 mg, 1.1 mmol) at 0° C. The mixture was warmed to room temperature and stirred for one hour. After one hour, silica gel (1 g) was added to reaction and the mixture filtered. The filtrate was concentrated, and the resulted oil purified on silica using 10-20% ethyl acetate in n-hexane as eluant to give (6Z,12Z,25Z,31Z)-heptatriaconta-6,12,25,31-tetraen-19-one, 4 (0.12 g, 0.23 mmol, 42%) as a clear oil.

$^1$H NMR (300 MHz, CDCl$_3$): 5.36-5.32 (m, 8H), 3.36-3.32, (m, 1H), 2.40-2.35 (t, J=6.6 Hz, 3H), 2.14-2.00 (m, 16H), 1.58-1.54 (m, 4H), 1.34-1.29 (m, 28H), 0.90-0.86 (t, J=6.6 Hz, 6H).

Synthesis of 2-((S)-2,2-di((9Z,12Z)-octadeca-9,12-dien-1-yl)-1,3-dioxolan-4-yl) ethan-1-ol, 7

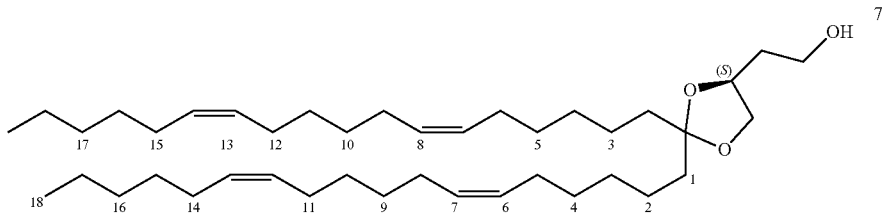

A mixture of (6Z,12Z,25Z,31Z)-heptatriaconta-6,12,25,31-tetraen-19-one, 4 (0.12 g, 0.23 mmol), (4S)-(+)-4-(2-hydroxyethyl)-2,2-dimethyl-1,3-dioxolane 5 (0.20 g, 1.38 mmol), and pyridinium p-toluene sulfonate (9 mg) in toluene (10 mL) was heated at reflux under nitrogen positive pressure. After 12 hours, the mixture was concentrated under vacuum to give a crude oil. The resulting crude oil was purified by chromatography on silica using 20-40% ethyl acetate in n-hexane as eluant to give 2-((S)-2,2-di((9Z,12Z)-octadeca-9,12-dien-1-yl)-1,3-dioxolan-4-yl) ethan-1-ol, 7 (0.11 g, 0.17 mmol, 77%) as a clear oil.

$^1$H NMR (300 MHz, CDCl$_3$): 5.36-5.32 (m, 8H), 4.25-4.20 (m, 1H), 4.10-4.06 (m, 1H), 3.82-3.77 (m, 1H), 3.54-3.49 (m, 1H), 2.23-2.19 (t, J=6.6 Hz, 3H), 2.14-2.00 (m, 16H), 1.84-1.78 (m, 2H), 1.62-1.51 (m, 6H), 1.34-1.29 (m, 28H), 0.90-0.86 (t, J=6.6 Hz, 6H).

Synthesis of 3-((S)-2,2-di((9Z,12Z)-octadeca-9,12-dien-1-yl)-1,3-dioxolan-4-yl)propan-1-ol, 8

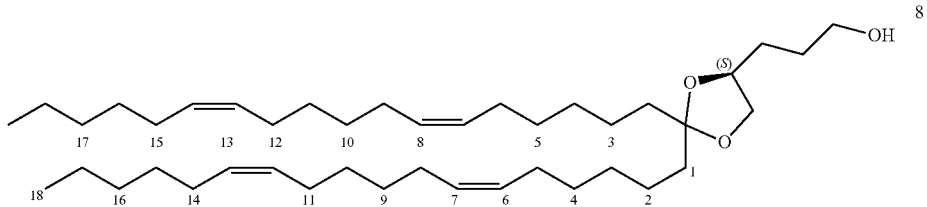

A mixture of (6Z,12Z,25Z,31Z)-heptatriaconta-6,12,25,31-tetraen-19-one, 4 (0.50 g, 0.95 mmol), (S)-(3)-(2,2-Dimethyl-1,3-dioxolane-4-yl)propanol 6 (0.76 g, 4.75 mmol), and pyridinium p-toluene sulfonate (36 mg) in toluene (10 mL) was heated at reflux under nitrogen positive pressure. After 12 hours, the mixture was concentrated under vacuum to give a crude oil. The resulting crude oil was purified by chromatography on silica using 20-40% ethyl acetate in n-hexane as eluant to 3-((S)-2,2-di((9Z,12Z)-octadeca-9,12-dien-1-yl)-1,3-dioxolan-4-yl)propan-1-ol, 8 (0.48 g, 0.76 mmol, 80%) as a clear oil.

$^1$H NMR (300 MHz, CDCl$_3$): 5.34-5.29 (m, 8H), 4.06-4.02 (m, 2H), 3.67-3.47 (m, 2H), 3.45-3.43 (m, 1H), 2.12-2.01 (m, 16H), 1.65-1.62 (m, 8H), 1.34-1.29 (m, 32H), 0.89-0.85 (t, J=6.6 Hz, 6H).

Synthesis of 2-((S)-2,2-di((9Z,12Z)-octadeca-9,12-dien-1-yl)-1,3-dioxolan-4-yl)-N,N-dimethylethan-1-amine, (AKG-KC2-01, O-12095)

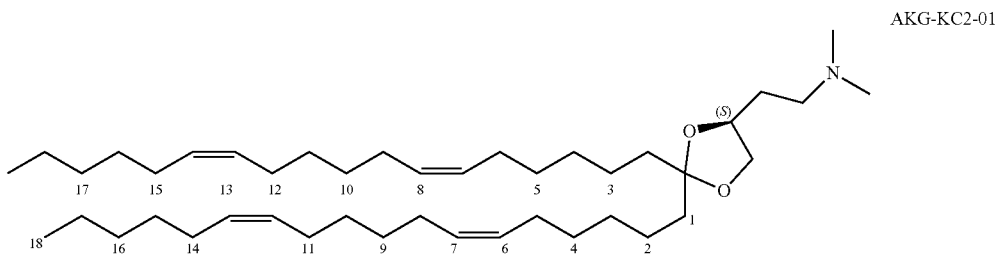

To a solution of 2-((S)-2,2-di((9Z,12Z)-octadeca-9,12-dien-1-yl)-1,3-dioxolan-4-yl) ethan-1-ol, 7 (0.49 g, 0.79 mmol) in dichloromethane (10 mL) at 0° C. was added methanesulfonyl chloride (73 μL, 0.95 mmol) and triethylamine (0.26 mL, 1.2 mmol). The solution was warmed to room temperature and stirred for an addition hour. The reaction was quenched with water and extracted with dichloromethane (2×100 mL). The organics were washed with brine then dried over magnesium sulfate and filtered. The filtrate was concentrated under vacuum to give a crude oil. A solution of 2M dimethylamine (10 mL) was added to the resulting crude oil and allowed to stir for 24 hours. The mixture was then quenched with water and extracted with dichloromethane (2×100 mL). The combined organics were washed with brine then dried over magnesium sulfate then filtered. The filtrate was concentrated under vacuum to give a crude oil. The crude oil was purified by chromatography on silica using 5-100% ethyl acetate in n-hexane as eluant to give 2-((S)-2,2-di((9Z,12Z)-octadeca-9,12-dien-1-yl)-1,3-dioxolan-4-yl)-N,N-dimethylethan-1-amine, (AKG-KC2-01, O-12095), (206 mg, 0.32 mmol, 41%) as a clear oil.

$^1$H NMR (300 MHz, CDCl$_3$): 5.35-5.32 (m, 8H), 4.08-4.03 (m, 2H), 3.47 (t, J=6.8 Hz, 1H), 2.36-2.27 (m, 2H), 2.21 (s, 6H), 2.01-1.99 (m, 16H), 1.88-1.77 (m, 2H), 1.68-1.53 (m, 6H), 1.42-1.19 (m, 34H), 0.96-0.86 (t, J=3.7 Hz, 6H).

MS(APCI) for C$_{43}$H$_{79}$NO$_2$: 642.6

Synthesis of 3-((S)-2,2-di((6Z, 12Z)-octadeca-6-12-dien-4-yl)-1,3-dioxolan-4-yl)-N,N-dimethylpropan-1-amine, AKG-KC3-01, O-12096)

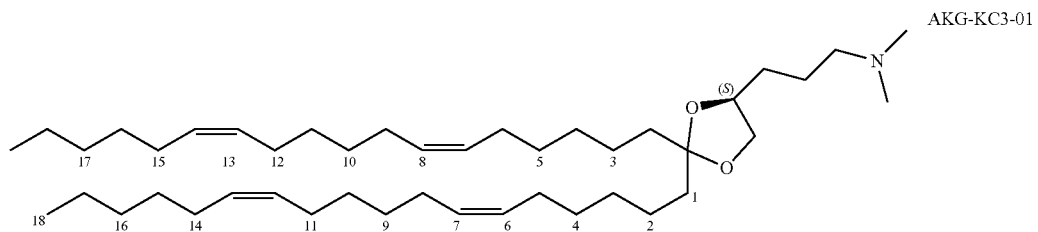

Procedure previously described.
3-((S)-2,2-di((6Z, 12Z)-octadeca-6-12-dien-4-yl)-1,3-dioxolan-4-yl)-N,N-dimethylpropan-1-amine, (AKG-KC3-01, 0-12096), (255 mg, 0.39 mmol, 51%) as a clear oil.
$^1$H NMR (300 MHz, CDCl$_3$): 5.39-5.32 (m, 8H), 4.06-4.02 (m, 2H), 3.48-3.44 (m, 1H), 2.35-2.30 (m, 2H), 2.25 (s, 6H), 2.01-1.98 (m, 16H), 1.70-1.51 (m, 12H), 1.35-1.25 (m, 32H), 0.90-0.85 (t, J=6.6 Hz, 6H).
MS(APCI) for C$_{44}$H$_{81}$NO$_2$: 656.6

Synthesis of 2-((S)-2,2-di((Z)-octadec-9-en-1-yl)-1,3-dioxolan-4-yl)-N,N-dimethylethan-1-amine (AKG-KC2-OA, O-11880)

2-((S)-2,2-di((Z)-hexadec-9-en-1-yl)-1,3-dioxolan-4-yl)-N,N-dimethylethan-1-amine (AKG-KC2-PA, O-11879)

3-((S)-2,2-di((Z)-octadec-9-en-1-yl)-1,3-dioxolan-4-yl)-N,N-dimethylpropan-1-amine (AKG-KC3-OA, O-11957)

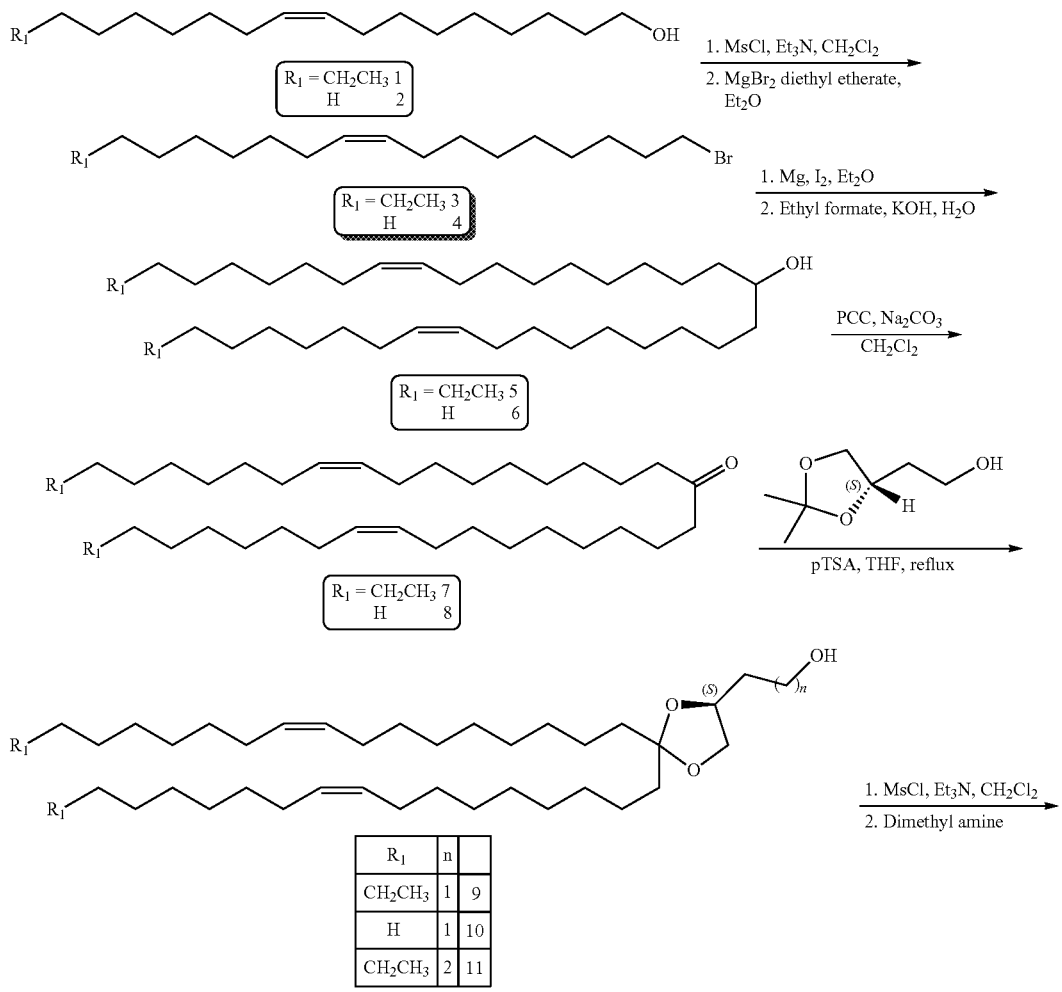

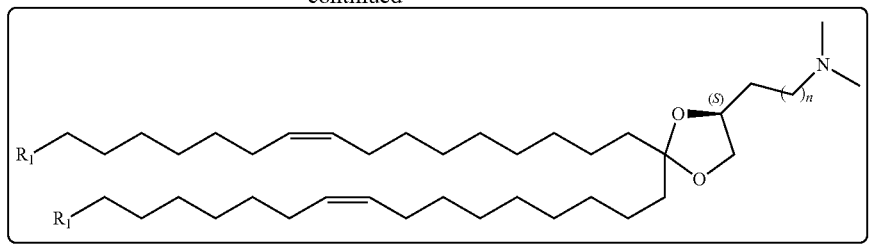

| Compounds | R₁ | n |
|---|---|---|
| AKG-KC2-OA | CH$_2$CH$_3$ | 1 |
| AKG-KC2-PA | H | 1 |
| AKG-KC3-OA | CH$_2$CH$_3$ | 2 |

Experimental Procedure (Refer to Previously Described Synthesis of AKG-KC2-01)

Synthesis of (Z)-1-bromooctadec-9-ene 3

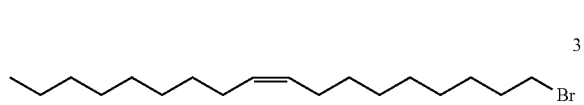 [SMILES: CCCCCCCC/C=C\CCCCCCCCBr]

Procedure previously described.
(Z)-1-bromooctadec-9-ene, (6.4 g, 19.33 mmol) as a clear oil.
¹H NMR (300 MHz, CDCl₃): 5.36-5.32 (m, 2H), 3.41 (t, J=7.5 Hz, 2H), 2.01-1.99 (m, 4H), 1.87-1.82 (m, 2H), 1.44-1.26 (m, 22H), 0.87 (t, J=6.6 Hz, 3H).

(Z)-16-bromohexadec-7-ene 4

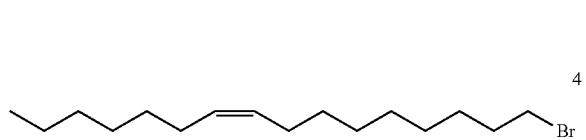 [SMILES: CCCCCC/C=C\CCCCCCCCBr]

¹H NMR (300 MHz, CDCl₃): 5.36-5.32 (m, 2H), 3.42 (t, J=7.5 Hz, 2H), 2.01-1.99 (m, 4H), 1.87-1.82 (m, 2H), 1.44-1.26 (m, 18H), 0.89 (t, J=6.6 Hz, 3H).

Synthesis of (9Z,28Z)-heptatriaconta-9,28-dien-19-ol 5

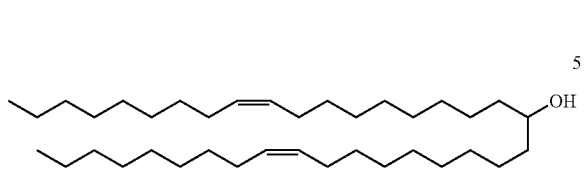 [SMILES: CCCCCCCC/C=C\CCCCCCCCC(O)CCCCCCCC/C=C\CCCCCCCC]

Procedure previously described.
(9Z,28Z)-heptatriaconta-9,28-dien-19-ol (1.2 g, 2.25 mmol, 47%) as a solid.
¹H NMR (300 MHz, CDCl₃): 5.36-5.29 (m, 4H), 3.57 (bs, 1H), 2.01-1.97 (m, 8H), 1.42-1.26 (m, 53H), 0.89 (t, J=6.6 Hz, 6H).

(7Z,26Z)-tritriaconta-7,26-dien-17-ol 6

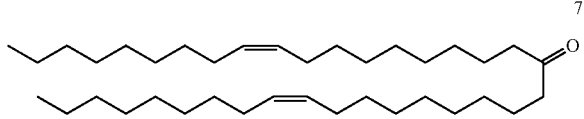 [SMILES: CCCCCCCC/C=C\CCCCCCCCC(=O)CCCCCCCC/C=C\CCCCCCCC]

¹H NMR (300 MHz, CDCl₃): 5.36-5.29 (m, 4H), 3.57 (bs, 1H), 2.01-1.97 (m, 8H), 1.42-1.26 (m, 45H), 0.89 (t, J=6.6 Hz, 6H).

Synthesis of (9Z,28Z)-heptatriaconta-9,28-dien-19-one 7

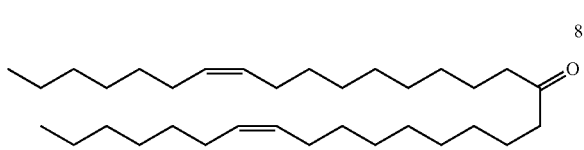 [SMILES: CCCCCC/C=C\CCCCCCCCC(=O)CCCCCCCC/C=C\CCCCCC]

Procedure previously described.
(9Z,28Z)-heptatriaconta-9,28-dien-19-one (0.89 g, 1.67 mmol, 74%) as a clear oil.
¹H NMR (300 MHz, CDCl₃): 5.36-5.29 (m, 4H), 2.03-1.98 (m, 8H), 1.42-1.26 (m, 52H), 0.90-0.89 (t, J=6.6 Hz, 6H).

(7Z,26Z)-tritriaconta-7,26-dien-17-one 8

¹H NMR (300 MHz, CDCl₃): 5.36-5.29 (m, 4H), 2.03-1.98 (m, 8H), 1.42-1.26 (m, 44H), 0.90-0.89 (t, J=6.6 Hz, 6H).

Synthesis of 2-((S)-2,2-di((Z)-octadec-9-en-1-yl)-1,3-dioxolan-4-yl) ethan-1-ol 9

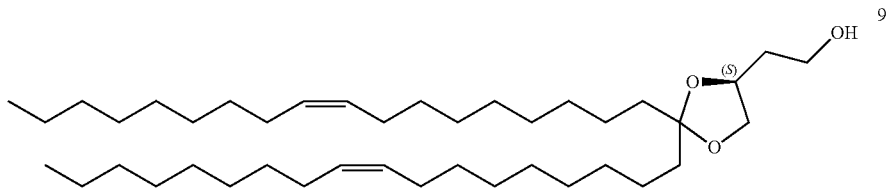

Procedure previously described.
2-((S)-2,2-di((Z)-octadec-9-en-1-yl)-1,3-dioxolan-4-yl) ethan-1-ol (0.39 g, 0.63 mmol, 74%) as a clear oil.
$^1$H NMR (300 MHz, CDCl$_3$): 5.36-5.28 (m, 4H), 4.22-4.10 (m, 1H), 4.08-4.05 (m, 1H), 3.82-3.79 (m, 2H), 3.48 (t, J=6.8 Hz, 1H), 2.24-2.21 (m, 1H), 2.01-1.99 (m, 8H), 1.81-1.80 (m, 2H), 1.59-1.54 (m, 6H), 1.34-1.26 (m, 45H), 0.87 (t, J=6.3 Hz, 6H).

Synthesis of 2-((S)-2,2-di((Z)-hexadec-9-en-1-yl)-1,3-dioxolan-4-yl)ethan-1-ol, 10

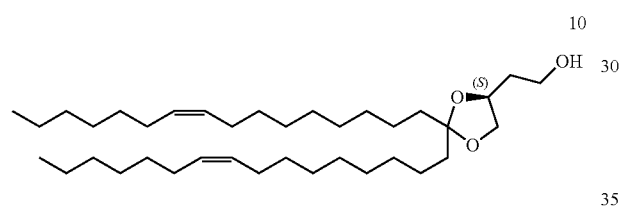

Procedure previously described.
2-((S)-2,2-di((Z)-hexadec-9-en-1-yl)-1,3-dioxolan-4-yl) ethan-1-ol (1.02 g, 1.65 mmol, 51%) as a clear oil.
$^1$H NMR (300 MHz, CDCl$_3$): 5.36-5.29 (m, 4H), 4.23-4.10 (m, 1H), 4.07-4.05 (m, 1H), 3.82-3.79 (m, 2H), 3.48 (t, J=6.6 Hz, 1H), 2.24-2.12 (m, 1H), 2.01-1.97 (m, 8H), 1.84-1.78 (m, 2H), 1.57-1.55 (m, 8H), 1.34-1.29 (m, 35H), 0.87 (t, J=6.3 Hz, 6H).

Synthesis of 3-((S)-2,2-di((Z)-octadec-9-en-1-yl)-1,3-dioxolan-4-yl)propan-1-ol, 11

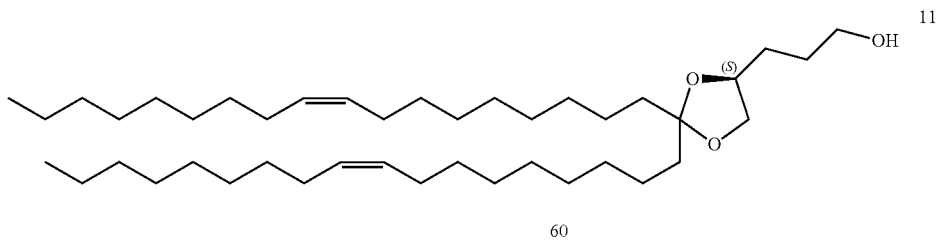

Procedure previously described.
3-((S)-2,2-di((Z)-octadec-9-en-1-yl)-1,3-dioxolan-4-yl) propan-1-ol (0.41 g, 0.65 mmol, 76%) as a clear oil
$^1$H NMR (300 MHz, CDCl$_3$): 5.39-5.32 (m, 4H), 4.06-4.03 (m, 2H), 3.71-3.67 (m, 2H), 3.47-3.46 (m, 1H), 2.01-1.99 (m, 10H), 1.66-1.59 (m, 4H), 1.56-1.54 (m, 6H), 1.34-1.26 (m, 44H), 0.87 (t, J=6.3 Hz, 6H).

Synthesis of 2-((S)-2,2-di((Z)-octadec-9-en-1-yl)-1,
3-dioxolan-4-yl)-N,N-dimethylethan-1-amine,
(AKG-KC2-OA, O-11880)

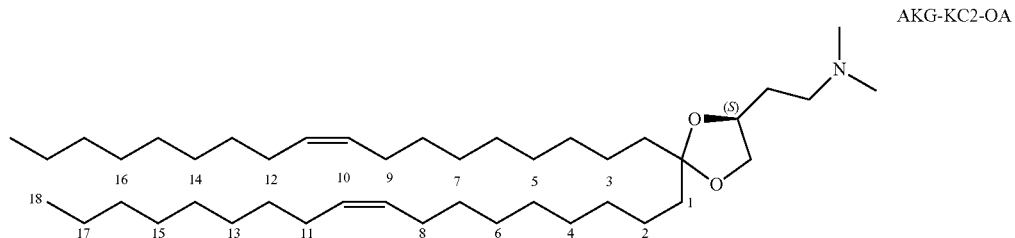

Procedure previously described.
2-((S)-2,2-di((Z)-hexadec-9-en-1-yl)-1,3-dioxolan-4-yl)-N,N-dimethylethan-1-amine, (AKG-KC2-OA, O-11880), (200 mg, 0.31 mmol, 49%) as a clear oil.
$^1$H NMR (300 MHz, CDCl$_3$): 5.38-5.28 (m, 4H), 4.08-4.01 (m, 2H), 3.48 (t, J=6.8 Hz, 1H), 2.39-2.24 (m, 2H), 2.21 (s, 6H), 2.01-1.97 (m, 8H), 1.82-1.77 (m, 2H), 1.68-1.52 (m, 6H), 1.34-1.26 (m, 46H), 0.87 (t, J=6.3 Hz, 6H).
MS(APCI) for C$_{43}$H$_{83}$NO$_2$: 646.7

Synthesis of 2-((S)-2,2-di((Z)-hexadec-9-en-1-yl)-1,
3-dioxolan-4-yl)-N,N-dimethylethan-1-amine,
(AKG-KC2-PA, O-11879)

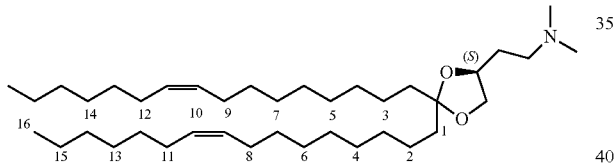

Procedure previously described.
2-((S)-2,2-di((Z)-hexadec-9-en-1-yl)-1,3-dioxolan-4-yl)-N,N-dimethylethan-1-amine, (AKG-KC2-PA, O-11879), (195 mg, 0.33 mmol, 18%) as a clear oil.
$^1$H NMR (300 MHz, CDCl$_3$): 5.35-5.28 (m, 4H), 4.08-4.02 (m, 2H), 3.48 (t, J=6.6 Hz, 1H), 2.38-2.27 (m, 2H), 2.20 (s, 6H), 2.01-1.99 (m, 8H), 1.97-1.80 (m, 2H), 1.77-1.52 (m, 6H), 1.34-1.29 (m, 38H), 0.87 (t, J=6.3 Hz, 6H).
MS(APCI) for C$_{39}$H$_{75}$NO$_2$: 590.6

Synthesis of 3-((S)-2,2-di((Z)-octadec-9-en-1-yl)-1,
3-dioxolan-4-yl)-N,N-dimethylpropan-1-amine,
(AKG-KC3-OA, O-11957)

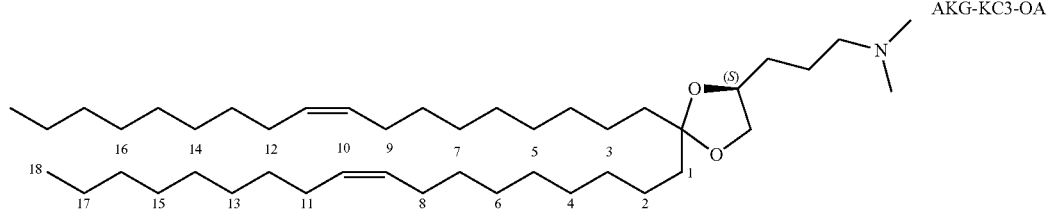

Procedure previously described.

3-((S)-2,2-di((Z)-octadec-9-en-1-yl)-1,3-dioxolan-4-yl)-N,N-dimethylpropan-1-amine, (AKG-KC3-OA, O-11957), (160 mg, 0.24 mmol, 37%) as a clear oil.

$^1$H NMR (300 MHz, CDCl$_3$): 5.39-5.28 (m, 4H), 4.06-4.01 (m, 2H), 3.44 (t, J=6.8 Hz, 1H), 2.26 (t, J=6.8 Hz, 2H), 2.20 (s, 6H), 2.01-1.97 (m, 8H), 1.82-1.77 (m, 2H), 1.60-1.43 (m, 8H), 1.34-1.26 (m, 46H), 0.87 (t, J=6.3 Hz, 6H).

MS(APCI) for C$_{44}$H$_{85}$NO$_2$: 660.6

Example 2. Assay for In Vitro Cytotoxicity in Human Hepatocyte or Cancer Cells LNPs can be tested in vitro over a series of 10 dilutions to determine IC50 in human hepatocyte/liver (HepG2; ATCC #HB8065) cells. As these formulations are generally expected to be nontoxic, a positive control of Lipofectamine™ 3000 (ThermoFisher #L3000015)-complexed mRNA (2 μl reagent/1 μg mRNA) is included in all studies. The mRNA used is CleanCap FLuc, EGFP, or MCherry reporter gene mRNA (5 moU; Trilink #L-7202, #L-7201, or #L-7203). Data is reported out as the full cell viability curve, as well as a calculation of the actual IC50 value for each compound.

Adherent cells are grown to ~80% confluency. The cells are trypsinized by adding 0.25% trypsin-EDTA (Gibco #25200-072) and the cells subsequently spun down, and 5 ml of growth medium (MEM media; Corning #10010 CM) added to disperse the cells. The cell density is determined using a hemocytometer. Growth medium (MEM media containing 10% FBS; Corning #35015 CV) is added to the cells to adjust to an appropriate concentration of cells. Then, 200 of the cells (5,000 cells/well) is added to a 96-well clear flat-bottom plate (Costar #9804) and incubated in the plate at 37° C. in a humidified incubator with 5% CO$_2$ for 24 h.

Serial dilutions of LNP formulations using growth medium as solvent are prepared. These compounds are provided as sterile aqueous with a concentration of 1 mg/ml mRNA. For making dilutions, each LNP stock was warmed to room temperature. These were further diluted to 4× in the growth media to the highest mRNA concentration tested of 250 ug/ml.

LNPs are added to the wells at a series of 1:3 dilutions from the initial 250 μg/ml concentration for each LNP by aspirating out the old media and replacing it with 200 μl of the LNP containing media. The plates were incubated at 37° C. in a humidified incubator with 5% CO$_2$ for 72 h. At the end of the LNP incubation period, replace the media in each well with 100 μl of 1× PrestoBlue Cell Viability Reagent (ThermoFisher Cat #A13261). Incubate the plate at 37° C. in a humidified incubator with 5% CO$_2$ 30 min to 2 h. Take readings at 30, 60, and 120 min. Read fluorescence with 560 nm excitation and 590 nm emission using SpectraMax M5 plate reader (Molecular Devices). Correct background by subtracting the RFU of the control containing only the culture medium (background control well) from all sample readings. Calculate the percentage of cytotoxicity using the formula below:

% Cytotoxicity=[(RFU$_{\cdot Medium}$−RFU$_{Treatment}$)/RFU$_{\cdot Medium}$]×100%

The IC50 was determined using GraphPad Prism using the following formula:

$Y=100/(1+10 \ ((\text{Log IC50}-X)*\text{Hill Slope}))$

The cytotoxicity of Lipofectamine™ 3000 (ThermoFisher #L3000015)-complexed mRNA (2 μl reagent/1 μg mRNA) positive control can in some embodiments be 5-100-fold more toxic than compounds disclosed here. This shows that disclosed compounds are less toxic than commercial transfection reagents in an in vitro hepatocytotoxicity assay. In some embodiments, the compounds described herein form less toxic LNPs in vivo than commercially available transfection reagents.

Example 3. Determination of pKa of Ionizable Lipid

The pKa of an ionizable cationic lipid can be calculated several ways. For lipids this is sometimes difficult because membrane structure and neighboring lipids in the membrane can influence the dissociation properties of the amino group, potentially giving inaccurate values. An in-situ measurement is ideal, where the apparent pKa of the ionizable lipid is measured while the lipid is within its intended environment, in this case as part of an LNP (Jayaraman 2012, Sabins 2018).

For each LNP formulation, amino lipid pKa values are determined by measuring the fluorescence of 2-(p-toluidino)-6-napthalene sulfonic acid (TNS) during titration from pH 3 to 12. TNS is an anionic molecule that does not fluoresce in solution but increases fluorescence when associated with a positive lipid membrane, and this property has been used in the past to probe membrane surface charge. A master buffer stock is prepared (10 mM sodium phosphate, 10 mM sodium borate, 10 mM sodium citrate, 150 mM sodium chloride) which are used to prepare buffers at various pH values for determining apparent pKa. Using 1 M sodium hydroxide and 1 M hydrochloric acid, ~20 unique buffers from the master buffer stock are prepared at different pH values between about 3 and 12. 300 mM 6-(p-Toluidino)-2-naphthalenesulfonic acid sodium salt (TNS reagent) solubilized in dimethyl sulfoxide (DMSO) is used as a stock. LNP are prepared and purified into the desired pH buffer with a final mRNA concentration of 0.04 mg/mL. Using a 96-well plate, preloaded with desired buffers, mRNA containing LNP are added to so that the final concentration of mRNA is 0.7 μg/mL. To each well, TNS is added so that the DMSO concentration is 1% (v/v). After mixing, the fluorescence of TNS in each well is measured (Ex/Em 331 nm/445 nm) and a sigmoidal best fit analysis is applied to the fluorescence data. The pKa is determined as the pH giving rise to half-maximal fluorescence intensity. The apparent pKa measured for compounds 1-36 is within the pH range 6.0-7.0.

Example 4. Measurement of Cell Uptake of LNPs

Measurement of LNP cellular uptake is achieved by fluorescent imaging and/or fluorescent quantification. There are many suitable fluorescent tracers available, such as 1,1'-Dioctadecyl-3,3,3',3'-Tetramethylindocarbocyanine Perchlorate (DiI), 3,3'-Dilinoleyloxacarbocyanine Perchlorate (DiO), 1,1'-Dioctadecyl-3,3,3',3'-Tetramethylindodicarbocyanine Perchlorate (DiD) and 1,1'-Dioctadecyl-3,3,3',3'-Tetramethylindotricarbocyanine Iodide (DiR) (Thermo). These lipids are weakly fluorescent in water but exhibit high fluorescence when incorporated into lipid membranes such as those present in LNPs. It is important that the lipids chosen are photostable and have high extinction coefficients.

LNPs containing these types of lipids are visualized under a fluorescent microscope. In one method, LNP lipid formulation contains a fluorescent lipid tracer such as 1,1'-Dioctadecyl-3,3,3',3'-Tetramethylindodicarbocyanine-5,5'-Disulfonic Acid (DiI5-DS) at 0.1-0.5 mol % total lipid. Cells of interest are grown in a suitable cell culture dish, such as a 24-well plate (Corning). The cells are seeded the day prior to the uptake study at 50% confluency and grown overnight under appropriate conditions, for example 37° C., 5% CO2, 90-100% humidity. LNPs are added to cell culture medium at 0.1-100 ug/mL mRNA, allowed to interact with the cells for some time (4-24 h), then the cells are washed with media three times to remove non-internalized LNPs before viewing. The cells are viewed with a microscope with fluorescent detection capabilities. The relative extent of LNP cellular uptake is determined from the fluorescent intensity signal from the cells, using non-treated cells as a background control. Alternatively, quantitative measurement of cellular fluorescent lipid may be achieved by pelleting cells, solubilizing them with a detergent such as Triton-X100, and quantifying fluorescence by a spectrofluorometer or quantifying fluorescent lipid tracer by HPLC.

In a similar manner, the quantitation of fluorescently labeled mRNA is achieved. For example, dye-labeled enhanced green fluorescent protein (EGFP) and Firefly luciferase (FLuc) mRNAs, both transcribed with Cyanine 5-UTP:5-Methoxy-UTP at a ratio of 1:3 is currently available from Trilink Biotechnologies. Cyanine 5 has an excitation maximum of 650 nm and an emission maximum of 670 nm. Substitution in this ratio results in mRNA that is easily visualized and that can still be translated in cell culture. By entrapping fluorescently labeled mRNA one can visualize the intracellular delivery of mRNA by methods described above.

LNP uptake in cells may be achieved by endogenous methods such as ApoE mediated, or through exogenous methods such as active targeting. It was found that the LNP systems containing ionizable cationic lipids take advantage of a "natural" targeting process where they adsorb apolipoprotein E (ApoE) in the blood (Cullis et al 2017) and are then actively taken up in hepatocytes by a number of receptors that contain ApoE binding ligands (Williams et al. 2010). By using non-overlapping fluorophores it is possible to independently track mRNA and LNP intracellular distribution and organelle accumulation kinetics.

mRNA cellular expression levels may be quantified by using reporter systems such as EGFP, FLuc or mCherry, available from Trilink Biotechnologies. In one embodiment, EGFP mRNA is encapsulated in LNPs, and added to cells of interest at 0.1-100 ug/mL mRNA. The cells may be washed free of non-internalized LNP by replacing the media after 4-24 h. At 24 h, GFP signal is quantified by fluorescence microscopy or flow cytometry. In this way it is possible to differentiate between a panel of LNP formulations based upon reporter protein expression levels.

Example 5. Transfection Selectivity Index

A Transfection selectivity Index (TSI) is calculated to determine the relative transfection efficiency in mammalian cells, compared to the relative toxicity in those same cells. The selectivity index was calculated using the formula below:

$$TSI=EF_{mammalian}/IC_{50,mammalian}$$

where $EF_{mammalian}$ is the transfection efficiency expressed in terms of ng protein/million cells and $IC_{50,mammalian}$ relates to the cell viability of the same formulation in terms of half maximal inhibitory concentration.

The LNPs using compounds described here (1-36) have a 50% higher TSI than LNPs made using otherwise identical LNPs made with control molecule DLin-MC3-DMA as the ICL Example 6. An Assay for Lipid Peroxidation The extent of oxidation can be determined using a forced degradation assay where LNP samples are treated with 3% $H_2O_2$ at 25° C., and sampled on days 0, 1, 3, and 5 for lipid oxidation products (Blessy et al. (2014) Journal of Pharmaceutical Analysis 4, 159-165). The oxidation reaction can be quenched by addition of 0.1 M butylated hydroxytoluene (BHT) in ethanol and stored frozen at −80° C. until measurement. Lipid oxidation products can be measured using a 2-thiobarbituric acid (TBA) reactivity assay (Gutteridge (1982) FEBS Letters 150, 454-458) to detect malondialdehyde (MDA), an end product of lipid peroxidation or by detection using an HPLC assay with evaporative light scattering detection (ELSD) or charged aerosol detection (CAD). Lipid oxidation and isomerization impurity structures can be assigned based on known literature precedent and are expected to be mixtures of isomers.

Generally, it is known in the art that lipids with multiple unsaturations in the acyl chain are more sensitive to oxidation (see Reis and Spickett (2012) Biochim Biophys Acta 1818, 2374-2387).

It is anticipated that compounds 1-36 described herein will have less susceptibility to oxidative damage or degradation when compared to a control LNPs containing the DLin-KC2-DMA lipid or when compared to a control LNPs containing DLin-MC3-DMA. In some embodiments, the compounds provided herein have greater than 30%, greater 50%, greater 75%, greater 90%, and greater 95% reduction in oxidation byproducts when compared to the control LNP.

Example 7. Preparing Ligand-Targeted LNPs

Antibody ligands providing for specific uptake of LNPs into the cells of interest, such as, immune cells, in the form of antibody Fab' fragments or single chain Fv fragments are prepared by any method known in the art (for example, as described in Drummond et al. U.S. Pat. Appl. 20180271998; Zhou et al. U.S. Pat. No. 10,406,225; Marks et al. U.S. Pat. No. 8,974,792, which are incorporated herein by reference in their entireties). To provide for conjugation of the ligands to LNPs, the ligands are constructed with a C-terminal sequence having a Cysteine residue, such as CAA, or GGSGGC. The ligands are expressed in bacterial or eukaryotic cells and isolated from the cellular mass or growth medium using standard methods such as protein affinity chromatography or metal chelation chromatography. To activate the thiol group of a terminal Cysteine residue, the ligands are incubated in the presence of 15 mM Cysteine in a 10 mM citrate buffer, pH 6.0-6.2, containing 140 mM NaCl, for 1 hour, and purified by gel-chromatography on a Sephadex G-25 or similar column, eluent 10 mM citrate buffer, pH 6.0-6.2, containing 140 mM NaCl. The protein concentration in the purified, cysteine-activated ligand solution is determined using UV spectrophotometry at 280 nm. The antibody ligand, at 1-10 mg/ml in the above named buffer, is mixed with the aqueous solution of a maleimide-terminated PEG-DSPE derivative (mal-PEG(2000)-DSPE, cat. No. 880126, Avanti Polar Lipids, AL, USA, or Sunbright® DSPE-020MA, NOF corporation, Japan) at the protein/lipid molar ratio of 4:1. Mal-PEG-lipids having PEG spacer with molecular weight or 3,400 (Sunbright® DSPE- 034MA) or 5,000, available from NOF Corporation (Sunbright® DSPE-050MA), can be used where longer distance between the LNP surface and the ligand moiety is desirable. The solution is incubated at ambient temperature for 2 hours, adjusted to 0.5 mM Cysteine to block unreacted maleimide groups, and the micellar ligand-PEG-DSPE conjugate is purified by gel chromatography on Ultrogel AcA 34 (if the ligand is a Fab) or Ultrogel AcA 44 (if the ligand is a scFv), eluent—144 mM NaCl buffered with 10 mM HEPES, pH 7.0-7.4. The conjugated protein is quantified by UV spectrophotometry, and the purity is confirmed by SDS gel-electrophoresis.

Ligand is appended to the surface of LNPs by one of the following methods.

Method 1. Preformed LNPs (obtained as described in Hope et al. U.S. Pat. No. 10,653,780 incorporated herein by reference in its entirety) are mixed with the micellar solution of the ligand-PEG-DSPE conjugate in a HEPES-buffered saline (10 mM HEPES, 140 mM NaCl, pH 7.0-7.2) to achieve the required ligand/lipid ratio in the range of 5-100 (typically 15-30) ligands per LNP particle. The mixture is incubated with slow agitation 2 hours at 37-40° C., or overnight at 2-8° C., during which time the conjugate is incorporated into the outer lipid layer of the LNPs. The ligand-conjugated LNPs are purified from unincorporated ligand-PEG-DSPE by gel chromatography on Sepharose CL-2B or CL-4B (hydrophilic size exclusion media with the same molecular weight cutoff can be also used); the LNP fraction appearing near the void volume is collected. The amount of ligand conjugated to the particles is determined by SDS gel-electrophoresis with Coomassie Blue or fluorescent staining and concurrently run ligand standards.

Method 2. A solution of the ligand-PEG-DSPE conjugate in 10 mM Na-citrate buffer pH 4.0 containing also the nucleic acid component of the LNP is mixed with the ethanolic solution of the LNP lipids to the final ethanol concentration of 40% by volume as described by Semple et al., U.S. Pat. No. 8,021,686, incorporated herein by reference in its entirety. Alternatively, a LNP-preparation protocol of Hope et al. U.S. Pat. No. 10,653,780 (incorporated herein by reference in its entirety) is employed. The amount of ligand-PEG-DSPE is 0.1-1 mol % of the lipid. The mixture is dialyzed against HEPES-buffered saline (10 mM HEPES, 140 mM NaCl, pH 7.0) to remove ethanol. Ligand-PEG-DSPE is incorporated in the resulting LNPs. Any residual ligand-PEG-DSPE is removed by gel chromatography using Sepharose CL-4B or CL-2B, eluent HEPES-buffered saline, or by buffer exchange for HEPES-buffered saline by tangential flow filtration on a polysulfone membrane (flat or hollow fiber cartridge) having 500 KD molecular weight cutoff.

Method 3. Mal-PEG-DSPE is combined with preformed LNPs in a citrate-buffered saline (10 mM Na— citrate buffer pH 6.0-6.2, 140 mM NaCl) in the amount of 0.1-1 mol % relative to the LNP lipid in the same manner as ligand-PEG-DSPE of Method 1. LNPs with incorporated mal-PE-DSPE are purified from unincorporated mal-PEG-DSPE by gel chromatography on Sepharose CL-4B in the same buffer, and incubated with thiol-activated antibody ligand (5-100 ligands pre LNP particle) for 2-24 hours. Ligand-conjugated LNP so obtained are purified from unconjugated ligand by Sepharose CL-4B gel chromatography using HEPES-buffered saline pH 7.0 as eluent.

Method 4. Mal-PEG-DSPE is incorporated into the LNPs at 0.1-1 mol % of the LNP lipid in the same manner as ligand-PEG-DSPE according to Method 2. The resulting Mal-PEG-conjugated LNPs are incubated with the thiol-activated ligand and purified as described in Method 3.

Method 5. The protocol of Method 4 is performed with the difference that instead of mal-PEG-DSPE a maleimide-conjugated lipid without a PEG spacer (mal-DSPE, Coatsome® FE-808MA3, NOF corporation, Japan) is added to the lipid solution. The resulting maleimide-LNPs are conjugated to thiol-activated ligand as per Method 3.

Method 6. A low-molecular ligand (e.g., mannose) is conjugated to LNP by the Methods 1 or 2 wherein a mannose-PEG-DSPE (Biochempeg Scientific, MA, USA, cat. No. 12169) is substituted for an antibody ligand-PEG-DSPE.

Example 8. Determining Optimal Ligand Density of the Ligand-Targeted LNPs

A panel of LNPs are prepared with the increasing ligand density in a given range (2-200 ligands per LNP particle, or 5-100 ligands per LNP particle) using any of the methods of Example 7. The LNPs are fluorescently labeled by incorporation of a fluorescently labeled lipid or fluorescently labeled nucleic acid as described in Example 4. The labeled ligand-conjugated LNPs are tested for the cell uptake according to Example 4, and the ligand content corresponding to the maximum of the ligand-specific cell uptake of the LNPs is determined. The nucleic acid intracellular function (such as mRNA expression) can be used as an assay output (Example 4), in which case the presence of a lipid or nucleic acid detectable label is not necessary.

Example 9. Preparation of Lipidic Nanoparticles (LNPs)

mRNA modified with 5-methoxyuridine (5moU) and coding for mCherry (Cat #L-7203) was obtained from Trilink Biotechnologies (San Diego, CA). All uridine nucleosides were substituted with N1-methyl-pseudouridine. To produce the mRNA, a synthetic gene encoding the mRNA sequence was cloned into a DNA plasmid. The synthetic gene was comprised of an RNA promoter, a 5' untranslated region, mCherry protein coding sequence, a 3' untranslated region, and a poly(A) tail region of approximately 120 As. The open reading frame sequence for the mCherry mRNA from Tri-Link (Cat #L-7203) corresponds to SEO ID NO: 1:

AUGGUGAGCAAGGGCGAGGAGGACAACAUGGCCAUCAUCAAGGAGUUCA

UGCGGUUCAAGGUGCACAUGGAGGGCAGCGUGAACGGCCACGAGUUCGA

GAUCGAGGGCGAGGGCGAGGGCCGGCCCUACGAGGGCACCCAGACCGCC

AAGCUGAAGGUGACCAAGGGCGGCCCCCUGCCCUUCGCCUGGGACAUCC

UGAGCCCCCAGUUCAUGUACGGCAGCAAGGCCUACGUGAAGCACCCCGC

CGACAUCCCCGACUACCUGAAGCUGAGCUUCCCCGAGGGCUUCAAGUGG

GAGCGGGUGAUGAACUUCGAGGACGGCGGCGUGGUGACCGUGACCCAGG

ACAGCAGCCUGCAGGACGGCGAGUUCAUCUACAAGGUGAAGCUGCGGGG

CACCAACUUCCCCAGCGACGGCCCCGUGAUGCAGAAGAAGACCAUGGGC

UGGGAGGCCAGCAGCGAGCGGAUGUACCCCGAGGACGGCGCCCUGAAGG

GCGAGAUCAAGCAGCGGCUGAAGCUGAAGGACGGCGGCCACUACGACGC

CGAGGUGAAGACCACCUACAAGGCCAAGAAGCCCGUGCAGCUGCCCGGC

-continued
GCCUACAACGUGAACAUCAAGCUGGACAUCACCAGCCACAACGAGGACU

ACACCAUCGUGGAGCAGUACGAGCGGGCCGAGGGCCGGCACAGCACCGG

CGGCAUGGACGAGCUGUACAAGAGCGGCAACUGA

Stock solutions of each lipid were prepared. Ionizable lipids were weighed out in 4 mL glass vials (Thermo B7999-2) and dissolved in ethanol (Sigma-Aldrich 200 proof, RNase free) to a final concentration of 10 mM. Other lipids such as DSPC, Cholesterol and PEG-DMG were weighed out and dissolved in ethanol to a concentration of 1 mM. DSPS was dissolved in methanol (Sulpelco, Omnisolve) at a concentration of 1 mM and briefly heated to 70° C. to complete its dissolution.

Lipid mixtures for each individual LNP were prepared by adding the desired volume of each lipid stock solution to a new vial, adding ethanol if needed to achieve a final volume of 1.2 mL. For example, an LNP formulation of AKG-UO-1/DSPC/DSPS/Chol/PEG-DMG (50/2.5/7.5/38.5/1.5 mol %), with an N/P of 5 contained 1500 nmol AKG-UO-1, 75 nmol DSPC, 225 nmol DSPS, 1155 nmol Chol and 45 nmol PEG-DMG for every 100 µg of mRNA used.

mRNA solutions were prepared by thawing frozen mRNA (mCherry mRNA, Trilink) vials and diluting mRNA in 6.25 mM sodium acetate (pH 5.0) to a final concentration of 0.033 mg/mL. To prepare LNPs, a NanoAssemblr Benchtop microfluidic device (from Precision Nanosystems) was used. If LNPs contained DSPS, the heating block accessory set to 70° C. was used, otherwise LNPs were mixed at room temperature. 3 mL of mRNA solution was loaded into a 3 mL disposable syringe (BD 309656) and 1 ml of lipid mixture in a 1 ml syringe (BD309659) and placed in the NanoAssemblr heating block for 4 min prior to mixing. LNP formation was achieved by pumping the liquid streams through a disposable microfluidics cassette at 3:1 aqueous: alcohol volume ratio at 6 mL/min mixing speed. After mixing, 3.6 mL of LNP mixture was collected, while the initial mixed volume of 0.35 mL and last 0.05 mL of mix was discarded. Ethanol was removed by buffer exchange using SpectraPor dialysis tubing (12-14 k MWCO) in PBS (Cytivia, SH30256.01) or by sequential concentration and dilution using Amicon Ultra-4 centrifugal concentrators (10 k MWCO, at 500 g).

LNPs were typically exchanged into PBS, pH 7.4 and then 15 mM Tris, pH 7.4, 20% sucrose, concentrated to 20-50 ug/mL mRNA, sterile filtered (Thermo Nalgene 0.2 um #720-1320) prior to freezing by immersion in liquid nitrogen for 5 min and long-term storage at −20° C.

Example 10. LNP Characterization

A. mRNA Concentration and Relative Encapsulation Efficiency Determination by Fluorescent Binding Dye Materials: Ribogreen reagent (Thermo #11491), 3×96-well plates with lids, PBS, dissociation buffer (PBS with 10% DMSO and 1% (wt/wt) Zwittergent 3-14 (Sigma-Aldrich #693017), mRNA, general pipette tips & repeater pipette tips.

1. 5 mL of 2 µg/mL mRNA stock were prepared in DPBS or PBS
2. Diluted standards were prepared as follows in single wells in a 96-well plate (Plate A);

| Final [mRNA] ng/mL | Vol. stock 2 µg/mL (µL) | Vol. PBS (µL) |
|---|---|---|
| 2000 | 400 | 0 |
| 1500 | 300 | 100 |
| 1000 | 200 | 200 |
| 500 | 100 | 300 |
| 0 | 0 | 400 |

3. Using different wells in Plate A, samples were diluted to be within the standard curve, you'll need one well per sample. For example, if the approximate mRNA concentration should be ~30 ug/mL in the sample, a 20× dilution was performed (Dilution Factor). (20 uL sample added to 380 µL PBS in a well). No lid was used on plate A. Samples were mixed by gentle pipetting up & down.

Example of Plate A

| | | | | | | | | |
|---|---|---|---|---|---|---|---|---|
| A | 0 | 500 | 1000 | 1500 | 2000 | | | |
| B | | | | | | | | |
| C | S 1 | S 2 | S 3 | S 4 | S 5 | S 6 | S 7 | S 8 Etc. |
| D | | | | | | | | |
| E | | | | | | | | |
| F | | | | | | | | |
| G | | | | | | | | |
| H | | | | | | | | |

4. Two more plates, plates B & C were used. Using a multichannel pipettor, 60 µL of each standard 2 were pipetted into wells each (duplicate), and sample into 3 wells each (triplicate)

Example of Plate B and C

| | | | | | | | | |
|---|---|---|---|---|---|---|---|---|
| A | 0 | 500 | 1000 | 1500 | 2000 | | | |
| B | 0 | 500 | 1000 | 1500 | 2000 | | | |
| C | S 1 | S 2 | S 3 | S 4 | S 5 | S 6 | S 7 | S 8 Etc. |
| D | S 1 | S 2 | S 3 | S 4 | S 5 | S 6 | S 7 | S 8 Etc. |
| E | S 1 | S 2 | S 3 | S 4 | S 5 | S 6 | S 7 | S 8 Etc. |
| F | | | | | | | | |
| G | | | | | | | | |
| H | | | | | | | | |

5. The number of wells used on each plate was counted and 4 was added to this number. For plate B, PBS was prepared with Ribogreen diluted 1:100. For example, for 40 wells, 44 was used as the number. 44×60 µL=2.64 mL Ribogreen solution needed, so that would be 2.61 mL PBS with 26.4 µL Ribogreen.
6. For plate C, 2.61 mL Dissociation buffer and 26.4 uL Ribogreen was pipetted.
7. Using a repeater pipette set for 60 µL, PBS+RiboGreen was added to each well on plate B and 60 µL Dissociation Buffer+Ribogreen to plate C. Both plates B and C were mixed on an orbital mixer (120 rpm) for 1 min. Plate B was placed in the dark for 15 min. Plate C was incubated at 37° C. in the dark for 10 min, followed by 5 min at RT.
8. Both plates were read one after the other, using Ex. 465, Em. 530 nm
9. Using the standard curve, the slope and intercept were calculated and by extrapolation the mRNA concentrations of the samples on plate B & C were calculated (average and std.dev)

10. Percent encapsulation efficiency (% EE) by [mRNA] plate B/[mRNA] plate C×100 was calculated
11. Total [mRNA] by taking [mRNA] plate C X dilution factor was calculated.

B. LNP Particle Size
1. 30 µL of LNP was mixed with 1.5 mL PBS in a polystyrene cuvette (Sarstedt, #67.754) and analyzed for size using a ZetaSizer Pro (Malvern) using ZS Xplorer software, version number 1.4.0.105. The Z-average size and polydispersity index value were recorded. Typically, size measurements of LNPs were taken post LNP mixing, post buffer exchange and post sterile filtering.

C. LNP Zeta Potential
1. 30 µL of LNP was mixed with 1.5 mL PBS and injected into a disposable folded capillary cell (Malvern Nano-series DTS1070) and zeta potential measured on a ZetaSizer Pro at 25° C.

Example 11. Determination of Transfection Efficiency in Murine Dendritic Cells of LNPs Using mCherry mRNA A. Cell Propagation, Transfection, Harvesting and Staining Protocol
1. MutuDC1940 cells (ABM) were grown according to supplier's instructions in T75 flasks. When required, they were plated at 180,000 cells/well into 24-well plate one day prior to transfection.
2. LNPs were added in triplicate to each well at 1 µg/mL in 1 mL media and after 24 h the cells were washed once with DPBS (VWR 02-0119-1000).
3. 0.2 mL of DPBS (plus 5 mM EDTA, pH 7.4) was then added to facilitate detachment.
4. The cells were placed at 37° C. for 3 min, until detached.
5. 0.5 ml DPBS added to each well and the liquid transferred to a flow cytometry tube (Falcon 5 mL #352054).
6. The tube was centrifuged at 1100 rpm for 3-5 min and the liquid poured off.
7. 100 µL of Zombie Violet (Biolegend) (diluted 1:500 in PBS) was added to each tube.
8. The tubes were gently tapped to resuspend cells and placed in the dark for 15 min at RT.
9. To the cells 0.5 mL of (paraformaldehyde 4% in PBS:DPBS 1:1) was added and the cells flicked gently to resuspend and put on ice for 30 min. Another 2 ml PBS was added.
10. The cells were pelleted as above and resuspended in 0.5 mL DPBS with 5% BSA and placed in the fridge until needed.

B. Cell Analysis
1. Cells suspensions were analyzed by an Attune NxT flow cytometer using the VL1 and YL2 for live/dead and mCherry fluorescence signals respectively. Gating analysis was performed on FloJo software.

Example 12. Impact of DSPS on Transfection Efficiency of Dendritic Cells Using LNPs with KC2 as Ionizable Cationic Lipid The aim of this study was to explore the effect of phosphatidylserine targeting using DSPS on transfection efficiency in murine dendritic cells. LNPs were prepared as described in Example 9, characterized for particle size and zeta potential as described in Example 10, and evaluated for transfection efficiency in murine dendritic cells as described in Example 11. The LNPs all had DLin-KC2-DMA constant at an N/P ratio of 5 and 50 mol % of total lipid, the PS lipid was varied initially from 0-2.5 mol % and the DSPC phospholipid varied from 0-7.5 mol % (Total mol % of DSPC and DSPS was constant at 10 mol %), and the cholesterol constant at 38.5 mol % (all mol % of total lipid). The particle size, Polydispersity Index (PDI), and entrapment efficiency for all formulations is shown below in Tables 5 and 6.

TABLE 5

Physicochemical properties of KC2-containing LNPs used in Example 12 varying from 0-2.5 mol % used in Example 12 and FIG. 3A.

| Mol % DSPS | Particle Size (nm) | PDI | % Encapsulation ± SD |
|---|---|---|---|
| 0 | 77.6 | 0.075 | 86.4 ± 2.8 |
| 0.1 | 82.0 | 0.171 | 87.0 ± 4.7 |
| 0.5 | 89.2 | 0.285 | 86.3 ± 3.2 |
| 2.5 | 72.2 | 0.263 | 87.1 ± 6.8 |

TABLE 6

Physicochemical properties of KC2-containing LNPs varying from 0-7.5 mol % used in Example 12 and FIG. 3B, FIG. 3C, and FIG. 3D.

| Mol % DSPS | Particle Size (nm) | PDI | % Encapsulation ± SD |
|---|---|---|---|
| 0 | 73.9 | 0.14 | 92.6 ± 6.2 |
| 1.25 | 80.3 | 0.13 | 90.9 ± 5.6 |
| 2.5 | 70.7 | 0.25 | 89.0 ± 7.4 |
| 5 | 78.7 | 0.12 | 85.1 ± 6.8 |
| 7.5 | 76.4 | 0.14 | 85.4 ± 3.6 |

An initial set of LNPs containing DLin-KC2-DMA and varying phosphatidylserine in the form of DSPS from 0-2.5 mol %, showed little transfection at 0 or 0.5 mol % DSPS, but increase by 18-fold when DSPS was incorporated at 2.5 mol % (FIG. 3A). A second series of LNPs prepared with DSPS from 0-7.5 mol % was evaluated at 0.1, 0.3, and 1 µg/mL mRNA concentrations (FIG. 3B, FIG. 3C and FIG. 3D). The transfection efficiency increased as the mol % of DSPS was increased above 2.5 mol %, with a maximum at 7.5 mol % at 1 µg/mL mRNA, and 5 mol % at both 0.1 and 0.3 µg/mL mRNA. These data demonstrate that the inclusion of phosphatidyl-L-serine can dramatically increase the transfection efficiency of mRNA-containing LNPs, and that maximal uptake occurs between 5-7.5 mol % of DSPS (as % of total lipid).

Example 13. Impact of ICL and Anionic Phospholipid Targeting Ligand on mRNA Transfection of Dendritic Cells The aim of this study was to see if other anionic phospholipids could also enhance the transfection efficiency of LNPs and how LNPs prepared with varying ICLs and PS targeting would transfect dendritic cells. LNPs were prepared as described in Example 9, characterized for particle size and zeta potential as described in Example 10, and evaluated for transfection efficiency in murine dendritic cells as described in Example 11. The LNPs had various ICLs (DLin-KC2-DMA, KC2-OA, KC3-OA, or SM-102) constant at an N/P ratio of 5 and 50 mol % of total lipid, the PS lipid was kept constant at 5 mol % and the DSPC at 5 mol %, and the cholesterol constant at 38.5 mol % (all mol % of total lipid). The particle size, PDI, and entrapment efficiency for all formulations is shown below in Table 7.

TABLE 7

Physicochemical properties of LNPs varying in ICL used and with anionic phospholipid at 5 mol %.

| Ionizable Cationic Lipid (ICL) | Anionic lipid | Particle Size (nm) | PDI | % Encapsulation ± SD |
|---|---|---|---|---|
| KC2 | 5% DSPS | 90.9 | 0.13 | 91.0 ± 5.8 |
| KC2-OA | 5% DSPS | 74.8 | 0.13 | 92.8 ± 8.0 |
| KC3-0A | 5% DSPS | 95.5 | 0.09 | 96.6 ± 18.3 |
| SM-102 | None | 77.5 | 0.05 | 92.6 ± 5.0 |
| SM-102 | 5% DSPS | 65.9 | 0.13 | 84.5 ± 7.7 |
| KC2 | 5% Glu-DSPE | 52.1 | 0.23 | 87.9 ± 6.8 |
| KC2 | 5% Suc-DSPE | 64.6 | 0.19 | 86.6 ± 3.6 |

The transfection results are shown in FIG. 4 show high transfection rates with three different KC-series ICLs (KC2, KC2-OA, and KC3-OA), and also with LNPs prepared with the branched ICL, SM-102. The encapsulation efficiency was high and the particle size below 100 nm for all formulations, including those prepared with alternate anionic phospholipids (Suc-DSPE or Glu-DSPE). The data demonstrate that DSPS (L-serine) can not be substituted with either N-glutaryl-distearoylphosphatidylethanolamine (Glu-DSPE) or N-succinyl-distearoylphosphatidylethanolamine (Suc-DSPE) and provide the same high level of mRNA transfection despite both phospholipids also containing two negative charges and both containing the same distearoyl (C18:0) fully saturated acyl chains. These studies also clearly show that the addition of DSPS can give rise to high transfection efficiencies for other ionizable cationic lipids, including those with a single unsaturated acyl gain (KC2-OA or KC3-OA) and those including a branched ICL, like SM-102. The addition of DSPS to SM-102 containing LNPs gave rise to a 22-fold increase in mCherry expression, for example.

Example 14. Dependence of PS Targeting on ICL and PS Structure

The aim of this study was to compare PS-targeted LNPs with KC2 and KC3 series ionizable cationic lipids of varying acyl chain composition. KC2 series lipids having a structure of dimethylaminoethyl headgroup structure were compared to the KC3 series containing a dimethylaminopropyl-derivatized head group. The LNPs contained various ICLs (KC2, KC2-01, KC2-OA, KC2-PA, KC3-OA, and KC3-01) as the ICL at an N/P ratio of 5 and 50 mol % ICL, and a constant 1.5 mol % PEG-DMG. The cholesterol content was held constant at 38.5 mol % and the DSPC content varied inversely with the mol % of DSPS at either 0 or 5 mol % (all lipid concentrations were used as mol % of total lipid). Transfection efficiency was evaluated in murine dendritic cells as described in Example 11.

TABLE 8

Physicochemical properties of LNPs varying in ICL used and with anionic phospholipid at 5 mol %.

| Ionizable Cationic Lipid (ICL) | PS content | Particle Size (nm) | PDI | % Encapsulation ± SD |
|---|---|---|---|---|
| KC2 | None | 95.6 | 0.08 | 91.7 ± 2.0 |
| KC2 | 5% DSPS | 82.5 | 0.09 | 87.1 ± 3.8 |
| KC2-01 | None | 82.4 | 0.08 | 91.6 ± 3.9 |
| KC2-01 | 5% DSPS | 76.0 | 0.10 | 90.5 ± 3.5 |
| KC2-OA | None | 89.5 | 0.08 | 88.6 ± 4.2 |
| KC2-OA | 5% DSPS | 85.9 | 0.10 | 92.4 ± 4.5 |
| KC2-PA | None/10% DPPC | 92.3 | 0.11 | 92.4 ± 4.4 |
| KC2-PA | 5% DSPS/5% DPPC | 85.2 | 0.10 | 95.5 ± 3.4 |
| KC3-01 | None | 88.2 | 0.10 | 94.3 ± 7.1 |
| KC3-01 | 5% DSPS | 101.2 | 0.16 | 95.2 ± 4.4 |
| KC3-OA | None | 105.9 | 0.08 | 86.6 ± 1.6 |
| KC3-OA | 5% DSPS | 103.0 | 0.13 | 93.8 ± 3.2 |
| KC2-PA | 5% DPPS/5% DPPC | 77.1 | 0.06 | 93.8 ± 3.7 |

The transfection results are shown in FIG. 5 and clearly show a positive impact of PS targeting on multiple KC-series ICLs. Here we show that ICLs containing both unsaturated C16 and C18 ICLs could be targeted with phosphatidyl-L-serine and give rise to high transfection rates for dendritic cells. The highest rate of transfection came when the PS and PC contained a mismatched acylchain composition, with 5 mol % DPPC and 5 mol % DSPS, and combined with a C16 ICL (KC2-PA).

Example 15. Impact of Phosphatidylserine Structure on Transfection Efficiency of LNPs The aim of this study was to explore the effect of different anionic phospholipid structures on transfection efficiency in dendritic cells. LNPs were prepared as described in Example 9, characterized for particle size and zeta potential as described in Example 10, and evaluated for transfection efficiency in murine dendritic cells as described in Example 11. The LNPs all had AKG-UO-1 constant at an N/P ratio of 5 and 50 mol % of total lipid, the anionic lipid was varied depending on the formulation and inversely to the DSPC phospholipid, and the cholesterol constant at 38.5 mol % except for the 20 mol % DSPS LNP (all mol % of total lipid). For samples that contained up to 10% phosphatidylserine component, the phosphatidylcholine composition was reduced accordingly from 10 mol %. For example, an LNP with 5 mol % DSPS, contained 5 mol % DSPS and 5 mol % DSPC, and those that contained 10 mol % DSPS had no DSPC. However, for the sample that contained 20 mol % DSPS, there was no DSPC in the formulation and the mol % cholesterol was reduced by 10 mol % to 28.5 mol %.

The entrapment efficiency for all formulations was between 84 and 90%, indicating highly efficiency mRNA entrapment in the LNP.

TABLE 9

Physicochemical properties and encapsulation for LNPs prepared with AKG-UO-1 as the ICL and varying anionic phospholipids.

| LNP Formulation (anionic lipid) | Particle Size (nm) | PDI | Zeta Potential at pH 5 (mV) | Zeta Potential at pH 7 (mV) | % Encapsulation |
|---|---|---|---|---|---|
| No Anionic lipid | 98.1 | 0.03 | 13.01 | −0.2 | 84.2 ± 4.2 |
| 2.5% L-DSPS | 96.8 | 0.03 | 3.4 | −1.7 | 86.1 ± 5.0 |
| 5% L-DSPS | 95.7 | 0.05 | 14.9 | −2.9 | 88.3 ± 3.2 |
| 7.5% L-DSPS | 95.1 | 0.10 | 17.0 | −4.2 | 89.1 ± 3.6 |

TABLE 9-continued

Physicochemical properties and encapsulation for LNPs prepared with AKG-UO-1 as the ICL and varying anionic phospholipids.

| LNP Formulation (anionic lipid) | Particle Size (nm) | PDI | Zeta Potential at pH 5 (mV) | Zeta Potential at pH 7 (mV) | % Encapsulation |
|---|---|---|---|---|---|
| 10% L-DSPS | 100.5 | 0.08 | 15.2 | −5.1 | 89.6 ± 3.1 |
| 7.5% L-DPPS | 96.3 | 0.07 | 17.8 | −7.6 | 88.1 ± 2.7 |
| 7.5% D-DSPS | 100.1 | 0.14 | 19.5 | −9.6 | 87.4 ± 4.4 |
| 7.5% L-DOPS | 110.4 | 0.07 | 15.1 | −3.5 | 89.5 ± 3.5 |
| 7.5% L-DMPS | 97.6 | 0.08 | 12.7 | −3.8 | 88.4 ± 1.3 |
| 20% L-DSPS | 97.7 | 0.07 | 7.0 | −7.0 | 88.5 ± 1.9 |
| 5% DSPG | 86.6 | 0.04 | 17.5 | −4.7 | 87.1 ± 3.1 |
| 7.5% DSPG | 85.0 | 0.08 | 16.6 | −4.1 | 90.1 ± 0.9 |
| 7.5% Glu-DSPE | 94.0 | 0.07 | 16.9 | −6.4 | 89.6 ± 9.1 |
| 7.5% Suc-DSPE | 96.9 | 0.05 | 14.3 | −5.6 | 88.4 ± 9.0 |

The effect of different phosphatidylserine chemical forms was evaluated in FIG. 6A showing the importance of saturation, acyl chain length, and serine stereochemistry on LNP transfection activity in murine dendritic cells. PS analogs with oleic acid acyl chains (DOPS) or where the stereochemistry as (D-serine) rather than L-serine gave rise to LNPs with transfection activity similar to that of LNPs prepared without any phosphatidylserine. However, LNPs prepared with PS containing the L-isomer of serine and saturated acyl chains are significantly better at transfecting dendritic cells compared to LNPs without any PS. Of the saturated series, those with C16 (DPPS) or C18 (DSPS), showed the highest activity, while those with C14 (DMPS) was lower, although still improved compared to dendritic cells treated with LNPs without any PS. In FIG. 6B the impact of other anionic phospholipids were evaluated with DSPG-containing formulations (5 or 7.5 mol %) showing activity similar to background, and N-glutaryl- or N-succinyl-distearoylphosphatidylethanolamine (Glu-DSPE or Suc-DSPE) showing a more modest 3-5-fold enhancement of activity when included in these AKG-UO1 containing LNPs. This example shows that LNPs prepared with saturated phosphatidyl-L-serines transfect dendritic cells significantly better than those containing the unsaturated dioleoylphosphatidyl-L-serine (DOPS) or the D-isomer of DSPS. LNPs containing the L-isomers of DSPS and DPPS showed the highest level of transfection compared to other forms of PS, anionic N-glutaryl or N-succinyl DSPE analogs, or distearoylphosphatidyglycerol (DSPG) at either 5 or 7.5 mol %.

Example 16. Optimizing the DSPS Density on AKG-UO-1 Containing LNPs

The aim of this study was to explore the impact of DSPS density on transfection efficiency of LNPs. LNPs were prepared as described in Example 9. The LNPs contained AKG-UO-1 as the ICL at an N/P ratio of 5 with between 0 and 20 mol % DSPS and a constant 1.5 mol % PEG-DMG. The cholesterol content was held constant at 38.5 mol % and the DSPC content varied inversely with the mol % of DSPS between 0-10 mol % (all lipid concentrations were used as mol % of total lipid). In the 20 mol % DSPS formulation, there was no DSPC and the cholesterol content decreased in the total by 10 mol % (from 38.5 to 28.5 mol %). Transfection efficiency was evaluated in murine dendritic cells as described in Example 11.

TABLE 10

Physicochemical properties and encapsulation for LNPs prepared with AKG-UO-1 as the ICL and varying anionic phospholipids.

| LNP Formulation | Particle Size (nm) | PDI | Zeta Potential at pH 5 (mV) | Zeta Potential at pH 7 (mV) | % Encapsulation |
|---|---|---|---|---|---|
| UO1 + 0% DSPS | 98.1 | 0.03 | 13.0 | −0.2 | 84.2 + 4.2 |
| UO1 + 2.5% DSPS | 96.8 | 0.03 | 3.4 | −1.7 | 86.1 + 5.0 |
| UO1 + 5% DSPS | 95.7 | 0.05 | 14.9 | −2.9 | 88.3 + 3.2 |
| UO1 + 7.5% DSPS | 95.1 | 0.10 | 17.0 | −4.2 | 89.1 + 3.6 |
| UO1 + 10% DSPS | 100.5 | 0.08 | 15.2 | −5.1 | 89.6 + 3.1 |
| UO1 + 20% DSPS | 97.7 | 0.07 | 7.0 | −7.0 | 88.5 + 1.9 |

The dependence of the LNP composition on DSPS concentration is shown in FIG. 7 for the AKG-UO1 containing LNPs. This study suggests that the presence of DSPS in the formulation allows for a high level of transfection of dendritic cells between 2.5 and 10 mol % DSPS, and an apparent peak around 5-7.5 mol % DSPS for AKG-UO-1 containing LNPs.

Example 17. Impact of PEG on Transfection Efficiency of AKG-UO-1 Containing LNPs The aim of this study was to explore the impact of PEG-lipid density on transfection efficiency of nontargeted and phosphatidyl-L-serine targeted LNPs. LNPs were prepared as described in Example 9. The LNPs contained AKG-UO-1 as the ICL at an N/P ratio of 5 with either 0 or 5 mol % DSPS and between 0.5-4.5 mol % PEG-DMG. The cholesterol content was held constant at 38.5 mol % and the DSPC content was 10 mol % for the formulations with no DSPS and 5 mol % for those with 5 mol % DSPS. At PEG-DMG content above 1.5 mol %, the total cholesterol content was reduced by the amount of PEG-DMG added, for example with a PEG-DMG content of 3.5 mol %, the cholesterol content was reduced to 36.5 mol % from 38.5 mol %. The particles with 0.5% PEG-DMG showed a negative zeta potential at pH 7.4, and a significant shift to a positive zeta potential at pH 5. The LNPs with 1.5-3.5 mol % PEG-DMG were essentially neutral at pH 7.

TABLE 11

Physicochemical properties of LNPs used in Example 17 and containing AKG-UO-1, 0 or 5 mol % DSPS

| % DSPS | % PEG-DMG | Particle Size (nm) | Zeta Potential at pH 7 (mV) | Zeta Potential at pH 5 (mV) |
|---|---|---|---|---|
| 0 | 0.5 | 98.9 | 0.27 | 25.92 |
| 0 | 1.5 | 75.0 | −0.87 | 12.07 |
| 0 | 2.5 | 73.8 | −0.51 | 11.86 |
| 0 | 3.5 | 81.0 | −0.30 | 6.34 |
| 0 | 4.5 | 143 | −1.47 | 14.51 |
| 5 | 0.5 | 106.1 | −1.35 | 9.30 |
| 5 | 1.5 | 73.7 | −0.21 | 3.23 |
| 5 | 2.5 | 70.7 | −0.20 | 4.75 |
| 5 | 3.5 | 65.6 | −0.10 | 7.54 |
| 5 | 4.5 | 63.1 | −1.12 | 3.73 |

The impact of PEG-DMG on transfection of dendritic cells by DSPS-targeted LNPs containing the AKG-UO-1 ICL is shown in FIG. 8. The formulation with 0.5% PEG-DMG showed a transfection efficiency in the presence of 5% DSPS that was between 6-7 fold higher than observed at 1.5-2.5 PEG-DMG. Transfection at 1.5 and 2.5 PEG-DMG was similar, but decreased dramatically at 3.5 and 4.5 mol % PEG-DMG. The ratio of targeted to nontargeted transfection at each PEG-density varied, and was 12-fold at 0. 5% PEG, 7-fold at 1.5% PEG, 37-fold at 2.5% PEG, and below 5-fold at 3.5 and 4.5% PEG, likely because of high PEG-shielding of the PS targeting moiety. The combination of these data show that the optimum range of PEG-densities is between 0.5-2.5% PEG-DMG, with the lower end of the range being optimum for overall transfection efficiency, while the 2.5% being optimal for target specificity.

Example 18. Oxidative Stability of ICLs

The aim of this studies was to compare stability of ionizable cationic lipids with conjugated olefins (such as KC2, KC3 and O-11769) and those with conjugated olefins (such as KC2-01, KC3-01 and UO-1) under accelerated oxidation.

Individual lipid stocks (10 mM) were prepared in ethanol and stored at −20° C. Prior to the experiment, 5 mM suspensions (KC2, KC2-01, KC3, KC3-01, O-11769 and UO-1) were prepared by mixing 45 µl of 10 mM lipid stock in ethanol (Sigma-Aldrich, cat #459836) with 45 µl of ultra-pure water (Rx Biosciences, cat #P01-UPW02-1000). Liposomal formulations based on AKG-UO-1 and O-11769 ionizable cationic lipids (Table 12) were prepared by combining lipid mixtures of desired composition in 1 mL ethanol with 3 mL 6.25 mM sodium acetate, pH 5.0 at 6 mL/min on a NanoAssemblr (Precision Nanosystems). 3.6 mL of the mixture was retained, while the initial 0.35 mL of the mixture and final 0.05 mL were discarded. Ethanol was removed by buffer exchange into PBS, pH 7.4 by concentrating each liposome preparation using an Aminon-Ultra 4 centrifugal concentrator at 500 g for 10 min at 4° C. and diluting back to the original volume with PBS. This cycle was repeated multiple times until the ethanol concentration was <1%. Finally, liposomes were sterile filtered through 0.2 µm PES (Nalgene) syringe filters and size measured by a ZetaSizer (Malvern). The AKG-UO-1 containing formulation (Lot #102021-6) had an average size of 81.8 nm and a PDI of 0.09, whereas the O-11769 containing formulation had an average size of 86.6 nm and a PDI of 0.10.

TABLE 12

LNP formulations used in the accelerated oxidation study.

| Lot# | Composition | MW | mol % | Estimated total lipid [mM] |
|---|---|---|---|---|
| 102021-6 | AKG-UO-1 | 658.1 | 50 | 1.5 |
| | DSPC | 790 | 10 | |
| | Cholesterol | 387 | 38.5 | |
| | PEG$_{2000}$-DMG | 2500 | 1.5 | |
| 102021-7 | O-11769 | 658.1 | 50 | 1.5 |
| | DSPC | 790 | 10 | |
| | Cholesterol | 387 | 38.5 | |
| | PEG$_{2000}$-DMG | 2500 | 1.5 | |

Aliquots of the liposomal formulations were stored at −80° C. and thawed before the experiment. A combined stock in water of 10% $H_2O_2$ (Sigma-Aldrich, cat #H1009) and 1 mM of Fe(III)Cl (Sigma-Aldrich, cat #372870) was freshly prepared prior to the treatment. To make 1% final concentration of $H_2O_2$ and 100 µM Fe(III)Cl, 10 µl of 10% $H_2O_2$/1 mM Fe(III)Cl stock was added to 90 µl of both liposomal formulations and individual lipids The liposomes and individual lipids were incubated with $H_2O_2$/Fe(III)Cl at 37° C. and then 5 µl from each sample was taken at different time points (0, 3, 24, 48 and 72 hours) and dissolved in 90 µl of MeOH for HPLC analysis. Degradation of the main lipid peak was analyzed using Thermo Scientific Vanquish Flex UHPLC occupied with Charged Aerosol Detector (CAD) and Thermo Scientific Accucore™ C18+ UHPLC column (L=50 mm, D=2.1 mm, Particle Size=1.5 µm). The UHPLC operating conditions are listed in Table 13.

TABLE 13

| Chromatographic Conditions | |
|---|---|
| HPLC Instrument | Thermo Scientific Vanquish Flex UHPLC |
| HPLC Column | Accucore ™ Vanquish ™ C18+ UHPLC column |
| Column Temperature | 55° C. |
| Flow Rate | 0.5 mL/min |
| Injection Volume | 5 µL |
| Absorbance detection | 210 nm |
| CAD | 10 Hz |
| Run Time | 15 min |
| Sample Temperature | 21° C. |
| Sample Solvent | MeOH |
| Mobile Phase | Mobile Phase A: 5 mM ammonium acetate in water (pH 4) |
| | Mobile Phase B: Methanol |

| Mobile phase program: | | |
|---|---|---|
| Time, min | Mobile Phase A,% | Mobile Phase B,% |
| −0.5 | 15 | 85 |
| 0 | 15 | 85 |
| 2 | 10 | 90 |
| 4 | 2 | 98 |
| 8 | 2 | 98 |
| 12 | 0 | 100 |
| 14 | 15 | 85 |
| 15 | 15 | 85 |

The data are presented as a percentage of the main lipid peak measured at different time points relative to the lipid peak measured at time zero.

TABLE 14

Degradation of ICLs with two olefins separated by one (KC2, KC3, or O-11769) or more (KC2-01, KC3-01, UO-1, UO-6, and UO-7) methylenes.

| | % of parent lipid peak at time 0 | | |
|---|---|---|---|
| Lipid/Formulation | 24 h | 48 h | 72 h |
| ICL Lipid Suspensions | | | |
| KC2 | 35 ± 0.7 | 6 ± 1.9 | 0 ± 0.0 |
| KC2-01 | 91 ± 0.3 | 87 ± 0.9 | 83 ± 0.3 |
| KC3 | 46 ± 1.8 | 1 ± 0.2 | 0 ± 0.0 |
| KC3-01 | 83 ± 4.3 | 80 ± 0.4 | 74 ± 2.2 |
| O-11769 | 31 ± 0.9 | 1 ± 0.2 | 0.3 ± 0.1 |
| UO-1 | 78 ± 0.6 | 74 ± 0.1 | 65 ± 2.5 |
| UO-6 | 58 ± 0.8 | 32 ± 1.3 | 22 ± 1.8 |
| UO-7 | 80 ± 1.7 | 71 ± 0.8 | 62 ± 1.0 |
| Liposome preparations | | | |
| UO-1 (102021-6) | 86 ± 6.2 | 85 ± 4.2 | 73 ± 0.1 |
| O-11769 (102021-7) | 27 ± 2.2 | 8 ± 1.4 | 4 ± 0.1 |

As shown in FIG. 9A and FIG. 9B, all ICLs with olefins that had four methylenes between the two olefins (KC2-01, KC3-01 and UO-1) demonstrate dramatically superior stability under accelerated oxidation with hydrogen peroxide comparing to their counterparts with a single methylene separating the two olefins (KC2, KC3 and O-11769 respectively). Even after 72 h treatment with hydrogen peroxide, the main peaks of KC2-01, KC3-01 and UO-1 stay above 70% relative to the start of the treatment, while KC2, KC3 and O-11769 are fully degraded after 48 hours of incubation with hydrogen peroxide. Two other polyunsaturated ICLs (UO-6 and UO-7) similarly showed good stability to oxidation, although the UO-7 with a hydroxyethyl substituent in the head group degraded more rapidly than then dimethylamino ICLs (Table 14).

The stability of ICLs with olefins separated by more than one methylene were studied as part of mRNA-free liposomal formulations using the structurally related UO-1 and O-11769 ICLs. Other ionizable cationic lipids (KC2, KC2-01, KC3 and KC3-01) were excluded from this study since their chromatographic peaks overleap with the peak of DSPC which compromises the data interpretation. The stability data of UO-1 and O-11769 based liposomal formulations are shown in FIG. 9A. UO-1 formulated in liposomes has 73±0.05% of main UO-1 peak after 72 hours of incubation in the presence of 1% hydrogen peroxide. In contrast, O-11769 based liposomes show only 3.9±0.06% of the O-11769 peak after 72 hours of the treatment.

The totality of this data suggests that in addition to the improved transfection efficiency demonstrated in Examples 14 and 20 or the ICLs with more than one methylene between their olefins, these lipids also display significantly improved stability to oxidative degradation.

Example 19. Impact of N/P Ratio on Transfection Efficiency of mCherry mRNA Containing LNPs The aim of this study was to explore the effect of different N/P ratios on transfection efficiency in dendritic cells. LNPs were prepared as described in Example 9, characterized for particle size and zeta potential as described in Example 10, and evaluated for transfection efficiency in murine dendritic cells as described in Example 11. The LNPs all used KC2-01 as the ICL but varied the cationic lipid-to-mRNA phosphate (N/P) ratio from 4-7, the PS lipid was constant at 5 mol % and the DSPC phospholipid constant at 5 mol %, and the cholesterol constant at 38.5 mol %. The entrapment efficiency for all formulations was between 84 and 90%, indicating highly efficiency mRNA entrapment in the LNP. Transfection efficiency was evaluated in murine dendritic cells as described in Example 11.

TABLE 15

Physicochemical properties of LNPs used in Example 19

| % DSPS | N/P | Particle Size (nm) | Zeta Potential at pH 7 (mV) | Zeta Potential at pH 5 (mV) |
|---|---|---|---|---|
| 0 | 4 | 85.4 | −10.8 | 16.3 |
| 0 | 5 | 84.9 | −6.9 | 20.9 |
| 0 | 6 | 81.1 | −7.0 | 21.6 |
| 0 | 7 | 75.7 | −6.1 | 21.5 |
| 5 | 4 | 84.1 | −17.5 | 13.8 |
| 5 | 5 | 80.9 | −17.2 | 20.4 |
| 5 | 6 | 82.2 | −15.5 | 15.8 |
| 5 | 7 | 79.5 | −13.9 | 16.6 |

Transfection activity was evaluated for both DSPS-targeted and nontargeted KC-01 LNP formulations at both 1 ug/ml (FIG. 10A) and 0.33 ug/ml (FIG. 10B). These data show high DSPS-mediated transfection efficiency for KC2-01 containing LNPs over a broad range of N/P ratios with the greatest transfection efficiency being observed at an N/P of 7.

Example 20. Impact of Ionizable Lipid Structure on Transfection Efficiency Containing LNPs The aim of this study was to explore the effect of different ICLs on transfection efficiency in dendritic cells. LNPs were prepared as described in Example 9, characterized for particle size and zeta potential as described in Example 10, and evaluated for transfection efficiency in murine dendritic cells as described in Example 11. The LNPs used the ionizable lipids in Table 16 in the ICL with a constant N/P ratio of 5, the PS lipid was either 0 or 7.5 mol % and the DSPC phospholipid constant at 10 or 2.5 mol % (total of DSPC and DSPC was 10 mol %), and the cholesterol constant at 38.5 mol %.

TABLE 16

Physicochemical properties of LNPs used in Example 20.

| ICL | % DSPS | Particle Size (nm) | Particle Size (nm) Post-Freeze/Thaw | Encapsulation Efficiency (%) |
|---|---|---|---|---|
| AKG-UO1 | 0 | 98.0 | 122.6 | 75.4 ± 2.2 |
| AKG-UO1 | 7.5 | 93.9 | 94.2 | 91.6 ± 2.9 |
| AKG-UO1A | 0 | 84.4 | 103.2 | 77.5 ± 0.9 |
| AKG-UO1A | 7.5 | 89.2 | 91.1 | 88.7 ± 4.1 |
| O-11769 | 0 | 83.0 | 89.6 | 87.5 ± 2.7 |
| O-11769 | 7.5 | 130.8 | 126.4 | 91.5 ± 6.2 |
| AKG-UO4 | 0 | 102.3 | 169.4 | 46.5 ± 1.8 |
| AKG-UO4 | 7.5 | 89.9 | 91.3 | 89.0 ± 7.6 |
| AKG-UO4A | 0 | 112.1 | 123.4 | 73.1 ± 4.1 |
| AKG-UO4A | 7.5 | 92.4 | 91.81 | 85.8 ± 4.3 |
| AKG-DM2-OA | 0 | 77.6 | 111.5 | 64.9 ± 3.4 |
| AKG-DM2-OA | 7.5 | 106.5 | 123.0 | 86.2 ± 5.5 |
| DODAP | 0 | 69.8 | 68.2 | 83.4 ± 7.7 |
| DODAP | 7.5 | 90.1 | 88.0 | 84.1 ± 2.3 |

The effect of targeting and ICL choice on transfection activity was evaluated using both nontargeted and 7.5 mol % DSPS-targeted LNPs (FIG. 11). All ICLs used in this study had a related diacyl structure that varied either in the degree and position of unsaturations in the acyl chains or the specific ionizable amine used, and thus it's apparent pKa. This data shows that the AKG-UO1 lipid with the two olefins separated by four methylenes (C18 total length) showed the highest activity when incorporated into LNPs. The O-11769 lipid (dilinoleic acid) showed activity that was approximately half of the AKG-UO-1 containing LNP, the latter having similar activity to the AKG-UO4 lipid with C16 acyl chains and the ICL with the same head group but oleic acid (single olefin) at both acyl chains (AKG-OA-DM2). However, the largest reductions in activity came from changing the dimethyl amine substituent in AKG-UO-1 to diethylamino in UO-1A, or in decreasing the number of methylenes between the two esters and dimethylamino group (DODAP). These two changes gave rise to large reductions in transfection activity, the latter even in the presence of DSPS targeting.

It is also worth noting that among this series, those LNPs that contained 7.5 mol % DSPS were less susceptible to adverse changes in particle size after they underwent a freeze-thaw process than those that did not contain DSPS. On average, those LNPs that did not contain DSPS changed 28.4 nm in diameter, whereas those that contained DSPS changed 3.9 nm. Since, storage stability is of major concern for mRNA vaccines, the addition of DSPS provides an important stabilizing effect to these LNPs.

Example 21. Measuring the Effect of Adding 10 and 25 Mol % DOPS on LNP Particle Formation and Activity in MutuDC1940 Dendritic Cell Line The aim of this study was to explore the impact of including DOPS into mRNA LNP formulations at compositions at or below the mol % previously shown in the literature (Gaitonde et al. (2011) Clin Immunol 138, 135-145; Rodriquez-Fernandez (2018) Front Immunol 9, 253) to enhance liposome (with) uptake into dendritic cells. LNPs were prepared as described in Example 9 at 25° C. and analyzed as in Example 10. The LNPs contained KC2 as the ICL at an N/P ratio of 5 with between 0, 10 and 25 mol % DOPS and a constant 1.5 mol % PEG-DMG. The cholesterol content was held constant at 38.5 mol % for the 0% and 10% DOPS formulations and the DSPC content varied inversely with the mol % of DOPS between 0-10 mol % (all lipid concentrations were used as mol % of total lipid). In the 25 mol % DOPS formulation, there was no DSPC and the cholesterol content decreased in the total by 15 mol (from 38.5 to 23.5 mol %). Transfection efficiency was evaluated in murine dendritic cells as described in Example 11.

TABLE 17

Physicochemical properties of DOPS containing LNP formulations

| LNP Formulation | Particle Size (nm) | PDI | Encapsulation Efficiency (%) |
|---|---|---|---|
| KC2/DSPC/DOPS/Chol/PEG-DMG (50/10/0/38.5/1.5) | 68.8 | 0.136 | 90.0 ± 3.5 |
| KC2/DSPC/DOPS/Chol/PEG-DMG (50/0/10/38.5/1.5) | 80.8 | 0.163 | 90.9 ± 3.5 |
| KC2/DSPC/DOPS/Chol/PEG-DMG (50/0/25/23.5/1.5) | Peak 1 = 62.6, Peak 2 = 416.3 | 0.398 | 77.3 ± 3.5 |

The impact of 10-25 mol % DOPS on targeting of LNPs to dendritic cells was evaluated in FIG. 12. This study shows that including 10 mol % DOPS in a KC2-based LNP formulation had a positive effect on mCherry expression levels in MutuDC1940 cells, while not adversely affecting either particle size or encapsulation of mRNA. However, when the DOPS content was increased to 25 mol % the expression of mCherry was lower than the formulation that had no DOPS and the size distribution widened as demonstrated by an increase in the PDI and gave rise to a distribution that contained particles >400 nm. Taken together, 25 mol % may have been shown in the literature to enhance liposome uptake into dendritic cells, while in an LNP formulation with mRNA it had a deleterious effect on both particle size and transfection activity. Importantly, the DOPS used here and in the literature contained unsaturated acyl chains, in this case oleic acid. This is similar to what is typical in many cells, where the phosphatidylserine acyl chains are often unsaturated in the sn-2 position, in many instances with multiple olefins (2-4). Although there is a small enhancement with a lower concentration of DOPS, this enhancement was shown in Example 15 to be significantly higher when the PS was comprised of saturated acyl chains, most preferably dipalmitoyl (C16) or distearoyl (C18).

Example 22. Impact of Pegylation and Phosphatidylserine Targeting on Immunogenicity of SARS-CoV-2 Spike Protein mRNA Vaccine Constructs Mice and study design. The in vivo study was carried out. Female BALB/c mice were purchased from Jackson Labs, allowed to acclimate in the vivarium for at least 7 days, and were 6-8 weeks at the start of the study. On study day 0 mice were injected intramuscularly in the right quadricep with 1 ug of vaccine candidate (quantity refers to mRNA) in a volume of 50 μL. Study groups consisted of 5 mice and included vehicle control, comparator vaccines, and experimental vaccine candidates. Mice were given a second injection of the same vaccine candidate 21 days later. Blood was collected and serum was isolated from 5 randomly selected control mice at the start of the study and from all mice on study day 21 and 34. Serum was stored at −80° C. until analysis for antibody titers. On study day 34, mice were euthanized and spleens were harvested.

Design and preparation of mRNA. mRNA encoding the SARS-CoV-2 full length spike protein and flanked with the same UTRs used in the BNT162b2 (Comirnaty) vaccine was purchased from Vernal Biosciences. All uridine nucleosides were substituted with N1-methyl-pseudouridine. To produce the mRNA, a synthetic gene encoding the mRNA sequence (VRN029; SEQ ID NO: 2, FIG. 13A) was cloned into a DNA plasmid. The synthetic gene was comprised of an RNA promoter, a 5' untranslated region, the SARS-COV2 Spike protein receptor binding domain, a 3' untranslated region, and a poly(A) tail region of approximately 120 As. The plasmid was propagated and expanded in a culture of *E. coli* and then isolated from the clarified *E. coli* lysate via anion exchange chromatography. The purified plasmid was linearized using a type IIs restriction enzyme that cut at a site at the end of the poly(A) tail encoding region. That plasmid was then incubated in a buffer with nucleotide triphosphates, RNA polymerase, and RNase inhibitor. To stop the reaction, DNase I was added to digest the linear plasmid template. The uncapped RNA was then purified using chromatography and then incubated in another buffer with GTP, S-adenosyl-methionine, a guanalyltransferase, 2'-O-methyltransferase, and RNase inhibitor. The capped mRNA was then purified using chromatography, buffer exchanged into water, and filled into vials.

Generation of lipid nanoparticles (LNP) containing mRNA. Stock solutions of each lipid were prepared. Ionizable lipids were weighed out in 4 mL glass vials (Thermo B7999-2) and dissolved in ethanol (Sigma-Aldrich 200 proof, RNase free) to a final concentration of 10 mM. Other lipids such as DSPC (Avanti Polar Lipids), Cholesterol (Dishman) and PEG-DMG (NOF) were weighed out and dissolved in ethanol to a concentration of 1 mM. DSPS-Na (NOF) was dissolved in methanol (Sulpelco, Omnisolve) at a concentration of 1 mM and briefly heated to 70° C. to complete its dissolution.

Lipid mixtures for each individual LNP were prepared by adding the desired volume of each lipid stock solution to a new vial, adding ethanol if needed to achieve a final volume of 1.2 mL. For example, a LNP formulation of AKG-UO-1/DSPC/DSPS/Chol/PEG-DMG (50/2.5/7.5/38.5/1.5 mol %), with an N/P of 5 contained 1500 nmol AKG-UO-1, 75 nmol DSPC, 225 nmol DSPS, 1155 nmol Chol and 45 nmol PEG-DMG for every 100 μg of mRNA used. mRNA solutions were prepared by thawing frozen mRNA (SARS-CoV-2 spike mRNA, Vernal) vials and diluting mRNA in 6.25 mM sodium acetate (pH 5.0) to a final concentration of 0.033 mg/mL, where the concentration is confirmed by absorbance on a Nanodrop.

To prepare LNPs, a NanoAssemblr Benchtop microfluidic device (from Precision Nanosystems) was used. If LNPs contained DSPS, the heating block accessory set to 70° C. was used, otherwise LNPs were mixed at room temperature. 3 mL of mRNA solution was loaded into a 3 mL disposable syringe (BD 309656) and 1 ml of lipid mixture in a 1 ml syringe (BD309659) and placed in the NanoAssemblr heating block for 4 min prior to mixing. LNP formation was achieved by pumping the liquid streams through a disposable microfluidics cassette at 3:1 aqueous:alcohol volume ratio at 6 mL/min mixing speed. After mixing, 3.6 mL of LNP mixture was collected, while the initial mixed volume of 0.35 mL and last 0.05 mL of mix was discarded. Ethanol was removed by buffer exchange using SpectraPor dialysis tubing (12-14 k MWCO) in PBS (Cytivia, SH30256.01). LNPs were typically exchanged into PBS, pH 7.4 and then 15 mM Tris, pH 7.4, 20% sucrose, concentrated to 20-50 ug/mL mRNA, sterile filtered (Thermo Nalgene 0.2 um #720-1320) prior to freezing by immersion in liquid nitrogen for 5 min and long-term storage at −20° C. For this study, samples were concentrated to >40 µg/mL mRNA, and diluted with varying volumes of 15 mM Tris, 20% Sucrose, pH 7.4 to a target concentration of 40 mRNA and then frozen on LN2. Characterization of LNPs was undertaken after an aliquot of the LNPs were thawed and diluted 1:1 (vol:vol) with 15 mM Tris, pH 7.4 such that the final concentration was 20 µg/mL mRNA in 15 mM Tris, 10% sucrose, pH 7.4. This simulated the conditions of sample preparation that were performed prior to dosing the animals with an injection of 1 µg mRNA in 50 µL volume via IM injection into a hind limb.

LNP characterization. mRNA encapsulation and mRNA concentration within the LNPs was measured using a Ribogreen assay. Nanoparticle size and zeta potential were measured by a zetasizer (Malvern).

SARS-CoV-2 anti-spike antibody titers. A standard indirect ELISA was performed to analyze serum samples for total IgG binding antibodies to the SARS-CoV-2 spike protein. For this assay, Nunc MaxiSorp 96-well plates were coated with 100 µL of SARS-CoV-2 spike protein (Sino Biological, cat. no. 40589-V08B1) diluted to 2 µg/mL in 1×PBS, pH 7.4. Plates were incubated statically for 12 hrs at 37° C. Unbound coating antigen was removed by washing plates 3× with 100 µL PBS+0.05% Tween-20. Plates were then blocked in PBS+5% skim milk for 1 hr at 37° C. Test and positive control samples were diluted in assay diluent (PBS, Tween-20, 1% skim milk) to starting point dilution 1:20 followed by four-fold serial dilutions using U-bottom dilution plates. Once blocking was completed, blocking buffer was removed by inversion and each sample was plated in duplicates. Plates were statically incubated for 2 hr at 37° C., followed by washing 3× with 100 µL of PBS+ 0.05% Tween-20 to remove unbound sera. 100 µL of secondary detection antibody (goat anti-mouse-HRP IgG, Abcam) was added to each well at a dilution of 1:10,000. Plates were incubated statically for 30 min at RT, and unbound antibodies were subsequently removed and plates were washed as described above. To develop, 100 µL of 1-Step Ultra TMB substrate was added to each well and the reaction was stopped after ~10 min with 50 µL of TMB stop solution (SeraCare, cat. no. 5150-0019). The plates were read within 30 min at 450 nm with a Thermo LabSystems Multiskan spectrophotometer. Titers were defined as the reciprocal of the dilutions that generated a specific cut-off value for OD 450 on the linear part of the titration curve.

Ex vivo T cell responses. On study day 34, spleens were mechanically dissociated to single-cell suspensions. Cells were resuspended in cell-stimulation media (RPMI with L-Glutamine and HEPES buffer, heat-inactivated fetal bovine serum, and Pen/Strep) and $2\times10^6$ cells were aliquoted in a volume of 100 µL into 96-well plates. Splenocytes from each mouse were stimulated for approximately 18 hrs at 37° C. with 100 µL of media alone, treated with positive control Cell Stimulation Cocktail (ThermoFisher, cat. #00-4970-93) containing PMA and ionomycin, or 1 µg/mL of a peptide pool covering the SARS-CoV-2 spike protein (JPT, cat. #PM-WCPV-S-2). After 1 hr of stimulation, Golgi Stop (BD Biosciences, cat. #554724) was added to each well.

Flow cytometry. After the stimulation, cells were washed with PBS and transferred to 96-well deep-well plates. Cells were stained with LIVE/DEAD near IR viability dye (ThermoFisher, cat. #L10119) diluted in PBS for 20 min at 4° C. Cells were washed with FBS staining buffer (BD Biosciences, cat. #554656) and incubated with Fc Block (BD Biosciences, cat. 553142) for 10 min at 4° C. Cells were then stained for 40 min at 4° C. with a cell surface antibody cocktail consisting of CD3 BV605 (BD, cat. #564009), CD4 BV421 (BD, cat. #562891), and CD8 APC (BD, cat. #553035). BD Brilliant Stain Buffer (cat. #563794) was included in the staining buffer. Cells were washed with FBS staining buffer and then fixed for 20 min at room temperature with Fix/Perm buffer (ThermoFisher, cat. #00-5523-00). Cells were washed with 1× Perm buffer, incubated with Fc Block, and then stained for 40 min at 4° C. with an intracellular cytokine antibody cocktail consisting of IFN-g PE/Cy7 (BD, cat. #557649), IL-2 PE (BioLegend, cat. #503808) and TNF-a FITC (BD, cat. #554418). Cells were then washed, resuspended in FBS stain buffer and acquired on a MACSQuant 16 flow cytometer (Miltenyi Biotec). Flow data was analyzed using FlowJo v10.8.1 (BD Biosciences).

TABLE 18

Physicochemical properties of LNPs used in evaluating the immunogenicity of SARS-CoV-2 spike protein mRNA vaccine construct

| LNP Formulation | Particle Size (nm) | Zeta Potential (mV) pH 5 | Zeta Potential (mV) pH 7 | Encapsulation Efficiency (%) |
| --- | --- | --- | --- | --- |
| 7.5% DSPS_UO1_PEG-DMG 1.5% | 80.3 | 5.3 | −2.6 | 90.7 ± 7.1 |
| 7.5% DSPS_UO1_PEG-DMG 2.5% | 71.0 | 5.5 | −1.0 | 89.1 ± 9.3 |
| 7.5% DSPS_UO1_PEG-DMG 3.5% | 61.9 | 6.6 | −3.6 | 89.3 ± 10.0 |
| 7.5% DSPS_UO1_PEG-DPPE 1.5% | 80.7 | 7.9 | −5.1 | 90.7 ± 14.2 |
| 7.5% DSPS_UO1_PEG-DPPE 2.5% | 68.4 | 2.7 | −2.4 | 91.0 ± 6.9 |
| 7.5% DSPS_UO1_PEG-DSG 1.5% | 100.7 | 9.6 | −6.7 | 88.8 ± 5.1 |
| 7.5% DPPS_UO1_PEG-DMG 1.5% | 89.8 | 14.4 | −1.4 | 93.8 ± 9.2 |
| UO1_PEG-DMG 1.5% | 116.0 | 20.2 | 2.5 | 86.5 ± 9.3 |
| 7.5% DSPS_KC2OA_PEG-DMG 1.5% | 80.0 | 11.7 | −3.5 | 90.9 ± 5.5 |
| 7.5% DSPS_KC2OA_PEG-DSG 1.5% | 88.5 | 9.0 | −3.9 | 92.2 ± 9.7 |
| ALC0315_1.5% PEG-DMG | 79.5 | 2.0 | −2.4 | 86.7 ± 9.3 |
| SM102_1.5% PEG-DMG | 92.6 | 11.8 | −0.1 | 92.0 ± 7.1 |

To evaluate the impact of PEG-lipid concentration on vaccine immunogenicity, BALB/c mice were immunized with mRNA-LNPs containing increasing amounts of PEG-lipid (PEG-DMG or PEG-DPPE). Blood serum was collected on day 21 post prime and on day 13 post boost (day 34 of study) for antibody analysis. Splenocytes were stimulated with Spike peptide pools and the percent of CD4 T cells producing IL-2 was quantified using flow cytometry (FIG. 13B and FIG. 13C). Both forms of PEG, PEG-DMG (FIG. 13B) or PEG-DPPE (FIG. 13C), inversely impacted mRNA-LNPA vaccine immunogenicity, with lower concentrations of PEG-lipid showing higher levels of both B-cell and T-cell responses.

To evaluate the impact of PEG-lipid acyl chain composition on mRNA-LNP immunogenicity, BALB/c mice were immunized with mRNA-LNPs containing different PEG formats (PEG-DMG or PEG-DSG). Blood serum was collected on day 21 post prime and on day 13 post boost (day 34 of study). Splenocytes were stimulated with Spike peptide pools and the percent of CD4 T cells producing IL-2 was quantified using flow cytometry. Antibody titer data were log-transformed prior to statistical analysis. Groups were compared using an unpaired t test. For LNPs made with the ionizable lipid KC2OA, either PEG format performed similarly (FIG. 13D). In contrast, LNPs using the ionizable lipid UO1 and PEG-DMG induced a superior antibody response than LNPs containing PEG-DSG (FIG. 13E).

To assess how the incorporation of phosphatidylserine influences mRNA-LNP immunogenicity, BALB/c mice were immunized with mRNA-LNPs containing various ionizable lipids with or without DSPS. On Day 34 (13 days post-boost), serum was collected for quantification of total IgG anti-spike antibodies by ELISA. Splenocytes were stimulated with peptide and the percent of CD4 T cells producing IL-2 was quantified using flow cytometry.

The inclusion of DSPS with comparator ionizable lipid ALC-0315 negatively impacted total IgG anti-spike antibody levels (FIG. 13F). DSPS had the opposite effect on LNPs containing the ionizable lipids UO1 and KC2OA and significantly increased geometric mean antibody levels 36- and 46-fold, respectively. DSPS also had an effect on CD4 T cell responses, with responses trending higher for LNPs containing UO1 and KC2OA, and significantly higher for SM-102. Taken together, inclusion of DSPS in lipid nanoparticles can substantially influence the immunogenicity of mRNA vaccines, and that the impact of DSPS is influenced by the type of ionizable cationic lipid.

The effects of different phosphatidylserine acyl chain composition on serum antibody titers (FIG. 13G, panel A) and the magnitude of the spike-specific CD4 T cell response in the spleen (FIG. 13G, panel B) was evaluated. Mice were immunized with LNPs using the ionizable lipid UO1 and either the DSPS or DPPS forms of phosphatidyl serine. On Day 34 (13 days post-boost), serum was collected for quantification of total IgG anti-spike antibodies by ELISA. Splenocytes were stimulated with peptide and the percent of CD4 T cells producing IL-2 was quantified using flow cytometry.

With regards to the impact of the PS acyl chain composition, both forms of PS comparably increased antibody levels over the base formulation lacking PS (FIG. 13G, Panel A). Both forms of PS also had a positive effect on the CD4 T cell response (FIG. 13G, Panel B), although only the formulation containing DPPS was significantly higher than the based formulation without PS. Taken together, both forms of PS included in our LNPs, DPPS or DSPS, had a similar positive effect on increasing the immunogenicity of mRNA-LNP vaccines.

Example 23. Measuring the Effect of Adding Either DSPS D-Isomer or L-Isomer at 7.5 Mol % in KC2-01 Based LNPs by Particle Characteristics and Activity in MutuDC1940 Dendritic Cell Line The aim of this study was to compare the impact of including the D and the L-isomers of DSPS into mRNA LNP formulations at 7.5 mol %. LNPs were prepared as described in Example 9 at 25° C. and analyzed as in Example 10. The LNPs contained KC2-01 as the ICL at an N/P ratio of 5 with 2.5 mol % DSPC, 7.5 mol % DSPS (D or L) and a constant 1.5 mol % PEG-DMG. Transfection efficiency was evaluated in murine dendritic cells as described in Example 11.

TABLE 19

Physicochemical properties of KC2-01 LNPs with mCherry mRNA and distearoylphosphatidyl-L-serine or distearoylphosphatidyl-D-serine.

| LNP Formulation | DSPS (serine isomer) | Particle Size (nm) | PDI | Zeta Potential mV, pH 5 | Zeta Potential mV, pH 7 | Encapsulation Efficiency (%) |
|---|---|---|---|---|---|---|
| KC2-01/DSPC/Chol/PEG-DMG (50/10/38.5/1.5) | N/A | 83.92 | 0.03 | 7.7 | −0.47 | 89.2 ± 5.7 |
| KC2-01/DSPC/DSPS/Chol/PEG-DMG (50/2.5/7.5/38.5/1.5) | D | 85.4 | 0.09 | 7.8 | −4.8 | 88.7 ± 3.5 |
| KC2-01/DSPC/DSPS/Chol/PEG-DMG (50/2.5/7.5/38.5/1.5) | L | 87.4 | 0.04 | 7.7 | −2.7 | 90.9 ± 6.0 |

This study shows that including 7.5 mol % DSPS (either isomer) in a KC2-01 based LNP formulation had no effect on the particle size or mRNA encapsulation. The zeta potential values are similar at pH 5, but the DSPS containing formulation have more negative values at pH 7 than the non-DSPS containing formulation, likely a result of the additional negative charge added by the DSPS. The impact of the stereochemistry on transfection was evaluated in FIG. 14A and FIG. 14B. An 8-fold increase in mCherry expression was observed when the D-isomer of DSPS was used compared to the L isomer at 1 µg/mL mRNA (and 4.7-fold at 0.33 µg/mL mRNA), indicating that the uptake or expression mechanism(s) of DSPS containing LNPs is likely stereo-specific.

Example 24. Measuring the Effect of Inclusion of DSPS in KC2-Based LNPs at 25° C. and 65° C. On Particle Characteristics and Activity in MutuDC1940 Dendritic Cell Line The aim of this study was to compare the impact of including the D-isomer of DSPS in KC2 based LNPs produced at two different temperatures. LNPs were prepared as described in Example 9 where those that contained DSPS were made at 65° C. at those that did not include DSPS were made at 25° C. and all LNPs were analyzed as in Example 10.

All LNPs contained ICL at an N/P ratio of 5 with a constant 1.5 mol % PEG-DMG. The cholesterol content was held constant at 38.5 mol % and the DSPC content varied inversely with the mol % of DSPS at 5 and 7.5 mol % (all lipid concentrations were used as mol % of total lipid). These mRNA LNPs all contained mCherry mRNA and the composition of comparator formulations using SM-102 based lipid formulation, the same lipid composition as that used in mRNA-1273 and that using ALC-0315, similar to that used in BNT162b2 were taken from their respective prescribing information. Note, the BNT162b2 comparator using ALC-0315 was made with an N/P of 5.0 in keeping with the other formulations in this study, which is different than the approved Covid vaccine Comirnaty.

This study shows that heating the lipid solution and mRNA solution in a heating block set to 65° C. had no deleterious effect on particle diameter or, zeta potential or mRNA encapsulation readings at either 5 or 7.5 mol % DSPS content. The impact of temperature on transfection of DSPS-targeted KC2 LNPs, and the comparison to SM102 and ALC-0315 containing LNPs is shown in FIG. 15. The 5 mol % DSPS formulation had a 2-fold higher mCherry expression than the exact same formulation made at 25° C. ($p<0.05$, T-Test). A comparison of the formulations with 7.5 mol % DSPS made at either temperature showed no significant difference. The 5 mol % DSPS containing LNP, made at 65° C. gave a 6.5-fold increase in mCherry expression over the SM102 formulation. It is likely that higher temperatures increase the solubility of DSPS in alcohol and allow better incorporation of the lipid in the particle, which allows for enhanced uptake in this in vitro study, while nor adversely affecting many of the LNP crucial particle characteristics such as size, encapsulation or mRNA expression.

Example 25. Comparing UO1, UO6 & 7 in LNPs with and without DSPS

The aim of this study was to evaluate AKG-UO-6 ("UO-6") and AKG-UO-7 ("UO-7") in LNPs with and without 7.5 mol % DSPS. Previously, it was found that 7.5 mol % DSPS produced the most optimal LNPs from a UO-1 series. Here 7.5 mol % DSPS was chosen as an initial amount of DSPS to include to compare the structurally similar UO-6 and 7 LNPs were prepared as described in Example 9 and analyzed as in Example 10.

The LNPs contained either UO-1, UO-6 or UO-7 as the ICL at 50 mol %. The formulations also contained 38.5 mol % cholesterol, and 1.5 mol % PEG-DMG. The non DSPS containing samples have 10 mol % DSPC, and to the 7.5 mol % DSPS containing LNPs, DSPS was added at 7.5 mol % and DSPC was included at 2.5 mol %. The N/P in all formulations was 5. Transfection efficiency was evaluated in murine dendritic cells as described in Example 11.

TABLE 20

Physicochemical properties of KC2 containing LNPs with 5 or 7.5% DSPS to similar LNPs prepared with SM102 or ALC-0315 ionizable cationic lipid.

| LNP Formulation | Mixing Temp ° C. | Particle Size (nm) | PDI | Zeta Potential mV, pH 5 | Zeta Potential mV, pH 7 | Encapsulation Efficiency (%) |
| --- | --- | --- | --- | --- | --- | --- |
| KC2 | 25 | 70.4 | 0.21 | 4.5 | −1.1 | 87.3 ± 3.2 |
| KC2 with 5% DSPS | 25 | 78.3 | 0.12 | 2.5 | −2.2 | 87.0 ± 2.2 |
| KC2 with 5% DSPS | 65 | 88.2 | 0.11 | 7.4 | −4.2 | 87.0 ± 3.8 |
| KC2 with 7.5% DSPS | 25 | 73.5 | 0.11 | 1.0 | −2.3 | 86.9 ± 3.8 |
| KC2 with 7.5% DSPS | 65 | 74.3 | 0.07 | 0.5 | −8.2 | 87.8 ± 2.2 |
| SM102 | 25 | 84.0 | 0.17 | 6.3 | −0.7 | 81.9 ± 3.9 |
| ALC-0315 | 25 | 72.1 | 0.08 | 3.3 | −3.0 | 80.7 ± 2.2 |

TABLE 21

Physicochemical properties and encapsulation efficiency of UO-1,
UO-6, and UO-7 LNPs with and without DSPS-targeting.

| LNP Formulation | Particle Size (nm) | PDI | Zeta Potential mV, pH 5 | Zeta Potential mV, pH 7 | Encapsulation Efficiency |
|---|---|---|---|---|---|
| UO1 | 72.8 | 0.11 | 14.5 | 5.6 | 89.6 ± 4.8 |
| UO1_7.5%_DSPS | 80.5 | 0.03 | 13.9 | −2.4 | 91.4 ± 4.2 |
| UO6 | 72.0 | 0.22 | 14.9 | 4.2 | 90.5 ± 11.1 |
| UOUO6_7.5%_DSPS | 86.1 | 0.13 | 14.3 | 1.7 | 92.8 ± 11.1 |
| UO7 | 79.3 | 0.16 | 18.2 | −2.6 | 91.4 ± 2.5 |
| UO7_7.5%_DSPS | 94.3 | 0.13 | 16.9 | −5.3 | 92.3 ± 5.0 |

This study shows that including DSPS in LNPs based on UO1, UO6 and UO7 caused an increase in expression of mCherry, without adverse changes in particle size or mRNA entrapment. The impact of 7.5 DSPS incorporation into LNPs on dendritic cell transfection activity was shown for formulations prepared with three different ICLs (UO-1, UO-6, and UO-7) (FIG. 16). For UO-1 with 7.5 mol % DSPS, the mCherry expression was 11-fold higher than UO6 with 7.5 mol % DSPS and 7-fold higher than UO7 with 7.5 mol % DSPS. UO-7 with DSPS had 1.5-fold more mCherry expression than UO6 with DSPS. Of the non DSPS containing formulations, UO7 was 2.2-fold more active than UO1 and 1.9-fold more active than UO6. However, LNPs prepared with all three ICLs maintained good encapsulation efficiencies, particle size, and zeta potential, while benefiting from targeting with DSPS inclusion in the formulation.

Example 26. Evaluating the Effect of Adding DSPS to UO1, SM102 and ALC-0315 Based LNPs by Comparing Particle Characteristics and Activity in MutuDC1940 Dendritic Cell Line The aim of this study was to evaluate the effect of including the L-isomers of DSPC into mRNA LNP formulations at 0, 5% and 7.5 mol %. LNPs were prepared as described in Example 9 at 25° C. and analyzed as in Example 10.

The LNPs contained either AKG-UO-1 ("UO-1"), SM102 as the ICL at 50 mol %. For UO1 and SM102 the formulations contained 38.5 mol % cholesterol, and 1.5 mol % PEG-DMG. The non DSPS containing samples have 10 mol % DSPC, and to the DSPS containing LNPs, DSPS was added at 5 or 7.5 mol % with a concomitant reduction in DSPC by the same mol %. For the ALC-0315 formulation, the ICL was 46.3 mol %, DSPC 9.4 mol %, cholesterol 42.7 mol % and PEG-DMG 1.5 mol %. DSPS was added with concomitant reduction in the DSPC mol % as above. The N/P in all formulations was 5. Transfection efficiency was evaluated in murine dendritic cells as described in Example 11.

TABLE 22

Physicochemical properties and encapsulation efficiency of PS-targeted
formulations of UO1, SM102, and ALC-0315 containing LNPs

| LNP Formulation | Particle Size (nm) | PDI | Zeta Potential mV, pH 5 | Zeta Potential mV, pH 7 | Encapsulation Efficiency (%) |
|---|---|---|---|---|---|
| UO1 | 72.8 | 0.11 | 10.2 | 3.6 | 89.6 ± 4.8 |
| UO1_5%_DSPS | 83.0 | 0.11 | 9.9 | −2.7 | 91.4 ± 4.2 |
| UO1_7.5%_DSPS | 80.5 | 0.03 | 11.0 | 1.4 | 91.1 ± 6.3 |
| SM102 | 80.7 | 0.04 | 13.0 | 1.6 | 90.1 ± 5.6 |
| SM102_5%_DSPS | 81.0 | 0.02 | 13.1 | −6.1 | 90.5 ± 1.4 |
| SM102_7.5%_DSPS | 80.1 | 0.05 | 13.0 | −4.0 | 90.1 ± 2.7 |
| ALC0315 | 74.6 | 0.06 | 6.2 | −0.9 | 72.3 ± 0.9 |
| ALC0315_5%_DSPS | 68.1 | 0.10 | 8.0 | −8.8 | 84.2 ± 1.3 |
| ALC0315_7.5%_DSPS | 75.0 | 0.02 | 7.9 | −11.8 | 84.9 ± 3.8 |

This study shows that including DSPS in LNPs based on UO1, SM102 and ALC-0315 caused an increase in expression of mCherry (FIG. 17), without adverse changes in particle size or mRNA entrapment. For UO-1 and SM102, 5 mol % DSPS looked maximal, while 7.5 mol % DSPS was maximal for the ALC-0315 formulation. For UO-1 and SM102 the increase in expression was 18.1 and 58.7-fold respectively for the 5 mol % DSPS samples. The increase was 80.9-fold for the ALC-0315 based sample for 7.5 mol % DSPS.

Example 27. Additional Exemplary Phosphatidyl-L-Serine Targeted LNP Formulations Additional formulations shown below could also be prepared using the methods described in the Examples above. All lipid concentrations are shown as mol % as a percentage of the total lipid in the LNP. The below compositions vary in conjugated lipid content from 0.5 to 2.5 mol %, in sterol content from 25-45 mol %, in ICL content from 40-65 mol %, in saturated phosphatidyl-L-serine content from 2-10 mol %, and in total noncationic phospholipid content from 5-20 mol %. Most compositions would contain two phospholipids, typically phosphatidyl-L-serine (DSPS or DPPS being preferred) and phosphatidylcholine, although some exemplary formulations may contain more than two phospholipids, including phosphatidylethanolamines, like dioleoylphosphatidylethanolamine (DOPE).

TABLE 23

Exemplary phosphatidyl-L-serine containing LNP formulations

| Formulation (#) | Ionizable Cationic Lipid (mol %) | PS (mol %) | Additional Phospholipid(s) (mol %) | Sterol (mol %) | Conjugated lipid (mol %) |
|---|---|---|---|---|---|
| 1 | AKG-UO-1 (47.5) | DSPS (7.5) | DSPC (3.5) | Chol (40) | PEG-DMG (1.5) |
| 2 | AKG-UO-1 (45) | DSPS (8) | DSPC (4) | Chol (42) | PEG-DMG (1) |
| 3 | AKG-KC2-01 (40) | DSPS (5) | DSPC (5) DOPE (5) | Chol (44) | PEG-DMG (1) |
| 4 | AKG-KC2-01 (42.5) | DSPS (7.5) | DSPC (6.5) | Chol (42) | PEG-DMG (1.5) |

TABLE 23-continued

Exemplary phosphatidyl-L-serine containing LNP formulations

| Formulation (#) | Ionizable Cationic Lipid (mol %) | PS (mol %) | Additional Phospholipid(s) (mol %) | Sterol (mol %) | Conjugated lipid (mol %) |
|---|---|---|---|---|---|
| 5 | AKG-KC2-01 (65) | DSPS (7.5) | DSPC (2.5) | Chol (24.5) | PEG-DMG (0.5) |
| 6 | AKG-KC2-01 (60) | DSPS (6) | DSPC (4) | Chol (29) | PEG-DMG (1) |
| 7 | AKG-KC2-01 (55) | DSPS (7) | DSPC (3) | Chol (34) | PEG-DMG (1) |
| 8 | AKG-KC2-01 (57) | DSPS (6.5) | DSPC (3.5) | Chol (28) | PEG-DMG (1) |
| 9 | AKG-KC2-01 (60) | DSPS (7.5) | DSPC (2.5) DOPE (4) | Chol (28.5) | PEG-DMG (1.5) |
| 10 | AKG-KC2-01 (48) | DSPS (6) | DSPC (4) | Chol (41.5) | PEG-DMG (0.5) |
| 11 | AKG-KC2-01 (48) | DPPS (6) | DSPC (4) | Chol (41.5) | PEG-DMG (0.5) |
| 12 | AKG-KC2-01 (48) | DSPS (6) | DPPC (4) | Chol (41.5) | PEG-DMG (0.5) |
| 13 | AKG-KC2-PA (47.5) | DSPS (6) | DSPC (4) | Chol (41.5) | PEG-DMG (1) |
| 14 | AKG-KC2-PA (47.5) | DPPS (6) | DSPC (4) | Chol (41.5) | PEG-DMG (1) |
| 15 | AKG-KC2-PA (47.5) | DSPS (6) | DPPC (4) | Chol (41.5) | PEG-DMG (1) |
| 16 | AKG-UO-04 (48) | DSPS (7.5) | DSPC (2.5) | Chol (41.5) | PEG-DMG (0.5) |
| 17 | AKG-UO-04 (48) | DPPS (7.5) | DSPC (2.5) | Chol (41.5) | PEG-DMG (0.5) |
| 18 | AKG-UO-04 (48) | DSPS (7.5) | DPPC (2.5) | Chol (41.5) | PEG-DMG (0.5) |
| 19 | AKG-UO-1 (47.5) | DSPS (7.5) | DSPC (4.5) | Chol (39) | PEG-DMG (1.5) |
| 20 | AKG-UO-1 (47.5) | DPPS (7.5) | DSPC (4.5) | Chol (39) | PEG-DMG (1.5) |
| 21 | AKG-UO-1 (47.5) | DSPS (7.5) | DSPC(2.5) | B-sitosterol (42) | PEG-DMG (0.5) |
| 22 | AKG-UO-1 (50) | DSPS (7.5) | DSPC (2.5) | B-sitosterol (39) | PEG-DMG (1) |
| 23 | AKG-UO-1 (52.5) | DSPS (7.5) | DSPC (2.5) | B-sitosterol (39) | PEG-DMG (1) |
| 24 | AKG-UO-1 (55) | DSPS (7.5) | DSPC (2.5) | B-sitosterol (39) | PEG-DMG (1) |
| 25 | AKG-UO-1 (55) | DSPS (7.5) | DSPC (2.5) | Chol (34) | PEG-DMG (1) |
| 26 | AKG-UO-1 (57) | DSPS (6.5) | DSPC (3.5) DOPE (4) | Chol (28) | PEG-DMG (1) |
| 27 | AKG-UO-1 (52.5) | DSPS (7.5) | DSPC (6.5) DOPE (4) | Chol (28) | PEG-DMG (1.5) |
| 28 | AKG-UO-1a (48) | DSPS (8) | DSPC (2) | Chol (41.5) | PEG-DMG (0.5) |
| 29 | AKG-UO-7 (48) | DSPS (7) | DSPC (3) | Chol (41) | PEG-DMG (1) |
| 30 | AKG-KC3-01 (45) | DSPS (6) | DSPC (4) | Chol (44) | PEG-DMG (1) |
| 31 | AKG-KC2-01 (42.5) | DSPS (7.5) | DSPC (6.5) | Chol (42) | PEG-DMG (1.5) |
| 32 | AKG-UO-2 (48) | DPPS (8) | DSPC (2) | Chol (41.5) | PEG-DMG (0.5) |
| 33 | Compound 29 (48) | DSPS (5) | DSPC (5) | Chol (41.5) | PEG-DMG (0.5) |
| 34 | Compound 33 (48) | DSPS (7.5) | DSPC (2.5) | Chol (41) | PEG-DMG (1) |
| 35 | Compound 29 (50) | DSPS (5) | DSPC (5) | Chol (39) | PEG-DMG (1) |
| 36 | Compound 33 (50) | DSPS (7.5) | DSPC(2.5) | Chol (39) | PEG-DMG (1) |
| 37 | KC3-OA (48) | DSPS (5) | DSPC (5) | Chol (41.5) | PEG-DMG (0.5) |
| 38 | ALC-0315 (46) | DSPS (5) | DSPC (5) | Chol (43) | PEG-DMG (1) |
| 39 | ALC-0315 (48) | DSPS (5) | DSPC (5) | Chol (41) | PEG-DMG (1) |
| 40 | SM-102 (50) | DSPS (5) | DSPC (5) | Chol (39.5) | PEG-DMG (0.5) |
| 41 | SM-102 (50) | DSPS (7.5) | DSPC (2.5) | Chol (39) | PEG-DMG (1) |
| 42 | SM-102 (48) | DSPS (5) | DSPC (5) | Chol (41) | PEG-DMG (1) |
| 43 | AKG-UO-1 (48) | DSPS (7.5) | – | Chol (43.5) | PEG-DMG (1) |
| 44 | AKG-UO-1 (48) | DSPS (7.5) | – | Chol (43.5) | PEG-DMG (1) |
| 45 | AKG-KC3-01 (48) | DSPS (5) | DSPC (5) DOPE (15) | Chol (26) | PEG-DMG (1) |
| 46 | AKG-KC3-01 (48) | DSPS (5) | DSPC (5) DOPE (10) | Chol (31) | PEG-DMG (1) |
| 47 | AKG-KC3-01 (48) | DSPS (6) | DSPC (4) | Chol (40) | PEG-DMG (2) |
| 48 | AKG-KC3-01 (48) | DSPS (6) | DSPC (4) | Chol (39.5) | PEG-DMG (2.5) |
| 49 | AKG-UO-1 (46) | DSPS (7) | DSPE (5) | Chol (41.5) | PEG-DMG (0.5) |
| 50 | AKG-UO-1 (48) | DSPS (7.5) | eggSM (2.5) | Chol (41.5) | PEG-DMG (0.5) |
| 51 | AKG-KC3-01 (48) | DSPS (5) | HSPC (5) | Chol (41.5) | PEG-DMG (0.5) |
| 52 | AKG-UO-1 (47.5) | DSPS (7.5) | DSPC (2.5) | Chol (42) | PEG-DPG (0.5) |
| 53 | AKG-UO-1 (47) | DSPS (7.5) | DSPC (2.5) | Chol (42) | PEG-DPG (1) |

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

While specific embodiments of the subject disclosure have been discussed, the above specification is illustrative and not restrictive. Many variations of the disclosure will become apparent to those skilled in the art upon review of this specification. The full scope of the disclosure should be determined by reference to the claims, along with their full scope of equivalents, and the specification, along with such variations.

All publications, patents and patent applications referenced in this specification are incorporated herein by reference in their entirety for all purposes to the same extent as if each individual publication, patent or patent application were specifically indicated to be so incorporated by reference.

What is claimed is:

1. An ionizable cationic lipid compound of the formula

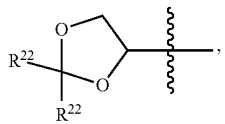

wherein
a. each $R^{22}$ is independently a linear polyunsaturated $C_{16}$-$C_{18}$ hydrocarbon lipid tail consisting of saturated alkyl groups on both ends of a pair of cis-oriented olefin double bonds separated by an unsaturated linear ethylene, n-propylene or n-butylene alkyl chain between the olefins within each $R_{22}$ hydrocarbon chain; and
b.

indicates attachment to a dialkyl amino alkyl group selected from the group consisting of: dimethylaminoethyl, diethylaminoethyl, and dimethylaminopropyl.

2. The compound of claim 1, wherein both $R_{22}$ hydrocarbon lipid tails are identical.

3. The compound of claim 1, wherein the pair of olefins in each hydrocarbon lipid tails are separated by a n-butylene alkyl chain within each $R_{22}$ hydrocarbon lipid tail.

4. The compound of claim 1, wherein each $R_{22}$ is a linear $C_{16}$ hydrocarbon chain.

5. The compound of claim 1, wherein each $R_{22}$ is a linear $C_{18}$ hydrocarbon chain.

6. The compound of claim 1, wherein the dialkyl amino group is dimethylaminopropyl.

7. The compound of claim 1, wherein both $R_{22}$ are identical; the pair of olefins in each hydrocarbon lipid tails are separated by a n-butylene alkyl chain and the saturated alkyl groups on either end of the pair of olefins each have the same number of carbons within each $R_{22}$ hydrocarbon chain.

8. The compound of claim 7, wherein the dialkyl amino group is dimethylaminopropyl.

9. The compound of claim 7, wherein each $R_{22}$ is a linear $C_{16}$ hydrocarbon chain.

10. The compound of claim 7, wherein each $R_{22}$ is a linear $C_{18}$ hydrocarbon chain.

11. An ionizable cationic lipid compound of the formula

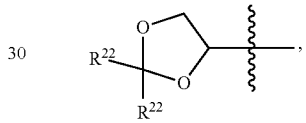

wherein
a. each $R^{22}$ is an identical linear polyunsaturated $C_{16}$-$C_{18}$ hydrocarbon lipid tail consisting of saturated alkyl groups on both ends of a pair of cis-oriented olefin double bonds separated by at least two methylene groups between the two olefin double bonds within each $R_{22}$ hydrocarbon chain; and
b.

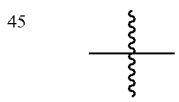

indicates attachment to a dialkyl aminoalkyl group.

12. The compound of claim 11, wherein the saturated alkyl groups on both ends of the pair of cis-oriented olefin double bonds within each $R_{22}$ have a different number of carbons.

13. The compound of claim 11, wherein the saturated alkyl groups on both ends of the pair of cis-oriented olefin double bonds within each $R_{22}$ have the same number of carbons.

14. The compound of claim 11, wherein the dialkyl aminoalkyl group is a dimethylaminoalkyl group or a diethylaminoalkyl group.

15. The compound of claim 11, wherein the dialkyl aminoalkyl group is a dialkylaminoethyl group or a dialkylaminopropyl group.

16. The compound of claim 11, wherein the dialkyl aminoalkyl group is a dimethylaminoethyl, diethylaminoethyl, or dimethylaminopropyl.

17. The compound of claim 16, wherein:
a. the ionizable cationic lipid compound has the formula

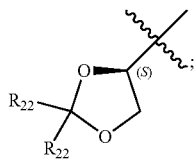

b. each $R^{22}$ is an identical linear polyunsaturated $C_{16}$ or $C_{18}$ hydrocarbon lipid tail; and
c. the saturated alkyl groups on both ends of the pair of cis-oriented olefin double bonds is separated by four methylene groups between the two olefin double bonds within each $R_{22}$ hydrocarbon chain.

18. An ionizable cationic lipid compound of the formula

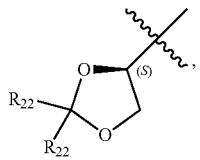

wherein
a. each $R^{22}$ is an identical, linear polyunsaturated $C_{16}$-$C_{18}$ hydrocarbon lipid tail consisting of saturated alkyl groups on both ends of a pair of cis-oriented olefin double bonds separated by an unsaturated linear n-butylene alkyl chain between the olefins within each $R_{22}$ hydrocarbon chain; and
b.

indicates attachment to a dialkyl amino alkyl group selected from the group consisting of: a dimethylaminoalkyl, diethylaminoalkyl, dialkylaminoethyl, or dialkylaminopropyl group.

19. The compound of claim 18, wherein
a. the dialkyl amino alkyl group is a dimethylaminopropyl or dimethylaminoethyl; and
b. each $R_{22}$ is a linear $C_{16}$ or $C_{18}$ hydrocarbon chain.

20. The compound of claim 19, wherein the saturated alkyl groups on both ends of the pair of cis-oriented olefin double bonds within each $R_{22}$ have the same number of carbons.

* * * * *

SEQUENCE LISTING

```
Sequence total quantity: 2
SEQ ID NO: 1              moltype = RNA    length = 720
FEATURE                   Location/Qualifiers
source                    1..720
                          mol_type = other RNA
                          organism = synthetic construct
SEQUENCE: 1
atggtgagca agggcgagga ggacaacatg gccatcatca aggagttcat gcggttcaag   60
gtgcacatgg agggcagcgt gaacggccac gagttcgaga tcgagggcga gggcgagggc  120
cggccctacg agggcaccca gaccgccaag ctgaaggtga ccaagggcgg ccccctgccc  180
ttcgcctggg acatcctgag cccccagttc atgtacggca gcaaggccta cgtgaagcac  240
cccgccgaca tccccgacta cctgaagctg agcttcccg agggcttcaa gtgggagcgg  300
gtgatgaact tcgaggacgg cggcgtggtg accgtgaccc aggacagcag cctgcaggac  360
ggcgagttca tctacaaggt gaagctgcgg ggcaccaact tccccagcga cggccccgtg  420
atgcagaaga gaccatggg ctgggaggcc agcagcgagc ggatgtaccc cgaggacggc  480
gccctgaagg gcgagatcaa gcagcggctg aagctgaagg acggcggcca ctacgacgcc  540
gaggtgaaga ccacctacaa ggccaagaag cccgtgcagc tgcccggcgc ctacaacgtg  600
aacatcaagc tggacatcac cagccacaac gaggactaca ccatcgtgga gcagtacgag  660
cgggccgagg gccggcacag caccggcggc atggacgagc tgtacaagag cggcaactga  720

SEQ ID NO: 2              moltype = RNA    length = 4319
FEATURE                   Location/Qualifiers
source                    1..4319
                          mol_type = other RNA
                          organism = synthetic construct
SEQUENCE: 2
gggaataaac tagtattctt ctggtcccca cagactcaga gagaaccgc caccatgttc   60
gtgttcctgg tgctgctgcc tctggtgtcc agccagtgtg tgaacctgac caccagaaca  120
cagctgcctc cagcctacac caacagcttt accagaggcg tgtactaccc cgacaaggtg  180
ttcagatcca gcgtgctgca ctctacccag gacctgttcc tgcctttctt cagcaacgtg  240
acctggttcc acgccatcca cgtgtccggc accaatggca ccaagagatt cgacaacccc  300
gtgctgccct tcaacgacgg ggtgtactt gccagcaccg agaagtccaa catcatcaga  360
ggctggatct tcggcaccac actggacagc aagacccaga gctgctgat cgtgaacaac  420
gccaccaacg tggtcatcaa agtggcgag ttccagttct gcaacgaccc cttcctgggc  480
gtctactacc acaagaacaa caagagctgg atggaaagcg agttccgggt gtacagcagc  540
gccaacaact gcaccttcga gtacgtgtcc cagcctttcc tgatggacct ggaaggcaag  600
cagggcaact tcaagaacct gcgcgagttc gtgtttaaga acatcgacgg ctacttcaag  660
atctacagca agcacacccc tatcaacctc gtgcgggatc tgcctcaggg cttctctgct  720
ctggaacccc tggtggatct gcccatcggc atcaacatca cccggtttca gactactgctg  780
gccctgcaca gaagctacct gacacctggc gatagcagcg gcggatggac agctggtgcc  840
gccgcttact atgtgggcta cctgcagcct agaaccttcc tgctgaagta caacgagaac  900
ggcaccatca ccgacgccgt ggattgtgct ctggatcctc tgagcgagac aaagtgcacc  960
ctgaagtcct tcaccgtgga aaagggcatc taccagacca gcaacttccg ggtgcagccc 1020
accgaatcca tcgtcgggt ccccaatatc accaatctgt gccccttcgg cgaggtgttc 1080
aatgccacca gattcgcctc tgtgtacgcc tggaaccgga gcggatcag caattgcgtg 1140
gccgactact ccgtgctgta caactccgcc agcttcagca ccttcaagtg ctacggcgtg 1200
tcccctacca agctgaacga cctgtgcttc acaaacgtgt acgccgacag cttcgtgatc 1260
cggggagatg aagtgcggca gattgcccct ggacagacga gcaagatcgc cgactacaac 1320
tacaagctgc ccgacgactt caccggctgt gtgattgcct ggaacagcaa caacctggac 1380
tccaaagtcg gcggcaacta caattacctg taccggctgt tccggaagtc caatctgaag 1440
cccttcgagc gggacatctc caccgagatc tatcaggccg gcagccccc ttgtaacggc 1500
gtggaaggct tcaactgcta cttcccactg cagtcctacg gctttcagcc cacaaatggc 1560
gtgggctatc agccctacag agtggtggtg ctgagcttcg aactgctgca tgcccctgcc 1620
acagtgtgcg gccctaagaa aagcaccaat ctcgtgaaga caaatgcgt gaacttcaac 1680
ttcaacggcc tgaccggcac cggcgtgctg acagagagca caagaagtt cctgccattc 1740
cagcagtttg gccgggatat cgccgatacc acagacgccg ttagagatcc ccagacactg 1800
gaaatcctgg acatcacccc ttgcagcttc ggcggagtgc tgtgatcac ccctggcacc 1860
aacaccagca tcaggtggc agtgctgtac caggacgtga actgtaccga agtgcccgtg 1920
gccattcacg ccgatcagct gacacctaca tggcgggtgt actccaccgg cagcaatgtg 1980
tttcagacca gagccggctg tctgatcgga gccgagcacg tgaacaatag ctacgagtgc 2040
gacatcccca tcggcgctgg aatctgcgcc agctaccaga cacagacaaa cagccctcgg 2100
agagccagaa gcgtggccag ccagagcatc attgcctaca caatgtctct gggcgccgag 2160
aacagcgtgg cctactccaa caactctatc gctatcccca caacttcac catcagcgtg 2220
accacagaga tcctgcctgt gtccatgacc aagaccagct ggactgcac catgtacatc 2280
tgcggcgatt ccaccgagtg ctccaacctg ctgctgcagt acggcagctt ctgcacccag 2340
ctgaatagag ccctgacagg gatcgccgtg gaacaggaca gaacaccga agaggtgttc 2400
gcccaagtga gcagatctca agaccccct ctatcaagg acttcggcgg cttcaatttc 2460
agccagattc tgcccgatcc tagcaagccc agcaagcgga gcttcatcga ggacctgctg 2520
ttcaacaaag tgacactggc cgacgccggc ttcatcaagc agtatggga ttgtctggc 2580
gacattgccg ccaggatct gatttgcgcc cagaagtta acggactgac agtgctgcct 2640
cctctgctga ccgatgagat gatcgcccag tacacatctg ccctgctggc cggcacaatc 2700
acaagcggct ggacatttgg agcaggcgcc gctctgcaga tccccttgc tatgcagatg 2760
gcctaccggt tcaacggcat cggagtgacc cagaatgtgc tgtacgagaa ccagaagctg 2820
atcgccaacc agttcaacag cgccatcggc aagatccagg acagcctgag cagcacagca 2880
agcgccctgg gaaagctgca ggacgtggtc aaccagaatg cccaggcact gaacaccctg 2940
gtcaagcagc tgtcctccaa cttcggcgcc atcagctctg tgctgaacga tatcctgagc 3000
agactggacc ctcctgaggc cgaggtgcag atcgacagac tgatcacagg cagactgcag 3060
agcctccaga catacgtgac ccagcagctg atcagagccg ccgagattag cctctctgcc 3120
```

```
aatctggccg ccaccaagat gtctgagtgt gtgctgggcc agagcaagag agtggacttt 3180
tgcggcaagg gctaccacct gatgagcttc cctcagtctg cccctcacgg cgtggtgttt 3240
ctgcacgtga catatgtgcc cgctcaagag aagaatttca ccaccgctcc agccatctgc 3300
cacgacggca aagcccactt tcctagagaa ggcgtgttcg tgtccaacgg cacccattgg 3360
ttcgtgacac agcggaactt ctacgagccc cagatcatca ccaccgacaa caccttcgtg 3420
tctggcaact gcgacgtcgt gatcggcatt gtgaacaata ccgtgtacga ccctctgcag 3480
cccgagctgg acagcttcaa agaggaactg gacaagtact ttaagaacca cacaagcccc 3540
gacgtggacc tgggcgatat cagcggaatc aatgccagcg tcgtgaacat ccagaaagag 3600
atcgaccggc tgaacgaggt ggccaagaat ctgaacgaga gcctgatcga cctgcaagaa 3660
ctggggaagt acgagcagta catcaagtgg ccctggtaca tctggctggg ctttatcgcc 3720
ggactgattg ccatcgtgat ggtcacaatc atgctgtgtt gcatgaccag ctgctgtagc 3780
tgcctgaagg gctgttgtag ctgtggcagc tgctgcaagt tcgacgagga cgattctgag 3840
cccgtgctga agggcgtgaa actgcactac acatgatgac tcgagctggt actgcatgca 3900
cgcaatgcta gctgcccctt tcccgtcctg ggtacccccga gtctccccccg acctcgggtc 3960
ccaggtatgc tcccacctcc acctgcccca ctcaccacct ctgctagttc cagacacctc 4020
ccaagcacgc agcaatgcag ctcaaaacgc ttagcctagc cacaccccca cgggaaacag 4080
cagtgattaa cctttagcaa taaacgaaag tttaactaag ctatactaac cccagggttg 4140
gtcaatttcg tgccagccac accctggagc tagcagcggc cgcggccgca aaaaaaaaaa 4200
aaaaaaaaaa aaaaaaaaaa aaaaaaaaaa aaaaaaaaaa aaaaaaaaaa aaaaaaaaaa 4260
aaaaaaaaaa aaaaaaaaaa aaaaaaaaaa aaaaaaaaaa aaaaaaaaaa aaaaaaaa    4319
```